(12) United States Patent
Hertz et al.

(10) Patent No.: US 8,586,298 B2
(45) Date of Patent: Nov. 19, 2013

(54) METHODS AND KITS FOR DIAGNOSING AND TREATING B-CELL CHRONIC LYMPHOCYTIC LEUKEMIA

(75) Inventors: Anne Mette Buhl Hertz, Rungsted Kyst (DK); Henrik Leffers, Copenhagen N (DK)

(73) Assignee: Clluone Diagnostics A/S, Aalborg Øst (DK)

( * ) Notice: Subject to any disclaimer, the term of this patent is extended or adjusted under 35 U.S.C. 154(b) by 472 days.

(21) Appl. No.: 10/535,500

(22) PCT Filed: Nov. 19, 2003

(86) PCT No.: PCT/DK03/00794
§ 371 (c)(1),
(2), (4) Date: May 26, 2006

(87) PCT Pub. No.: WO2004/046376
PCT Pub. Date: Jun. 3, 2004

(65) Prior Publication Data
US 2006/0281697 A1  Dec. 14, 2006

(30) Foreign Application Priority Data
Nov. 19, 2002  (DK) .................................. 2002-01792

(51) Int. Cl.
*C12Q 1/68* (2006.01)
*A61K 49/00* (2006.01)

(52) U.S. Cl.
USPC .............................. 435/6.1; 424/9.1; 435/6.14

(58) Field of Classification Search
None
See application file for complete search history.

(56) References Cited

U.S. PATENT DOCUMENTS

| | | | |
|---|---|---|---|
| 4,554,101 | A | 11/1985 | Hopp |
| 5,681,729 | A | 10/1997 | Kudo et al. |
| 2003/0190659 | A1 | 10/2003 | LaCasse et al. |

FOREIGN PATENT DOCUMENTS

| | | |
|---|---|---|
| EP | 1 033 401 A2 | 9/2000 |
| WO | WO 00/44788 A1 | 8/2000 |
| WO | WO 00/67795 A1 | 11/2000 |
| WO | WO 00/64886 A2 | 9/2001 |

OTHER PUBLICATIONS

Shanafelt, T.D., Byrd, J.C., Call, T.G., Zent, C.S., and Kay, N.E. Narrative review: initial management of newly diagnosed, early-stage chronic lymphocytic leukemia. Annals of Internal Medicine, 2006. vol. 145, pp. 435-447.*
Rosenwald, Alizadeh, Widhopf, Simon, Davis, Yu, Yang, Pickeral, Rassenti, Powell, Botstein, Byrd, Grever, Cheson, Chiorazzi, Wilson, Kipps, Brown, and Staudt. Relation of gene expression phenotype to immunoglobulin mutation genotype in b cell chronic lymphocytic leukemia. Journal of Experimental Medicine, 2001. vol. 194, pp. 1639-1647.*
Burger et al. (2002) Chemokine Receptors and Stromal Cells in the Homing and Homeostasis of Chronic Lymphocytic Leukemia B Cells. Leukemia & Lymphoma, 43(3):461-466.*
Orchard et al. (2004) ZAP-70 expression and prognosis in chronic lymphocytic leukaemia. Lancet, 363:105-111.*
Damie et al., "B-Cell Chronic Lymphocytic Leukemia Cells Express a Surface Membrane Phenotype of Activated, Antigen-Experienced B Lymphocytes", Blood, vol. 99, No. 11, p. 4087-4090, 2002.
Hamblin, "Chronic Lymphocytic Leukaemia: One Disease of Two?", Ann Hematol, vol. 81, p. 299-303, 2002.
Kröber, et al., "$V_H$ Mutation Status, CD38 Expression Level, Genomic Aberrations, and Survival in Chronic Lymphocytic Leukemia", Blood, vol. 100, No. 4, p. 1410-1416, 2002.
Lin et al., "Relationship between p53 Dysfuction, CD38 Expression, and $IgV_H$ Mutation in Chronic Lymphocytic Leukemia", Blood, vol. 100, No. 4, p. 1404-1409, 2002.
Jensen et al., "'Rapid Tumor Lysis in a Patient with B-Cell Chronic Lymphocytic Leukemia and Lymphocytosis Treated with an Anti-CD20 Monoclonal Antibody (IDEC-C2B8, Rituximab), Ann Hematol, vol. 77, p. 89-91, 1998.
Muzny et al., "*Homosapiens*", 12 BAC RP11-693J15, Database EMBL, accession No. AC063949, 2000.
Andrews et al., "Reconstruction of a Functional Human Type II IL-4/IL-13 Receptor in Mouse B Cells: Demonstration of Species Specificity" J Immunol, vol. 166, No. 3, p. 1716-1722, 2001.
Bouteiller et al., "Isolation of an IL-13-dependent Subclone of the B9 Cell Line Useful for the Estimation of Human IL-13 Bioactivity", Journal of Immunological Methods, vol. 181, p. 29-36, 1995.
Chaouchi et al., "Interleukin-13 Inhibits Interleukin-2-Induced Proliferation and Protects Chronic Lymphocytic Leukemia B Cells from In Vitro Apoptosis", Blood, vol. 87, No. 3, p. 1022-1029, 1996.
Damie et al., "Ig V Gene Mutation Status and CD38 Expression as Novel Prognostic Indicators in Chronic Lymphocytic Leukemia", Blood, vol. 94, No. 6, p. 1840-1847, 1999.
Dancescu et al., "Interleukin 4 Protects Chronic Lymphocytic Leukemic B Cells from Death by Apoptosis and Upregulates Bcl-2 Expression" J. Exp. Med., vol. 176, p. 1319-1326, 1992.
Dohner et al., "Genomic Aberrations and Survival in Chronic Lymphocytic Leukemia", The New England Journal of Medicine, vol. 343, No. 26, p. 1910-1916, 2000.
Fluckiger et al., "IL-13 has only a subset of IL-4-like Activities on B Chronic Lymphocytic Leukaemia Cells", Immunology, vol. 83, No. 3, p. 397-403, 1994.
Hamblin, et al., "Unmutated Ig $V_H$ Genes are Associated with a More Aggressive Form of Chronic Lymphocytic Leukemia", Blood, vol. 94, No. 6, p. 1848-1854, 1999.
Jorgensen et al., Differential Display Competitive Polymerase Chain Reaction: An Optimal Tool for Assaying Gene Expression, Electrophoresis, vol. 20, p. 230-240, 1999.

(Continued)

Primary Examiner — Anne Gussow
Assistant Examiner — Neil P Hammell
(74) Attorney, Agent, or Firm — Hunton & Williams LLP

(57) ABSTRACT

The present invention relates to methods and kits for detecting several polynucleotide sequence found to be indicative of a poor prognosis of B-CLL. All the polynucleotides are transcribed from a region on human chromosome 12p21-22. Most of the polynucleotides do not encode larger polypeptides, but may encode small peptides, they may function as RNAs. Four polynucleotides encode a novel protein, which in one preferred embodiment can be used as a cytokine, preferably as an interleulkin. Furthermore the invention relates to methods and compositions for treating B-CLL in particular poor prognosis B-CLL.

13 Claims, 13 Drawing Sheets

(56) References Cited

OTHER PUBLICATIONS

Kim et al., "The Emerging Fields of Suicide Gene Therapy and Virotherapy", Trends in Molecular Medicine, vol. 8, No. 4, p. S68-S73, 2002.

Kröber et al., "$V_H$ Mutation Status, CD38 Expression Level, Genomic Aberrations, and Survival in Chronic Lymphocytic Leukemia", Blood, vol. 100, No. 4, p. 1410-1416, 2002.

Kyte et al., "A Simple Method for Displaying the Hydropathic Character of a Protein", Journal of Molecular Biology, vol. 157, p. 105-132, 1982.

Liang et al., "Differential Display of Eukaryotic Messenger RNA by Means of the Polymerase Chain Reaction", Science, vol. 257, p. 967-971, 1992.

Lundin et al., "Interleukin 4 Therapy for Patients with Chronic Lymphocytic Leukaemia: a phase I/II Study", British Journal of Haematology, vol. 112, p. 155-160, 2001.

Luo et al., Antiproliferative Effect of Interleukin-4 in B Chronic Lymphocytic Leukemia, Journal of Immunotherapy, vol. 10, p. 418-425, 1991.

Merrifield, "Solid Phase Peptide Synthesis. I. The Synthesis of a Tetrapeptide", J. Am. Chem. Soc., vol. 85, p. 2149-2154, 1963.

Panayiotidis et al., "Interleukin-4 Inhibits Apoptotic Cell Death and Loss of the bcl-2 Protein in B-Chronic Lymphocytic Leukaemia Cells in vitro", British Journal of Haematology, vol. 85, p. 439-445, 1993.

Petersen et al., "Optimisation of the CT.h4S Bioassay for Detection of Human Interleukin-4 Secreted by Mononuclear Cells Stimulated by Phytohaemaglutinin or by Human Leukocyte Antigen Mismatched Mixed Lymphocyte Culture", Immunology Letters, vol. 84, p. 29-39, 2002.

Yazawa et al., "Current Progress in Suicide Gene Therapy for Cancer", World J. Surg., vol. 26, No. 7, p. 783-789, 2002.

Oscier et al., Multivariate Analysis of Prognostic Factors in CLL: Clinical Stage, *IGVH* gene mutational status, and Loss or Mutation of the *p53* gene are Independent Prognostic Factors, Blood, vol. 100, No. 4, p. 1177-1184, 2002.

Standard Search Report in DK2002 01792, dated Jul. 22, 2003.

International Search Report in PCT/DK03/00794, dated Augst 16, 2004.

Written Opinion issued in International Application No. PCT/DK03/00794, dated Oct. 27, 2004.

EP Divisional Application No. 07115891.9 Extended EP Search Report dated Sep. 30, 2008.

EP Patent Application No. 03773581.8 Examination Report dated Oct. 29, 2008.

XP-002490020, "Direct Submission", Aug. 29, 2002 Database Embase, Elsevier Science Publisher, Amsterdam.

XP-002490021, "Mammalian Gene Collection Program Team", Jun. 19, 2007 Database Embase, Elsevier Science Publisher, Amsterdam.

Buhl, A. et. al., Identification of a gene on chromosome 12q22 uniquely overexpressed in chronic lymphocytic leukemia, Blood Journal, 107(7): 2904-2911, Jan. 4, 2006.

Josefsson, P. et al., CLLU1 Expression analysis adds prognostic information to risk prediction in chronic lymphocytic leukemia, Blood Journal, 109(11): 4973-4979, Jan. 6, 2007.

Celis, J. et al., Gene expression profiling: monitoring transcription and translation products using DNA microarrays and proteomics, FEBS Letters, 480: 2-16, 2000.

Orntoft, T. et al., Genome-wide Study of Gene Copy Numbers, Transcripts, and Protein Levels in Pairs of Non-invasive and Invasive Human Transitional Cell Carcinomas, Molecular & Cellular Proteomics, 1(1): 37-45, Jan. 1, 2001.

Buhl, et al. (2009) The CLLU1 Expression Level Is a Stable and Inherent Feature of the Chronic Lymphocytic Leukemia Clone, Leukemia, v. 23, pp. 1182-1186.

Caligaris-Cappio, F. (2000) Biology of Chronic Lymphocytic Leukemia, Rev. Clin. Exp. Hematol. v.4 pp. 5-21.

BLAST alignment of SEQ ID No. 11, [retrived on Jan. 1, 2010], Retrieved from the Internet: <http://blast.ncbi.nlm.nih.gov/Blast.cgj>.

Entrez Gene information for CLLU1 [retrieved on Jan. 1, 2010]; Retrieved from the Internet: <http://www.ncbi.nlm.nih.gov/sites/entrez>.

\* cited by examiner

Fig.4

| Fold Library | Template Length | Model | PSSM E-value | SAM/TED E-value | Biotext | Class | Fold | SuperFamily | Family | Protein |
|---|---|---|---|---|---|---|---|---|---|---|
| d1pd212 23%i.d. | 75 | | 2.98 | 1 | n/a | Alpha and beta proteins (a/b) | Thioredoxin fold | Thioredoxin-like | Glutathione S-transferases, N-terminal domain | Glutathione S-transferase |
| d1iara_ 17%i.d. | 129 | | 3.05 | 1 | n/a | All alpha proteins | 4-helical cytokines | 4-helical cytokines | Short-chain cytokines | Interleukin-4 (IL-4) |
| d1dgna_ 17%i.d. | 89 | | 5.34 | 1 | n/a | not in SCOP 1.53 | PDB header: hydrolase inhibitor. | Chain: A; PDB Molecule:iceberg (protease inhibitor). | | PDBTitle: solution structure of interleukin-2 1beta generation. |
| d1am9a_ 22%i.d. | 80 | | 5.57 | 1 | n/a | All alpha proteins | Helix-loop-helix DNA-binding domain | Helix-loop-helix DNA-binding domain | Helix-loop-helix DNA-binding domain | SREBP-1a |

Fig.5

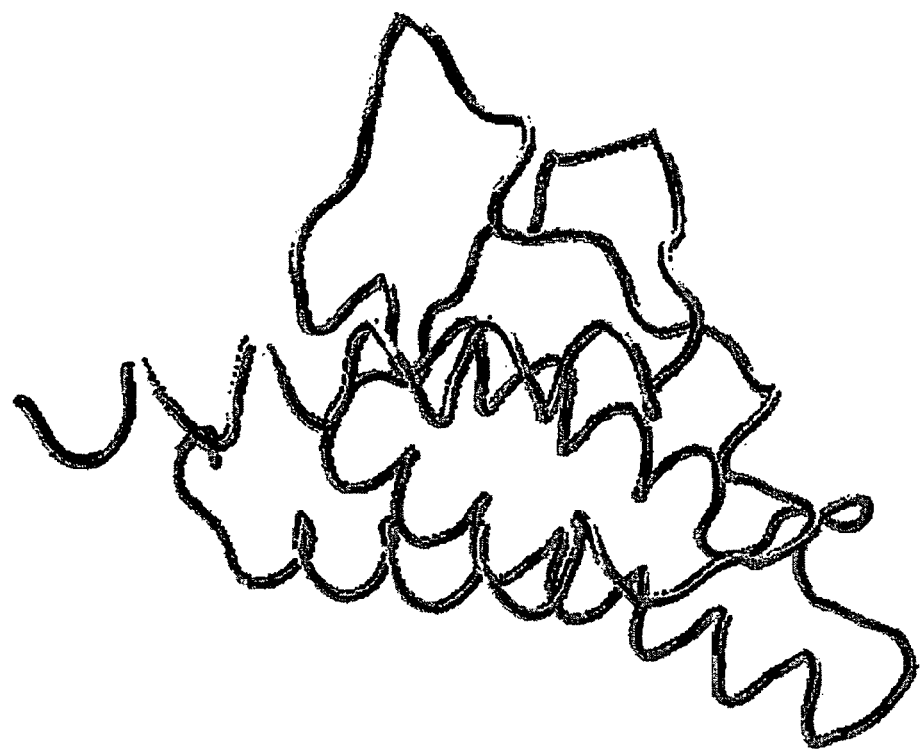
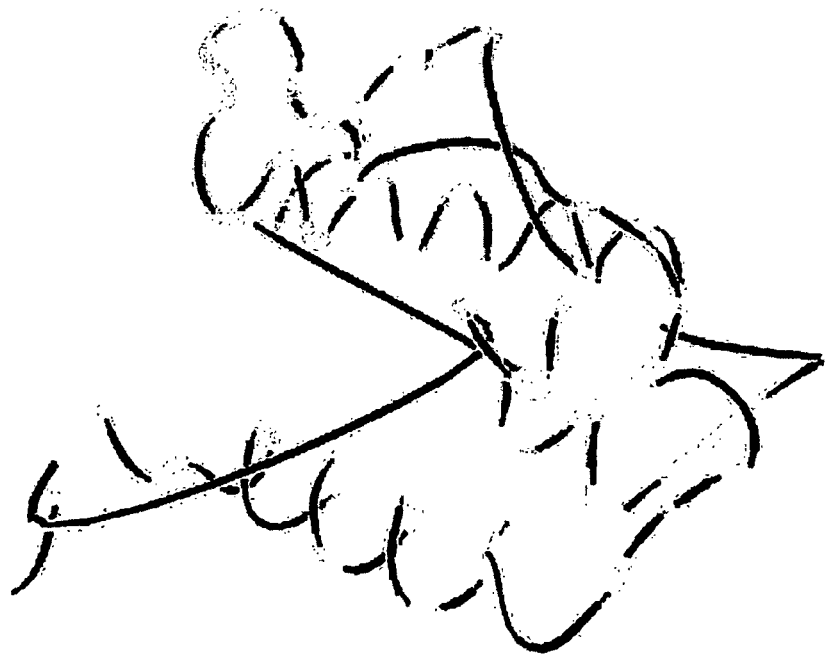
Fig.6
Human IL4
AMB1

```
AMB1 IL4 IL3 GM-CSF

AMB1    ------MFNKCSFHSSIYRPADNSASSLCAIICF---LNLVIECDLE-TNS-EINKLIIY-LFSQNNRIRFSKLLLKILFYI-SIFSYPE---IMC------EQYVTFIK---------------PGIHYGQVSKKH-IIYS---TFLSKNFKFQLLRVCW
IL4     -------------------------------------HKDITLQEIIKT---LNSL------TE-QKT-LCTELTVTDIFAASKNTTEKEIFCRAATVLRQFYSHHEKDTRC---LGATAQQFHRHKQLIREFLKRLDRNLWGL------AGLNSCPVKEANQSTLE---NFLERLKTIMREKYSKCSS-
IL3     ------------------------------------------ANCSIMIDE-----IIHH-------LKRPNPLLDPN-----------------NLLN-SEDMDILMERNLRTPNLLAFVRAVKHLENASAIES------ILKNLLPCL

| | 1 | 2 | 3 | 4 | 5 | 6 | 7 | 8 | 9 | 10 | 11 | 12 |
|---|---|---|---|---|---|---|---|---|---|---|---|---|
| A | whole brain | cerebellum left | substantia nigra | heart | esophagus | colon, transverse | kidney | lung | liver | leukemia, HL-60 | fetal brain | yeast total RNA |
| B | cerebral cortex | cerebellum right | accumbens nucleus | aorta | stomach | colon, desending | skeletal muscle | placenta | pancreas | HeLa S3 | fetal heart | yeast tRNA |
| C | frontal lobe | corpus callosum | thalamus | atrium, left | duodenum | rectum | spleen | bladder | adrenal gland | leukemia K-562 | fetal kidney | E.coli rRNA |
| D | parietal lobe | amygdala | pituitary gland | atrium, right | jejunum | | thymus | uterus | thyroid gland | leukemia, MOLT-4 | fetal liver | E.coli DNA |
| E | occipital lobe | caudate nucleus | spinal cord | ventricle left | ileum | | peripheral blood leukocyte | prostate | salivary gland | Burkitt's lymphoma, Raji | fetal spleen | Poly r(A) |
| F | temporal lobe | hippo-campus | | ventricle right | ilocecum | | lymph node | testis | mammary gland | Burkitt's lymphoma, Daudi | fetal thymus | human C₀t-1 DNA |
| G | p.g.* of cerebral cortex | medulla oblongata | | inter-ventricular septum | appendix | | bone marrow | ovary | | colorectal adeno-carcinoma SW480 | fetal lung | human DNA 100 ng |
| H | pons | putamen | | apex of the heart | colon, ascending | | trachea | | | lung carcinoma A549 | | human DNA 500 ng |

METHODS AND KITS FOR DIAGNOSING AND TREATING B-CELL CHRONIC LYMPHOCYTIC LEUKEMIA

CROSS-REFERENCE TO RELATED APPLICATIONS

This patent application is a U.S. national phase application of International Application No. PCT DK/2003/000794, filed Nov. 19, 2003, which claims priority of Denmark Patent Application PA 2002 01792, filed Nov. 19, 2002. All of the above applications are incorporated herein by reference in their entireties.

All patent and non-patent references cited in the present application, are hereby incorporated by reference in their entirety.

FIELD OF INVENTION

The present invention relates to methods and kits for detecting several polynucleotide sequence found to be indicative of a poor prognosis of B-CLL. All the polynucleotides are transcribed from a region on human chromosome 12p21-22. Most of the polynucleotides do not encode larger polypeptides, but may encode small peptides, they may function as RNAs. Four polynucleotides encode a novel protein, which in one preferred embodiment can be used as a cytokine, preferably as an interleukin. Furthermore the invention relates to methods and compositions for treating B-CLL in particular poor prognosis B-CLL.

BACKGROUND OF INVENTION

B-CLL is the most common form of leukaemia in Denmark, with more than 250 new cases diagnosed every year. The disease results in accumulation of CD19+CD5+CD23+ lymphocytes in the blood, bone marrow and organs of the patients. B-CLL cells are long-lived, slowly dividing and locked in the $G_1$ phase of the cell cycle. At this time it is unknown how or why B-CLL occurs and no cure is known for B-CLL. The application of more aggressive treatment strategies has been hampered by the inability to identify reproducible and reliable prognostic predictors in patients with poor outcome in this disease. In many patients the diagnosis does not affect morbidity or mortality. Other patients suffer from an incurable cancer that inevitably results in death, regardless of treatment. Until recently this latter group of patients could not be identified at the time of diagnosis. Recently, two studies established the mutational status of immunoglobulin variable region of the heavy chain (Ig $V_H$) genes in B-CLL as independent prognostic markers, within each clinical stage (Damle, et al. & Hamblin, et al.). Patients without somatic hypermutation show much shorter survival than patients with somatic hypermutation. FISH-studies of cytogenetic aberrations in B-CLL established specific abnormalities on chromosomes 11 (ATM), 12 (?), 13 (Leu-1 and -2) and 17 (p53) as independent prognostic markers, within each clinical stage (Dohner, et al.). Very recent studies have demonstrated that independent risk prediction, using a combined analysis of Ig $V_H$ gene mutational analysis and cytogenetics, can identify subgroups of B-CLL with median survival ranging from less than 2.5 years to more than 15 years (Krober, et al., Lin, et al., & Oscier, et al.) (see FIG. 1). Since the process of characterising the Ig VH gene mutational status of an individual patient is cumbersome, it is desirable to provide easier tests based on diagnostic markers for use in the differential diagnosis of such cancer patients.

SUMMARY OF INVENTION

It is an object of preferred embodiments of the present invention to provide differentially expressed transcription products, which can be used as prognostic markers of disease and give information about the differences in etiology between different groups of B-CLL patients. These differentially expressed transcription products are genetic markers that can be used in an easy assay to distinguish between subgroups of B-CLL patients and especially identify B-CLL patients with a poor prognosis.

This method for diagnosing a subtype of B-cell chronic lymphocytic leukaemia (B-CLL) comprises the steps of determining the presence or absence of at least one expression product such as a transcriptional product which comprise a nucleotide sequence selected from the group consisting of SEQ ID No:12, SEQ ID No:13, SEQ ID No:14, SEQ ID No:15, SEQ ID No:16, SEQ ID No:17 and SEQ ID No:18 in a biological sample isolated from a individual. As evidenced by the appended examples, the present inventors have determined that the expression products of this invention are present in one subtype of B-CLL having poor prognosis and thus of great diagnostic value and independent prognostic value. Equally important, an expression product comprising a nucleotide sequence selected from the group consisting of SEQ ID No:12, SEQ ID No:13, SEQ ID No:14, SEQ ID No:15, SEQ ID No:16, SEQ ID No:17 and SEQ ID No:18 has not been found in any of the other tissue types tested (see e.g. FIG. 8).

The vast majority of patients which show expression of the AMB-1 gene in form of at least one of the expression products selected from the group consisting of SEQ ID No:12, SEQ ID No:13, SEQ ID No:14, SEQ ID No:15, SEQ ID No:16, SEQ ID No:17 and SEQ ID No:18 show unmutated Ig V(H) genes which is consistent with poor prognosis B-CLL. The presence of an expression product of the AMB-1 gene can be determined easily using standard laboratory procedures and equipment. Therefore the diagnostic method provided by the present inventors provides an easy method of diagnosis as compared to the determination of the mutation status of Ig V(H) genes and can furthermore give additional information about the prognosis.

Accordingly, a further object of preferred embodiments of the present invention is a method for determining the progress of B-CLL comprising determining the amount of at least one expression product which comprise a nucleotide sequence selected from the group consisting of SEQ ID No:12, SEQ ID No:13, SEQ ID No:14, SEQ ID No:15, SEQ ID No:16, SEQ ID No:17 and SEQ ID No:18 in a biological sample isolated from an individual. The method may be used e.g. for determining the efficiency of a treatment, i.e. to see whether the amount of the expression product decreases or increases in response to a curative treatment.

The expression products of the present invention are all transcripts of SEQ ID NO:1 and/or SEQ ID No:5, the gene of the present invention called AMB-1 which also encodes a novel polypeptide (SEQ ID NO:3).

A further object of preferred embodiments of the present invention is to provide a cure and/or treatment of patients with B-CLL, in particular of patients with poor prognosis B-CLL such as the sub-type of B-CLL which is characterised by the presence of an expression product of the present invention.

The method for treating B-CLL comprises administering to an individual with a B-CLL diagnosis a compound capable of decreasing or inhibiting the formation of an expression product of SEQ ID NO:1 and/or SEQ ID NO:5. This expression product preferably comprises a nucleotide sequence selected from the group consisting of SEQ ID No:12, SEQ ID No:13, SEQ ID No:14, SEQ ID No:15, SEQ ID No:16, SEQ ID No:17 and SEQ ID No:18. The present inventors believe that the presence of at least one of said expression products is an etiological factor in B-CLL and that the disease can be treated or cured by inhibiting the expression of at least one of such products and/or by inhibiting the effect of such product by e.g. rendering it inactive.

A further preferred object of embodiments of the present invention is to destroy or to eliminate the transcription of at least one expression product comprising at least one nucleotide sequence selected form the group consisting of SEQ ID No:12, SEQ ID No:13, SEQ ID No:14, SEQ ID No:15, SEQ ID No:16, SEQ ID No:17 and SEQ ID No:18 for the treatment of cancer, such as a poor prognosis sub-type of B-CLL.

The above destruction or elimination is obtained by applying polynucleotides or oligonucleotides in the form of small interfering RNA molecules (siRNA), antisense molecules or ribozymes.

In one aspect the invention relates to a gene therapy vector capable of inhibiting or decreasing the formation of an expression product of SEQ ID NO:1 and/or SEQ ID NO:5, said gene therapy vector preferably encoding a specific siRNA molecule, a specific antisense molecule or a specific ribozyme being capable of decreasing or inhibiting the formation of an expression product of SEQ ID NO:1 and/or SEQ ID NO:5. This gene therapy vector can be used for treating B-CLL based on the finding that the AMB-1 gene encoded by SEQ ID No:1 and/or SEQ ID No:5 is an etiological factor in B-CLL.

Both SEQ ID No 1 which is a 20,000 nucleotide long sequence and SEQ ID No 5 which is a 80,000 nucleotide long sequence provides several transcriptional products in B-CLL cells in patients with poor prognosis B-CLL. Some of the transcriptional products e.g. SEQ ID No 2 and SEQ ID No 4 consists of two exons (SEQ ID No: 15 and SEQ ID No: 16) separated by the same intron. Both mRNA sequences encode an open reading frame (SEQ ID No: 17) encoding a 121 amino acid peptide (SEQ ID No 3).

Accordingly, yet another object of preferred embodiments of the present invention relates to a novel class of polypeptides. These may be described as a group of isolated polypeptides or proteins comprising or essentially consisting of the amino acid sequence of SEQ ID No. 3, or a fragment thereof, or a polypeptide functionally equivalent to SEQ ID No. 3, or a fragment thereof, wherein said fragment or functionally equivalent polypeptide has at least 60% sequence identity with the polypeptide of SEQ ID No 3. The polypeptides of the present invention may have interleukin or cytokine activity.

In a still further aspect the invention relates to an isolated polynucleotide selected from the group consisting of:

i) a polynucleotide comprising nucleotides of SEQ ID No 5, ii) a polynucleotide encoding a polypeptide having the amino acid sequence of SEQ ID No 3, iii) a polynucleotide, the complementary strand of which hybridises, under stringent conditions, with a polynucleotide as defined in any of i) and ii).

iv) a polynucleotide which is degenerate to the polynucleotide of iii), and v) the complementary strand of any such polynucleotide.

The polypeptides encoded by the polynucleotides may furthermore a) have at least 60% sequence identity with the amino acid sequence of SEQ ID No 3 and have interleukin or cytokine activity, b) be recognised by an antibody, or a binding fragment thereof, which is capable of recognising an epitope, wherein said epitope is comprised within a polypeptide having the amino acid sequence of SEQ ID No 3; and/or c) be competing with a polypeptide having the amino acid sequence as shown in SEQ ID No 3 for binding to at least one predetermined binding partner such as a cytokine receptor.

One further therapeutic application of the present invention is a method of vaccination against B-CLL said method comprising immunising an individual against a translational product of SEQ ID No:1 and/or SEQ ID No:5. By stimulating the immune system of an individual to produce antibodies against the translational product the individual can become immune towards B-CLL and/or the method can be used as part of therapy. The state of the art describes various ways of immunising an individual against a particular protein.

Finally, the invention provides a method for determining an increased or decreased predisposition for B-CLL comprising determining in a biological sample from an individual a germline alteration in a target nucleic acid sequence comprising 150,000 nucleotides, said target nucleic acid sequence comprising at least 10 nucleotides of SEQ ID No:1 and/or SEQ ID No:5. This aspect is based on the finding of the importance of the expression product of SEQ ID No:1 and/or SEQ ID No:5, and the absence of any detectable expression product of SEQ ID No:1 and/or SEQ ID No:5 in healthy tissue and in patients with good prognosis B-CLL. It is highly likely that the difference is caused by a germline alteration. A germline alteration can be targeted by gene therapy methods and by the methods provided in the present invention.

DESCRIPTION OF DRAWINGS

FIG. 4. Alignment of AMB1 with IL4 based on structurel similarity. IL4 is called d1iara in the alignment. The additional lines indicate the structural similarity.

FIG. 5. A 3D search, where the peptide sequence has been searched for similarity to known protein or peptide 3D-structures.

FIG. 6. Predicted 3-D structure of AMB-1 compared to the known 3-D structure of human IL4. Prediction is performed using SEQ ID No:3 and the method described in: Enhanced Genome Annotation using Structural Profiles in the Program 3D-PSSM. Kelley L A, MacCallum R M & Sternberg M J E (2000). J. Mol. Biol. 299(2), 499-520.

FIG. 7. Alignment of the AMB1 peptide sequence with the sequences of IL4, IL3, IL13 and GM-CSF, based on their structures.

FIG. 8. A table showing the tissue types on the MTE array used for dot blotting of AMB-1 to check for expression in other tissue types.

DETAILED DESCRIPTION OF THE INVENTION

Figure 1:
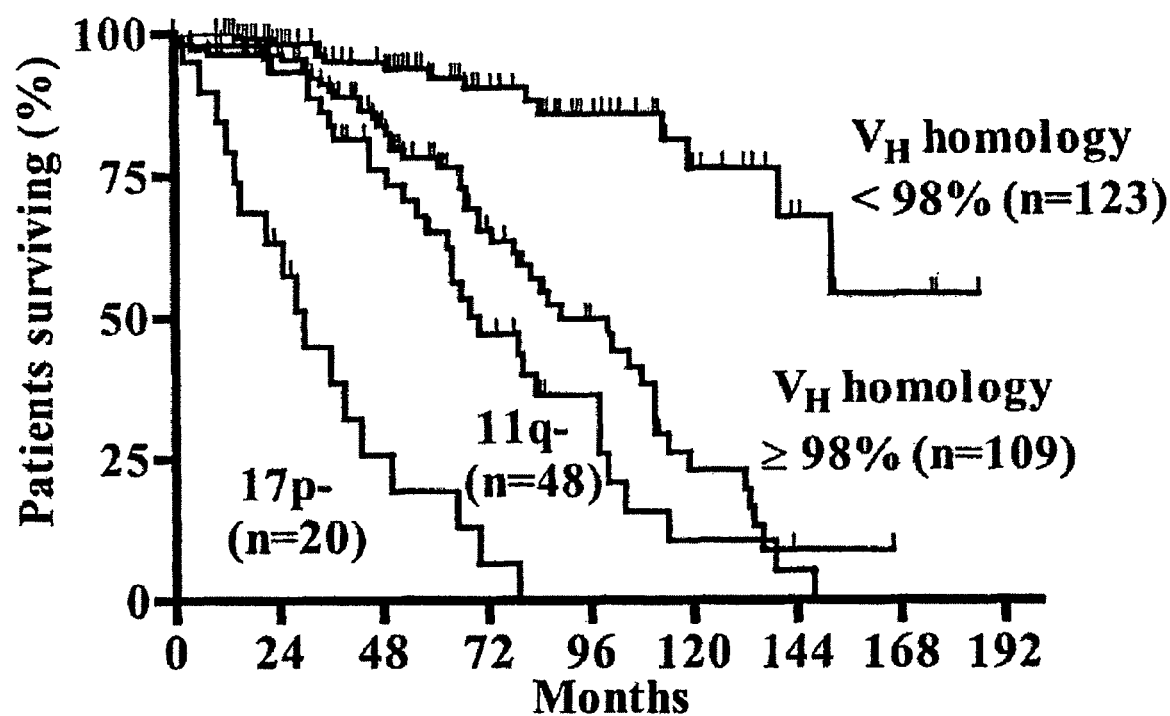
FIG. 1: Overall survival of B-CLL patients by genotype (all stages) The prognostic significance of $V_H$ homology and cytogenetic aberrations is independent of clinical stage (from Kröber et al., 2002 (4)).
Figure 2A:
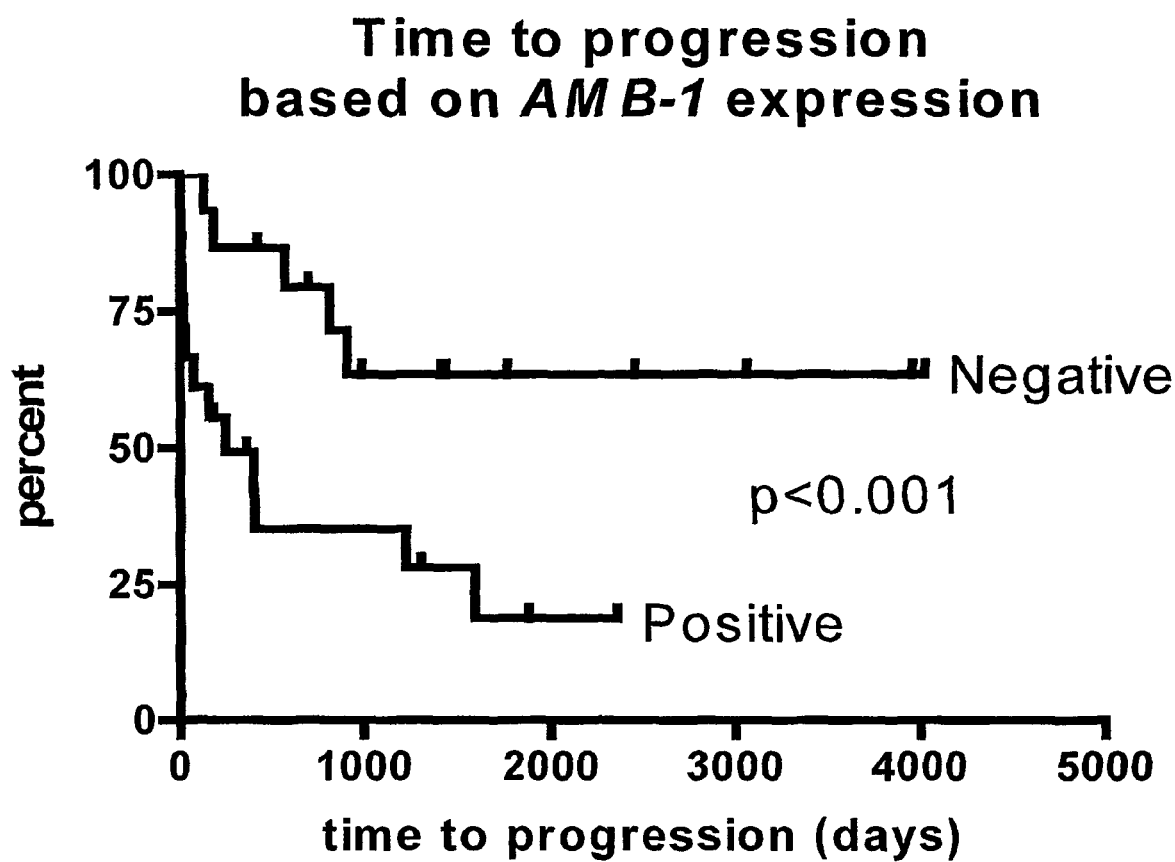
FIG. 2(a-d): Survival curves for survival or time to progression based on AMB-1 expression or $IgV_H$ mutational status respectively. Patients are newly diagnosed, untreated B-CLL patients (n=34).
Figure 2B:
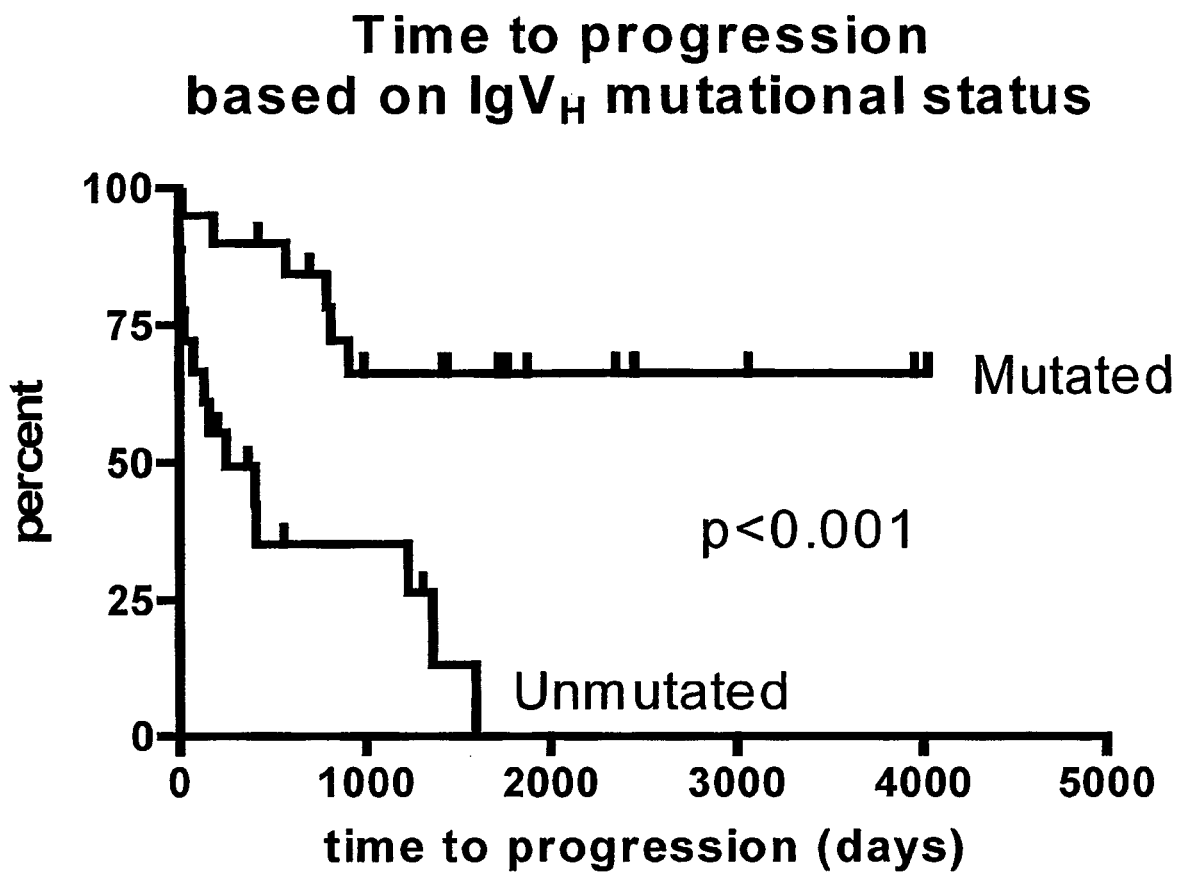
Figure 2C:
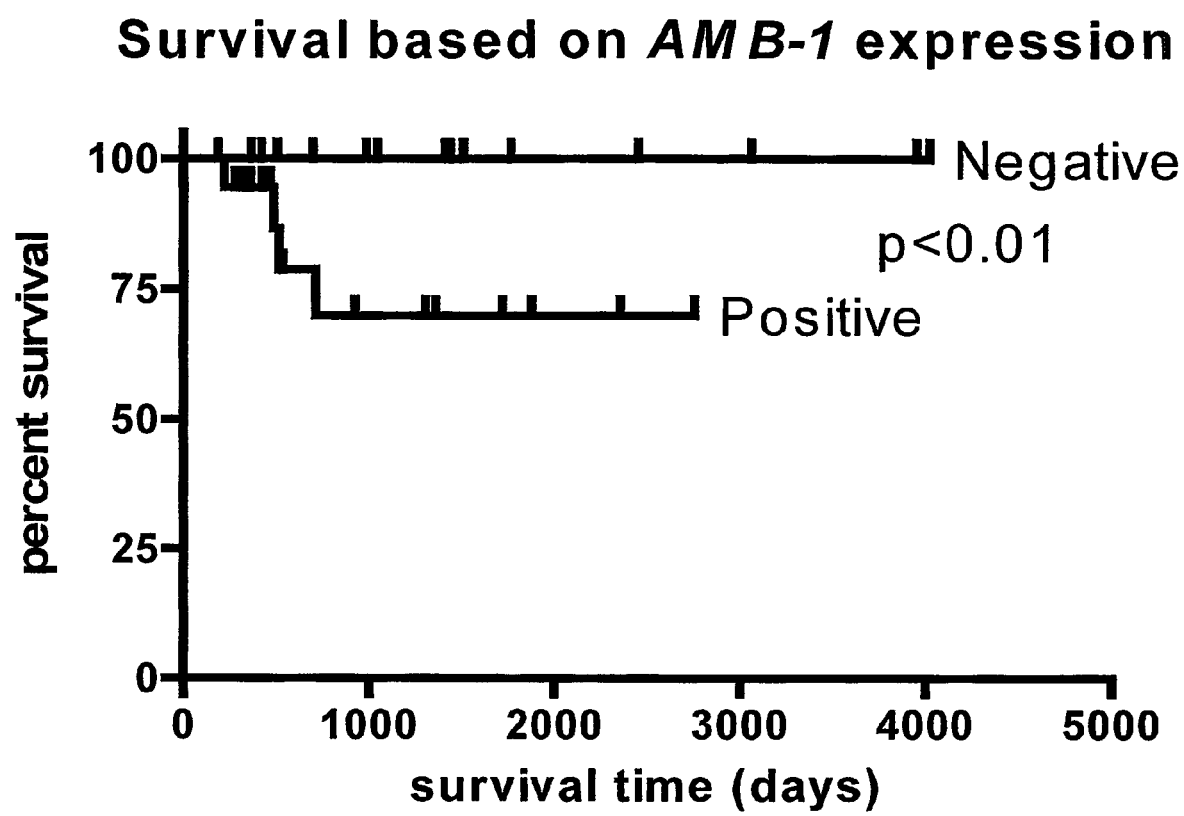
Figure 2D:
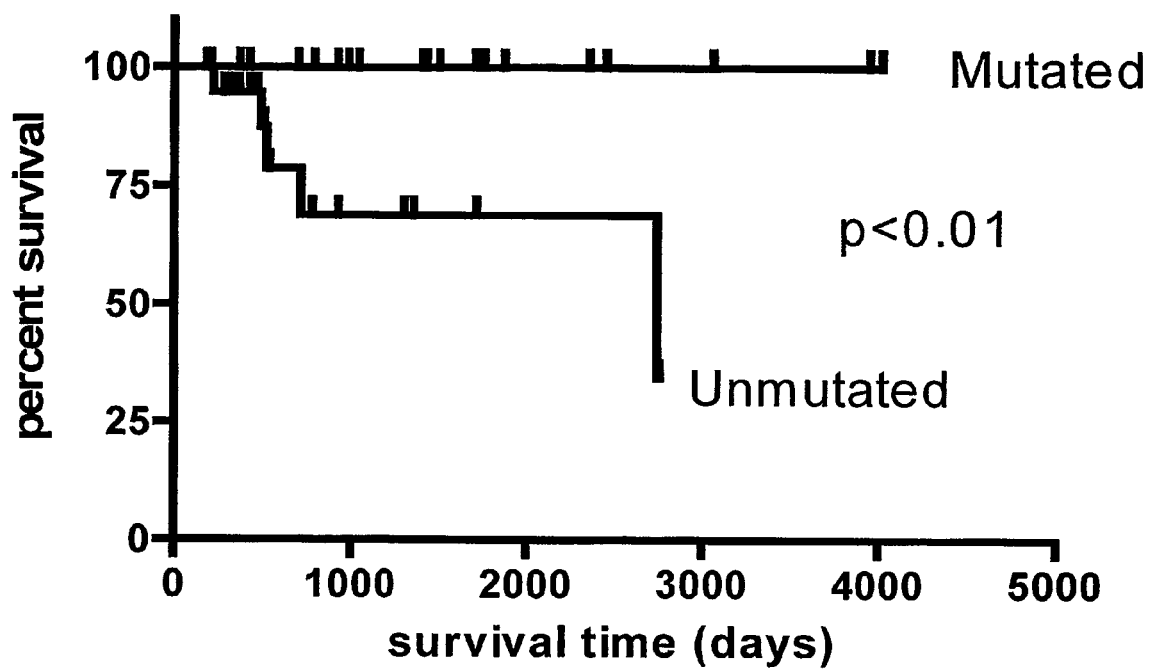

The present invention in particular relates to polynucleotide sequences found to be indicative of a poor prognosis of B-CLL and new methods and compositions for treating B-CLL in particular poor prognosis of B-CLL. An overview of the sequences disclosed by the present invention is present here:

SEQ ID No:1 includes 20.000 bp human genome sequence, derived from BAC clone acc. no. AC063949. It includes the region encoding the mRNAs corresponding to the cDNAs described in Seq ID Nos:2, 4, 6, 7, 8, 9, 10, and 11 and possible up- and down-stream regulatory sequences. Seq ID No:1 includes a subset of the sequence described in Seq ID No:5. The sequence is derived from human 12q21-22.

SEQ ID No:2 includes a cDNA corresponding to a putative mRNA transcript that includes the region encoding the peptide sequence in Seq ID No:3 and up- and downstream regions. It is transcribed from the +strand of Seq ID No:1 and Seq ID No:5 from human 12q21-22. From position 2317, this sequence is identical to Seq ID No:4.

Seq ID No:3 contains a peptide sequence encoded by some mRNAs transcribed from the region on human chromosome 12q21-22 included in Seq ID No:1 and Seq ID No:5. It is encoded by the mRNA sequences identified as cDNAs in Seq ID Nos 02, 04, 09 and 11.

Seq ID No:4 includes a cDNA corresponding to a putative mRNA transcript that includes the region encoding the peptide sequence in Seq ID No:3 and up- and downstream regions. It is transcribed from the +strand of Seq ID No:1 and Seq ID No:5 from human 12q21-22.

Seq ID No:5 includes 80.000 bp human genome sequence, derived from BAC clone acc. no. AC063949. It is an expansion of the genomic sequence included in Seq ID No:1. which is contained within this sequence. It includes the region encoding the mRNAs corresponding to the cDNAs described in Seq ID Nos 02, 04, 06, 07, 08, 09, 10 and 11 and possible up- and down-stream regulatory sequences. The sequence is derived from human 12q21-22.

Seq ID No:6 corresponds to a cDNA detected by cDNA cloning, corresponding to an mRNA transcript. It includes two exons. It is transcribed from the +strand of Seq ID No:1 and Seq ID No:5 from human 12q21-22.

Seq ID No:7 corresponds to a cDNA detected by cDNA cloning, corresponding to an mRNA transcript. It includes three exons, the first and third are identical to the two exons in Seq ID No:6. It is transcribed from the +strand of Seq ID No:1 and Seq ID No:5.doc from human 12q21-22.

Seq ID No:8 corresponds to a cDNA detected by cDNA cloning, corresponding to an mRNA transcript. It includes two exons, the last is also present as exon-2 in a human cDNA clone (sequence acc. no. BC036936) (Seq ID No:9.doc). It is transcribed from the +strand of Seq ID No:5.doc from human 12q21-22.

Seq ID No:9 corresponds to a human cDNA sequence (sequence acc. no. BC036936). It is transcribed from the +strand Seq ID No:5 from 12q21-22. We have not cDNA cloned this cDNA, but a splice variant (Seq ID No:8), where exon-2 of this sequence was spliced to exon-1 of Seq ID No:6 was detected by cDNA cloning. It is transcribed from the +strand of Seq ID No:5 from human 12q21-22.

Seq ID No:10 corresponds to a cDNA detected partly by cDNA cloning, partly by PCR analysis, corresponding to an mRNA transcript. It includes two exons, exon-1 includes the region encoding Seq ID No:3 and exon-1 from Seq ID No:6; exon-2 is identical to exon-2 in Seq ID No:6 and exon-3 in Seq ID No:7. It is transcribed from the +strand of Seq ID No:1.doc and Seq ID No:5 from human 12q21-22.

Seq ID No:11 corresponds to a cDNA detected by cDNA cloning, corresponding to an mRNA transcript. It includes one exon. The sequence includes the the region that encodes Seq ID No:3, exons 2 and 3 from Seq ID No:7 and the region between those exons. It is transcribed from the +strand of Seq ID No:1 and Seq ID No:5 from human 12q21-22.

Seq ID No:12 Is an exon sequence. It corresponds to the first exon in Seq ID No: 9 It is transcribed from the +strand of Seq ID No:5 from human 12q21-22.

Seq ID No:13 Is an exon sequence. It corresponds to the first exon in Seq ID No: 6, 7, 8, and it is included in Seq ID No: 2. It is transcribed from the +strand of Seq ID No:1 and 5 from human 12q21-22.

Seq ID No:14 Is an exon sequence. It is identical to Seq ID No:13, but with an additional GT dinucleotide at the 3'end, caused by the use of an alternative splice site. It can replace Seq ID No:13 as the first exon in Seq ID No: 6, 7, 8, and be included in Seq ID No: 2. It is transcribed from the +strand of Seq ID No:1 and 5 from human 12q21-22.

Seq ID No:15 Is an exon sequence. It corresponds to the second exon in Seq ID No:7 and it is included in Seq ID No: 2, 4, 10 and 11. It is transcribed from the +strand of Seq ID No:1 and 5 from human 12q21-22.

Seq ID No:16 Is an exon sequence. It corresponds to the third exon in Seq ID No:7, it is the second exon in Seq ID No:6 and 11 and it is included in Seq ID No:2 and 4. It is transcribed from the +strand of Seq ID No:5 from human 12q21-22.

Seq ID No:17 Is the sequence encoding the peptide in Seq ID No: 3. It is included in Seq ID No:2, 4, 10 and 11. It is transcribed from the +strand of Seq ID No:5 from human 12q21-22.

Seq ID No:18 Is an exon sequence. It corresponds to the second exon in Seq ID No:8 and 9. It is transcribed from the +strand of Seq ID No:5 from human 12q21-22.

Methods of Diagnosis

One important aspect of the present invention relates to diagnosis of a subtype of B-cell chronic lymphocytic leukaemia (B-CLL) having poor prognosis. A further important aspect of the invention relates to prognosis of B-CLL. These methods are based on the discovery by the present inventors that an expression product which comprise at least one nucleotide sequence selected from the group consisting of SEQ ID No:12, SEQ ID No:13, SEQ ID No:14, SEQ ID No:15, SEQ ID No:16, SEQ ID No:17 and SEQ ID No: 18 is (are) only present in particular subtypes of B-CLL associated with poor prognosis and completely absent in other subtypes of B-CLL and in healthy tissue (see in particular example 2). By completely absent is meant that the expression products are not detected in any of the other tissue types with the methods used in the appended examples. This is indicative of a complete absence of any transcript or a very low level of transcript in the other tissue types.

The expression product is encoded by SEQ ID No 1 and/or SEQ ID No 5, and the expression product is selected from the group consisting of transcriptional products and translational products.

Thus, the present invention relates to a method for detecting the presence or absence of at least one expression product, wherein the at least one expression product comprise a nucleotide sequence selected from the group consisting of SEQ ID No:12, SEQ ID No:13, SEQ ID No:14, SEQ ID No:15, SEQ ID No:16, SEQ ID No:17 and SEQ ID No:18 in a biological sample isolated from an individual for establishing a differential diagnosis of B-CLL or for determining the prognosis of the B-CLL.

"Expression product" is herein meant to be a product which is the result of the expression of a polynucleotide such as DNA sequence, e.g. a genomic DNA sequence, and is in the form of either a polypeptid or in the form of a polynucleotide, i.e. an expression product can be selected from the group consisting of a transcriptional product and a translational product. In the case where the expression product is a polynucleotide, said polynucleotide is preferably mRNA selected from the group consisting of mRNA, pre-mRNA, pre-pro-mRNA.

A "transcriptional product" or a "transcription product" is herein meant to be a product resulting from a transcription of a polynucleotide such as a DNA molecule, preferably a genomic DNA molecule. A transcriptional product is inherently a nucleotide, such as an oligonucleotide or a polynucleotide.

A "translational product" or a "translation product" is herein meant to be a product resulting from a translation of a transcriptional product such as a mRNA. A translational product is inherently a oligopeptide or a polypeptide.

The expression product of the present invention has almost exclusively been found as transcription products in patients with poor B-CLL prognosis. Based on the experimental data presented in the herein, the inventors expect that it turns out that the subtype of B-CLL is characterised solely or better by the presence of a transcriptional or translational product which comprise a sequence selected from the group consisting of SEQ ID No:3, SEQ ID No:12, SEQ ID No:13, SEQ ID No:14, SEQ ID No:15, SEQ ID No:16, SEQ ID No:17 and SEQ ID No:18.

Preferably the individual is a mammal, more preferably a human. It is also expected that the gene encoded by SEQ ID No 1 and/or SEQ ID No 5 and the expression products derived from said gene can be used as a diagnostic tool in other species in particular in mammals selected from the group: domestic animals such as cow, horse, sheep, pig; and pets such as cat or dog.

In the case that the expression product is a transcriptional product, this transcriptional product just needs to comprise at least one of the nucleotide sequences selected from the group consisting of SEQ ID No:12, SEQ ID No:13, SEQ ID No:14, SEQ ID No:15, SEQ ID No:16, SEQ ID No:17 and SEQ ID No:18. These transcriptional products will preferably be derived from SEQ ID No 1 and/or SEQ ID No 5 and may be in the form of mRNA or any pre- or pro-forms of said mRNA.

As described, the transcriptional product may comprise at least one of the nucleotide sequences selected from the group consisting of SEQ ID No:12, SEQ ID No:13, SEQ ID No:14, SEQ ID No:15, SEQ ID No:16, SEQ ID No:17 and SEQ ID No:18, such as one of the nucleotide sequences selected from the group consisting of SEQ ID No:12, SEQ ID No:13, SEQ ID No:14, SEQ ID No:15, SEQ ID No:16, SEQ ID No:17 and SEQ ID No:18, such as two of the nucleotide sequences selected from the group consisting of SEQ ID No:12, SEQ ID No:13, SEQ ID No:14, SEQ ID No:15, SEQ ID No:16, SEQ ID No:17 and SEQ ID No:18, such as 3 of the nucleotide sequences selected from the group consisting of SEQ ID No:12, SEQ ID No:13, SEQ ID No:14, SEQ ID No:15, SEQ ID No:16, SEQ ID No:17 and SEQ ID No:18, e.g. 4 of the nucleotide sequences selected from the group consisting of SEQ ID No:12, SEQ ID No:13, SEQ ID No:14, SEQ ID No:15, SEQ ID No: 16, SEQ ID No:17 and SEQ ID No:18, such as 5 of the nucleotide sequences selected from the group consisting of SEQ ID No:12, SEQ ID No:13, SEQ ID No:14, SEQ ID No:15, SEQ ID No:16, SEQ ID No:17 and SEQ ID No:18 and ultimately the transcriptional product may comprise all of the six nucleotide sequences selected from the group consisting of SEQ ID No:12, SEQ ID No:13, SEQ ID No:14, SEQ ID No:15, SEQ ID No:16, SEQ ID No:17 and SEQ ID No:18. The transcriptional product of the present invention can have any sequence which is a result of combining the nucleotide sequences selected from the group consisting of SEQ ID No:12, SEQ ID No:13, SEQ ID No:14, SEQ ID No:15, SEQ ID No:16, SEQ ID No:17 and SEQ ID No:18 as long as the specific nucleotide sequences selected from the group consisting of SEQ ID No:12, SEQ ID No:13, SEQ ID No:14, SEQ ID No:15, SEQ ID No:16, SEQ ID No:17 and SEQ ID No:18 can be identified as intact sequences in the transcriptional product.

Examples of transcriptional products in the form of specific mRNAs which comprise at least one of the nucleotide sequences selected from the group consisting of SEQ ID No:12, SEQ ID No:13, SEQ ID No:14, SEQ ID No:15, SEQ ID No:16, SEQ ID No:17 and SEQ ID No:18 are the sequences corresponding to SEQ ID No 2 (short cDNA clone) SEQ ID No 4 (long cDNA clone) SEQ ID No 6, SEQ ID No 7, SEQ ID No 8, SEQ ID No 9, SEQ ID No 10 and SEQ ID No 11. These mRNA sequences have been found in patients with poor prognosis.

It is obvious for a person skilled in the art that any fragments of SEQ ID No:2, SEQ ID No:4, SEQ ID No:6, SEQ ID No:7, SEQ ID No:8, SEQ ID No:9, SEQ ID No:10 and SEQ ID No:11 will have the same diagnostic value as long as the nucleotide sequences selected from the group consisting of SEQ ID No:12, SEQ ID No:13, SEQ ID No:14, SEQ ID No:15, SEQ ID No:16, SEQ ID No:17 and SEQ ID No:18 can be found in the fragments.

The mRNA sequence may be detected In a sample using hybridisation techniques. In particular when more than one analysis is to be performed at the same time it is advantageous to use a DNA array comprising e.g. an oligomer of at least 15 consecutive bases selected from the group consisting of SEQ ID No:2, SEQ ID No:4, SEQ ID No:6, SEQ ID No:7, SEQ ID No:8, SEQ ID No:9, SEQ ID No:10, SEQ ID No:11, SEQ ID No:12, SEQ ID No:13, SEQ ID No:14, SEQ ID No:15, SEQ ID No:16, SEQ ID No:17 and SEQ ID No:18.

Another way of detecting the presence or absence of the transcriptional product is by specifically amplifying the transcriptionals product having a sequence corresponding to SEQ ID No 2, 4, 6, 7, 8, 9, 10 or 11 or fragments thereof. This can be done by selecting primer pairs which cause only the amplification of these sequences.

Generally, hybridisation techniques are selected from not limited to the group consisting of in situ hybridisation, northern blots, Southern blots, dot blots and PCR based techniques.

A non-limiting list of PCR based techniques include rt-PCR, quantitative PCR and realtime PCR.

According to yet another embodiment, the translational product is a protein encoded by a polynucleotide selected from the group consisting of SEQ ID No:1, SEQ ID No:5, SEQ ID No:2, SEQ ID No:4, SEQ ID No:6, SEQ ID No:7, SEQ ID No:8, SEQ ID No:9, SEQ ID No:10 and SEQ ID No:11. Detection of this protein can be done with state of the art methods including the detection with an antibody directed against said protein, such as Western blotting, more preferably by using a fluorescently labelled antibody, preferably wherein the method comprises the use of flowcytometry, such as FACS. Other methods include but are not limited to gel electrophoresis, gel filtration, ion exchange chromatography, FPLC, mass spectrometry and immunohistochemistry.

Preferably, said protein is selected from the group comprising SEQ ID No 3 (protein), or a protein sharing at least 60% sequence identity with SEQ ID No 3. The protein with the amino acid sequence set forth in SEQ ID No 3 is the longest open reading frame in the cDNA sequence of SEQ ID No 2 or 4.

In a specific embodiment of the present invention is a method for determining whether an individual has a B-CLL sub-type with poor prognosis, the method comprising determining the level of an expression product which comprise a nucleotide sequence selected from the group consisting of SEQ ID No:12, SEQ ID No:13, SEQ ID No:14, SEQ ID No:15, SEQ ID No:16, SEQ ID No:17 and SEQ ID No:18 of said individual, and indicating the individual as having a B-CLL sub-type with poor prognosis if the level of the expression product is at or beyond a discriminating value and indicating the individual as not having a B-CLL sub-type with poor prognosis if the level of the expression product is not at or beyond the discriminating value, the discriminating value being a value which has been determined by measuring the level of the expression product which comprise a nucleotide sequence selected from the group consisting of SEQ ID No:12, SEQ ID No:13, SEQ ID No:14, SEQ ID No:15, SEQ ID No:16, SEQ ID No:17 and SEQ ID No:18 in both a healthy control population and a population with known B-CLL sub-type with poor prognosis, thereby determining said discriminating value which identifies the B-CLL sub-type population having a poor prognosis.

In this method the individual may be a member of an unselected population or be a member of a population already identified as having a B-CLL sub-type with a poor prognosis.

The above method may be performed such that the determination is performed at several time points at intervals as part of a monitoring of a cancer patient after or during the treatment for primary cancer.

The methods described so-far relate to the determination of the presence or absence of an expression product which comprise a nucleotide sequence selected from the group consisting of SEQ ID No:12, SEQ ID No:13, SEQ ID No:14, SEQ ID No:15, SEQ ID No:16, SEQ ID No:17 and SEQ ID No:18. By quantitatively measuring the amount of an expression product which comprise a nucleotide sequence selected from the group consisting of SEQ ID No:12, SEQ ID No:13, SEQ ID No:14, SEQ ID No:15, SEQ ID No:16, SEQ ID No:17 and SEQ ID No:18 in a biological sample isolated from an individual, it is possible to predict the progression of B-CLL in an individual.

In one embodiment the quantitative measurement is performed during treatment to estimate the efficiency of such treatment.

A preferred embodiment of the above diagnostic and prognostic methods is a method for detecting the presence or absence an expression product, wherein said at least one expression product comprise the nucleotide sequence of SEQ ID No:15 in a biological sample isolated from an individual for establishing a differential diagnosis of B-CLL or for determining the prognosis of the B-CLL.

A further preferred embodiment of the above diagnostic and prognostic methods is a method for detecting the presence or absence an expression product, wherein said at least one expression product comprise the nucleotide sequence of SEQ ID No:16 in a biological sample isolated from an individual for establishing a differential diagnosis of B-CLL or for determining the prognosis of the B-CLL.

Yet a further preferred embodiment of the above diagnostic and prognostic methods is a method for detecting the presence or absence an expression product, wherein said at least one expression product comprise the nucleotide sequence spanning the junction sequence between Exon-2 (SEQ ID No:15) and Exon-3 (SEQ ID No:16) in a biological sample isolated from an individual for establishing a differential diagnosis of B-CLL or for determining the prognosis of the B-CLL.

The nucleotide sequence spanning the junction between Exon-2 and Exon-3 is the last 20 nucleotides of the 3'-end of SEQ ID No:15 and the first 20 nucleotides of the 5'-end of SEQ ID No:16.

The "junction sequence" between two nucleotide sequences, such as two exons, is herein defined as the at least 20 3'-nucleotides of the first exon which is located 5' relative to the second exon and the at least 20 5'-nucleotides of the second exon which is located 3' relative to the first exon.

For all diagnostic applications of the present invention, the biological sample may be selected from the group comprising blood, serum, plasma, urine, saliva, lymph node biopsy, bone marrow, spinal liquid, spleen biopsy, and liver biopsy. The cells to be assessed in a sample are preferably leukocytes, mononuclear leukocytes or lymphocytes or B-lymphocytes.

A further embodiment of the present invention also includes a diagnostic kit for ex vivo or in situ diagnosis of a subtype of B-cell chronic lymphocytic leukaemia (B-CLL) in a individual, the kit comprising a detector molecule capable of detecting the presence or absence of at least one expression product, wherein said at least one expression product comprise a nucleotide sequence selected from the group consisting of SEQ ID SEQ ID No:12, SEQ ID No:13, SEQ ID No:14, SEQ ID No:15, SEQ ID No:16, SEQ ID No:17 and SEQ ID No:18 in a biological sample isolated from the individual.

The detector molecule is preferably a nucleotide and even more preferably a nucleotide capable of hybridising to a nucleotide sequence selected from the group consisting of SEQ ID SEQ ID No:12, SEQ ID No:13, SEQ ID No:14, SEQ ID No:15, SEQ ID No:16, SEQ ID No:17 and SEQ ID No:18 under stringent condition.

B-CLL Therapy

With the identification of a new sub-type of B-CLL having a poor prognosis, the present inventors also provide methods for treatment of B-CLL in such patients. This method is based on the finding that transcription products comprising these sequence products are present in B-CLL cells of patients with the poor prognosis. By modifying the activity and/or level of these transcription products, a treatment and/or cure for B-CLL is provided.

Accordingly, in a therapeutic aspect of the present invention there is provided a method of treating a B-CLL sub-type with poor prognosis comprising administering to an individual with a poor prognosis B-CLL diagnosis a compound capable of decreasing or inhibiting the formation of an expression product which comprise a nucleotide sequence selected from the group consisting of SEQ ID No:12, SEQ ID No:13, SEQ ID No:14, SEQ ID No:15, SEQ ID No:16, SEQ ID No:17 and SEQ ID No:18.

One such method is based on administering an oligonucleotide capable of inhibiting transcription from SEQ ID No 1 and/or SEQ ID No 5. Said oligonucleotide may comprises at least 8-10 consecutive nucleotides from the sequence of SEQ ID No 1. These sequences constitute the putative promoter sequences controlling the transcription transcription products which comprise a nucleotide sequence selected from the group consisting of SEQ ID No:12, SEQ ID No:13, SEQ ID No:14, SEQ ID No:15, SEQ ID No:16, SEQ ID No:17 and SEQ ID No:18. The oligonucleotides bind specifically to the promoter sequences and inhibit transcription of the gene. Such oligonucleotides may comprises nucleotide monomers selected from the group: DNA, RNA, LNA, PNA, methylated DNA, methylated RNA, more preferably PNA or LNA.

In a more preferred embodiment the therapeutic methods comprise administering an oligonucleotide capable of binding to a transcriptional product and preventing translation by destroying the transcriptional product. One particularly preferred embodiment of this aspect is RNA interference (RNAi) oligonucleotides.

The discovery of the phenomenon RNAi has revealed an entirely new level of gene regulation in eukaryotic cells. It is based on the observation that the presence of long double stranded RNA (dsRNA) in a cell almost completely eliminates the expression of the gene having the same sequence, whereas expression of other unrelated genes are left undisturbed. Although this observation had been know for time in plants as posttranscriptional gene silencing (PTGS) it was not before it was characterised as a general mechanism throughout the animal kingdom that its potentials were fully appreciated. Over the last few years it has been developed as a robust technique to knock down any desirable gene in worms and flies, and quickly a large body of information was gathered about the function of genes in these organisms. Due to the activation of the interferon system by long dsRNA the RNAi method was at that time not applicable in a mammalian system.

A key observation that allowed the harnessing of RNAi as a tool for regulating gene expression in mammals was the observation that chemically synthesised oligo-mer small interfering RNAs (siRNA) effectively suppress gene expression in several human cell lines without inflecting interferon response. This has triggered new promises for siRNA as a therapeutic drug in humans.

RNAi works by hybridising specifically to the mRNA transcribed by the cell to form a (partly) double stranded RNA molecule. This is recognised as a double stranded molecule by the cell's own nucleases, which degrade them.

In order for the technique to work efficiently, the siRNA oligonucleotide comprises a sequence of 5-30 consecutive nucleotides which is the complementary sequence of the nucleotide sequences selected from the group consisting of SEQ ID No:12, SEQ ID No:13, SEQ ID No:14, SEQ ID No:15, SEQ ID No:16, SEQ ID No:17 and SEQ ID No:18. By targeting at least one of the nucleotide sequences selected from the group consisting of SEQ ID No:12, SEQ ID No:13, SEQ ID No:14, SEQ ID No:15, SEQ ID No:16, SEQ ID No:17 and SEQ ID No:18, the transcriptional products characterised by the nucleotide sequences from the group of SEQ ID No:2, SEQ ID No:4, SEQ ID No:6, SEQ ID No:7, SEQ ID No:8, SEQ ID No:9, SEQ ID No:10 and SEQ ID No:11 will be eliminated. Example 5 shows that cells characteristic for the poor prognosis B-CLL sub-type can be eliminated by destroying the herein mentioned transcription products.

By "complementarity" is meant a nucleic acid that can form hydrogen bond(s) with other DNA or RNA sequence by either traditional Watson-Crick or other non-traditional types of base-paired interactions, e.g. Hoogsteen type.

Preferred siRNA molecules of the present invention are between 5 to 30 nucleotides long, such as 8-30 nucleotides long, such as 8-25 nucleotides, e.g. 8-24 nucleotides, e.g. 8-23 nucleotides, e.g. 8-22 nucleotides, e.g. 8-21 nucleotides, such as 8-20 nucleotides, e.g. 9-23 nucleotides, e.g. 10-23 nucleotides, such as 11-23 nucleotides, e.g. 12-23 nucleotides such as 13-23 nucleotides, e.g. 14-23 nucleotides, e.g. 15-23 nucleotides, such as 16-23 nucleotides, such as 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, such as 30 nucleotides long.

RNAi oligonucleotides may be administered to the cell, or a vector may be transfected into the cells, said vector comprising a promoter region capable of directing the expression of at least one RNAi oligonucleotide. Due to the very restricted expression of the AMB-1 gene, it is not important only to target the RNAi oligos or the vectors to B-CLL cells.

One way of targeting to blood cells comprises using a heparin receptor for targeting to blood cells.

Another way of targeting the transcriptional products which comprise at least one nucleotide sequence selected from the group consisting of SEQ ID No:12, SEQ ID No:13, SEQ ID No:14, SEQ ID No:15, SEQ ID No:16, SEQ ID No:17 and SEQ ID No:18 is to use an antisense construct comprising a promoter sequence capable of directing the transcription of at least part of the antisense equivalent of SEQ ID No 1 or 2 or 4 or 5 or 6 or 7 or 8 or 9 or 10 or 11 specifically to the poor prognosis B-CLL sub-type.

When desired targeting to B-CLL cells can be performed using the CD19 or CD20 receptor. The CD19 receptor is particularly preferred since it internalises its ligand.

In a further therapeutic embodiment the compound is a gene therapy vector comprising a promoter sequence operably linked to a sequence coding for a protein capable of inhibiting cell division in the cell and/or capable of killing the cell, said promoter sequence being a tissue specific promoter capable of directing expression only in B cells, more preferably only in B-CLL cells. One particularly preferred promoter sequence is the extremely cell specific promoter of SEQ ID No:1 or SEQ ID No:5. When this promoter is used targeting of the suicide vector is not very important, since it will only be active in the cells in which AMB-1 is expressed and these are the cells to be targeted by the suicide gene.

Deletion studies will determine the exact length of the promoter sequence counted from the transcription start site. Accordingly, the promoter may comprise at least 100 nucleotides of Seq_ID:1 or Seq_ID:5, such as at least 200 nucleotides, for example at least 300 nucleotides, such as at least 400 nucleotides, for example at least 500 nucleotides, such as at least 600 nucleotides, for example at least 700 nucleotides, such as at least 800 nucleotides, for example at least 900 nucleotides, such as at least 1000 nucleotides, for example at least 1100 nucleotides, such as at least 1200 nucleotides, for example at least 1300 nucleotides, such as at least 1400 nucleotides, for example at least 1500 nucleotides, such as at least 1600 nucleotides, for example at least 1700 nucleotides, such as at least 1800 nucleotides, for example at least 1900 nucleotides, such as at least 2000 nucleotides, for example at least 2500 nucleotides, such as at least 3000 nucleotides, for example at least 3500 nucleotides, such as at least 5000 nucleotides, for example at least 10,000 nucleotides.

The specificity of expression of mRNAs described by the present invention are striking. The RT-PCR data and the Northern blot data using the dot-blot disclose that the mRNAs of the present invention are expressed either at very low levels in other tissues or only in the B-CLL patients where one can detect it.

Thus one embodiment of the present invention is the use of the promotor region for use in gene therapy. The promotor is defined as any sequence within SEQ ID No:1 and SEQ ID No:5 that directs the formation of an expression product which comprise a nucleotide sequence selected from the group consisting of SEQ ID No:12, SEQ ID No:13, SEQ ID No:14, SEQ ID No:15, SEQ ID No:16, SEQ ID No:17 and SEQ ID No:18, said expression product being any of the sequences selected from the group consisting of SEQ ID No:2, SEQ ID No:4, SEQ ID No:6, SEQ ID No:7, SEQ ID No:8, SEQ ID No:9, SEQ ID No:10 and SEQ ID No:11 in B-CLL cells or any other cell or tissue types in which any of the sequences are transcribed.

One way that one can use the promotor region in gene therapy is to make a gene therapy construct where the promotor drives the expression of a cell suicide gene such as but not limited to the gene for HSV-1 thymidine kinase, the varicelia-zoster, virus thymidine kinase gene, *E.Coli* cytosine deaminase, the nitroreductase gene or the *E.Coli* Deo gene (Yazawa et al. & Kirn D. et al.). This would allow for selective expression of the suicide genes in B-CLL cells.

Alternatively, the promotor could be used for a selective expression of genes that could have curative effects when expressed in B-CLL cells, but unwanted effects if expressed ubiquitously.

Also, one embodiment of the present invention relates to the use of the promotor region for use in screening assays where the promotor is linked to a reporter gene and transfected into B-CLL cells in which the reporter gene will be expressed. This approach would allow for easy screening for compounds that would turn off the expression of the reporter gene for example by killing the cell.

A presently preferred embodiment relates a gene therapy vector of the present invention comprising an oligonucleotide capable of inhibiting transcription from SEQ ID No 1 and/or SEQ ID No 5, wherein the promoter is a B-CLL specific promoter, which may or may not be operably linked to a protein selected from the group comprising HSV-1 thymidine kinase, the varicella-zoster, virus thymidine kinase gene, *E.Coli* cytosine deaminase, the nitroreductase gene or the *E.Coli* Deo gene.

In one embodiment the compound is a therapeutic antibody directed against a polypeptide having the amino acid sequence of SEQ ID No 3, preferably wherein said antibody is a human or humanised antibody. Another possibility is to identify a modulator of binding of SEQ ID No 3 to its receptor within or outside the cell and to administer this modulator to the cells.

4-helical Cytokines

A further object of preferred embodiments of the present invention is an isolated polypeptide comprising an amino acid sequence selected from the group consisting of:
 i) an amino acid sequence of SEQ ID NO: 3,
 ii) an amino acid sequence having at least 60% sequence identity compared to the full length sequence of SEQ ID NO:3
 ii) a fragment of SEQ ID NO:3 having at least 60% sequence identity compared to the full length sequence of SEQ ID NO:3.

The protein encoded by SEQ ID No 1 and/or SEQ ID No 5 shares a very small sequence identity with any known protein. However, it has been possible to use 2D and 3D analytical tools to identify the protein as a 4-helical cytokine. The 3D structure of the protein is very similar to 4-helical cytokines and in particular to IL4.

IL4 is a very important cytokine in B-CLL biology. IL4 is not expressed by B-CLL cells, but the IL4 receptor is found on the cells. The IL4 that stimulates B-CLL cells is believed to be produced by T-lymphocytes. The role of IL4 in B-CLL biology is complicated. It has been suggested that IL4 can inhibit B-CLL DNA synthesis and proliferation. Other reports demonstrated that IL4 protects B-CLL cells from apoptosis by upregulating Bcl-2, and IL4 was shown to inhibit apoptosis without stimulating proliferation. Recently, a clinical study in Sweden has confirmed these in vitro studies since IL4 administration to B-CLL patients resulted in increased numbers of B-CLL cells in the blood, suggesting that IL4 had a stimulatory or anti-apoptotic effect on the B-CLL cells in vivo (Lundin, et al.).

In many systems the effects of IL13 are largely similar to those of IL4, but IL13 is slightly less potent that IL4. It is unclear whether B-CLL cells express IL13, but the cells do express the IL13 receptor. The effects of IL13 in B-CLL are controversial. While Chaouchi et al. suggested that IL13, like IL4 protects B-CLL cells from apoptosis (Chaouchi et al), studies by Fluckiger et al. suggest that this is not the case (Fluckiger et al.).

The combined finding of 2D and 3D structure similarity to 4-helical cytokines and the importance of IL4 in B-CLL strongly suggests that the novel class of proteins of which the AMB-1 protein is one representative are cytokines.

These polypeptides constitute a novel class of proteins sharing 2D and 3D structure similarities with 4-helical cytokines. In a preferred embodiment, the isolated polypeptide comprises or essentially consists of the amino acid sequence of SEQ ID No. 3 or a fragment thereof. This particular protein at least can be used for diagnosis, for raising antibodies for use in therapy against B-CLL, and for protective or therapeutic immunisation of an individual against B-CLL.

Consequently, the isolated polypeptide preferably has interleukin activity or interleukin like activity, such as having IL3, IL13, GM-CSF, TGF-β, IGF activity, more preferably having IL4 activity or IL4 like activity.

Probably the isolated polypeptides are capable of forming homo- or hetero-oligomer with each other and among themselves. Such oligomers are also within the scope of the present invention. Such oligomers may comprise at least one isolated polypeptides as defined in any the present invention, such as a dimer, a trimer, a quatramer, a quintamer, a hexamer, an octamer, a decamer, a dodecamer. In biological systems the activity may be attributed only to dimer or higher-mer.

The protein defined by SEQ ID No 3 shares very little sequence identity with known cytokines and interleukines and as a matter of fact very little sequence identity with any known protein. Consequently the present inventors contemplates that the group comprises functionally equivalent polypeptide sharing at least 60% sequence identity with SEQ ID No 3, more preferably at least 70% sequence identity, more preferably at least 80% sequence identity, such as at least 90% sequence identity, for example at least 95% sequence identity, such as at least 97% sequence identity, for example at least 98% sequence identity.

Activity as a cytokine or interleukin can be assessed in a biological assay where the polypeptide is contacted with a cytokine dependent cell line. Accordingly, polypeptides with cytokine or interleukin like activity can also be identified by similar methods.

One approach to assess cytokine/interleukin activity in a biological assay is to express the CDS (SEQ ID No:17) reading frame in a baculovirus system (Invitrogen, Carlsbad, USA) and purify the protein. The recombinant protein can be assayed in cytokine induced proliferation assays as described in general in the eBioscience catalog & Reference Manual 2002 p.260-262 (eBioscience, San Diego, USA). In particular IL4 activity can be determined using the CTh4S cell line as described by Petersen et al (see Example 8).

The promoter sequence (which forms part of SEQ ID No 1 and/or SEQ ID No 5) and the coding sequences (SEQ ID No:3) can be used in various aspects of gene therapy and immunotherapy.

Further polynucleotide sequences from other individuals or other species with the same function can be isolated by one of the following methods, which each form independent aspects of the present invention.

A first method for identifying a nucleotide sequence encoding a 4-helical cytokine comprises the steps of:
i) isolating mRNA from a biological sample,
ii) hybridising the mRNA to a probe comprising at least 10 nucleotides of the coding sequence of SEQ ID No 1 and/or SEQ ID No 5 under stringent conditions,
iii) determining the nucleotide sequence of a sequence capable of hybridising under step ii), and
iv) determining the presence of an open reading frame in the nucleotide sequence determined under step iii).

A second method for identifying a nucleotide sequence encoding a 4-helical cytokine is a computer assisted method comprising the steps of
i) performing a sequence similarity search of at least 10 nucleotides of the coding sequence SEQ ID No 1 and/or SEQ ID No 5,
ii) aligning "hits" to said coding sequence,
iii) determining the presence of an open reading frame in the "hits".

It is highly likely that other similar polypeptides encoding further 4-helical cytokines can be found in other individuals and/or other species of mammals. In particular, individuals of other geographical origin may carry genes which differ from the polynucleotides of the present invention. It is also conceivable that similar sequences can be found in closely and even in distantly related species.

Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the genetic code.

For example, certain amino acids may be substituted for other amino acids in a protein structure without appreciable loss of interactive binding capacity with structures such as, for example, antigen-binding regions of antibodies, binding sites of receptors, or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, ie. still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within +2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Functional equivalents and variants are used interchangably herein. In one preferred embodiment of the invention there is also provided variants of a 4-helical cytokine, and variants of fragments thereof. When being polypeptides, variants are determined on the basis of their degree of identity or their homology with a predetermined amino acid sequence, said predetermined amino acid sequence being SEQ ID No. 3 or a fragment thereof.

Accordingly, variants preferably have at least 60% sequence identity, for example at least 65% sequence identity, such as at least 70% sequence identity, for example at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity # of identical positions/total # of positions (e.g., overlapping positions)×100). In one embodiment the two sequences are the same length. The sequence identity is preferably calculated relative to the full length sequence of the molecule of the present invention.

A degree of "sequence identity" of amino acid sequences is a function of the number of identical amino acids at positions shared by the amino acid sequences. A degree of "sequence homology" or "sequence similarity" of amino acid sequences is a function of the number of amino acids, i.e. structurally related, at positions shared by the amino acid sequences. Sequence identity is determined by the alignment algorithm that performs global alignments which has been described by Smith T F and Waterman M S (Smith T F et al.)

A list of the standard qualifiers and the default values for the alignment algorithm is given below:

|  |  | Allowed values | Default |
|---|---|---|---|
| Standard (Mandatory) qualifiers | | | |
| [-asequence] (Parameter 1) | Sequence USA | Readable sequence | Required |
| [-bsequence] (Parameter 2) | Sequence database USA | Readable sequence(s) | Required |
| -gapopen | The gap open penalty is the score taken away when a gap is created. The best value depends on the choice of comparison matrix. The default value assumes you are using the EBLOSUM62 matrix for protein sequences, and the EDNAFULL matrix for nucleotide sequences. | Number from 1.000 to 100.000 | 10.0 for any sequence |
| -gapextend | The gap extension penalty is added to the standard gap penalty for each base or residue in the gap. This is how long gaps are penalized. Usually you will expect a few long gaps rather than many short gaps, so the gap extension penalty should be lower than the gap penalty. An exception is where one or both sequences are single reads with possible sequencing errors in which case you would expect many single base gaps. You can get this result by setting the gap open penalty to zero (or very low) and using the gap extension penalty to control gap scoring. | Number from 0.100 to 10.000 | 0.5 for any sequence |
| [-outfile] (Parameter 3) | Output alignment file name | Alignment output file | |
| Additional (Optional) qualifiers | | | |
| -datafile | This is the scoring matrix file used when comparing sequences. By default it is the file 'EBLOSUM62' (for proteins) or the file 'EDNAFULL' (for nucleic sequences). These files are found in the 'data' directory of the EMBOSS installation. | Comparison matrix file in EMBOSS data path | EBLOSUM62 for protein EDNAFULL for DNA |
| Advanced (Unprompted) qualifiers | | | |
| -[no]brief | Brief identity and similarity | Boolean value Yes/No | Yes | such as at least 98% sequence identity, for example 99% sequence identity with the predetermined sequence.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or An "unrelated" or "non-homologous" sequence shares less than 40% identity, though preferably less than 25% identity, with one of the 4-helical cytokine sequences of the present invention. The term "substantial identity" means that two peptide sequences, when optimally aligned, such as by the Smith and Waterman algorithm using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Additionally, variants are also determined based on a predetermined number of conservative amino acid substitutions as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:

Amino acids having polar side chains (Asp, Glu, Lys, Arg, His, Asn, Gln, Ser, Thr, Tyr, and Cys,)
Amino acids having non-polar side chains (Gly, Ala, Val, Leu, Ile, Phe, Trp, Pro, and Met)
Amino acids having aliphatic side chains (Gly, Ala Val, Leu, Ile)
Amino acids having cyclic side chains (Phe, Tyr, Trp, His, Pro)
Amino acids having aromatic side chains (Phe, Tyr, Trp)
Amino acids having acidic side chains (Asp, Glu)
Amino acids having basic side chains (Lys, Arg, His)
Amino acids having amide side chains (Asn, Gln)
Amino acids having hydroxy side chains (Ser, Thr)
Amino acids having sulphor-containing side chains (Cys, Met),
Neutral, weakly hydrophobic amino acids (Pro, Ala, Gly, Ser, Thr)
Hydrophilic, acidic amino acids (Gln, Asn, Glu, Asp), and
Hydrophobic amino acids (Leu, Ile, Val)

Preferred conservative amino acids substitution groups are: valine-leucine-isoleucine, phenylalanine-tyrosine, lysine-arginine, alanine-valine, and asparagine-glutamine.

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

The addition or deletion of at least one amino acid may be an addition or deletion of from preferably 2 to 250 amino acids, such as from 10 to 20 amino acids, for example from 20 to 30 amino acids, such as from 40 to 50 amino acids. However, additions or deletions of more than 50 amino acids, such as additions from 50 to 100 amino acids, addition of 100 to 150 amino acids, addition of 150-250 amino acids, are also comprised within the present invention. The deletion and/or the addition may—independently of one another—be a deletion and/or an addition within a sequence and/or at the end of a sequence.

The polypeptide fragments according to the present invention, including any functional equivalents thereof, may in one embodiment comprise less than 250 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues.

"Functional equivalency" as used in the present invention is according to one preferred embodiment established by means of reference to the corresponding functionality of a predetermined fragment of the sequence.

Functional equivalents or variants of a 4-helical cytokine will be understood to exhibit amino acid sequences gradually differing from the preferred predetermined 4-helical cytokine, as the number and scope of insertions, deletions and substitutions including conservative substitutions increases. This difference is measured as a reduction in homology between the preferred predetermined sequence and the fragment or functional equivalent.

All fragments or functional equivalents of SEQ ID No. 3 are included within the scope of this invention, regardless of the degree of homology that they show to the respective, predetermined 4-helical cytokines disclosed herein. The reason for this is that some regions of the 4-helical cytokines are most likely readily mutatable, or capable of being completely deleted, without any significant effect on the binding activity of the resulting fragment.

A functional variant obtained by substitution may well exhibit some form or degree of native cytokine activity, and yet be less homologous, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of identity is not a principal measure of a fragment being a variant or functional equivalent of a preferred predetermined fragment according to the present invention.

One particularly preferred method of determining the degree of functional equivalence is by performing a biological or chemical assay such as the assays described in the appended examples. Preferred functional equivalents of SEQ ID No 3 are those that have a $K_D$ with respect to a predefined receptor which is less than 10 times higher than the $K_D$ of the polypeptide of SEQ ID No 1 with respect to the same receptor, more preferably less than 5 times higher, more preferably less than 2 times higher.

With respect to functional equivalence this may be defined in a biological assay based on a cytokine dependent or stimulated cell line. Such cell lines are e.g. available from American Type Culture Collection, P.O.Box 1549, Manassas, Va. 20108 USA. The following cell lines at least are available for testing cytokines and in particular interleukins:

| Accession number | Description | Activity |
|---|---|---|
| CRL-1841 | TH-2 clone A5E | IL2 dependent, IL4 stimulated |
| CRL-2003 | TF-1 | IL3 dependent |
| CRL-2407 | NK-92 | IL2 dependent |
| CRL-2408 | NK-92MI | IL2 dependent |
| CRL-2409 | NK92CI | IL2 dependent |
| CRL-9589 | AML-193 | IL3 stimulated, GM-CSF dep. |

-continued

| Accession number | Description | Activity |
|---|---|---|
| CRL-9591 | MV-4-11 | GM-CSF dependent |
| TIB-214 | CTLL-2 | IL2 dependent |

The following cell lines are available from DSMZ—Deutsche Sammiung von Mikroorganismen und Zelikulturen GmbH, Mascheroder Weg 1b, D-38124 Braunschweig, GERMANY. As can be seen from the table, some of the cell lines can be used to broadly assess cytokine activity whereas others are only reported to respond to one or a few specific cytokines.

| Accession number | Description | Acvitity |
|---|---|---|
| ACC 211 | Mouse hybridoma, B9 | IL6 dependent |
| ACC 137 | Human acute myeloid leukemia, UT-7 | Constitutively cytokine responsive to various cytokines. |
| ACC 104 | Human acute megakaryoblastic leukemia | Respond with proliferation to: GM-CSF, IFN-alpha, IFN-á, IFN-gamma, IL2, IL3, IL4, IL6, IL15, NG F, SCF, TNF-alpha, TPO |
| ACC 247 | Human acute myeloid leukemia, OCI-AML5 | G-GSF, GM-CSF, IL3, FTL3-ligand |
| ACC 271 | Human acute myeloid leukemia, MUTZ-2 | IL3, SCF, G-CSF, M-CSF, IFN-gamma |
| ACC 334 | Human erythroleukemia, TF-1 | GM-CSF, IFN-gamma, IL3, IL4, IL5, IL6, IL13, LIF, NGF, OSM, SCF, TNF-alpha, and TPO |

The TF-1 cell line mentioned above can be used for assaying IL13 function. This cell line is sensitive to various different cytokines but gives a very strong proliferative response when exposed to IL13. This cell line can in particular be used if there is no response in the IL4 sensitive cell line (CT.h4S). Further cell lines which can be used for distinguishing between IL4 and IL13 activity include cell lines/hybridomas such as B-9-1-3 (Bouteiller et al.) and A201.1 (Andrews et al.).

Pharmaceutical uses of Isolated Polypeptides

Apart from being used for diagnosis, it is also within the scope of the present invention to use an isolated polypeptide as defined in the invention for a pharmaceutical composition ogether with a pharmaceutically acceptable carrier. Such pharmaceutical compositions may be used for any of the purposes for which cytokines and in particular interleukin is used at present.

Examples of such uses include the treatment of bone disorders, inflammation, for lowering blood serum cholesterol, allergy, infection, viral infections, hematopoietic disorders, preneoplastic lesions, immune related diseases, autoimmune related diseases, infectious diseases, tuberculosis, cancer, viral diseases, septic shock, reconstitution of the haematopoietic system, induction of the granulocyte system, pain, cardial dysfunction, CNS disorders, depression, artheritis, psoriasis, dermatitis, collitis, Crohn's disease, diabetes, in an individual in need thereof.

It is also within the scope of the present invention to use an isolated polypeptide according to the invention as an adjuvant or as an immune anhancer, for regulating TH2 immune responses, and for suppressing Th1 immune responses.

A further use of an isolated polypeptide of the invention is as a growth factor for administration to cell cultures or as a growth factor for veterinary use, e.g. for stimulating the growth of livestock.

Immunotherapy

Having identified a transcriptional and/or translational product of SEQ ID No 1 and/or SEQ ID No 5 as an etiological factor in B-CLL it is also within the scope of the present invention to perform an immunisation of a patient in need thereof against B-CLL, wherein the immunisation generates an immune response in the patient which recognises a translational product of SEQ ID No 2, SEQ ID No 4, SEQ ID No 6, SEQ ID No 7, SEQ ID No 8, SEQ ID No 9, SEQ ID No 10 and SEQ ID No 11. A preferred immunotherapy is a vaccination against B-CLL by immunising an individual against a translational product of SEQ ID No 1 and/or SEQ ID No 5. In this way the individual builds up antibodies directed against said translational product and any developing B-CLL will be stopped by these antibodies.

Immunisation may be performed in various ways, such as by immunising said individual with at least one isolated polypeptide as defined the present invention and optionally adjuvants and carriers or immunising with an expression construct capable of expressing an isolated polypeptide according to the invention in the cells (DNA vaccination).

Another method comprises peptide loading of dendritic cells, or ex vivo expansion and activation of T-cells, or inducing a CTL response that targets cells expressing the polypeptide encoded by SEQ ID No 1 and/or SEQ ID No 5.

Antibodies

Antibodies against any of the polypeptides belonging to the novel class of proteins identified by the present inventors can be produced by any known method of immunisation.

In one embodiment, the antibodies are produced in a non-human mammal, or in an insect. If antibodies are to be used for therapy in human beings they are preferably subsequently humanised. In one embodiment, the antibody is formulated into a single-chain antibody.

In another embodiment, in particular for therapeutic purposes, the host organism is a human being and the antibody is subsequently produced recombinantly in a non-human mammal, such as a mouse. The antibody may also be produced as a monoclonal antibody in a hybridoma. One way of producing a monoclonal antibody is described in U.S. Pat. No. 5,681,729 in which a human lymphocyte producing an antibody is generated by the steps, in the order mentioned, comprising 1. transplanting human lymphocytes to a mouse lacking both functional T and B cells so that said human lymphocytes take in said mouse's body;
2. immunizing said mouse with a desired antigen so as to generate human lymphocytes producing an antibody specific to said antigen;
3. administering to said mouse an antiserum to mouse cells;
4. recovering lymphocyte containing cells from said mouse;
5. separating human lymphocytes from the recovered cells by centrifugation; and
6. separating said human lymphocytes producing said antibody.
7. immortalizing said human lymphocytes
8. cloning the obtained immortalized human-derived lymphocytes producing said antibody; and recovering a monoclonal antibody specific to said desired antigen from the cloned immortalized human-derived lymphocytes.

The antibodies of the present invention may be provided as part of a pharmaceutical composition. Such a pharmaceutical composition may be used for treating cancer, preferably for treating leukaemia, more preferably for treating B-CLL leukaemia, more preferably for treating poor prognosis B-CLL leukaemia.

Use of Antibodies in Therapy

Antibodies directed against epitopes can be used for prevention and/or therapy of for example B-CLL. Antigenic epitopes can be used in vaccines to stimulate an immunological response in a mammal that is directed against cells having the B-CLL-associated epitope found in the AMB-1 protein(s) or functional equivalents. Antibodies directed against the antigenic epitopes of the invention can combat or prevent B-CLL.

An antigenic epitope may be administered to the mammal in an amount sufficient to stimulate an immunological response against the antigenic epitope. The antigenic epitope may be combined in a therapeutic composition and administered in several doses over a period of time that optimizes the immunological response of the mammal. Such an immunological response can be detected and monitored by observing whether antibodies directed against the epitopes of the invention are present in the bloodstream of the mammal.

Such antibodies can be used alone or coupled to, or combined with, therapeutically useful agents. Antibodies can be administered to mammals suffering from any B-CLL that displays the B-CLL-associated epitope. Such administration can provide both therapeutic treatment, and prophylactic or preventative measures. For example, therapeutic methods can be used to determine the spread of a B-CLL and lead to its remission.

Therapeutically useful agents include, for example, leukeran, adrimycin, aminoglutethimide, aminopterin, azathioprine, bleomycin sulfate, bulsulfan, carboplatin, carminomycin, carmustine, chlorambucil, cisplatin, cyclophosphamide, cyclosporine, cytarabidine, cytosine arabinoside, cytoxin dacarbazine, dactinomycin, daunomycin, daunorubicin, doxorubicin, esperamicins, etoposide, fluorouracil, ifosfamide, interferon-α, lomustine, melphalan, mercaptopurine, methotrexate, mitomycin C, mitotane, mitoxantrone, procarbazine HCl, taxol, taxotere (docetaxel), teniposide, thioguanine, thiotepa, vinblastine sulfate, vincristine sulfate and vinorelbine. Additional agents include those disclosed in Chapter 52, Antineoplastic Agents (Paul Calabresi and Bruce A. Chabner), and the introduction thereto, pp.1202-1263, of Goodman and Gilman's "The Pharmacological Basis of Therapeutics", Eighth Edition, 1990, McGraw-Hill, Inc. (Health Professions Division). Toxins can be proteins such as, for example, pokeweed anti-viral protein, cholera toxin, pertussis toxin, ricin, gelonin, abrin, diphtheria exotoxin, or Pseudomonas exotoxin. Toxin moieties can also be high energy-emitting radionuclides such as cobalt-60, I-131, I-125, Y-90 and Re-186, and enzymatically active toxins of bacterial, fungal, plant or animal origin, or fragments thereof.

Chemotherapeutic agents can be used to reduce the growth or spread of B-CLL cells and tumors that express the AMB-1 associated epitope of the invention. Animals that can be treated by the chemotherapeutic agents of the invention include humans, non-human primates, cows, horses, pigs, sheep, goats, dogs, cats, rodents and the like. In all embodiments human B-CLL antigens and human individuals are preferred.

Species-dependent antibodies can be used in therapeutic methods. Such a species-dependent antibody has constant regions that are substantially non-immunologically reactive with the chosen species. Such species-dependent antibody is particularly useful for therapy because it gives rise to substantially no immunological reactions. The species-dependent antibody can be of any of the various types of antibodies as defined above, but preferably is mammalian, and more preferably is a humanized or human antibody.

Compositions

Therapeutically useful agents can be formulated into a composition with the antibodies of the invention and need not be directly attached to the antibodies of the invention. However, in some embodiments, therapeutically useful agents are attached to the antibodies of the invention using methods available to one of skill in the art, for example, standard coupling procedures.

Compositions may contain antibodies, antigenic epitopes or trypsin-like protease inhibitors. Such compositions are useful for detecting the AMB-1 protein (for example antigenic epitopes) and for therapeutic methods involving prevention and treatment of B-CLLs associated with the presence of the AMB-1 (for example antigenic epitopes).

The antibodies, (and for example antigenic epitopes and protease inhibitors) can be formulated as pharmaceutical compositions and administered to a mammalian host, such as a human patient in a variety of forms adapted to the chosen route of administration. Routes for administration include, for example, intravenous, intra-arterial, subcutaneous, intramuscular, intraperitoneal and other routes selected by one of skill in the art.

Solutions of the antibodies, (and for example antigenic epitopes and protease inhibitors) can be prepared in water or saline, and optionally mixed with a nontoxic surfactant. Formulations for intravenous or intra-arterial administration may include sterile aqueous solutions that may also contain buffers, liposomes, diluents and other suitable additives.

The pharmaceutical dosage forms suitable for injection or infusion can include sterile aqueous solutions or dispersions comprising the active ingredient that are adapted for administration by encapsulation in liposomes. In all cases, the ultimate dosage form must be sterile, fluid and stable under the conditions of manufacture and storage.

Sterile injectable solutions are prepared by incorporating the antibodies, antigenic epitopes and protease inhibitors in the required amount in the appropriate solvent with various of the other ingredients enumerated above, as required, followed by filter sterilization.

Polynucleotides

In a still further aspect the invention relates to an isolated polynucleotide selected from the group consisting of:
i) a polynucleotide comprising nucleotides of SEQ ID No 5,
ii) a polynucleotide encoding a polypeptide having the amino acid sequence of SEQ ID No 3,
iii) a polynucleotide, the complementary strand of which hybridises, under stringent conditions, with a polynucleotide as defined in any of i) and ii).
iv) a polynucleotide which is degenerate to the polynucleotide of iii), and
v) the complementary strand of any such polynucleotide.

The polypeptides encoded by the polynucleotides may furthermore
a) have at least 60% sequence identity with the amino acid sequence of SEQ ID No 3 and have interleukin or cytokine activity,
b) be recognised by an antibody, or a binding fragment thereof, which is capable of recognising an epitope, wherein said epitope is comprised within a polypeptide having the amino acid sequence of SEQ ID No 3; and/or c) be competing with a polypeptide having the amino acid sequence as shown in SEQ ID No 3 for binding to at least one predetermined binding partner such as a cytokine receptor.

Specific examples of fragments of SEQ ID No 1 include the nucleotide sequence selected from the group consisting of SEQ ID No:12, SEQ ID No:13, SEQ ID No:14, SEQ ID No:15, SEQ ID No:16, SEQ ID No:17 and SEQ ID No:18.

Hybridisation

The entire nucleotide sequence of the coding sequence of SEQ ID No 1 and/or SEQ ID No 5 or portions thereof can be used as a probe capable of specifically hybridising to corresponding sequences. To achieve specific hybridisation under a variety of conditions, such probes include sequences that are unique and are preferably at least about 10 nucleotides in length, and most preferably at least about 20 nucleotides in length. Such probes can be used to amplify corresponding sequences from a chosen organism or individual by the well-known process of polymerase chain reaction (PCR) or other amplification techniques. This technique can be used to isolate additional nucleotide sequences from a desired organism or as a diagnostic assay to determine the presence of the coding sequence in an organism or individual. Examples include hybridisation screening of plated DNA libraries (either plaques or colonies; see e. g. Innis et al. (1990) PCR Protocols, A Guide to Methods and Applications, eds., Academic Press).

The terms "stringent conditions" or "stringent hybridisation conditions" include reference to conditions under which a probe will hybridise to its target sequence, to a detectably greater degree than other sequences (e.g., at least twofold over background). Stringent conditions are target sequence dependent and will differ depending on the structure of the polynucleotide. By controlling the stringency of the hybridisation and/or washing conditions, target sequences can be identified which are 100% complementary to a probe (homologous probing).

Alternatively, stringency conditions can be adjusted to allow some mismatching in sequences so that lower degrees of similarity are detected (heterologous probing).

Generally, probes for hybridisation of this type are in a range of about 1000 nucleotides in length to about 250 nucleotides in length.

An extensive guide to the hybridisation of nucleic acids is found in Tijssen, Laboratory Techniques in Biochemistry and Molecular Biology-Hybridization with Nucleic Acid Probes, Part I, Chapter 2, "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, N.Y. (1995). See also Sambrook et al. (1989) Molecular Cloning: A Laboratory Manual (2nd ed. Cold Spring Harbor Laboratory, Cold Spring Harbor, N.Y.).

Specificity is typically the function of post-hybridisation washes, the critical factors being the ionic strength and temperature of the final wash solution.

Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature.

Formulas are available in the art for the determination of melting temperatures.

Preferred hybridisation conditions for the nucleotide sequence of the invention include hybridisation at 42° C. in 50% (w/v) formamide, 6×SSC, 0.5% (w/v) SDS, 100 mg/ml salmon sperm DNA. Exemplary low stringency washing conditions include hybridization at 42° C. in a solution of 2×SSC, 0.5% (w/v) SDS for 30 minutes and repeating. Exemplary moderate stringency conditions include a wash in 2×SSC, 0.5% (w/v) SDS at 50° C. for 30 minutes and repeating.

Exemplary high stringency conditions include a wash in 2×SSC, 0.5% (w/v) SDS, at 65° C. for 30 minutes and repeating. Sequences that correspond to the AMB-1 gene or fractions thereof according to the present invention may be obtained using all the above conditions. For purposes of defining the invention, the high stringency conditions are used.

Mutations

Finally, the invention provides a method for determining an increased or decreased predisposition for B-CLL comprising determining in a biological sample from an individual a germline alteration in a target nucleic acid sequence comprising 150,000 nucleotides, said target nucleic acid sequence comprising at least 10 nucleotides of SEQ ID No 1 and/or SEQ ID No:5. This aspect is based on the finding of the importance of the expression product of SEQ ID No 1 and/SEQ ID No:5, and the complete absence of any detectable expression product of SEQ ID No 1 and/or SEQ ID No:5 in healthy tissue and in patients with good prognosis B-CLL. It is highly likely that the difference is caused by a germline alteration. A germline alteration can be targeted by gene therapy methods and by the methods provided in the present invention.

Preferably, said predisposition is a predisposition for poor prognosis of B-CLL.

EXAMPLES

Example 1 cDNA Cloning

By Differential Display (Pardee et al., 1992, Jorgensen et al., 1999) part of a gene (hereafter referred to as AMB-1) was found that is expressed in unmutated B-CLL patients with poor prognosis. This gene is not found in the mutated B-CLL patients. When AMB-1 was sequenced and aligned to known sequences in GenBank, perfect homology was found to 225 base pairs (bp) of human genomic DNA from chromosome 12.

RNA was prepared using the RNEASY® (RNA Extraction) kit from Qiagen, as described by the manufacturer (Qiagen, Hilden, Germany). RNA was prepared from patients with B-CLL without hyper mutation who, by PCR analysis, using primers FDP5 (CCTTTATGTGTGTGACAAGTG; SEQ ID No:29) and F10 (ATCCAGCCAGGATGAAATA-GAA; SEQ ID No:30), showed a high level of the resulting PCR fragment. Poly-A+RNA was isolated from total RNA by the MICROPOLY(A)PURIST® (RNA Purification) kit from Ambion, as described by the manufactor (Ambion, Inc., Texas, USA). Cloning-ready cDNA was prepared from 8 µg poly-A+RNA using the ZAP EXPRESS® XR Library Construction Kit from Stratagene as described by the manufacturer (Stratagene, San Diego, USA). The cDNA was size fractionated and two size fractions (fraction-1: >2500 by and fraction-2 300-2500 bp) were independently ligated to pre-digested lambda Zap vectors and packed into phage particles as described by the manufacturer (Stratagene, San Diego, USA). The titer was determined for each library and 200,000 pfu of from the fraction-1 library were plated onto two 22×22 cm screening plates (100,000 pfu on each plate) and 750,000 pfu of the fraction-2 library were plated on five 22×22 cm screening plates (150,000 pfu on each) as described by Stratagene, San Diego, USA. The plates were incubated at 37° C. for 18 hours and the plaques transferred to replica nylon filters (Amersham) and denatured and renatured to allow hybridisation. All procedures were made as described by the manufacturers (Stratagene, San Diego, USA & Amersham Biosciences, Buckinghamshire, UK).

The filters were screened by independent hybridisations with alpha[$^{32}$P]-dATP-labelled DNA fragments; alpha[$^{32}$P]-dATP was purchased from Amersham Biosciences, Buckinghamshire, UK. Between succesive hybridisations, the old probe was removed by incubation for 20 min in 21 90-100° C. water containing 0.1% SDS. The DNA fragments used as probes were (all positions relate to sequence ID#X): 1) pos. 48978-49250; 2) pos. 50011-51591; 3) pos. 51461-52182; 4) pos. 51901-52589; 5) pos. 53121-56521; 6) pos. 58163-59408. All hybridisations and washes were made according to the instructions from Stratagene, San Diego, USA and Amersham Biosciences, Buckinghamshire, UK; Washing was done at a high stringency (0.1×SSC at 65° C. for 20 min).

A total of 38 plaques that showed a positive response from one or more of the screenings, were excised from the screening plates and grown as plasmids as described (Stratagene, San Diego, USA).

A total of 8 cDNAs were identified by cDNA cloning or by a combination of cDNA cloning, PCR analysis and RACE (rapid amplification of cDNA ends-polymerase chain reaction) using the SMART™ RACE cDNA amplification kit (Clontech, Palo Alto, Calif.) according to the manufacturer's instructions.

Example 2

Bioinformatic Analysis of AMB-1

The DNA and protein sequence data bases (GenBank and EBI) have been searched for sequences with similarity to AMB1. There is no significant DNA sequence similarity to any known gene. In particular, the coding region of the AMB1 mRNA (SEQ ID no 3) is not present in any known EST. The only significant match to the complete mRNA sequences and the DNA sequence of the putative coding region were BAC clones derived from the region on human chromosome 12 where the gene is located. The "AMB-1 gene" had not been annotated as a gene on the chromosome. Searches with the peptide sequence in the sptrnr data base of peptide sequences (includes Sprot and nrtrembl) showed a low similarity to putative intron maturases from cloroplasts and to bovine IL4. The percentage similarity to both maturases and bovine IL4 was low (25.6% and 30.3%, respectively) and the similarity to maturases only included a match to 75 amino acids of the much larger maturases. In contrast, the match to bovine IL4 extended over the full peptide sequence. IL4, and other 4-helical cytokines, include a leader peptide sequence (signal peptide) allowing the proteins to be secreted. The AMB1 peptide sequence includes a N-terminal peptide sequence with similarity to signal peptide sequences, however, it is not a typical sequence.

A 3D search has been performed, where a peptide sequence is searched for similarity to known protein or peptide 3D-structures. The two best matches were the thioredoxin fold and the human 4-helical cytokine IL4 (FIG. 5). The two matches had almost similar probability scores (2.88 and 3.05, respectively). Searches with 4-helical cytokine peptide sequences (IL4, IL3, IL13 and GM-CSF) revealed that all could be folded into both a 4-helical cytokine structure and the thioredoxin fold. Alignment based on the structural similarity between IL4 (dliara) and AMB-1 is shown in FIG. 5. Thus, the AMB1 peptide sequence share this property with 4-helical cytokines. The structural similarity is not perfect (FIG. 6) and there are no obvious glycosylation sites in the AMB1 sequence, however, the similarity is significant. Alignment of the AMB1 peptide sequence with the sequences of IL4, IL3, IL13 and GM-CSF, based on their structures, showed very little sequence conservation but a high degree of structural conservation (FIG. 7). Based on this alignment, AMB1 has similarities to all the 4-helical cytokines, and the length of AMB1 and the position of gaps in the alignment could suggest a higher similarity to e.g. IL13, but searches at 3D-PSSM only identified a significant similarity to the structure of IL4, not IL13, IL3 or GM-CSF. However, the search algorithms are not perfect and may therefore not detect a possible low structural similarity.

Example 3

Differential Expression of AMB-1

Patient Material

Blood samples were collected from newly diagnosed untreated patients with B-CLL. Mononuclear cells were isolated by Lymphoprep separation (Nycomed Pharma, Oslo, Norway), and the percentage of CD5+CD20+ B-CLL cells in the mononuclear fraction was >90% in all samples as determined by flow cytometric analysis.

Isolation of RNA and Conversion to cDNA.

Material for RNA production was isolated mononuclear cells from B-CLL patients or mononuclear cells from lymphoprep separated buffy coats from normal donors. Total RNA was isolated from $5 \times 10^7$ or more cells using the QIAamp RNA Blood Mini kit (Qiagen, Valencia, Calif.) with DNAse treatment. RNA (1 ug) was converted to cDNA by incubation with a mixture of random-primers (1 µg) and T24-primer (1 µg) for 5 minutes at 70° C. After cooling on ice, the reaction mixture was added to a final volume of 25 µl containing 30U of AMV Reverse Transcriptase HC (Promega, Madison, Wis., USA), 1× First Strand Buffer (50 mM Tris-HCl, pH 8.3, 50 mM KCl, 10 mM MgCl$_2$, 10 mM DTT, 0.5 mM spermidine), 2.5 mM of each dNTP and 60U rRNasin ribonuclease inhibitor (Promega, Madison, Wis., USA). The reaction was performed for 60 minutes at 37° C.

Determination of Somatic Hypermutation Status

Two µl of cDNA was amplified using a GeneAmp PCR System 2700 (Applied Biosystems, Warrington, UK) with a 40 µmol specific upstream primer corresponding to 1 of the 6 human VH family leader sequences (VH1 (SEQ ID No:31): 5'-CCATGGACTGGACCTGGAGG-3', VH2 (SEQ ID No:32): 5'-ATGGACATACTTTGTTCCAGC-3', VH3 (SEQ ID No:33): 5'-CCATGGAGTTTGGGCTGAGC-3', VH4 (SEQ ID No:34): 5'-ATGAAACACCTGTGGTTCTT-3', VH5 (SEQ ID No:35): 5'-ATGGGGTCAACCGCGATCCT-3', VH6 (SEQ ID No:36): 5'-ATGTCTGTCTCCTTCCT-CAT-3') and a 40 pmol downstream primer (Cu (SEQ ID No:37):5'-GAGGCTCAGCGGGAAGACCTT-3' or Cy (SEQ ID No:38):5'-GGGGAAGACCGATGGGCCCCT-3') corresponding to a consensus sequence of the constant region of IgM or IgG respectively. The Reverse Transcription (RT)-PCR reaction contained 1xPCR buffer (10 mM Tris-HCl, pH 9.0, 50 mM KCl, 0.1% Triton X-100), 2.5 mM MgCl$_2$, 0.2 mM of each dNTP and 1.5U Taq DNA Polymerase (Promega, Madison, Wis., USA) in a final volume of 100 µl. The RT-PCR was performed under the following conditions: 1 cycle of 94° C. for 5 minutes, 30 cycles of denaturation at 94° C. for 30 secs, annealing at 62° C. for 30 sec. and extension at 72° C. for 30 sec, and a final extension at 72° C. for 7 minutes. The RT-PCR products were analysed on 2% agarose gels and sequenced in an HBI Prism 310 Genetic Analyzer (Perkin Elmer, Foster City, Calif., USA) using the BigDye Terminator Cycle Sequencing Ready Reaction kit (Applied Biosystems, Warrington, UK) following the manufacturer's instructions.

Sequences obtained from each sample were compared to germ line sequences in the V base sequence directory (I. M. Tomlinson, MRC Center for Protein Engineering, Cambridge, UK) using BLAST, and the closest germ line sequence was assigned. A gene sequence was considered to be mutated if it had equal or more than 2% sequence alterations when compared to the closest published germ line sequence.

RT-PCR that Amplifies the Exon 2-Exon 3 Junction

To evaluate the mRNA expression pattern of AMB1 in unmutated and mutated B-CLL patients RT-PCR was performed. Exon-overlapping oligonucleotide primers were: 5'-ATCCAGCCAGGATGAAATAGAA-3' (SEQ ID No:30) and 5'-CACTTGTCACACACATAAAGG-3' (SEQ ID No:28). The RT-PCR was performed in a GeneAmp PCR System 2700 thermal cycler with an initial denaturation at 94° C. for 2 minutes, 40 cycles of 96° C. for 25 sec., 62° C. for 25 sec. and 72° C. for 90 secs, and a final extension at 72° C. for 5 minutes. The reactions contained 20 cDNA, 1×DDRT-PCR buffer (10 mM Tris-HCI, pH 8.3, 50 mM KCI, 1.8 mM $MgCl_2$, 0.1% Triton X-100, 0.005% gelatine), 0.25 mM of each dNTP, 30 pmol of each primer and 0.5U Taq DNA Polymerase (Promega, Madison, Wis., USA) in a 30 µl final volume. RT-PCR products were analyzed by gelelectrophoresis on 2% agarose gels and visualized with a Gene Genius Bio Imaging System (Syngene, Frederick, Md.) after staining with ethidium bromide. An actin control RT-PCR was performed using the primers: 5'-TGACGGGGTCACCCA-CACTGTGCCCATCTA-3' (SEQ ID NO: 42) and 5'-CTA-GAAGCATTTGCGGTGGACGATGGAGGG-3' (SEQ ID NO: 43).

RT-PCR that Amplifies the Exon 1-Exon 3 Junction:

To evaluate the mRNA expression pattern of AMB1 in unmutated and mutated B-CLL patients RT-PCR was performed. Exon-overlapping oligonucleotide primers were: 5'-AGACGGCTCTCACC AATAAG-3' (SEQ ID No:27) and 5'-CACTTGTCACACACATAAAGG-3' (SEQ ID No:28). The RT-PCR was performed in a GeneAmp PCR System 2700 thermal cycler with an initial denaturation at 94° C. for 2 minutes, 40 cycles of 96° C. for 25 sec., 62° C. for 25 sec. and 72° C. for 90 secs, and a final extension at 72° C. for 5 minutes. The reactions contained 2 µl cDNA, 1×DDRT-PCR buffer (10 mM Tris-HCI, pH 8.3, 50 mM KCI, 1.8 mM $MgCl_2$, 0.1% Triton X-100, 0.005% gelatine), 0.25 mM of each dNTP, 30 pmol of each primer and 0.5U Taq DNA Polymerase (Promega, Madison, Wis., USA) in a 30 µl final volume. RT-PCR products were analyzed by gel electrophoresis on 2% agarose gels and visualized with a Gene Genius Bio Imaging System (Syngene, Frederick, Md.) after staining with ethidium bromide (Continental Lab Products, San Diego, USA).

Statistical Analysis

Statistical significance of the correlation between somatic hypermutation status and AMB1 expression was analyzed using Fisher's exact test.

Northern Blotting.

RNA from spleen, bone marrow and colon was purchased from Clontech. The AMB1 probe was an 896 base pair fragment (57661-56766) obtained by RT-PCR as described above with the primers 5'-TCACCTGGGAGCTCAGAGGA-3' (SEQ ID No:39) and 5'-GTGATCCTGGGAGAATCTCT-3' (SEQ ID No:40). For Northern blotting, 5 µg of RNA was run on a 1% agarose-gel with 6% formaldehyde dissolved in 1×MOPS (20 mM 3-(N-morpholino)-propane-sulfonic acid, 5 mM sodium acetate, 1 mM EDTA, pH 7.0) for size separation. The presence of equal amounts of RNA in each lane was ensured by ethidium bromide staining. The RNA was transferred to a Hybond-N membrane (Amersham, Little Chalfont, UK) by capillary blotting and fixed by UV-irradiation. The filters were pre-hybridized for 1-2 hours at 42° C. in 6 ml ULTRAhyb (Ambion, Austin, Tex., USA) preheated to 68° C. and hybridized overnight at 42° C. after addition of further 4 ml containing the $^{32}$P-labeled probe and sheared salmon sperm DNA (10 µg/ml). The membranes were washed for 2×15 min. at 42° C. in 2×SSC, 0.1% SDS followed by 1×15 min. in 0.2×SSC, 0.1% SDS and 2×15 min. in 0.1×SSC, 0.1% SDS at 42° C. The blot was developed and quantified by a phosphoimager. The sizes of the mRNAs were determined by reference to 18S and 28S ribosomal RNA, which were visualized by ethidium bromide staining. The AMB1 probe used for hybridization was radiolabeled with [$\alpha$-$^{32}$P] dCTP using the Random Primers DNA Labeling System (Gibco BRL).

Dot Blot of Multiple Tissue Expression (MTE) Array.

An MTE array (Clontech, Palo Alto, Calif., USA) was hybridised to AMB1 at 65° C. in ExpressHyb (Clontech) supplemented with sheared salmon sperm DNA (7.5 µg/ml) and human $C_o$t-1 DNA (1.5 µg/ml) according to the manufacturers recommendations. The tissue types represented on the MTE array are shown in FIG. 11. Following hybridisation the filter was washed 5×20 min. at 65° C. in 2×SSC (1×SSC=150 mM NaCl, 15 mM sodium citrate, pH 7.0), 1% SDS and 2×20 min at 65° C. in 0.1×SSC, 0.5% SDS. The blot was developed and quantified by a phosphoimager (Fuji Imager Analyzer BAS-2500, Image Reader ver. 1.4E, Image Gauge ver. 3.01 software, Fuji, Stockholm, Sweden). The membranes were stripped by boiling in 0.5% SDS for 10 min. before rehybridization. The probe used for hybridization were radiolabeled with [$\alpha$-$^{32}$P] dCTP using the Random Primers DNA Labeling System (Gibco BRL, Rockville, ML, USA).

Results

Figure 10:
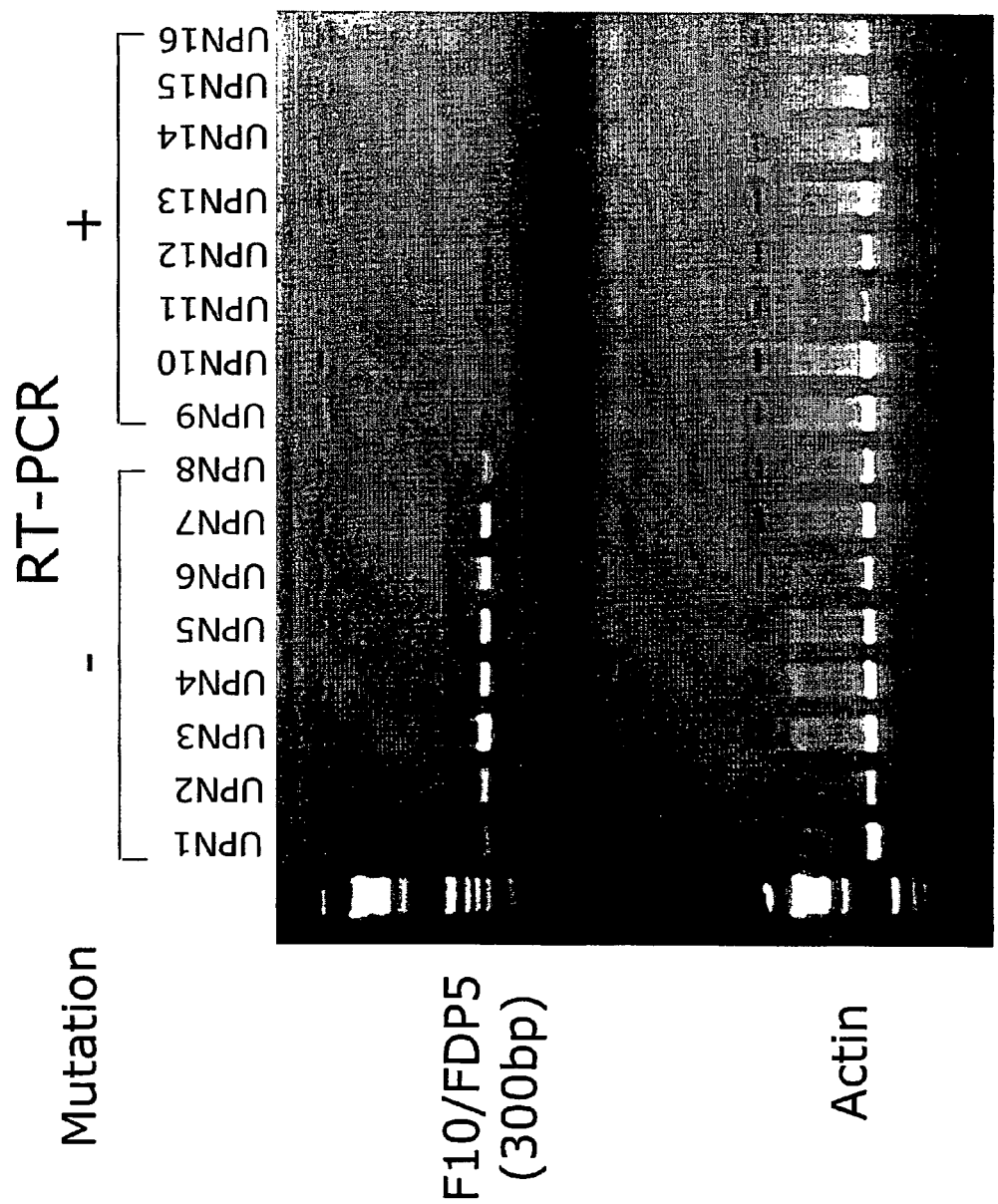
FIG. 10. RT-PCR demonstrating the expression of AMB-1 in B-CLL patients by RT-PCR. UPN1-UPN8 are unmutated patients, UPN9-UPN16 are mutated patients.

Based on the known sequence of the AMB-1 cDNA RT-PCRs with primers that extend across the Exon 2-Exon 3 junction and the Exon 1-Exon 3 junction were set up. As shown in FIG. 10, where the Exon 2-Exon 3 junction has been amplified, AMB-1 is expressed in the unmutated patients (UPN1-8) while no expression of AMB-1 is seen in mutated patients (UPN9-16).

Figure 3:
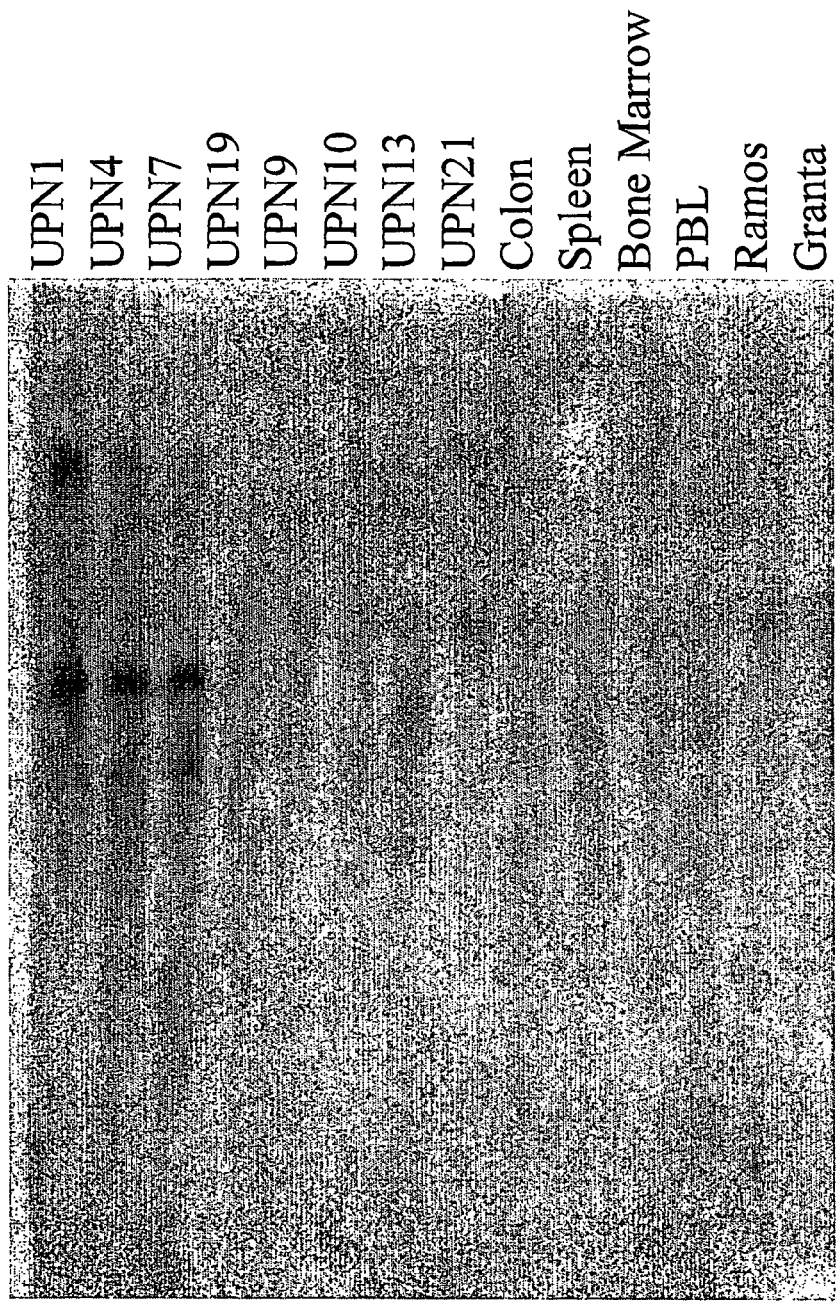
FIG. 3: Northern blotting demonstrating the expression level of AMB-1 in various tissue samples using as a probe an 875 base pair fragment of Exon 3/Seq ID No:16. UPN 1, 4 and 7 are unmutated B-CLL patients, UPN 19, 9, 10, 13 and 21 are mutated B-CLL patients. Included are RNA samples from normal Colon, Spleen, Bone Marrow and PBL (peripheral blood lymphocytes) and RNA from the Ramos and Granta cell lines. Equal loading of lanes was confirmed by re-probing with an actin probe (results not shown).
Figure 9:
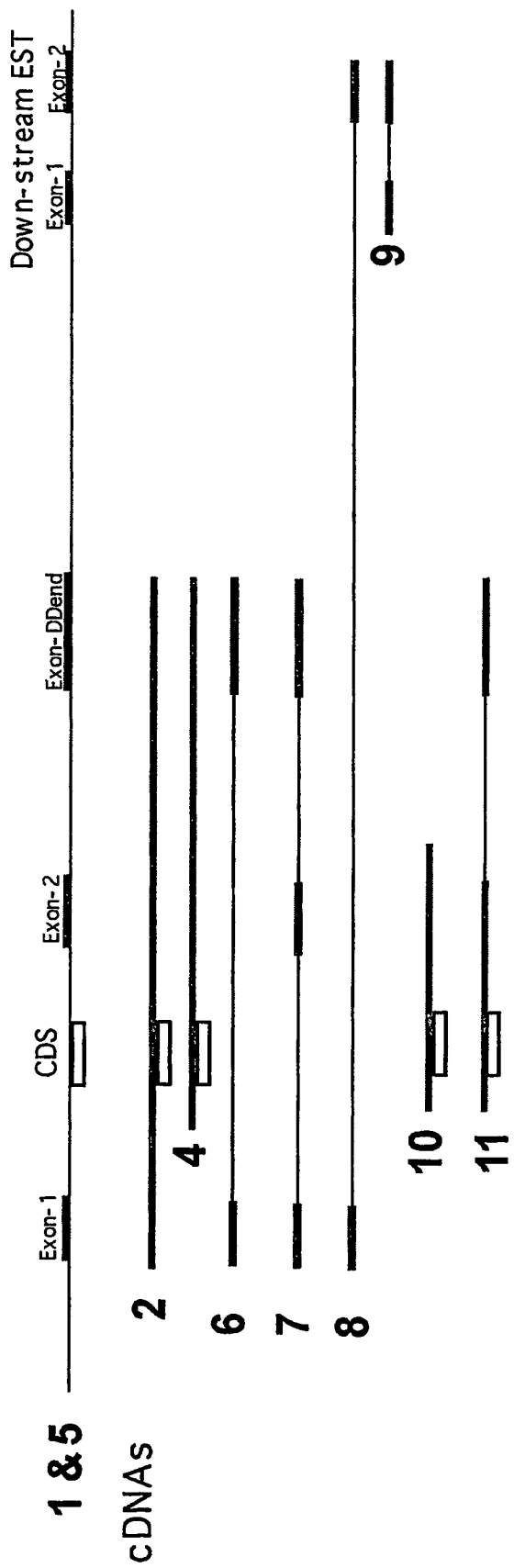
FIG. 9. Schematic representation of the transcriptional products of the present invention compared to the genomic AMB1 sequence (1 & 5). 2 is mRNA short form (SEQ ID No 2). 4 is mRNA long form (SEQ ID No 4). 6 (SEQ ID No:6), 7 (SEQ ID No:7), 8 (SEQ ID No:8), 9 (SEQ ID No:9), 10 (SEQ ID No:10) and 11 (SEQ ID No:11) are alternative transcription products all comprising at least one nucleotide sequence selected form the group consisting of SEQ ID No:12, SEQ ID No:13, SEQ ID No:14, SEQ ID No:15, SEQ ID No:16, SEQ ID No:17 and SEQ ID No:18.

Northern blot analysis was performed to determine the size of AMB-1's mRNA transcript. As shown in FIG. 3 the probe identifies transcripts in the samples from the three patients without somatic hypermutation (UPN1, UPN4 and UPN7). However, the probe does not recognise any transcripts from the patients with somatic hypermutation (UPN9, UPN10, UPN13, UPN21) or the various cell lines and tissue samples. Similar results were obtained when cell lines and tissue samples were investigated by RT-PCR (results not shown).

Dot blot analysis on a purchased filter with 96 different RNA samples (FIG. 8) only revealed specific binding to the total DNA control dot, but not to any specific tissue (results not shown). Thus AMB-1 is only expressed in B-CLL cells without hypermutation or AMB-1 is expressed at extremely low levels in other tissues.

We next tested the predictive value, in terms of $IgV_H$ mutational status, of expression of AMB-1 in 29 consecutive newly diagnosed patients. At present 13 somatically unmutated and 16 somatically mutated patients have been included in our prospective patient database. The sensitivity and specificity for expression of AMB-1 in predicting mutational status is well above 90% ($p<0.0001$), which is at the level obtained by sequencing.

Example 4

Investigation of the Prognostic Significance of AMB-1 in Terms of Patient Survival To obtain information about the ability of AMB-1 to predict survival or time to progression for B-CLL patients survival curves were made. For each patient the following data were collected: clinical stage at time of diagnosis (Rai and Binet staging), date of diagnosis, date of first time of treatment and last follow up date. Time to treatment (progression free survival) and survival time were calculated based on these dates using the Microsoft Excel software. Survival times and progression free survival times were plotted be the Kaplan-Meier Method and compared using the log-rank test (Prism 3.0 Graph Pad software).

34 newly diagnosed, untreated B-CLL patients were investigated as described above. As shown in FIG. 2a-d AMB-1 expression is a good predictor of B-CLL patient survival and B-CLL patient time to progression.

Example 5 siRNA Assays

Materials and Methods:

Frozen cells from unmutated or mutated B-CLL patients pruified and characterized for mutational status as previously described were thawed and Ficoll separated to obtain the live cells. Cells were counted and resuspended at $2\times10^6$ cells/ml in RPMI 1640 medium with glutamax-1 (RPMI, GIBCO, Paisley, UK). $1\times10^6$ cells (500 µl of cell suspension) were incubated on ice for 10 minutes with the appropriate siRNA or combination of siRNAs at a final concentration of 100 nM each. The suspension was electroporated using a 4 mm cuvette (Molecular BioProducts, San Diego, Calif., USA) in a BioRad Gene Pulser. Following electroporation the cells were incubated on ice for 10 minutes, washed once in RPMI with 20% FCS and 100 units/ml Penicillin and 100 µg/ml Streptomycin (GIBCO, Paisley, UK), resuspended at a concentration of $4\times10^6$ cells/ml in the same medium and incubated for 48 hours. For each patient the optimal voltage allowing for maximum siRNA uptake was determined by making a voltage curve (300-450V, 960 µF) using a FITC-labeled unspecific probe (Xeragon, Qiagen, Hilden, Germany) at a final concentration of 200 nM and the uptake was followed by flow cytometry.

The siRNAs were produced using the SilencerTM siRNA Construction Kit, (Ambion, Texas, USA) according to the manufacturers instructions. SiRNAs had the following target sequences:

TABLE 1

Overview of the siRNAs used in electroporation experiments

| siRNA name: | mRNA target sequence: |
|---|---|
| Exon 1 A | 5'- AAUAAGGGCAGGCAUCAUCCA -3' SEQ ID No: 19 |
| Exon 1 B | 5'- AAUUACACUGCCAGGUUUCCU -3' SEQ ID No: 20 |
| Exon 2 A | 5'- AAUUCAUUCACAAUGAUUGCU -3' SEQ ID No: 21 |
| Exon 2 B | 5'- AAUUUCUCUUGGGUAAUUCAG -3' SEQ ID No: 22 |
| Exon 3 (DDend) A | 5'- AAAAUCAGAAUCUGCGCAGCA -3' SEQ ID No: 23 |
| Exon 3 (DDend) B | 5'- AAUGAUGAUGGGAAGAAGGAA -3' SEQ ID No: 24 |
| CDS A | 5'- AAACUUAGUAAUUGAGUGUGA -3' SEQ ID No: 25 |
| CDS B | 5'- AAUAUGUCACUUUCAUAAAGC -3' SEQ ID No: 26 |
| Transcript on -strand A | 5'- AAUGAUGAUGGGAAGAAGGAA -3' |
| Transcript on -strand B | 5'- AAACUAUGAGAUUUCAGAAGG -3' |

After 48 hours of incubation the various B-CLL samples were counted and live and dead cells were distinguished by nigrosin exclusion (0.1% in Nigrosin in PBS from Fluka, Buchs, Switzerland).

Results:

Following 48 hours of incubation with control GFP siRNA or siRNAs against various regions of the cDNAs (see table 1), the viable cells and dead cells were counted based on the ability of the cells to exclude nigrosin. As shown in table 2, in 3 out of 4 patients introduction of siRNAs against Exon 1, Exon 2 and Exon 3 resulted in an increase of dead cells as compared to the controls (no siRNA or GFP siRNA).

TABLE 2

Percent dead cells of total cells following electroporation and incubation with siRNAs.

| Treatment: | UPN 67 | UPN 66 | UPN 62 | UPN 73 |
|---|---|---|---|---|
| No siRNA | 33.0% | 19.7% | 30.9% | 20.2% |
| Control siRNA | 28.4% | 26.7% | 24.0% | 16.0% |
| CDS siRNA | 23.7% | 25.5% | 21.0% | 13.3% |
| Ex1–3 SiRNA | 47.3% | 54.1% | 17.2% | 29.1% |

Example 6

Identification of Possible Cytogenetic Aberrations Near or within the Region Encoding AMB-1 on Chromosome 12

Rationale: The limited expression profile of AMB-1 suggests that it may be a result of a genetic aberration (e.g. deletion, translocation or alternative splicing) or that the promotor region controlling the expression of AMB-1 is uniquely activated in unmutated B-CLL. Another gene is situated about 200.000 bases upstream of the AMB-1 gene (SEQ ID No 1) on chromosome 12 and the inventors we have determined that this gene is expressed at equal levels in unmutated and mutated patients.

Methods: Using primers, initially spaced about 20.000 bp apart; this region on chromosome 12 is characterised in unmutated B-CLL patients. If genetic aberrations within the region are detected by PCR analysis of chromosomal DNA, detailed molecular genetic studies using FISH, microsatellite analysis and Southern blotting will be employed. The whole region from unmutated patients is sequenced.

Example 7

Polyclonal Antibodies

Production of Polyclonal Antibodies:

Synthetic peptides CDLETNSEINKLIIYLFSQNNRIRF (SEQ ID NO: 44) and CQVSKKHIIYSTFLSKNF (SEQ ID NO: 45) were synthesized and conjugated to KLH (K. J. Ross-Petersen Aps, Holte, Denmark). Polyclonal antibodies were produced by immunization of rabbits with these conjugated peptides by DAKO (DAKO Cytomation A/S, Glostrup, Denmark).

Testing of Polyclonal Antibodies:

At the present time we have produced polyclonal antibodies from three rabbits that have been immunized with peptides representing predicted immunogenic regions of the protein that can be predicted from the CDS sequence (SEQ ID No:17) (cDNA 4). The antibodies are tested in various ways. The proposed reading frame of CDS (SEQ ID No:17) is expressed in 293 cells and the binding of antibodies to lanes on a western blot with non-transfected 293 cells versus transfected 293 cells are compared. The size of the band in the lanes with transfected 293 cells is compared to the size of western blot bands in lanes with proteins from B-CLL patients. Specificity of the bands is secured by peptide blocking experiments.

Additionally the polyclonal antibodies are tested in B-CLL Immunoprecipitation experiments where the antibodies are used to immunoprecipitate the protein produced from the CDS sequence and the immunoprecipitates are analyzed by western blotting.

Example 8

Assay for the Biological Activity of 4-helix Cytokines

The assay is based on the use of a cytokine dependent or stimulated cell line, for example an IL4 dependent cell line ("Optimisation of the CT.h45 bioassay for detection of human interleukin-4 secreted by mononuclear cells stimulated by phytohaemaglutinin or by human leukocyte antigen mismatched mixed lymphocyte culture", Petersen, S. L., Russell, C. A., Bendtzen, K. & Vindeløv, L. L., Immunology Letters 84 (2002) 29-39). Other examples of cytokine dependent cell lines include IL13 dependent cell lines. A list of commercially available cytokine dependent cell lines is disclosed in the general part of the description. These can all be used for assessing cytokine activity. The most preferred cell lines are those that are IL4 dependent.

The assay can be performed in two ways. The first assay comprises providing recombinantly produced AMB1 protein or a functional equivalent thereof and determine the proliferation rate of the cell line. The proliferation rate (either rate of proliferation or ±proliferation) can be compared to the proliferation rate of the cell line exposed to IL4 or another known 4-helical cytokine or interleukin.

If a positive result is obtained with a polypeptide an assay will be performed on the same cell line with the IL4 receptor blocked. This will check whether the stimulus goes through IL4R.

The second assay is based on transfection of a gene encoding a 4-helix cytokine according to the invention into cytokine dependent cells and observe proliferation or non-proliferation during transient expression.

Example 9

Cytokine Receptor Binding Assays

The following is a description of the layout of a cytokine receptor binding assay used to determine the cytokine activity of the 4-helix cytokines according to the present invention.

The assays can be performed with any cytokine receptor. Preferred receptors include but is not limited to the receptors for IL4 IL13, IL3, and GM-CSF.

The ability of recombinant cytokine receptor to bind to 4-helical cytokine is assessed in a competitive binding ELISA assay as follows. Purified recombinant cytokine receptor (IL4, IL13, IL3 or GM-CSF receptors) (20 µg/ml in PBS) is bound to a Costar EIA/RIA 96 well microtiter dish (Costar Corp, Cambridge Mass., USA) in 50 µL overnight at room temperature. The wells are washed three times with 200 µL of PBS and the unbound sites blocked by the addition of 1% BSA in PBS (200 µl/well) for 1 hour at room temperature. The wells are washed as above. Biotinylated AMB-1 (1 µg/ml serially diluted in twofold steps to 15.6 ng/mL; 50 µL) is added to each well and incubated for 2.5 hours at room temperature. The wells are washed as above. The bound biotinylated AMB-1 is detected by the addition of 50 µl/well of a 1:2000 dilution of streptavidin-HRP (Pierce Chemical Co., Rockford, Ill.) for 30 minutes at room temperature. The wells are washed as above and 50 µL of ABTS (Zymed, Calif.) added and the developing blue color monitored at 405 nm after 30 min. The ability of unlabelled 4-helical cytokine to compete with biotinylated AMB-1, respectively, is assessed by mixing varying amounts of the competing protein with a quantity of biotinylated AMB-1 shown to be non-saturating (i.e., 70 ng/mL; 1.5 nM) and performing the binding assays as described above. A reduction in the signal (Abs 405 nm) expected for biotinylated 4-helical cytokine indicates a competition for binding to immobilised cytokine receptor.

The above identified assays can be used to identify 4-helical cytokines with similar binding affinities as AMB-1 (SEQ ID No. 3). In the competitive binding assays biotinylated IL4, IL13, IL3, or GM-CSF can be used to identify 4-helical cytokines which can compete with these cytokines.

The sequence listing in the file named "10535500 (55320.001041).TXT" having a size of 179103 bytes and created Apr. 17, 2008 is hereby incorporated by reference in its entirety.

REFERENCES

1. U.S. Pat. No. 4,554,101
2. U.S. Pat. No. 5,681,729
3. Antineoplastic Agents (Paul Calabresi and Bruce A. Chabner
4. Andrews, R., L. Rosa, M. Daines, and G. Khurana Hershey. 2001. Reconstitution of a functional human type II IL4/IL13 receptor in mouse B cells: demonstration of species specificity. *J Immunol* 166, no. 3:1716
5. Ausubel, et al., Current Protocols in Molecular Biology, Chapter 2, Eds., Greene Publishing and Wiley-Interscience, New York (1995).
6. Bouteiller, C. L., R. Astruc, A. Minty, P. Ferrara, and J. H. Lupker. 1995. Isolation of an IL13-dependent subclone of the B9 cell line useful for the estimation of human IL13 bioactivity. *J Immunol Methods* 181, no. 1:29
7. Chaouchi, N., C. Wallon, C. Goujard, G. Tertian, A. Rudent, D. Caput, P. Ferrera, A. Minty, A. Vazquez, and J. F. Delfraissy. 1996. Interleukin-13 inhibits interleukin-2-induced proliferation and protects chronic lymphocytic leukemia B cells from in vitro apoptosis. *Blood* 87, no. 3:1022
8. Damle, R. N., T. Wasil, F. Fais, F. Ghiotto, A. Valetto, S. L. Allen, A. Buchbinder, D. Budman, K. Dittmar, J. Kolitz, S. M. Lichtman, P. Schulman, V. P. Vinciguerra, K. R. Rai, M. Ferrarini, and N. Chiorazzi. 1999. Ig V gene mutation status and CD38 expression as novel prognostic indicators in chronic lymphocytic leukemia. *Blood* 94, no. 6:1840
9. Dancescu, M., M. Rubio-Trujillo, G. Biron, D. Bron, G. Delespesse, and M. Sarfati. 1992. Interleukin 4 protects chronic lymphocytic leukemic B cells from death by apoptosis and upregulates Bcl-2 expression. *J Exp Med* 176, no. 5:1319
10. Dohner, H., S. Stilgenbauer, A. Benner, E. Leupolt, A. Krober, L. Bullinger, K. Dohner, M. Bentz, and P. Lichter. 2000. Genomic aberrations and survival in chronic lymphocytic leukemia. *N Engl J Med* 343, no. 26:1910
11. Fluckiger, A. C., F. Briere, G. Zurawski, J. M. Bridon, and J. Banchereau. 1994. IL13 has only a subset of IL4-like activities on B chronic lymphocytic leukaemia cells. *Immunology* 83, no. 3:397
12. Goodman and Gilman's "The Pharmacological Basis of Therapeutics", Eighth Edition, 1990, McGraw-Hill, Inc. (Health Professions Division)
13. Hamblin, T. J., Z. Davis, A. Gardiner, D. G. Oscier, and F. K. Stevenson. 1999. Unmutated Ig V(H) genes are associated with a more aggressive form of chronic lymphocytic leukemia. *Blood* 94, no. 6:1848
14. Innis et al. (1990) PCR Protocols, A Guide to Methods and Applications, eds., Academic Press
15. Jørgensen M, Bévort M, Kledal T S, Hansen B V, Dalgaard M, and Leffers H (1999) Differential Display Competitive PCR: An Optimal Tool for Assaying Gene Expression. Electrophoresis 20:230-240
16. Kirn D. et al., "The emerging fields of suicide gene therapy and virotherapy", Trends Mol. Med. 2002, 8:568-573
17. Kröber, A., T. Seiler, A. Benner, L. Bullinger, E. Bruckle, P. Lichter, H. Dohner, and S. Stilgenbauer. 2002. V(H) mutation status, CD38 expression level, genomic aberrations, and survival in chronic lymphocytic leukemia. *Blood* 100, no. 4:1410
18. Kyte J and Doolittle R F. 1982. A simple method for displaying the hydropathic character of a protein. *J. Mol. Biol.* 157, no. 1:105
19. Liang P, and Pardee A B (1992) Differential Display of eukaryotic messenger RNA by means of the polymerase chain reaction. Science 257:967-71
20. Lin, K., P. D. Sherrington, M. Dennis, Z. Matral, J. C. Cawley, and A. R. Pettitt. 2002. Relationship between p53 dysfunction, CD38 expression, and IgV(H) mutation in chronic lymphocytic leukemia. i Blood 100, no. 4:1404
21. Lundin, J., E. Kimby, L. Bergmann, T. Karakas, H. Mellstedt, and A. Osterborg. 2001. Interleukin 4 therapy for patients with chronic lymphocytic leukaemia: a phase I/II study. *Br J Haematol* 112, no. 1:155
22. Luo, H. Y., M. Rubio, G. Biron, G. Delespesse, and M. Sarfati. 1991. Antiproliferative effect of interleukin-4 in B chronic lymphocytic leukemia. *J Immunother* 10, no. 6:418
23. Merrifield, J. Am. Chem. Soc. 85:2149-2146, 1963)
24. Oscier, D. G., A. C. Gardiner, S. J. Mould, S. Glide, Z. A. Davis, R. E. Ibbotson, M. M. Corcoran, R. M. Chapman, P. W. Thomas, J. A. Copplestone, J. A. Orchard, and T. J. Hamblin. 2002, Multivariate analysis of prognostic factors in CLL: clinical stage, IGVH gene mutational status, and loss or mutation of the p53 gene are independent prognostic factors. *Blood* 100, no. 4:1177
25. Panayiotidis, P., K. Ganeshaguru, S. A. Jabbar, and A. V. Hoffbrand. 1993. Interleukin-4 inhibits apoptotic cell death and loss of the bcl-2 protein in B-chronic lymphocytic leukaemia cells in vitro. *Br J Haematol* 85, no. 3:439
26. Petersen, S. L., Russell, C. A., Bendtzen, K. & Vindeløv, L. L., Optimisation of the CT.h45 bioassay for detection of human interleukin-4 secreted by mononuclear cells stimulated by phytohaemaglutinin or by human leukocyte antigen mismatched mixed lymphocyte culture", *Immunology Letters* 84 (2002) 29-39)
27. Sambrook et al. (1989) Molecular Cloning: A Laboratory Manual (2nd ed. Cold Spring Harbor Laboratory, Cold Spring Harbor, N.Y.).
28. Tijssen, Laboratory Techniques in Biochemistry and Molecular Biology-Hybridization with Nucleic Acid Probes, Part I, Chapter 2, "Overview of principles of hybridization and the strategy of nucleic acid probe assays", Elsevier, N.Y. (1993)
29. Yazawa et al., Current Progress in suicide gene therapy for cancer, World J. Surg. 2002, 26(7):783-789.

SEQUENCE LISTING

<160> NUMBER OF SEQ ID NOS: 45

<210> SEQ ID NO 1
<211> LENGTH: 19999
<212> TYPE: DNA
<213> ORGANISM: Homo Sapiens
<220> FEATURE:
<221> NAME/KEY: gene
<222> LOCATION: (1)...(19999)
<223> OTHER INFORMATION: Sequence of ac063949.emhum

<400> SEQUENCE: 1

| | | | | | |
|---|---|---|---|---|---|
| cacacgtagg | ctacgagtgg | ccctcagcct | gcctcatcat | ggacctgtgt | tataataaat | 60 |
| atgtttaatt | gtgctgtttt | cttatagagg | aaagtcctga | tgttagttgc | cttgaagtca | 120 |
| gacacccaga | gagaatcaca | ggttttcaga | ttaattcatc | gcttgattct | tatccctgaa | 180 |
| gtcatatctc | tggatctctg | gttctcacat | tataaatttc | aatgattctt | tttctatatg | 240 |
| gccatgtcat | tcatatcctg | tgtaatatgg | ggaaactgag | gtatgaatga | catcattcaa | 300 |
| aaagcacctg | caattttttct | ttgccaagca | cttacagctt | tttctcatgt | tgctttcaaa | 360 |
| aagtcattga | atattgttc | acatattttg | cagatgagga | aatgaatatt | caaatgcatt | 420 |
| aggtatcttg | tccaagttct | tacagccaga | aagtagagaa | atgaatttga | attacaaatc | 480 |
| ttctacctct | tggcttatgc | tctttttcatg | acactgggaa | taaatgtctg | aacaagcatg | 540 |
| acttcatgtt | tcaactattt | atcaaatact | tgttttctac | taagatcttg | cactcactca | 600 |
| gtgggatccc | ctgaagcctg | ctgattattt | gtcctttggc | atttatcact | ctctgtggga | 660 |
| ccttactctc | ctatggtaaa | gttttattgt | tattaaaagt | attatttgac | aataaatgta | 720 |
| gaaatcctac | agatcatact | caacaacatg | tctaatgtca | gcacacaatg | tctaacaatc | 780 |
| atttatgaat | actttatgtc | aaacataagc | aataacctaa | ttaaggaagg | tatttttaat | 840 |
| aaattgacac | ttttgacat | aaccatattt | caagtggctc | cattgttttg | tttatttatt | 900 |
| tatttattta | tttatttatt | tatttttgag | aaagggtctc | actctgttgc | ccagactgga | 960 |
| gtgcagtggc | aacatcatag | ctcactacag | cctcgacctc | tctgggctca | agcaatcctc | 1020 |
| ccatctcagc | ttcccaagta | gctgggacta | caggtgtgta | ccatcatgcc | aggctaattt | 1080 |
| ttcgtatttt | gtagagacgg | ggttttgcct | ggtcgtccgg | gttggtctca | aactcctggg | 1140 |
| tgttccgccc | accttggcct | cccaaagtgc | tgggattata | ggcatgagcc | tcaagtggct | 1200 |
| acttttagg | gttgaaattt | atattgactg | tcaactagct | tccctagtta | gtatttggga | 1260 |
| tctgctaact | aatttatatt | accatccaac | ttgtcaacat | ttgttgaaat | ataactgtcc | 1320 |
| tcactttttt | tgtgtgaaca | ttgaatacac | tttcagacta | aatttggttt | attacttaat | 1380 |
| gtcttattct | ttattagagt | taataatatt | tcttaatact | ttgccttcca | caaatgaata | 1440 |
| acttgtttgt | gatggctacc | tcttttttttc | tcttagcctg | tcacaggtat | tatgaataaa | 1500 |
| aattagcacg | gctgggcaaa | aacaatgaaa | gaaatacact | tgcctgggaa | agctggggag | 1560 |
| gggtaaatga | atataattca | aaataccata | tattattca | acactgttgg | aatatatgtc | 1620 |
| ctgttggaaa | tgtaaaagtg | acatatgttc | tcttcctggg | tctcagactt | ttaggatcta | 1680 |
| gttgagggaa | ctggacttat | acacaaaata | caattcaaca | acattatgag | ctagaaaatc | 1740 |
| catgagctaa | agtctttggc | aaagacatta | ggtaacatga | ggagtcagga | aaaggagaaa | 1800 |
| ttactgtggg | ctgaatggt | ctgggaacat | gagatggagg | aagtggcttg | ttactggaga | 1860 |
| aaggatgagg | ttcaaagaga | tgggaaaaaa | agaaagagag | aagaaagaaa | agaaatgagg | 1920 |

```
aaaaacaagt tgccagaaag aacaaggaag aatagaggca ggtaagcagt ggattttgcc      1980
ctagggaagg taatataact agagacggca gtttctaaca ggccatgatg aataagatac      2040
actttagccc tcattggtac gtgcagaaat tcaaatttgg aaattcaagc ttacatgaca      2100
gtaaatatat gttgggaaaa aaataaccgg taaacattta catcagctct ttttcctaaa      2160
gagaaaccta ttccatgcta tgaaatattt gtcacaattc tgttttcaaa atacttgctc      2220
tacttttcca agccacaaga ggaaacattt tctctgccaa cactctctga ccttaaccag      2280
tttctccact acgtctactc ttaagctctc tttagagctg tgtgtatctc gtctttatgt      2340
aaacctccta gatgatatac ttatggaaat attcaggcaa cttttttcatg aactttacca     2400 ggaaagacat ttctagcagg agagcatgaa tagaaatgga ctcttcccca gtctctgctg      2460
ggttctgact gtggtcactc taactataaa aagtgtgtaa aaatcatgag cagattattt      2520
catttccttg gggtccctaa aaatttcaag gtatctgtat tagcacagga agatttaaat      2580
tgatttctca acacattcag atatcttatg aactttatta agataaattt cctccagcat      2640
tcagaaactc atatattaca gaataaaaaa taaagcagaa aattagtgta cctggctaaa      2700
aatgagagca gggttctatt tcatttttgga aagtcactaa gacagtaata ataccattaa     2760
tgataaaatg ttaacattag ttaattatta gatgtgtttt tgtatgccag ccacataata     2820 tatacttta tatgtatcac ctacatttct agatgtaaat gtgagggaat tatagtagta      2880
tctacctcgt atgattgctg gatgatttaa atgagctgtt gtctcaaaaa cttggtatag     2940
aaagcagaaa cttttagtta ttaagattct tactattcca atatttgaat aaaacagtga     3000
cctgctaaga aaccccaata atattctgat acatcaaaac cttctggcat tagatgtttc     3060
taatctaaca tcttcatatt aattttttta tgttttgatt atctacattc agtagtgaat     3120
gtgtttctaa acgctggatg cattttttaac taaatgtgtt ttgtaccaca ttttgacaac    3180
ttttgtttta actatgattc agcttataac aaaacaaaac aatgcatctt ctctccactg     3240
ttaataaggt taatgaaaag ttgacttatg aaaaaaatcc taatttatgc acattctcat     3300
tgttttcctt gctaaggata ttagtacttg acgattctgt aacaaagaat tatcatggga    3360
tgaaactttg atgcaaatat cttatcaata caatgtgctt gattttaccct agatgagatt    3420 tttcttttct tctttctttt ttgagacagg ttttgctgt gttacccagg ctagcctcaa     3480 accccctggcc cctggcctca agtgatcctc tcacctctgc ctcccaaagt gctgggtatt    3540
acagatgtga gtcactgaat ccagcctcac ttagttggct ttcttagtga attatttat     3600 ctggttctaa aacttttttga taatactctc aaatatttat ggattttata acataattta   3660
tggattacgt agttatgaat ttcataaatg attttgtgat attgccacag atcatcacca    3720
ttatacagga tgtataacat aaccatggtt taatatattt tcataaacta tagaccaaac    3780
aaagactggt caggaccagg gcacgcatgc attttatatg tgtggtgcct attggaatat    3840
gccaggcctc ctgtgaaaaa aatcagtaag tgccttatctc ataggaccaa cggcccaaca   3900
ttcctgaagt cactaccaca ctttgcactt atctccatgt ggaaatagat agccactgtt    3960
gaattctggt gagaacgaca cgtctgaaat ctctcagctt cacaacccct attacagccc   4020
tcagagaatc ttctcacata gcgccaaaca acaactttag gaagtgatgt tcctagaatg    4080
aatcaatttc taaaattaaa agtgaaaaca atgacaagga gaagggaggg tcagagagga   4140
aaggctgatg ttactaaaag acaaaagaca gtataacctc ttatgaggat ggtccagaca    4200
ctcagggaaa tgcaggaaga aataaaagat aggagtttga accacactgt gatggctaac    4260
tttatgtgtg gacccgaccg atctatggga cacccagata gcttgtaaag cactatttct    4320
```

```
gggtgcgtca gtgagggtgt ttttggaaga gatcaacact tgagtcagta gactgagtaa    4380
agcagatggt cctcaccaat gtgggtgcac attgtttaat ctgttgagtg cctggataga    4440
caaaaaaggc aaaagaaggg tgaattccct ttctcgtctt aagctgggac agccatcctt    4500
tcctaccctc agacatgaga ggtttggatt cttggatctt tggtcccaag ggctgacact    4560
ggtggccacc tctggtttca ggtctttggc cccagattgt aagttacacc atcagcttcc    4620
ttggttcttg ggccttgaga ctcaagctaa aatacactac cagcttccct tgttctctag    4680
tgtagggaca gcaaatcatg aaaccttctg cctccataat catataagtc aattcccgta    4740
ataaatctgt gcttatatat ctatagcttt ccttttggtc tgtttctcca aagaacctta    4800
atgtacacac tatatgacct aacctgtagt aatgataacc ttatgcaggt ttgaataaga    4860
tgatggtatt ctcagtatct gggaggtatg ggctagagtg atgaaccacc gccatgagcc    4920
taggactgag gagatttctg aaatgtggaa tatttggtgt caaaaccaag agataatata    4980
gccatgtgga aacatgtag aactatcgta tgattcagca acccaaccac tgggaattta     5040
cccaaaggaa aggaaaccag tatattaaag agaatctgca ctcccatggt tattgcagca    5100
ttattctcaa tagcctagat atggactcaa cctaggagat tagatgaatg gacaaagaaa    5160
atgtggcata tgtacaccat gaaatactta ccagctataa aaaagaatta gccaaagcag    5220
tggtgtgtgc ctgtcatccc agctccttgg gaggctgagg tgggaagatc tcgaggccag    5280
aagtttgaga ccagcctggg caaaataata agactcggtc tctaaaacaa tttaaaaata    5340
ggccttcctt aaaaaagaa taaaatcatg tcattcacgg caacatagat gggactggag     5400
gatattactg ttaagtgaaa ttagccagga acagcaagtt aaaccccaca tattctgatt    5460
catatgcgga agctaaaaaa acgttgatct catagaagta aaagtagaa cagaggatgc      5520 tggagactag aaaaggtagg gagaaggaag ggagagggaa aaatttgtta acaggtacaa    5580
aaacaaaatt acagttagtt agggagaatt aattccagca tcctgtagca ctataggatg    5640
actatagtta ataataatac tttaattagt ctcaaatagc tagaaggagg atattgaatg    5700
ttcccaacac acacaaaaaa atgataatgt atgagatgat ggatatggta gttatcctga    5760
tctgatcact ctacattata tgtatcaaca catcactatg taccccacaa atatgtagaa    5820
tttttatttg tccatttaaa aaagataaca aatttaaaaa taaataaaa actaaattag      5880 tgttccatgt aaacctggat gaactggtca ccctacgtct gcccatctag atggctggtc    5940
aaagtttccc aggctccaca tcaagttgtt ccactgctca ctggaacttc cctagtcagg    6000
ttgggcaaat agtaatttac agcaaatagtg aattatcac tgacatttct tcagttcccc    6060
tctttggcat ctgcttcttc ttttctgtaa tgctgtttgt tgaaatgccc aacattcttt    6120
ttcttcccta gagctattca gggtgacctt tcttttcgca ttttcccatg ccacttccat    6180
tatatcaaaa taaaacagtc ctgtgtggcc actgctcatg accttgtttc ctgccatgtg    6240
aagataggat cggctgctct ttcttctcct ccttttttt cagagacagg atctctccct      6300
gtcacccaga ctggagtgca atggcacagt cgtagcttgc tgcagcctcg aactcctgga    6360
cctcctcagc ctcctgagta gctgggacta caggtgcaca ccaccatgcc ttcctaatct    6420
gatatatata tatatatata ttatatatat aaaatatata tataaatata tatattttat    6480
atattatata tataatatat atattttata tataaaatat atatattata tatatatatt    6540
atatataaaa tatatatatt atatatatat atatatatta tagagatggg gtcttgctct    6600
gtcacccagg ctgaagatca gctgctcttt ctaatctgtg gttagataag atctgtctcc    6660
caggggataa aatactacct ggaataaagg tatctttaaa ataatcccag agaagaaaac    6720
```

```
atttttatag tatgacagag gcagagaaaa cagagaatat ttgttaaggc aggactttca    6780
ccactcccag tacaatcatc tgtctgttac ctgcatacct tacacgggct ggcactgctg    6840
ggggtacaaa gtagatgcca aacttcacaa tggttagatt catgtttaaa aagccattgg    6900
atcaaacctt tgtgaaagtt tccagctttt ttctgttcca aatatgtgtc cattataaaa    6960
gaatctcaag agcataattg ccaagatagt ctatgtccat gagtatttca acatctctca    7020
tgaaatctgt tcccatcatt actcaagata ttgtatgaac agtattccac ataaactagg    7080
tgctcaataa tgattgattg gccaatggag ggtcattatt taatgcacta caatcttttta   7140
tgcaaggggc ccacaggaat cagtatgatc ccataggaat cctttctttt tccattgaaa    7200
aagaaacaga tagtggcttg tattaggttt cttgtgtgtg ttgtgaggtg aaagatatg     7260
aaaagaaatt tgatcagagc ataaatctga gcccatggga taggaaagaa tgagggaata    7320
aggaagaaaa cacagattat agacaggaaa atcaaaccta ttaaaactga taattttcga    7380
atactaaaaa tgtacattca tttgaacaaa aagattctat aaagcaagat ttctctgttc    7440
ttaccagcac taccatgccc aaactacctt aggaaatgaa tagcagagtc aaacttaaaa    7500
gcacctgaaa tttaaaacaa aaaccaattt acattttatt taagaaaagc aaacagatgg    7560
gcctgctaac aatgtcaaag tctcgtttac aaagaaaaaa acaaatctgg aacctgaagt    7620
caaacgagtt caaaataaaa agcaaaccaa taaacagaaa ccaacataaa cagaagttac    7680
taccatctcc ctcagcctgt gaaattctgg aacttctctt tctttctcgc cttcttcttc    7740
tctcacctgg aagacgagca gagtgaacac atcaggggtt gtcagttccc cagatggcac    7800
cacattcata aaccaccgac tccaggagaa tgtaggaagc ttagttaagg ccaaagttct    7860
ctttggatct tcctcatggg cttcaaggca aagaaaaaa aagtttgctt gagaatatct    7920
tcatatctat tagtttgaac catgcaaaat tacagttttt ataggtaaaa tgagtgcata    7980
ttggcaattt caaatgatta accctaatac attatgcttt tgggtataga aatattcaga    8040
tcttaaacat atgctgttac atacaaaatc aggtatattc ctgcttctat aattaaagca    8100
aagagaattt cttttggtca ctactccttc tgacatgagg tatgaaccaa gttcaggacc    8160
cctaaaggtc tgggtctggg tcatttctcc acctctaact tgtgccgctt tcttggtcag    8220
tcattgtgtt ctgagctgtc tcataaaaca tctgctatga cttactttc tcctgatagg    8280
gtggcttttcc atcgttggca cttcgttggc cttattggta tgcttatac actggttctc    8340
gtttccaaat tggcattatt attgttatga ttcctgctgc tctcccacat ttcccatctt    8400
tctcctgatc tctctcacct gtacatttct tacatttct cctgtgcttc cttcttccca    8460
tcatcattgc ccaagtgtgt cttctttctt ctccttgtca catttccttt gcccgctctc    8520
acatatgcag agatggctct tggttttcct tctgaaatct catagtttgg aggtaaactt    8580
gttagcaagg ccactgagaa gagaacaaaa gggaaacata agagaaacca agtcactatc    8640
tctctcattt cctggtttct agaagtaaga cccaaagaac tcactgtttc agtgctttca    8700
gctcaggcca aactagggtg atcaaactga gcttctgagt gctgatcaaa acctataaaa    8760
ccaagtagac agaccatcta caaatcttca ctgttaaata ccataaagaa tgaaaaggtc    8820
actaattggt aagactatat gtgtgataat taaatttatg catcaacctg gctaggctaa    8880
aggatgacca ggtagctggt aaaacattat tctgggtgtg tccataagag tgttttcgga    8940
agagatcagc atttgaattg gtgaacttag taaagcagac ggctctcacc aataagggca    9000
ggcatcatcc aatctgtcga aagcttgaat aaaacaaaaa gaggaaggga aaatttgctt    9060
ctttttcttct tgatctagta tatcatcttc tcctgcccct ggatgtgagt gggccttcag   9120
```

```
acttaaaacca ggagttacac ctttggcttc cctggttctc agttctttgg acttggactg    9180
aattacactg ccaggtttcc tggttctcca gcttgcagat ggcagatcat gggacttctt    9240
ggcctccata attgtgtgag tcaatttcca ttttatttac atatccagtt atgcattgct    9300
taacaatgga gacaggttct gagaaatgca ttgttaagtg atttcatcat tgtgcaaaca    9360
tcatagagtg taactacaca aacctggaca gcatagacta ctacacatct aggctacatg    9420
gtgtagcttg taacctcatg ataagtatgt ataacatcat gataagtatg tatgtatcta    9480
ccatatctaa atgtagaaaa ggtacagtaa aaatatggta taatcttatg ggatcaccat    9540
catatatgca atcctttgta gactgaaatg tcattgtgta gtgcatgact gtatacgcac    9600
acatacacaa acacacacaa atatactatt ggttcttttt ctctgaagag ccctaataca    9660
atatgttata catttatatt gactctattt caaaatttat ggttttggtg aaacatatgt    9720
ggagatgggg cataggtgtg tgaactggga tagtgtcctg ctgatgaatg ggtgggaggc    9780
atcatttggg acaagcccag ggcatcagct tatagatatc aagagctcaa caagagcact    9840
ttatggcaaa acctcccaca agacctctca gaagttgaga aactgctaaa agtttcttta    9900
tgacagatga catttatgga taaaataggg attagcagga ttctttaaat actttcgaac    9960
actaaccttc atttctacca ggcagtgggg ccccaagtgc agggccatag gaagtacaag   10020
tctgggagat actaggctgc actgtctgta gagaatctga aaaataata gagtcactga   10080 aatgcagttt ggtataatta ttgccatgca tcataattct aaatcatact agtggtcaaa   10140
tactcttccc tgaaaaaaca ttttcttggt ttgaattcta ataattgtt gtggtcacca   10200 ctgagctttt aaatatataa atactttcaa gtttgcatat ttttattacc tgttccttaa   10260
caaacattga attcaacatg aaaatgatta tgggaaacat tcgggtatac agtccctgac   10320
tcttaaggac tcaggtaaat acttagggta tttcatggcc ctagtctttg gggtaccaca   10380
tgtttcttct tcaaatcaca gattcaaaat caagaatgat aacacagtga ttgtgtagac   10440
aaaataagtg aaccaaaatt gcttgcttct gtcattctat ggaaccactg agagttttta   10500
cttgtgctta aaattttgaa tagtaaaaca gagtgtcaac ttcatgctgg aatattttg    10560 gcttttaga cacaatttta agtacatgaa gtatttttac aagactaagt aacatcactg    10620
aaattacagc tttcttcttt ttaaaactgg tatttgttat aaaactaaag agcgaatcaa   10680
gaaaagcata attattactg attattacag gattattact gaaaagaaa tgtacggaat    10740 agaggaggaa ggagttaaca aatgatccac tctgggtgtt gaaaacacca ataagcctgc   10800
ttccaggaag tgcctaagac agagctggct cagcttgctg ggtcacagca tgtaaggaaa   10860
ctgctgggct acatgccacc atcctcagtt gtccagatag ataatcccat agccccatgg   10920
ggaaataatc tttaattatg atatagctga caccattcaa agcactatgc taagtccttt   10980
atgtgaatta acttttgtca aatttatttt tcataaataa cccaaatatg tataccacta   11040
ttatcctacc ttaaagagga gaaactgagc tcctaaagtt taaatatcta acccaagtta   11100
agactgctag tcaccctagg ctattaactc aggcagtcta actcaggtat aataacatta   11160
tgctactgtt tgcagctttg actatgcctg aattataacg tcatgctatc taactaaaaa   11220
gctaagggaa ataaaatgag ccatagggct caatttcata aaaggagaga aaatactggg   11280
gaaaagtgat aatgcagagt ttaaatatt tttgtaaaag tgccagagat tgagtataac   11340
aagtgtgacc aaaaaaaaaa aaaaaaaaa aaaaggaaga aggtaaaaaa aagagggagg   11400
tctgagaaat agaatatca gaggaaggaa ataaggagg gtgagagtaa attctctttt     11460
agcattcaga ttccacagat tccacaaatc acatttcttt ttttaccaac taaggaaaaa    11520
```

```
taacacttga cctaacattt cattgcagtt agctaaagga tgctagaaaa actatgttgc   11580
agtggtttgc tctaatttct tcaggaatag agaaaagtga caaaaagatc agagaagaga   11640
agaaaggaaa ctatcagaaa aatacagaat tggagtagga tataacatat ttggggttgaa  11700 ggtaaaattt tatattgtaa tcttaagtat cttgctactt cagtttggtc cctggaacag   11760
cagcatcaga atctgccgag ggcttgttaa aaaggcagaa tctcaggtcc catcccagac   11820
tcactgaatc agaatataaa tactgacaag atgccccggg attcatatgc acagtagagc   11880
tggcgaagtt ccattgtagc ctgtgattgt tttctgcaac ttagtatttc tgagttttcc   11940
caaggaagaa aacccaggcc ttagcttctg gcagacttgt gtttctcctt tacttactag   12000
ctgcatgact catgagcaag gaaatcaaac tttatgtgcc tgagtttcct catctataaa   12060
atggagacta taataatcat ctcctaggct tgttttgagg atgttcaaca aatgctcctt   12120
tcattcctct atttacagac ctgccgcaga caattctgct agcagccttt gtgctattat   12180
ctgttttcta aacttagtaa ttgagtgtga tctggagact aactctgaaa taataagct    12240 gattatttat ttattttctc aaaacaacag aatacgattt agcaaattac ttcttaagat   12300
attattttac atttctatat tctcctaccc tgagttgatg tgtgagcaat atgtcacttt   12360
cataaagcca ggtatacatt atggacaggt aagtaaaaaa catattattt attctacgtt   12420
tttgtccaaa aattttaaat ttcaactgtt gcgcgtgtgt tggtaatgta aaacaaactc   12480
agtacagtag tattcagtac agtatttaag cccctgtact taaacatatt cctcgtacca   12540
atgaagttac atgaaaagca aatttgtgtg agatatcgta gatggaagta aattagtctt   12600
tatgttcccc acaaattgaa atgcatttca aaaactctgt gtgtgtatgt gtgtgtgtga   12660
cagagtgtgt gtgagagaga gacagagaga tacgctttgg ttgcctccat aagctggctg   12720
ctatgattaa taagaccaag ttttctaaag aaaatgagat cataacaaaa gccctcttta   12780
tgactatctt ttatcagggg caaaaaggaa agagacaaaa cagcatgaaa tgatgagacc   12840
aagtgatgaa aattcattca caatgattgc tttcaagagt aatttctctt gggtaattca   12900
gcagcctgtt actatggctc tctggagtga tagctaatgt aaatgaagcc tctaaaagtg   12960
gattatcctg acaagaatat actcagccaa taatgcaaca gaaatccatt caaagcattc   13020
gggaaaaatt caaagaata aatattcttt ttttttttt aaagttaatg acctacgatc     13080
catttcttcc ctgactaaca agcagcaagc acttaaaaat atccagccag gatgaaatag   13140
aaacccacct gacttgttaa tattttttgtt tggtcccagg gactcagatt ctaagccaaa   13200
ttctttgaat gatcttggca aatgtctcga attattttg ccaacttttc tttatcttgg    13260
aaaaaaagtt tcatgaatgg gtgtcaaaat tgattagttt taaaaacctt tcttgcagat   13320
acgtatggca ccctaaaact gtattagaaa aaaagtaagt actctgtagt gtgaaaaatt   13380
cttaaaggac accctctttt acaaactcac aaaaacagcc tttggaatac ccacatgaag   13440
tagctgttgt tattgctttc tatataccta catcttgtct attataaaaa gactggtttt   13500
tggcaggtgt ggtggctcac acctgtaatt ccagcacttt gggaggccaa ggcgggcgga   13560
tcacctgaga tcaggagttc aggaccagcc tgatcaatat ggtgaaaccc agtctttact   13620
gaaaatacaa aaatcacccg ggtgtggtga cgggcgcctg tagtcccagc tactcgggta   13680
gctgaggcag gagaatcact tgaactcagg agtcagaggt tgcagtgagc tgagatcatg   13740
ccactgcact ccagcctggg tgacagagca agactccatc tcaaaaaaaa aaaaaaaaaa   13800
gactggtttt tcaacagcta ttcccacccc tctgcatgga atattcacc cagtcaattg    13860 ttttcctagt ttgggtaatg gccctctggg caggactgga gtgggcaca caggagaagc    13920
```

```
tgcaaactat gtttagaagc atgtctggga aatgtcatgc aagaaaagac atatttaaag   13980
gtaggctttg catgaatgga aaaggagagt aattctatgt agagcagagc ctcttacttg   14040
cagtgagaga agcaaaagtg gggaagcaag aggaattatg cttttcatca gccaaatttg   14100
caggtaggag gattggctca gtcatcttgg ctgaggctca tgaaaccagg tgtaaagaaa   14160
gtggactaga ttaatttcat ccattacagg aagaggagcc gtgaaagata tccagaaat   14220 cattgggatt tgatggtaga aggtattttg ggactattcc atttgaaatg agaaggtacc   14280
tgacattctt tgaattcctt tcaagcaaag gattaaattt acccatgagt tgactcagaa   14340
aaaacataaa aagtattgtt gctctgctca gagttttatc taactcattc tcacttctta   14400
ttccatgatg aaatgacata aatgaggttt ttattgttg ttgttgttgt tttctggaca   14460
caaggcaagg tagctacctg gcagagctg ttttatttct ctatgccgtg gagagaaatt   14520
ggttaattgg ccatggaagg cagtcattaa gatgttccca tgcgagtgaa cttccaggg   14580 ttcccagctt ctgcatcctt ccctgtccct caattccatt gttggtgatg acaatgtctc   14640
tcccatcagc ctcatgaagt tctctctcat ttattaaaat ttgctttcag gaaaaatttt   14700
gaaaatgtgt ccagtaatgc ctgattggcc cctatccta aaggcttaaa ctggaggaag   14760
gaagctaaac tgagaaatct tgcaaatcat tgagccaaaa acgtattaat agcaagatct   14820
atcatttatt gactagtatg tggcaggcag tgccctttta tttaggcagg gagagttgat   14880 gggggggcg gggttcacac atcttaaaga ggtgctatct cctcctatat aaatcatgta   14940
agtcaagaga gtaaggaatt gtctttgttt ggttatattc aggggattag agtatacagt   15000
agaagatccc aagaaacctt gggatcattt tagactaaga aatgccaata ccgccgggcg   15060
cggtggctca cgcctgtaat cccagcactt tgagaggccg aggtgggcgg atcacaaggt   15120
caggagattg agaccgtcct ggctaacgtg gtgaaaccct gtctactaa aaaatacaaa   15180 aaattagccg ggcgtggtgg cgggcgcctg tagtcccagc tactcgggag gcggaggcag   15240
gagaatggtg tgaactcagg aggcggagct tgcagtcagc cgagattgcc ccaatgcact   15300
ccagcctggg cgacagaacg agactccgtc tcagaacaaa acaaaaggaa atgccaatac   15360
cagcagaaat agagccaaat catgaacata agctaaacaa atgttggcag tgtagcctag   15420
tggttaagag agcagactct taactagaac actgcactcc atgtcctcac tgtagaccct   15480
cactgtgggg ttctaattaa cccctgttac ttaccagtgg cagtcttaag gcattcctta   15540
agttcgttgt gccccaattt gttcatctgt agaagggta ggatgacagt agtgtttact   15600
ttataggctt actgtgagca ttaaatgagt tactactgta tttgtaaagt gcttaaaatg   15660
ctgctccaaa agagtttgtt aaacacttaa gaactgattt acttgcatct aaactgacag   15720
ctctcaataa ctggaaatga tcaagcatag gccctggaat ataagcaggt ctacatgaag   15780
gcaaaaatgt tcgtttcttt tgttcagccc tgtgcctaga tcaatatcta gtgatcatgc   15840
tcaagaaata ttgttgaatg aatcaatgaa cctaccgagg tagttacata aaagagttct   15900
gcatgagtac aaatctgggc aaagtgacct ccaaggaaat ttccactttt agattctgtg   15960
atttccttaa ggaactgata aattggtgtg atacaatgta aaaaatgtg cctatatgat   16020 ttgagaaaaa cttatttct ctccctcttt tttccttcct tcttcctcc ctcccttcct   16080 tccttcctcc ctcccttcct tcctcccctcc ctcccttcct tccttctctt tcttcttttc   16140 tttcttctt tctttctttc tttctttctt tctttctttc tttctttctt ctcttctctt   16200
tcctttcttt cttcctttct tgtgcctttt ctttctttct ttctttcttc tctgtccttt   16260
ctttcttcct ttctttcttt ctgcctttct ttctctttgt tttctttct ttccttcttt   16320
```

```
tttcctttaa gcagaccatg tctgttagat gaatgccttt ttctagttaa aaggttaaac   16380
aggaaagtga agcacaatta tcaagggtct ccagtcatct ccacatgttc ttaatcatta   16440 tcttcttta cagtttcata tctccaggcc tttcattggg tcaggttggc atttcgctgc   16500
cctttatgtg tgtgacaagt gaaaataagg aaagaaaaaa actcaagtga agaaaatcag   16560
aatctgcgca gcagttcctg ggcgtttcag ctgcttccca catcacctgc ctcatcaagc   16620
cccagcatcc atctccttgc tcatcttaca ccctgtgtgc atgacaggcc caccattcat   16680
ttatcagagc aaaggctctc ccactattct ggttcacccc cctacttagc cagatataca   16740
agaatatctg cacggatgac ctgcctcacc tgggagctca gaggagctca gattccatta   16800
ctatcgcacc aaggacagat ctcccagcaa gaatgacaga aaagactaac tgcccccaaa   16860
atctcccttc caaacacag ttctcttaat tctcccaaga aaccagaatg tgactgctca   16920
cctctctaag gacctgaaaa caactggcca tttcagctat ttaaatcaac tttaaaaaat   16980
ccaaccgcca aaatattaaa ccattttggt tggaatgata acataactaa cctgctgaca   17040
gctgcttctg ctaggtgcaa aaatggaaaa aaaaatactt ctaatcaggt caaatcactc   17100
tacctttggg attctaaatt tactcatatt ctcaaagaaa tatattcagt catagtgggg   17160
aaaataggat tattcctta gctcgataag caaccagaag ttcttccttc aaatcttgac   17220
atttaatcaa tcagaaattg attttggaa aactgtttcc tatgaagcta tctctgcctg   17280
aaggattttt cttttacaat ccagactata gaaggaaatt cacaacctgg actttcacct   17340
ccattggtca gagttttact gaccaattcc cacctctgcc ttacacctaa cggaagttta   17400
tgcctgtttt ctcttcacat accccaacag ttacaaatgg ttgttattat taagcatctt   17460
ttattttgtg gcctctgatt acatggtccc ctaaattttg acctaatcac aaaagattgg   17520
taaaatttct taacatatta ataatatttt gtttatgtgt caatatctta gcatgtatca   17580
attaagacag aggtcttaac gttctctttt tgaaagagaa tattaggatt cagagatatt   17640
aagagattct cccaggatca cagttaggta acagagctgg attttagtcc aggtctgtct   17700
acagctctaa cgtatataca ccctttgtat aacatgtcac gaattcagca taaagggatc   17760
ttcagtgatc taagtcaggg gtcagcaacc ttttctaaaa aggaccaaat agtaatattt   17820
caggctttgt ggaccctatg gtctctatca taactgttca aatcaccatg tagtgtaaaa   17880
ggagccataa gcaaaatata aactaacgaa tgtggctgtt ttatgggatt tttttttaac   17940
tctttattta caaaagcagg tggcagatca gaactcactt atgggccata gttctctgac   18000
ccctgacctg agaaaatctt atatttatgg acaacattta gactgtgact tgccaagtaa   18060
gaacaagaag ctctgtcaac tgaaggtcaa ggctggagtt ctgaaagcaa agagctgtct   18120
ggtgttaatg ataagtgaaa tagttaaagt tagaagatcc cagttataag aagcacaaag   18180
aataatgacc atagactcct gaacaagaat gtctggactt ctggcttagg cactcttgtt   18240
gtatggtcca ggccaagtta cctaatctct ccaggcctcc attttcttat cattaaatga   18300
agataataaa agtattttcc tcagagagct gtaagaataa actgagctaa cccatgtcaa   18360
gcacatagaa tagggcccag cctatattaa tttatcaata aatgccagct acatattagt   18420
tctctatatt tttattcatt atcataaaat gtttatctac agattggcat tgtaaggatg   18480
gagttaaaat tgtatgtatg tgaagggaaa ttattcctgt tactattgat ctgcatcaca   18540
ttaccccaaa tttgatggct taaagtaaca acattcattt tgcaaacaaa tttgaaattt   18600
gaggagggct tgtctgggaa gacttgtctc tgccctatgt ggtatcagca gggggaggct   18660
tgacggactg gcacatgccc ttccagaatg gcccactcgc atgcctgcca agttggtgct   18720
```

-continued

```
ggctcttggc tgggagctca gctggggctg agtgctaggg tccctgggag gttccttgtg    18780
gcctgaactt cctcaccaca aggcggctgc ggtgcgagag tgagcatttc aagatagagc    18840
caagatgaca ctgtattact gtgtaagacc cagcctggga attaatgtag cctcacttcc    18900
atcccactct atttttaaaa agtgaattat taaggtcacc ccatattcaa ggggatagga    18960
attagacttc atctgtatta agaaaaatgt ttttaaaaat tgtagacatg ttttaaaatt    19020
ctaaagtcca cttactggct gcagattatt tatatataca tgcaagatac actcctacat    19080
tctcttctta gaaggctcag ttgcaggtac agatgaagct cttcaagtga gatttcttat    19140
gtatttatcc tctcaatctg aagacttgta aactaagaga caagttattt gcaacctaca    19200
tacgcaatat tcaatggtaa agtatacata ggacagccac tacagacact cttgttttaa    19260
atagaggaaa atgagagcac ataacagtca ttggctcata gcaactctga tatccagaca    19320
gcaaacacaa gcaggtcttt ttttaggtct cagtcctact gcctggattc cctactgctc    19380
ttgggtcttc cctccaggtt cttggttctt ggacctcttt tcatttaata ctatttctgt    19440
tcctttaagt tcaagctggc aaaatatgat tgtacaattc tgtttaaaat tccaggactt    19500
cctgtgattc ttattgggga atactccatt agacaagaat ctctttgaca taagccattc    19560
tctacctgag atccctgtaa ggctgtgatg ggaccacata accttaaaat tattagaaga    19620
ctcattgttt actgagagaa tatgcctagc atatgcttag atcctagag gaactctgtt     19680
tcaaagggct tatgagacat taccttatat ctttctaagg tacaaacaaa aggtctttgg    19740
cttttgagtt tgatctttga gctgacacct tttcttaatt tgagaatccc ctgctctatg    19800
gagagactga caaagagaaa tagttttata tttgaatgta acatcttgga tctttaatag    19860
attatcttaa aattttcctg aaaatgtaac agttcctttt tttaaaattc attctcccta    19920
cacacttatt atatatgact aaaagaaact ccctggcatt tcaacattc tggttagaat      19980
ttttcttagc ccaatctac                                                  19999
```

```
<210> SEQ ID NO 2
<211> LENGTH: 3893
<212> TYPE: RNA
<213> ORGANISM: Homo sapiens
<220> FEATURE:
<221> NAME/KEY: mRNA
<222> LOCATION: (1)...(3893)
<223> OTHER INFORMATION: short version of  mRNA

<400> SEQUENCE: 2
```

```
aucagaggaa ggaauaaag gagggugaga guaaauucuc uuuuagcauu cagauccac      60
agauccaca aaucacauuu cuuuuuuac caacuaagga aaaauaacac uugaccuaac    120
auuucauugc aguuagcuaa aggaugcuag aaaaacuaug uugcaguggu uugcucuaau    180
uucuucagga auagagaaaa gugacaaaaa gaucagagaa gagaagaaag gaaacuauca    240
gaaaauaca gaauuggagu aggauauaac auauuugggu ugaagguaaa auuuauauu     300
guaaucuuaa guaucuugcu acuucaguuu ggucccugga acagcagcau cagaaucugc    360
cgagggcuug uuaaaaaggc agaaucucag gucccauccc agacucacug aaucagaaua    420
uaaauacuga caagaugccc cgggauucau augcacagua gagcuggcga aguuccauug    480
uagccuguga uuguuuucug caacuuagua uuucugaguu uucccaagga agaaaaccca    540
ggccuuagcu ucuggcagac uuguguuucu ccuuuacuua cuagcugcau gacucaugag    600
caaggaaauc aaacuuuaug ugccugaguu uccucaucua uaaaauggag acuauaauaa    660
ucaucuccua ggcuuguuuu gaggauguuc aacaaaugcu ccuuucauuc cucuauuuac    720
```

| | |
|---|---|
| agaccugccg cagacaauuc ugcuagcagc cuuugugcua uuaucuguuu ucuaaacuua | 780 |
| guaauugagu gugaucugga gacuaacucu gaaauaaaua agcugauuau uuauuuauuu | 840 |
| ucucaaaaca acagaauacg auuuagcaaa uuacuucuua agauauuauu uuacauuucu | 900 |
| auauucuccu acccugaguu gaugugugag caauaugauca cuuucauaaa gccagguaua | 960 |
| cauuauggac agguaaguaa aaaacauauu auuuauucua cguuuuuguc caaaauuuuu | 1020 |
| aaauuucaac uguugcgcgu gugugguaa uguaaaacaa acucaguaca guauauuca | 1080 |
| guacaguauu uaagccccug uacuuaaaca uauuccucgu accaaugaag uuacaugaaa | 1140 |
| agcaaauuug gugagauau cguagaugga aguaaauuag ucuuuauguu ccccacaaau | 1200 |
| ugaaaugcau uucaaaaacu cugugugugu augugugugu gugacagagu gugugugaga | 1260 |
| gagagacaga gagauacgcu uugguugccu ccauaagcug gcugcuauga uuaauaagac | 1320 |
| caaguuuucu aaagaaaaug agaucauaac aaaagcccuc uuuaugacua ucuuuauca | 1380 |
| ggggcaaaaa ggaaagagac aaaacagcau gaaaugauga gaccaaguga ugaaaauuca | 1440 |
| uucacaauga uugcuuucaa gaguaauuuc ucuugggaaa uucagcagcc uguuacuaug | 1500 |
| gcucucugga gugauagcua auguaaauga agccucuaaa aguggauuau ccugacaaga | 1560 |
| auauacucag ccaauaaugc aacagaaauc cauucaaagc auucgggaaa aauucaaaag | 1620 |
| aauaaauauu cuuuuuuuu uuuuaaaguu aaugaccuac gauccauuuc ucccugacu | 1680 |
| aacaagcagc aagcacuuaa aaauauccag ccaggaugaa auagaaaccc accugacuug | 1740 |
| uuaauauuuu uguuuggucc cagggacuca gauucaagc caaauucuuu gaaugaucuu | 1800 |
| ggcaaaugc ucgaauuauu uuugccaacu uuucuuuauc ugaaaaaa aguucauga | 1860 |
| augguguca aaauugauua guuuuaaaaa ccuuucuugc agauacguau ggcaccucuaa | 1920 |
| aacuguauua gaaaaaaauu ucauaucccc aggccuuuca uugggucagg uuggcauuuc | 1980 |
| gcugcccuuu augugugugu caagugaaaa uaaggaaaga aaaaacuca agugaagaaa | 2040 |
| aucagaaucu gcgcagcagu uccugggcgu ucagcugcu ucccacauca ccugccucau | 2100 |
| caagccccag cauccaucuc cuugcucauc uuacacccug ugcaugac aggcccacca | 2160 |
| uucauuuauc agagcaaagg cucucccacu auucugguuc accccccuac uuagccagau | 2220 |
| auacaagaau aucugcacgg augaccugcc ucaccuggga gcucagagga gcucagauuc | 2280 |
| cauuacuauc gcaccaagga cagaucuccc agcaagaaug acagaaaaga cuaacugccc | 2340 |
| ccaaaaucuc ccuuccaaaa cacaguucuc uuaauucucc caagaaacca gaaugugacu | 2400 |
| gcucaccucu cuaaggaccu gaaaacaacu ggccauuuca gcuauuuaaa ucaacuuuaa | 2460 |
| aaaauccaac cgccaaaaua uuaaaccauu uggguuggaa ugauaacaua acuaaccugc | 2520 |
| ugacagcugc uucugcuagg ugcaaaaaug gaaaaaaaaa uacuucuaau caggucaaau | 2580 |
| cacucuaccu uugggauucu aaauuuacuc auauucuacaa agaaauauau ucagucauag | 2640 |
| uggggaaaau aggauuauuc cuuuagcucg auaagcaacc agaaguucuu ccuucaaauc | 2700 |
| uugacauuua aucaaucaga aauugauuuu uggaaaacug uuccuauga agcuaucucu | 2760 |
| gccugaagga uuuucuuuu acaauccaga cuauagaagg aaauucacaa ccuggacuuu | 2820 |
| caccuccauu ggucagaguu uuacugacca auucccaccu cugccuuaca ccuaacggaa | 2880 |
| guuuaugccu guuuucucuu cacauaccc aacaguuaca aauggugugu auuauuaagc | 2940 |
| aucuuuauu uuguggccuc ugauuacaug gucccuaaaa uuuugaccua aucacaaaag | 3000 |
| auuggaaaaa uuucuaaaca uauuaauau auuuuguuua ugucaauua ucuuagcaug | 3060 |
| uaucaauuaa gacagagguc uuaacguucu cuuuuugaaa gagaauauua ggauucagag | 3120 |

-continued

| | | | | | |
|---|---|---|---|---|---|
| auauuaagag | auucucccag | gaucacaguu | agguaacaga | gcuggauuuu | aguccagguc | 3180 |
| ugucuacagc | ucuaacguau | auacacccuu | uguauaacau | gucacgaauu | cagcauaaag | 3240 |
| ggaucuucag | ugaucuaagu | caggggucag | caaccuuuuc | uaaaaaggac | caaauaguaa | 3300 |
| uauuucaggc | uuuguggacc | cuauggucuc | uaucauaacu | guucaaauca | ccauguagug | 3360 |
| uaaaaggagc | cauaagcaaa | auauaaacua | acgaaugugg | cuguuuuaug | ggauuuuuuu | 3420 |
| uuaacucuuu | auuucaaaaa | gcagguggca | gaucagaacu | cacuuauggg | ccauaguucu | 3480 |
| cugaccccug | accgagaaaa | aucuuauauu | uauggacaac | auuuagacug | ugacuugcca | 3540 |
| aguaagaaca | agaagcucug | ucaacugaag | gucaaggcug | gaguucugaa | agcaaagagc | 3600 |
| ugucuggugu | uaaugauaag | ugaaauaguu | aaaguuagaa | gaucccaguu | auaagaagca | 3660 |
| caaagaauaa | ugaccauaga | cuccugaaca | agaaugucug | gacuucuggc | uuaggcacuc | 3720 |
| uuguuguaug | guccaggcca | aguuaccuaa | ucucuccagg | ccuccauuuu | cuuaucauua | 3780 |
| aaugaagaua | auaaaaguau | uuccucagg | gagcuguaag | aauaaacuga | gcuaacccau | 3840 |
| gucaagcaca | uagaauaggg | cccagccuau | auuaauuuau | caauaaaugc | cag | 3893 |

<210> SEQ ID NO 3
<211> LENGTH: 121
<212> TYPE: PRT
<213> ORGANISM: Homo sapiens
<220> FEATURE:
<221> NAME/KEY: PEPTIDE
<222> LOCATION: (1)...(121)

<400> SEQUENCE: 3

Met Phe Asn Lys Cys Ser Phe His Ser Ser Ile Tyr Arg Pro Ala Ala
1               5                   10                  15

Asp Asn Ser Ala Ser Ser Leu Cys Ala Ile Ile Cys Phe Leu Asn Leu
            20                  25                  30

Val Ile Glu Cys Asp Leu Glu Thr Asn Ser Glu Ile Asn Lys Leu Ile
        35                  40                  45

Ile Tyr Leu Phe Ser Gln Asn Asn Arg Ile Arg Phe Ser Lys Leu Leu
    50                  55                  60

Leu Lys Ile Leu Phe Tyr Ile Ser Ile Phe Ser Tyr Pro Glu Leu Met
65                  70                  75                  80

Cys Glu Gln Tyr Val Thr Phe Ile Lys Pro Gly Ile His Tyr Gly Gln
                85                  90                  95

Val Ser Lys Lys His Ile Ile Tyr Ser Thr Phe Leu Ser Lys Asn Phe
            100                 105                 110

Lys Phe Gln Leu Leu Arg Val Cys Trp
        115                 120

<210> SEQ ID NO 4
<211> LENGTH: 6209
<212> TYPE: RNA
<213> ORGANISM: Homo sapiens
<220> FEATURE:
<221> NAME/KEY: mRNA
<222> LOCATION: (1)...(6209)
<223> OTHER INFORMATION: long version of mRNA

<400> SEQUENCE: 4

| | | | | | |
|---|---|---|---|---|---|
| ggaugugagu | gggccuucag | acuuaaacca | ggaguuacac | cuuuggcuuc | ccugguucuc | 60 |
| aguucuuugg | acuggacug | aauuacacug | ccagguuucc | ugguucucca | gcuugcagau | 120 |
| ggcagaucau | gggacuucuu | ggccuccaua | auugugugag | ucaauuucca | uuuuauuuac | 180 |
| auauccaguu | augcauugcu | uaacaaugga | gacagguucu | gagaaaugca | uuguuaagug | 240 |

-continued

| | |
|---|---|
| auuucaucau ugugcaaaca ucauagagug uaacuacaca aaccuggaca gcauagacua | 300 |
| cuacacaucu aggcuacaug guguagcuug uaaccucaug auaaguaugu auaacaucau | 360 |
| gauaaguaug uauguaucua ccauaucuaa auguagaaaa gguacaguaa aaauauggua | 420 |
| uaaucuuaug ggaucaccau cauauaugca auccuuugua gacugaaaug ucauugugua | 480 |
| gugcaugacu guauacgcac acauacacaa acacacacaa auauacuauu gguucuuuuu | 540 |
| cucugaagag cccaaauaca auauguuaua cauuuauauu gacucuauuu caaaauuuau | 600 |
| gguuuugguu aaacauaugu ggagaugggg cauaggugug ugaacuggga uaguguccug | 660 |
| cugaugaaug gguggggaggc aucauuuggg acaagcccag ggcaucagcu auagauauc | 720 |
| aagagcucaa caagagcacu uuauggcaaa accucccaca agaccucuca gaaguugaga | 780 |
| aacugcuaaa aguucuuuua ugacagauga cauuuaugga uaaaauaggg auuagcagga | 840 |
| uucuuuaaau acuuucgaac acuaaccuuc auuucuacca ggcaguggggg ccccaagugc | 900 |
| agggccauag gaaguacaag ucuggagau acuaggcugc acugucugua gagaaucuga | 960 |
| aaaaauaaua gagucacuga aaugcaguuu gguauaauua uugccaugca ucauaauucu | 1020 |
| aaaucauacu aguggucaaa uacucuuccc ugaaaaaaca uuuucuuggu uugaauucua | 1080 |
| aauaauuguu guggucacca cugagcuuuu aaauauauaa auacuuucaa guuugcauau | 1140 |
| uuuuauuacc uguccuuaa caaacauuga auucaacaug aaaaugauua ugggaaacau | 1200 |
| ucggguauac aguccccugac ucuuaaggac ucagguaaau acuagggua uuucauggcc | 1260 |
| cuagucuuug ggguaccaca uguuucuucu ucaaaucaca gauucaaaau caagaaugau | 1320 |
| aacacaguga uuguguagac aaaauaagug aaccaaaauu gcuugcuucu gucauucuau | 1380 |
| ggaaccacug agaguuuuua cuugugcuua aaauuuugaa uaguaaaaca gagugucaac | 1440 |
| uucaugcugg aauauuuuug gcuuuuaga cacaauuuua aguacaugaa guauuuuuac | 1500 |
| aagacuaagu aacaucacug aaauuacagc uuucuucuuu uuaaaacugg uauuuguuau | 1560 |
| aaaacuaaag agcgaaucaa gaaaagcaua auuauacug auuauuacag gauuauuacu | 1620 |
| gaaaagaaa uguacggaau agaggaggaa ggaguuaaca aaugauccac ucugggguguu | 1680 |
| gaaaacacca auaagccugc uuccaggaag ugccuaagac agagcuggcu cagcuugcug | 1740 |
| ggucacagca uguaaggaaa cugcugggcu acaugccacc auccccaguu guccagauag | 1800 |
| auaaucccau agccccaugg ggaaauaauc uuuaauuaug auauagcuga caccauucaa | 1860 |
| agcacuaugc uaagucccuuu augugaauua acuuuugca aauuuauuuu ucauaaauaa | 1920 |
| cccaaauaug uauaccacua uuaccuacc uuaaagagga gaaacugagc uccuaaaguu | 1980 |
| uaaauaucua acccaaguua agacugcuag ucaccuuagg cuauuaacuc aggcagucua | 2040 |
| acucagguau aauaacauua ugcuacuguu ugcagcuuug acuaugccug aauuauaacg | 2100 |
| ucaugcuauc uaacuaaaaa gcuaagggaa auaaaaugag ccauagggcu caauuucaua | 2160 |
| aaaggagaga aaauacuggg gaaagugau aaugcagagu uuaaauauu uuuguaaaag | 2220 |
| ugccagagau ugaguauaac aagugugacc aaaaaaaaaa aaaaaaaaaa aaaggaaga | 2280 |
| agguaaaaaa aagagggagg ucugaaaau agaaauauca gaggaaggaa auaaggagg | 2340 |
| gugagaguaa auucucuuuu agcauucaga uccacagau uccacaaauc acauuucuuu | 2400 |
| uuuuaccaac uaaggaaaaa uaacacuuga ccuaacauuu cauugcaguu agcuaaagga | 2460 |
| ugcuagaaaa acuauguugc aguggguuugc ucuaauuucu ucaggauag agaaagugaa | 2520 |
| caaaagauc agagaagaga agaaggaa cuacagaaaa auacagaau uggaguagga | 2580 |
| uauaacauau uugggguugaa ggugaaaauuu uauauuguaa ucuuaaguau cuugcuacuu | 2640 |

```
caguuugguc ccuggaacag cagcaucaga aucugccgag ggcuuguuaa aaaggcagaa    2700
ucucaggucc caucccagac ucacugaauc agaauauaaa uacugacaag augcccgggg    2760
auucauaugc acaguagagc uggcgaaguu ccauuguagc cugugauugu uuucugcaac    2820
uuaguauuuc ugaguuuucc caaggaagaa acccaggcc uuagcuucug gcagacuugu     2880
guuucuccuu uacuuacuag cugcaugacu caugagcaag gaaaucaaac uuuaugugcc    2940
ugaguuuccu caucuauaaa auggagacua uaauaaucau cuccuaggcu uguuugagg     3000 auguucaaca aaugcuccuu ucauuccucu auuuacagac cugccgcaga caauucugcu    3060
agcagccuuu gugcuauuau cuguuuucua aacuaguaa uugaguguga ucuggagacu     3120
aacucugaaa uaaauaagcu gauuauuuau uuauuuucuc aaacaacag aauacgauuu     3180 agcaaauuac uucuuaagau auuauuuuac auuucuauau ucuccuaccc ugaguugaug    3240
ugugagcaau augucacuuu cauaaagcca gguauacauu auggacaggu aaguaaaaaa    3300
cauuauauuu auucuacguu uuuguccaaa aauuuuaaau ucaacuguu gcgcgugugu     3360 ugguaaugua aaacaaacuc agacaguag uauucaguac aguauuuaag ccccuguacu     3420
uaaacauauu cccgguacca augaaguac augaaaagca auuugugug agauaucgua      3480 gauggaagua aauuagucuu uauguucccc acaaauugaa augcauuuca aaaacucugu    3540 gguguaugu guguguguga cagagugugu gugagagaga gacagagaga uacgcuuugg     3600
uugccuccau aagcuggcug cuaugauuaa uaagaccaag uuuucuaaag aaaaugagau    3660
cauaacaaaa gcccucuuua ugacuaucuu uuaucagggg caaaaaggaa agagacaaaa    3720
cagcaugaaa ugaugagacc aagugaugaa aauucauuca caaugauugc uuucaagagu    3780
aauuucucuu gggaauuca gcagccuguu acuauggcuc ucggagauga uagcuaaugu     3840
aaaugaagcc ucuaaaagug gauuauccug acaagaauau acucagccaa uaaugcaaca    3900
gaaauccauu caaagcauuc gggaaaaauu caaagaauaa aauauucuuu uuuuuuuuu    3960 aaaguuaaug accuacgauc cauuucuucc cugacuaaca agcagcaagc acuuaaaaau    4020
auccagccag gaugaaauag aaacccaccu gacuuguuaa uauuuuguu uggcccagg      4080 gacucagauu cuaagccaaa uucuuugaau gaucuuggca aaugucucga auuauuuuug    4140
ccaacuuuuc uuuaucuugg aaaaaaaguu ucaugaaugg gugucaaaau ugauuaguuu    4200
uaaaaaccuu ucuugcagau acguauggca cccuaaaacu guauuagaaa aaaauuucau   4260
aucuccaggc cuuucauugg gucagguugg cauuucgcug cccuuuaugu gugugacaag    4320
ugaaaauaag gaaagaaaaa aacucaagug aagaaaauca gaaucugcgc agcaguuccu   4380
gggcguuuca gcugcuuccc acaucaccug cccaucaag ccccagcauc caucuccuug     4440
cucaucuuac acccugugug caugacaggc ccaccauuca uuuaucagag caaaggcucu   4500
cccacuauuc ugguucaccc cccuacuuag ccagauauac aagaauaucu gcacggauga   4560
ccugccucac cugggagcuc agaggagcuc agauccauu acuaucgcac caaggacaga    4620
ucucccagca agaaugacag aaaagacuaa cugcccccaa aaucccccuu ccaaaacaca   4680
guucucuuaa uucccccaag aaaccagaau gugacugcuc accucucuaa ggaccugaaa   4740
acaacuggcc auuucagcua uuuaaaauca cuuuaaaaa uccaaccgcc aaaauauuaa     4800
accauuuugg uuggaaugau aacauaacua accugcugac agcugcuucu gcuaggugca   4860
aaaauggaaa aaaaaauacu ucuaaucagg ucaaucacu cuaccuuugg gauucuaaau     4920
uuacucuauu ucucaaagaa auauauucag ucauagugg gaaauaagga uuauccuuu     4980 agcucgauaa gcaaccagaa guucuuccuu caaaucuuga cauuuaauca aucagaaauu   5040
```

-continued

| | |
|---|---|
| gauuuuugga aaacuguuuc cuaugaagcu aucucugccu gaaggauuuu ucuuuuacaa | 5100 |
| uccagacuau agaaggaaau ucacaaccug gacuuucacc uccauugguc agaguuuuac | 5160 |
| ugaccaauuc ccaccucugc cuuacaccua acggaaguuu augccuguuu ucucuucaca | 5220 |
| uaccccaaca guuacaaaug guuguuauua uuaagcaucu uuuauuuugu ggccucugau | 5280 |
| uacauggucc ccuaaauuuu gaccuaauca caaaagauug guaaaauuuc uuaacauauu | 5340 |
| aauaauauuu uguuuaugug ucaauaucuu agcauguauc aauuaagaca gaggucuuaa | 5400 |
| cguucucuuu uugaaagaga auauuaggau ucagagauau uaagagauuc ucccaggauc | 5460 |
| acaguuaggu aacagagcug gauuuuaguc caggucuguc uacagcucua acguauauac | 5520 |
| acccuuugua uaacauguca cgaauucagc auaaagggau cuucagugau cuaagucagg | 5580 |
| ggucagcaac cuuuucuaaa aaggaccaaa uaguaauauu ucaggcuuug uggacccuau | 5640 |
| ggucucuauc auaacuguuc aaaucaccau guaguguaaa aggagccaua agcaaaauau | 5700 |
| aaacuaacga augugggcugu uuaugggau uuuuuuuuaa cucuuuauuu acaaaagcag | 5760 |
| guggcagauc agaacucacu uaugggccau aguucucuga ccccugaccu gagaaaaucu | 5820 |
| uauauuuaug gacaacauuu agacugugac uugccaagua agaacaagaa gcucugucaa | 5880 |
| cugaagguca aggcuggagu ucugaaagca aagagcuguc uggguguuaau gauaagugaa | 5940 |
| auaguuaaag uuagaagauc ccaguuauaa gaagcacaaa gaauaaugac cauagacucc | 6000 |
| ugaacaagaa ugucuggacu ucuggcuuag gcacucuugu uguauggucc aggccaaguu | 6060 |
| accuaaucuc uccaggccuc cauuuucuua ucauuaaaug aagauaauaa aaguauuuuc | 6120 |
| cucagagagc uguaagaaua aacugagcua acccauguca agcacauaga auagggccca | 6180 |
| gccuauauua auuuaucaau aaaugccag | 6209 |

<210> SEQ ID NO 5
<211> LENGTH: 80000
<212> TYPE: DNA
<213> ORGANISM: Homo sapiens
<220> FEATURE:
<221> NAME/KEY: gene
<222> LOCATION: (1)...(80000)
<223> OTHER INFORMATION: human genome sequence

<400> SEQUENCE: 5

| | |
|---|---|
| cacacgtagg ctacgagtgg ccctcagcct gcctcatcat ggacctgtgt tataataaat | 60 |
| atgtttaatt gtgctgtttt cttatagagg aaagtcctga tgttagttgc cttgaagtca | 120 |
| gacacccaga gagaatcaca ggttttcaga ttaattcatc gcttgattct tatccctgaa | 180 |
| gtcatatctc tggatctctg gttctcacat tataaatttc aatgattctt tttctatatg | 240 |
| gccatgtcat tcatatcctg tgtaatatgg ggaaactgag gtatgaatga catcattcaa | 300 |
| aaagcacctg caattttcct ttgccaagca cttacagctt tttctcatgt tgctttcaaa | 360 |
| aagtcattga atattgttc acatattttg cagatgagga aatgaatatt caaatgcatt | 420 |
| aggtatcttg tccaagttct tacagccaga aagtagagaa atgaatttga attacaaatc | 480 |
| ttctacctct tggcttatgc tcttttcatg acactgggaa taaatgtctg aacaagcatg | 540 |
| acttcatgtt tcaactattt atcaaatact tgttttctac taagatcttg cactcactca | 600 |
| gtgggatccc ctgaagcctg ctgattattt gtcctttggc atttatcact ctctgtggga | 660 |
| ccttactctc ctatggtaaa gttttattgt tattaaaagt attatttgac aataaatgta | 720 |
| gaaatcctac agatcatact caacaacatg tctaatgtca gcacacaatg tctaacaatc | 780 |
| atttatgaat actttatgtc aaacataagc aataacctaa ttaaggaagg tatttttaat | 840 |

```
aaattgacac ttttttgacat aaccatattt caagtggctc cattgttttg tttatttatt    900
tatttattta tttatttatt tatttttgag aaagggtctc actctgttgc ccagactgga    960
gtgcagtggc aacatcatag ctcactacag cctcgacctc tctgggctca agcaatcctc   1020
ccatctcagc ttcccaagta gctgggacta caggtgtgta ccatcatgcc aggctaattt   1080
ttcgtatttt gtagagacgg ggttttgcct ggtcgtccgg gttggtctca aactcctggg   1140
tgttccgccc accttggcct cccaaagtgc tgggattata ggcatgagcc tcaagtggct   1200
acttttttagg gttgaaattt atattgactg tcaactagct tccctagtta gtatttggga   1260
tctgctaact aatttatatt accatccaac ttgtcaacat ttgttgaaat ataactgtcc   1320
tcactttttt tgtgtgaaca ttgaatacac tttcagacta aatttggttt attacttaat   1380
gtcttattct ttattagagt taataatatt tcttaatact ttgccttcca caaatgaata   1440
acttgtttgt gatggctacc tcttttttttc tcttagcctg tcacaggtat tatggataaa   1500
aattagcacg gctgggcaaa acaatgaaa gaaatacact tgcctgggaa agctggggag   1560
gggtaaatga atataattca aaataccata tatttattca acactgttgg aatatatgtc   1620
ctgttggaaa tgtaaaagtg acatatgttc tcttcctggg tctcagactt ttaggatcta   1680
gttgagggaa ctggacttat acacaaaata caattcaaca acattatgag ctagaaaatc   1740
catgagctaa agtcttttggc aaagacatta ggtaacatga ggagtcagga aaggagaaa   1800
ttactgtggg ctggaatggt ctgggaacat gagatggagg aagtggcttg ttactggaga   1860
aaggatgagg ttcaaagaga tgggaaaaaa agaaagagag aagaaagaaa agaaatgagg   1920
aaaaacaagt tgccagaaag aacaaggaag aatagaggca ggtaagcagt ggattttgcc   1980
ctagggaagg taatataact agagacggca gtttctaaca ggccatgatg aataagatac   2040
actttagccc tcattggtac gtgcagaaat tcaaatttgg aaattcaagc ttacatgaca   2100
gtaaatatat gttgggaaaa aaataaccgg taaacattta catcagctct ttttcctaaa   2160
gagaaaccta ttccatgcta tgaaatattt gtcacaattc tgttttcaaa atacttgctc   2220
tacttttcca agccacaaga ggaaacattt tctctgccaa cactctctga ccttaaccag   2280
tttctccact acgtctactc ttaagctctc tttagagctg tgtgtatctc gtctttatgt   2340
aaacctccta gatgatatac ttatggaaat attcaggcaa cttttttcatg aactttacca   2400
ggaaagacat ttctagcagg agagcatgaa tagaaatgga ctcttcccca gtctctgctg   2460
ggttctgact gtggtcactc taactataaa aagtgtgtaa aaatcatgag cagattattt   2520
catttccttg gggtccctaa aaatttcaag gtatctgtat tagcacagga agatttaaat   2580
tgatttctca acacattcag atatcttatg aactttatta agataaattt cctccagcat   2640
tcagaaactc atatattaca gaataaaaaa taaagcagaa aattagtgta cctggctaaa   2700
aatgagagca gggttctatt tcattttgga aagtcactaa gacagtaata ataccattaa   2760
tgataaaatg ttaacattag ttaattatta gatgtgtttt tgtatgccag ccacataata   2820
tatactttta tatgtatcac ctacatttct agatgtaaat gtgagggaat tatagtagta   2880
tctacctcgt atgattgctg gatgatttaa atgagctgtt gtctcaaaaa cttggtatag   2940
aaagcagaaa cttttagtta ttaagattct tactattcca atatttgaat aaaacagtga   3000
cctgctaaga aaccccaata atattctgat acatcaaaac cttctggcat tagatgtttc   3060
taatctaaca tcttcatatt aattttttta tgttttgatt atctacattc agtagtgaat   3120
gtgtttctaa acgctggatg catttttaac taaatgtgtt ttgtaccaca ttttgacaac   3180
ttttgtttta actatgattc agcttataac aaaacaaaac aatgcatctt ctctccactg   3240
```

```
ttaataaggt taatgaaaag ttgacttatg aaaaaaatcc taatttatgc acattctcat   3300
tgttttcctt gctaaggata ttagtacttg acgattctgt aacaaagaat tatcatggga   3360
tgaaactttg atgcaaatat cttatcaata caatgtgctt gattttacct agatgagatt   3420
tttcttttct tctttctttt ttgagacagg gttttgctgt gttacccagg ctagcctcaa   3480
acccctggcc cctggcctca agtgatcctc tcacctctgc ctcccaaagt gctgggtatt   3540
acagatgtga gtcactgaat ccagcctcac ttagttggct ttcttagtga attattttat   3600
ctggttctaa aacttttga taatactctc aaatatttat ggattttata acataattta   3660
tggattacgt agttatgaat ttcataaatg attttgtgat attgccacag atcatcacca   3720
ttatacagga tgtataacat aaccatggtt aatatatttt tcataaacta tagaccaaac   3780
aaagactggt caggaccagg gcacgcatgc attttatatg tgtggtgcct attggaatat   3840
gccaggcctc ctgtgaaaaa aatcagtaag tgcttatctc ataggaccaa cggcccaaca   3900
ttcctgaagt cactaccaca cttttgcactt atctccatgt ggaaatagat agccactgtt   3960
gaattctggt gagaacgaca cgtctgaaat ctctcagctt cacaaacccct attacagccc   4020
tcagagaatc ttctcacata gcgccaaaca acaactttag gaagtgatgt tcctagaatg   4080
aatcaatttc taaaattaaa agtgaaaaca atgacaagga aagggaggg tcagagagga   4140
aaggctgatg ttactaaaag acaaaagaca gtataacctc ttatgaggat ggtccagaca   4200
ctcagggaaa tgcaggaaga aataaaagat aggagtttga accacactgt gatggctaac   4260
tttatgtgtg gacccgaccg atctatggga cacccagata gcttgtaaag cactatttct   4320
gggtgcgtca gtgagggtgt ttttggaaga gatcaacact tgagtcagta gactgagtaa   4380
agcagatggt cctcaccaat gtgggtgcac attgtttaat ctgttgagtg cctggataga   4440
caaaaaggc aaaagaaggg tgaattccct ttctcgtctt aagctgggac agccatcctt   4500
tcctaccctc agacatgaga ggtttggatt cttggatctt tggtcccaag ggctgacact   4560
ggtggccacc tctggtttca ggtctttggc cccagattgt aagttacacc atcagcttcc   4620
ttggttcttg ggccttgaga ctcaagctaa aatacactac cagcttccct tgttctctag   4680
tgtagggaca gcaaatcatg aaaccttctg cctccataat catataagtc aattcccgta   4740
ataaatctgt gcttatatat ctatagcttt ccttttggtc tgtttctcca aagaacctta   4800
atgtacacac tatatgacct aacctgtagt aatgataacc ttatgcaggt ttgaataaga   4860
tgatggtatt ctcagtatct gggaggtatg ggctagagtg atgaaccacc gccatgagcc   4920
taggactgag gagatttctg aaatgtggaa tatttggtgt caaaaccaag agataatata   4980
gccatgtgga aaacatgtag aactatcgta tgattcagca acccaaccac tgggaattta   5040
cccaaaggaa aggaaaccag tatattaaag agaatctgca ctcccatggt tattgcagca   5100
ttattctcaa tagcctagat atggactcaa cctaggagat tagatgaatg gacaaagaaa   5160
atgtggcata tgtacaccat gaaatactta ccagctataa aaaagaatta gccaaagcag   5220
tggtgtgtgc ctgtcatccc agctccttgg gaggctgagg tgggaagatc tcgaggccag   5280
aagtttgaga ccagcctggg caaaataata agactcggtc tctaaaacaa tttaaaaata   5340
ggccttcctt aaaaaagaa taaaatcatg tcattcacgg caacatagat gggactggag   5400
gatattactg ttaagtgaaa ttagccagga acagcaagtt aaaccccaca tattctgatt   5460
catatgcgga agctaaaaaa acgttgatct catagaagta aaaagtagaa cagaggatgc   5520
tggagactag aaaaggtagg gagaaggaag ggagagggaa aaatttgtta acaggtacaa   5580
aaacaaaatt acagttagtt agggagaatt aattccagca tcctgtagca ctataggatg   5640
```

```
actatagtta ataataatac tttaattagt ctcaaatagc tagaaggagg atattgaatg   5700
ttcccaacac acacaaaaaa atgataatgt atgagatgat ggatatggta gttatcctga   5760
tctgatcact ctacattata tgtatcaaca catcactatg taccccacaa atatgtagaa   5820
tttttatttg tccatttaaa aaagataaca aatttaaaaa taaaataaaa actaaattag   5880
tgttccatgt aaacctggat gaactggtca ccctacgtct gcccatctag atggctggtc   5940
aaagtttccc aggctccaca tcaagttgtt ccactgctca ctggaacttc cctagtcagg   6000
ttgggcaaat agtaatttac agcaatagtg aatttatcac tgacatttct tcagttcccc   6060
tctttggcat ctgcttcttc ttttctgtaa tgctgtttgt tgaaatgccc aacattcttt   6120
ttcttcccta gagctattca gggtgacctt tcttttcgca ttttcccatg ccacttccat   6180
tatatcaaaa taaacagtc ctgtgtggcc actgctcatg accttgtttc ctgccatgtg   6240
aagataggat cggctgctct ttcttctcct ccttttttt cagagacagg atctctccct   6300
gtcacccaga ctggagtgca atggcacagt cgtagcttgc tgcagcctcg aactcctgga   6360
cctcctcagc ctcctgagta gctgggacta caggtgcaca ccaccatgcc ttcctaatct   6420
gatatatata tatatatata ttatatatat aaaatatata tataaatata tatattttat   6480
atattatata tataatatat atattttata tataaaatat atatattata tatatatatt   6540
atatataaaa tatatatatt atatatatat atatatatta tagagatggg gtcttgctct   6600
gtcacccagg ctgaagatca gctgctcttt ctaatctgtg gttagataag atctgtctcc   6660
caggggataa aatactacct ggaataaagg tatctttaaa ataatcccag agaagaaaac   6720
atttttatag tatgacagag gcagagaaaa cagagaatat ttgttaaggc aggactttca   6780
ccactcccag tacaatcatc tgtctgttac ctgcatacct tacacgggct ggcactgctg   6840
ggggtacaaa gtagatgcca aacttcacaa tggttagatt catgtttaaa aagccattgg   6900
atcaaacctt tgtgaaagtt tccagctttt ttctgttcca aatatgtgtc cattataaaa   6960
gaatctcaag agcataattg ccaagatagt ctatgtccat gagtatttca acatctctca   7020
tgaaatctgt tccatcatt actcaagata ttgtatgaac agtattccac ataaactagg   7080
tgctcaataa tgattgattg gccaatggag ggtcattatt taatgcacta caatctttta   7140
tgcaaggggc ccacaggaat cagtatgatc ccataggaat cctttcttt tccattgaaa   7200 aagaaacaga tagtggcttg tattaggttt cttgtgtgtg ttgtgaggtg gaaagatatg   7260
aaaagaaatt tgatcagagc ataaatctga gcccatggga taggaaagaa tgagggaata   7320
aggaagaaaa cacagattat agacaggaaa atcaaaccta ttaaaactga taattttcga   7380
atactaaaaa tgtacattca tttgaacaaa aagattctat aaagcaagat ttctctgttc   7440
ttaccagcac taccatgccc aaactacctt aggaaatgaa tagcagagtc aaacttaaaa   7500
gcacctgaaa tttaaaacaa aaaccaattt acatttatt taagaaaagc aaacagatgg   7560
gcctgctaac aatgtcaaag tctcgtttac aaagaaaaaa acaaatctgg aacctgaagt   7620
caaacgagtt caaataaaa agcaaaccaa taaacagaaa ccaacataaa cagaagttac   7680
taccatctcc ctcagcctgt gaaattctgg aacttctctt tctttctcgc cttcttcttc   7740
tctcacctgg aagacgagca gagtgaacac atcaggggtt gtcagttccc cagatggcac   7800
cacattcata aaccaccgac tccaggagaa tgtaggaagc ttagttaagg ccaaagttct   7860
ctttggatct tcctcatggg cttcaaggca aagaaaaaa aagtttgctt gagaatatct   7920
tcatatctat tagtttgaac catgcaaaat tacagttttt ataggtaaaa tgagtgcata   7980
ttggcaattt caaatgatta accctaatac attatgcttt tgggtataga aatattcaga   8040
```

```
tcttaaacat atgctgttac atacaaaatc aggtatattc ctgcttctat aattaaagca     8100
aagagaattt cttttggtca ctactccttc tgacatgagg tatgaaccaa gttcaggacc     8160
cctaaaggtc tgggtctggg tcatttctcc acctctaact tgtgccgctt tcttggtcag     8220
tcattgtgtt ctgagctgtc tcataaaaca tctgctatga ctttactttc tcctgatagg     8280
gtggctttcc atcgttggca cttcgttggc cttattggta tgctttatac actggttctc     8340
gtttccaaat tggcattatt attgttatga ttcctgctgc tctcccacat ttcccatctt     8400
tctcctgatc tctctcacct gtacatttct tacattttct cctgtgcttc cttcttccca     8460
tcatcattgc ccaagtgtgt cttctttctt ctccttgtca catttccttt gcccgctctc     8520
acatatgcag agatggctct tggttttcct tctgaaatct catagtttgg aggtaaactt     8580
gttagcaagg ccactgagaa gagaacaaaa gggaaacata agagaaacca agtcactatc     8640
tctctcattt cctggtttct agaagtaaga cccaagaac tcactgtttc agtgctttca     8700
gctcaggcca aactagggtg atcaaactga gcttctgagt gctgatcaaa acctataaaa     8760
ccaagtagac agaccatcta caaatcttca ctgttaaata ccataaagaa tgaaaaggtc     8820
actaattggt aagactatat gtgtgataat taaatttatg catcaacctg gctaggctaa     8880
aggatgacca ggtagctggt aaaacattat tctgggtgtg tccataagag tgttttcgga     8940
agagatcagc atttgaattg gtgaacttag taaagcagac ggctctcacc aataagggca     9000
ggcatcatcc aatctgtcga aagcttgaat aaaacaaaaa gaggaaggga aaatttgctt     9060
cttttcttct tgatctagta tatcatcttc tcctgcccct tggatgtgagt gggccttcag     9120 acttaaaacca ggagttacac ctttggcttc cctggttctc agttctttgg acttggactg     9180
aattacactg ccaggtttcc tggttctcca gcttgcagat ggcagatcat gggacttctt     9240
ggcctccata attgtgtgag tcaatttcca ttttatttac atatccagtt atgcattgct     9300
taacaatgga gacaggttct gagaaatgca ttgttaagtg atttcatcat tgtgcaaaca     9360
tcatagagtg taactacaca aacctggaca gcatagacta ctacacatct aggctacatg     9420
gtgtagcttg taacctcatg ataagtatgt ataacatcat gataagtatg tatgtatcta     9480
ccatatctaa atgtagaaaa ggtacagtaa aaatatggta taatcttatg ggatcaccat     9540
catatatgca atcctttgta gactgaaatg tcattgtgta gtgcatgact gtatacgcac     9600
acatacacaa acacacacaa atatactatt ggttcttttt ctctgaagag ccctaataca     9660
atatgttata catttatatt gactctattt caaaatttat ggttttggtg aaacatatgt     9720
ggagatgggg cataggtgtg tgaactggga tagtgtcctg ctgatgaatg ggtgggaggc     9780
atcatttggg acaagcccag ggcatcagct tatagatatc aagagctcaa caagagcact     9840
ttatggcaaa acctcccaca agacctctca gaagttgaga aactgctaaa agtttcttta     9900
tgacagatga catttatgga taaaatagggg attagcagga ttctttaaat actttcgaac     9960
actaaccttc atttctacca ggcagtgggg ccccaagtgc agggccatag gaagtacaag    10020
tctgggagat actaggctgc actgtctgta gagaatctga aaaataata gagtcactga    10080 aatgcagttt ggtataatta ttgccatgca tcataattct aaatcatact agtggtcaaa    10140
tactcttccc tgaaaaaaca ttttcttggt ttgaattcta ataattgtt gtggtcacca    10200 ctgagctttt aaatatataa atactttcaa gtttgcatat ttttattacc tgttccttaa    10260
caaacattga attcaacatg aaaatgatta tgggaaacat tcgggtatac agtccctgac    10320
tcttaaggac tcaggtaaat acttagggta tttcatggcc ctagtctttg gggtaccaca    10380
tgtttcttct tcaaatcaca gattcaaaat caagaatgat aacacagtga ttgtgtagac    10440
```

```
aaaataagtg aaccaaaatt gcttgcttct gtcattctat ggaaccactg agagttttta   10500
cttgtgctta aaattttgaa tagtaaaaca gagtgtcaac ttcatgctgg aatattttg    10560 gcttttaga  cacaatttta agtacatgaa gtattttac  aagactaagt aacatcactg   10620
aaattacagc tttcttcttt ttaaaactgg tatttgttat aaaactaaag agcgaatcaa   10680
gaaaagcata attattactg attattacag gattattact gaaaagaaa  tgtacggaat   10740 agaggaggaa ggagttaaca aatgatccac tctgggtgtt gaaaacacca ataagcctgc   10800
ttccaggaag tgcctaagac agagctggct cagcttgctg ggtcacagca tgtaaggaaa   10860
ctgctgggct acatgccacc atcctcagtt gtccagatag ataatcccat agccccatgg   10920
ggaaataatc tttaattatg atatagctga caccattcaa agcactatgc taagtccttt   10980
atgtgaatta acttttgtca aatttatttt tcataaataa cccaaatatg tataccacta   11040
ttatcctacc ttaaagagga gaaactgagc tcctaaagtt taaatatcta acccaagtta   11100
agactgctag tcaccctagg ctattaactc aggcagtcta actcaggtat aataacatta   11160
tgctactgtt tgcagctttg actatgcctg aattataacg tcatgctatc taactaaaaa   11220
gctaagggaa ataaaatgag ccatagggct caatttcata aaaggagaga aaatactggg   11280
gaaaagtgat aatgcagagt ttaaaatatt tttgtaaaag tgccagagat tgagtataac   11340
aagtgtgacc aaaaaaaaa  aaaaaaaaa  aaaaggaaga aggtaaaaaa aagagggagg   11400
tctgagaaat agaaatatca gaggaaggaa ataaaggagg gtgagagtaa attctctttt   11460
agcattcaga ttccacagat tccacaaatc acatttcttt ttttaccaac taaggaaaaa   11520
taacacttga cctaacattt cattgcagtt agctaaagga tgctagaaaa actatgttgc   11580
agtggtttgc tctaatttct tcaggaatag agaaaagtga caaaaagatc agagaagaga   11640
agaaaggaaa ctatcagaaa aatacagaat tggagtagga tataacatat ttgggttgaa   11700
ggtaaaattt tatattgtaa tcttaagtat cttgctactt cagtttggtc cctggaacag   11760
cagcatcaga atctgccgag ggcttgttaa aaaggcagaa tctcaggtcc catcccagac   11820
tcactgaatc agaatataaa tactgacaag atgccccggg attcatatgc acagtagagc   11880
tggcgaagtt ccattgtagc ctgtgattgt tttctgcaac ttagtatttc tgagttttcc   11940
caaggaagaa aacccaggcc ttagcttctg gcagacttgt gtttctcctt tacttactag   12000
ctgcatgact catgagcaag gaaatcaaac tttatgtgcc tgagtttcct catctataaa   12060
atggagacta taataatcat ctcctaggct tgttttgagg atgttcaaca aatgctcctt   12120
tcattcctct atttacagac ctgccgcaga caattctgct agcagccttt gtgctattat   12180
ctgttttcta aacttagtaa ttgagtgtga tctggagact aactctgaaa taaataagct   12240
gattatttat ttattttctc aaaacaacag aatacgattt agcaaattac ttcttaagat   12300
attattttac atttctatat tctcctaccc tgagttgatg tgtgagcaat atgtcacttt   12360
cataaagcca ggtatacatt atggacaggt aagtaaaaaa catattattt attctacgtt   12420
tttgtccaaa aattttaaat ttcaactgtt gcgcgtgtgt tggtaatgta aaacaaactc   12480
agtacagtag tattcagtac agtatttaag cccctgtact taaacatatt cctcgtacca   12540
atgaagttac atgaaaagca aatttgtgtg agatatcgta gatggaagta aattagtctt   12600
tatgttcccc acaaattgaa atgcatttca aaaactctgt gtgtgtatgt gtgtgtgtga   12660
cagagtgtgt gtgagagaga gacagagaga tacgctttgg ttgcctccat aagctggctg   12720
ctatgattaa taagaccaag ttttctaaag aaaatgagat cataacaaaa gccctctttta  12780 tgactatctt ttatcagggg caaaaaggaa agagacaaaa cagcatgaaa tgatgagacc   12840
```

```
aagtgatgaa aattcattca caatgattgc tttcaagagt aatttctctt gggtaattca   12900
gcagcctgtt actatggctc tctggagtga tagctaatgt aaatgaagcc tctaaaagtg   12960
gattatcctg acaagaatat actcagccaa taatgcaaca gaaatccatt caaagcattc   13020
gggaaaaatt caaaagaata aatattcttt tttttttttt aaagttaatg acctacgatc   13080
catttcttcc ctgactaaca agcagcaagc acttaaaaat atccagccag gatgaaatag   13140
aaacccacct gacttgttaa tattttttgtt tggtcccagg gactcagatt ctaagccaaa   13200
ttctttgaat gatcttggca aatgtctcga attattttg ccaacttttc tttatcttgg    13260 aaaaaagtt tcatgaatgg gtgtcaaaat tgattagttt taaaaacctt tcttgcagat    13320
acgtatggca ccctaaaact gtattagaaa aaagtaagt actctgtagt gtgaaaaatt    13380
cttaaaggac accctctttt acaaactcac aaaaacagcc tttggaatac ccacatgaag   13440
tagctgttgt tattgctttc tatataccta catcttgtct attataaaaa gactggtttt   13500
tggcaggtgt ggtggctcac acctgtaatt ccagcacttt gggaggccaa ggcgggcgga   13560
tcacctgaga tcaggagttc aggaccagcc tgatcaatat ggtgaaaccc agtctttact   13620
gaaaatacaa aaatcacccg ggtgtggtga cgggcgcctg tagtcccagc tactcgggta   13680
gctgaggcag gagaatcact tgaactcagg agtcagaggt tgcagtgagc tgagatcatg   13740
ccactgcact ccagcctggg tgacagagca agactccatc tcaaaaaaaa aaaaaaaaa    13800 gactggtttt tcaacagcta ttcccacccc tctgcatgga aatattcacc cagtcaattg   13860
ttttcctagt ttgggtaatg gccctctggg caggactgga gtgggcaca caggagaagc    13920 tgcaaactat gtttagaagc atgtctggga aatgtcatgc aagaaaagac atatttaaag   13980
gtaggctttg catgaatgga aaaggagagt aattctatgt agagcagagc ctcttacttg   14040
cagtgagaga agcaaaagtg gggaagcaag aggaattatg ctttttcatca gccaaatttg   14100 caggtaggag gattggctca gtcatcttgg ctgaggctca tgaaaccagg tgtaaagaaa   14160
gtggactaga ttaatttcat ccattacagg aagaggagcc gtgaaagata tccagaaat    14220 cattgggatt tgatggtaga aggtattttg ggactattcc atttgaaatg agaaggtacc   14280
tgacattctt tgaattcctt tcaagcaaag gattaaattt acccatgagt tgactcagaa   14340
aaaacataaa aagtattgtt gctctgctca gagttttatc taactcattc tcacttctta   14400
ttccatgatg aaatgacata aatgaggttt tttattgttg ttgttgttgt tttctggaca   14460
caaggcaagg tagctacctg ggcagagctg ttttatttct ctatgccgtg gagagaaatt   14520
ggttaattgg ccatggaagg cagtcattaa gatgttccca tgcgagtgaa ctttccaggg   14580
ttcccagctt ctgcatcctt ccctgtccct caattccatt gttggtgatg acaatgtctc   14640
tcccatcagc ctcatgaagt tctctctcat ttattaaaat ttgctttcag gaaaaatttt   14700
gaaaatgtgt ccagtaatgc ctgattggcc ccttatccta aaggcttaaa ctggaggaag   14760
gaagctaaac tgagaaatct tgcaaatcat tgagccaaaa acgtattaat agcaagatct   14820
atcatttatt gactagtatg tggcaggcag tgcccttta tttaggcagg gagagttgat    14880 gggggggggcg gggttcacac atcttaaaga ggtgctatct cctcctatat aaatcatgta   14940
agtcaagaga gtaaggaatt gtctttgttt ggttatattc aggggattag agtatacagt   15000
agaagatccc aagaaccttt gggatcattt tagactaaga aatgccaata ccgccgggcg   15060
cggtggctca cgcctgtaat cccagcactt tgagaggccg aggtgggcgg atcacaaggt   15120
caggagattg agaccgtcct ggctaacgtg gtgaaaccct gtctctacta aaaatacaaa   15180
aaattagccg ggcgtggtgg cgggcgcctg tagtcccagc tactcgggag gcggaggcag   15240
```

```
gagaatggtg tgaactcagg aggcggagct tgcagtcagc cgagattgcc ccaatgcact   15300
ccagcctggg cgacagaacg agactccgtc tcagaacaaa acaaaaggaa atgccaatac   15360
cagcagaaat agagccaaat catgaacata agctaaacaa atgttggcag tgtagcctag   15420
tggttaagag agcagactct taactagaac actgcactcc atgtcctcac tgtagaccct   15480
cactgtgggg ttctaattaa cccctgttac ttaccagtgg cagtcttaag gcattcctta   15540
agttcgttgt gccccaattt gttcatctgt agaaggggta ggatgacagt agtgtttact   15600
ttataggctt actgtgagca ttaaatgagt tactactgta tttgtaaagt gcttaaaatg   15660
ctgctccaaa agagtttgtt aaacacttaa gaactgattt acttgcatct aaactgacag   15720
ctctcaataa ctggaaatga tcaagcatag gccctggaat ataagcaggt ctacatgaag   15780
gcaaaaatgt tcgtttcttt tgttcagccc tgtgcctaga tcaatatcta gtgatcatgc   15840
tcaagaaata ttgttgaatg aatcaatgaa cctaccgagg tagttacata aaagagttct   15900
gcatgagtac aaatctgggc aaagtgacct ccaaggaaat ttccactttt agattctgtg   15960
atttccttaa ggaactgata aattggtgtg atacaatgta aaaaaatgtg cctatatgat   16020
ttgagaaaaa cttattttct ctccctcttt tttccttcct tccttcctcc ctcccttcct   16080
tccttcctcc ctcccttcct tcctccctcc ctcccttcct tccttctctt tcttcttttc   16140
tttctttctt tctttctttc tttctttctt tctttctttc tttctttctt ctcttctctt   16200
tcctttcttt cttcctttct ttgtgccttt cttcttct ttcttcttc tctgtccttt   16260 cttt cttcct ttcttt ctt ctgccttt ct ttct ct ttgt tt tctttct ttccttcttt   16320 tttccttta a gcagaccatg tctgttagat gaatgccttt ttctagttaa aaggttaaac   16380
aggaaagtga agcacaatta tcaagggtct ccagtcatct ccacatgttc ttaatcatta   16440 tcttcttttta cagtttcata tctccaggcc tttcattggg tcaggttggc atttcgctgc   16500
cctttatgtg tgtgacaagt gaaaataagg aaagaaaaaa actcaagtga agaaaatcag   16560
aatctgcgca gcagttcctg ggcgtttcag ctgcttccca catcacctgc ctcatcaagc   16620
cccagcatcc atctccttgc tcatcttaca ccctgtgtgc atgacaggcc caccattcat   16680
ttatcagagc aaaggctctc ccactattct ggttcacccc cctacttagc cagatataca   16740
agaatatctg cacggatgac ctgcctcacc tgggagctca gaggagctca gattccatta   16800
ctatcgcacc aaggacagat ctcccagcaa gaatgacaga aaagactaac tgcccccaaa   16860
atctcccttc caaacacag ttctcttaat tctcccaaga aaccagaatg tgactgctca   16920
cctctctaag gacctgaaaa caactggcca tttcagctat ttaaatcaac tttaaaaaat   16980
ccaaccgcca aaatattaaa ccattttggt tggaatgata acataactaa cctgctgaca   17040
gctgcttctg ctaggtgcaa aaatggaaaa aaaaatactt ctaatcaggt caaatcactc   17100
tacctttggg attctaaatt tactcatatt ctcaaagaaa tatattcagt catagtgggg   17160
aaaataggat tattcctta gctcgataag caaccagaag ttcttccttc aaatcttgac   17220
atttaatcaa tcagaaattg attttttggaa aactgtttcc tatgaagcta tctctgcctg   17280 aaggatttt cttttacaat ccagactata gaaggaaatt cacaacctgg actttcacct   17340
ccattggtca gagttttact gaccaattcc cacctctgcc ttacacctaa cggaagttta   17400
tgcctgtttt ctcttcacat accccaacag ttacaaatgg ttgttattat taagcatctt   17460
ttattttgtg gcctctgatt acatggtccc ctaaattttg acctaatcac aaaagattgg   17520
taaaatttct taacatatta ataatatttt gtttatgtgt caatatctta gcatgtatca   17580
attaagacag aggtcttaac gttctctttt tgaaagagaa tattaggatt cagagatatt   17640
```

```
aagagattct cccaggatca cagttaggta acagagctgg attttagtcc aggtctgtct   17700
acagctctaa cgtatataca cccttttgtat aacatgtcac gaattcagca taaagggatc   17760
ttcagtgatc taagtcaggg gtcagcaacc ttttctaaaa aggaccaaat agtaatattt   17820
caggctttgt ggaccctatg gtctctatca taactgttca aatcaccatg tagtgtaaaa   17880
ggagccataa gcaaaatata aactaacgaa tgtggctgtt ttatgggatt ttttttttaac   17940 tctttattta caaaagcagg tggcagatca gaactcactt atgggccata gttctctgac   18000
ccctgacctg agaaaatctt atatttatgg acaacattta gactgtgact tgccaagtaa   18060
gaacaagaag ctctgtcaac tgaaggtcaa ggctggagtt ctgaaagcaa agagctgtct   18120
ggtgttaatg ataagtgaaa tagttaaagt tagaagatcc cagttataag aagcacaaag   18180
aataatgacc atagactcct gaacaagaat gtctggactt ctggcttagg cactcttgtt   18240
gtatggtcca ggccaagtta cctaatctct ccaggcctcc attttcttat cattaaatga   18300
agataataaa agtattttcc tcagagagct gtaagaataa actgagctaa cccatgtcaa   18360
gcacatagaa tagggcccag cctatattaa tttatcaata aatgccagct acatattagt   18420
tctctatatt tttattcatt atcataaaat gtttatctac agattggcat tgtaaggatg   18480
gagttaaaat tgtatgtatg tgaagggaaa ttattcctgt tactattgat ctgcatcaca   18540
ttaccccaaa tttgatggct taaagtaaca acattcattt tgcaaacaaa tttgaaattt   18600
gaggagggct tgtctgggaa gacttgtctc tgccctatgt ggtatcagca ggggaggct   18660 tgacggactg gcacatgccc ttccagaatg gcccactcgc atgcctgcca agttggtgct   18720
ggctcttggc tgggagctca gctggggctg agtgctaggg tccctgggag gttccttgtg   18780
gcctgaactt cctcaccaca aggcggctgc ggtgcgagag tgagcatttc aagatagagc   18840
caagatgaca ctgtattact gtgtaagacc cagcctggga attaatgtag cctcacttcc   18900
atcccactct attttaaaa agtgaattat taaggtcacc ccatattcaa ggggatagga   18960
attagacttc atctgtatta agaaaatgt ttttaaaaat tgtagacatg ttttaaaatt   19020
ctaaagtcca cttactggct gcagattatt tatatataca tgcaagatac actcctacat   19080
tctcttctta gaaggctcag ttgcaggtac agatgaagct cttcaagtga gatttcttat   19140
gtatttatcc tctcaatctg aagacttgta aactaagaga caagttattt gcaacctaca   19200
tacgcaatat tcaatggtaa agtatacata ggacagccac tacagacact cttgttttaa   19260
atagaggaaa atgagagcac ataacagtca ttggctcata gcaactctga tatccagaca   19320
gcaaacacaa gcaggtcttt ttttaggtct cagtcctact gcctggattc cctactgctc   19380
ttgggtcttc cctccaggtt cttggttctt ggacctcttt tcatttaata ctatttctgt   19440
tcctttaagt tcaagctggc aaaatatgat tgtacaattc tgtttaaaat tccaggactt   19500
cctgtgattc ttattgggga atactccatt agacaagaat ctctttgaca taagccattc   19560
tctacctgag atccctgtaa ggctgtgatg ggaccacata accttaaaat tattagaaga   19620
ctcattgttt actgagagaa tatgcctagc atatgcttag atcctagag gaactctgtt   19680 tcaaagggct tatgagacat taccttatat ctttctaagg tacaaacaaa aggtctttgg   19740
cttttgagtt tgatctttga gctgacacct tttcttaatt tgagaatccc ctgctctatg   19800
gagagactga caaagagaaa tagttttata tttgaatgta acatcttgga tctttaatag   19860
attatcttaa aattttcctg aaaatgtaac agttcctttt tttaaaattc attctcccta   19920
cacacttatt atatatgact aaaagaaact ccctggcatt tcaacattc tggttagaat   19980 ttttcttagc ccaatctacc agtttattag gtatatttgt attttccacg tcactgtagg   20040
```

```
tgacaatctt gctaaacttt ctgccactac ataacaagga tcccttctc cagttttcag    20100 taacaatcta ccaatagcct cctcaaggtc taccaagctt ctactaaaaa tctctttcag    20160
ccccttccaa cttctgccca ccaactagtc ccagaagcaa tacccatgtt ttaggtttca    20220
ttatagcagc atctagtttc gagttctcag aacctgtttc gatcatgttt cactgtttcc    20280
aaaacatccc aaaacagtag cttaagacag taacacttat tttgctcaca ggctgtacgg    20340
gaagcatggc tggagaggtc tcaggaaata tacaatcatg gtggaaggca agaggaagg     20400 aggtatgtct tacatggcca gagcaggaga aagagaaggg gaaggtgcca cacttttt      20460 agaaacccag atctcatgag aacttactca ctatcatgag aacagcaaag aagaaatctg    20520
tctccatgat ccaatcacct cccaccaggc ccctcctccc acactgggga ttacaattcg    20580
acatgagatt tgggcaggga cacaaatcca aaccataaca gttggcaacc ctttttaaa     20640 gaaagtaatg acatcaactc cttggggatg tggattgggg gagaatattg gagaggatcc    20700
aggggaagtg aagatatcaa gttctttata cataaataga tctatctttt tagggaagta    20760
gaatatgtca tttaggatag ggaaagttga agatgttact ctattcagct ttagggaaac    20820
tccaagatgt aacactatgt cctgtgaata ttagtcttgt ggaaagtgct ccattggaag    20880
aagacagaaa atgtcctgct gcacagagat ccatatcttc atgccacgtc ttgcaaatgc    20940
agtcagggag cttgctctaa attcgtgttg cctttaggα agttacagag catatttctt    21000
tatatcttct ttattttgc ccttgatagg agactgccag ggattcagtt attataattt     21060
tacatttatt tatccttttc tgggagcatc tcataccttt tttactagag aggccaaggt    21120
cacaattaag attagggaga caatacagag tcaagacacc tgaattttgc cacactactc    21180
ttgggccact ttaattggtg tttctgggcc tcattttat tactattatt attaattatt     21240
ttatggtgtg tataggagct ggaagatagt gacttctatt agaatttatt cttataaaca    21300
atgctgtatg gctcttggat taagaagtaa atagaaaaca aaaagggtct ttgaactgct    21360
gtctcttcta ggtcttctca gagtgctact gggaattaga tgggattaga tgggtgaatt    21420 tccttttttct tttgtttgag aggtctagat ttttgaagta tctaaaccat ctttagatct   21480
aagttaatct ccaaaaagct ttattgcctg aaacattcca gttctaggaa gtttgcattt    21540
ctctgagtgt aagggtctgg tctgtaactc cttgagatca ggaatgtgtc tttttatccc    21600
catagttcag cgcctaccct agtgtcttcc ctacaagtga tcattgaatg aagaaaggaa    21660
taaattcctt cttctctaac atacatcaga gacctctgac ccttattggg tccccttcc     21720 ctattgatat acctctccat ctccagacat ccacatggcc tcctagggt atgggattct     21780 tcactcttct cctggtacaa gctccttgcc tgaaattttt ctgacccacc cccatttcta    21840
accgtcacag gtttagattt tctgaagcaa acatacagac agagttcgag ttacaagaca    21900
tttaatagga atcgactctt gtgaaaggaa gaggggaaga tgtgggactg ggctcagtga    21960
gaagccaagc tgtgacacaa tgaaaacctc agcccaccct gcacagagct caggaatgag    22020
tgtcacgtgt tagagctgac ctgggtcagg tcaacattgc tgggtgtttc tgcttctgcc    22080
tcgttcagtt gtcagatgca agctgacctg ggaagggttt gactgggcaa gatggctgtc    22140
tgcagatgag gtcaatcaga aggggctgac agccaaaagt ggtttgctca tctcactacc    22200
cacagctggg tggcaagtcc ttcaagaggg agctggatga tgcttctcca cctctaccac    22260
accaaacaaa gcatttcttt cttattcttt ttcttcctgt ctcccttccc cctcccccct    22320
ctcccctttt ctcctcctcc tcctcctcct ccttcttctt cttcttcctc ttttttctcc    22380
ttcctctttc tttagagaca gggtcttgct tggttgccca ggctggagtg cagtggcaag    22440
```

```
gtcatagctc actgcagcct caacctcctg tgtttaagca atcctctcac cttggcctcc   22500
caagtagctg ggactacagg catgtgctat catgcccgac taattttttta attttttacta  22560 gagacagtct cactatgttg cctgggctgg agcatttcta ttcatgggtt ttgttcctct   22620
ggagctgtgc tgttctcttt gataacatga atatggattt gtatttaccc ccttctggcc   22680
atcttaacta atgggcccaaa ggaaggccag tggtgaagat gtttctctac agggaagttt   22740
ctaagtgttt ctcagcctac atgtgtgagt gtattaatgg gaatactggg gataattgga   22800
tagaatgtat gaaattagga ttggcctaaa ctatctggtc caaagtttat cctagtggcc   22860
ctaataacat ctccagtgat ggtctttcct gaggttatag aatgagctat aggaaagagt   22920
gatagtacag gaatgagagg attggatcgt cttttctctt tgttctattc ctctatgatt   22980
atttgatttc tttttttttgt gatggagtct cactctgtcg attatttgat ttttgtttca   23040
gattaaggcc agcttttcttt gactgagcag acccacgtat atgggaaacg gccacacacc   23100
aaattaaacc attcactgac acccgggcac acccattttc accactctgc tcttgcccgt   23160
gccattgcct ttgcatccaa gggattcttc cttctgtggc aatctgtatg acatccttac   23220
taagaaggcc tccctcagtg cccttggccc tctcacagcc cttccatgg ccttctccac    23280 tagactgtga ggaacccagt gtctggaaca gttcatggca ttgttgttag tgttgtcatt   23340
ttgttgttaa gccttctgct gtcagtggtc atttcatatg tttgcatatt tacgccctgc   23400
ctctttttgg tatgcagtgt ggaccctatt gcacggctac ttgtgtttca gtggctttgt   23460
cctattccac cttctatgcc acttactctg aatgcctggc acattggtag gtgcccaata   23520
ccaacttgga aagtgaatga atttgttttc tcattacctt ttgaaatgcc tatacagatg   23580
ttcctccact tatgatggag ttcattctga aaagctcatg ataagtagaa gatattatgt   23640
cagaaatgta ttttattgta tttttttattt tttaatcttt cttctctctttt ctttctttct  23700 ttcattcatt cattctttct ttctttcttt tctttcttt cctttcatct ttcttttagt     23760
agagacaatg tctcactata ttgcctaggc tggtcttgaa ctcttgggct aaaagcaatt   23820
ctcctgcctt gctctgccaa agggctgaga ttacaggcat caactactgc acctagttga   23880
aaaatgcatt taatgctcca ataaacccat cataaagtca aaccatcagc agtcagtgac   23940
tatctgtata ccttaggact aagttagaag ttggagatgg taaagtttct aaattagtac   24000
aagcacagga gctcttattc ctgccatttt atgaaagtca tgtgagtatt ggtgaccatc   24060
actaatgggg ctggtagaaa ctttaggacc agtctgtctt agtcagctgg gctgctacaa   24120
taaaaaacca tggactgagt gggttaaaca atggacattt acttctcaca gttctggaag   24180
atgggaagtc caagatcaag aagccaacat ggctggattc tgatgagggc ttttttctgga  24240 atgcagatga tcaccttctt gccttgtcct catgtggaag agagagcaaa ctctctagtc   24300
tctctttctt ttcttaaagg acaataatcc cattatggag gcctcatgct catgacctca   24360
tctaaaccta gttacttctt aaaggctcca actccaaata ccatcacact gaaggttagg   24420
gtttccacat ataaacttcg gagggacaca aacattcggt tcataacaag tgcattctac   24480
aggactccag ggagtgtgtt ggctacccctt catcccacac agctgcaaca atcctaatcc   24540
actgatatca agtcaccata tatttgaaat tcactcagtt cccaagaaaa tatctgcttt   24600
cataatcatt tctcagctaa ggaatgaaag ctatgataag aaagtctagc acttagtggg   24660
aaacaaactt gaattaggcc aggacccctt aaatattgtc actatgaaat ccaagggcag   24720
tatttacatg cttttccttc atgatgacct tagatttcgc ttctttatgc tgcaatcaac   24780
tgaaaacatt ccactgttgg taatcctttta tcttctaaca aatctaatttt agtagatctt  24840
```

```
gttactcctt attttgaaa atattaaact aaacaataag tgatctttca gggaaattct    24900
gcaagggaag tggcttctag agaatgcctc ttctccaaaa ggcctagttc tatttctgat    24960
atctaatcag ttctgctccc tttaaataat tactgaaact agtttattgt ttaaatgacc    25020
tcatttgaaa gtgggacttt cccctttgcc ttcttccctt ttaatttctg ttttaatta    25080 atgtaagtgc agtcagaact gacggtgtca accttcctg taactgtgat tgccacttgt    25140
ggacattctg tactcataag agtgattctc acaagttctt taagttttt ggaagtgcaa    25200 acccaacagg aagaaagaat aggactccct gcattctatt ttgctctgca gtgaagatgc    25260
attgttgagt aatttgcttt acattcagat atacccagat tcccatcttc ccaatccatg    25320
tgacttggct aagttacaac tcttataag cctcaatgcc tgcaactgaa taagaaagtg    25380
gtaaccatct catgggcat tgggtaaatg agataatact tatgaagtat gcagcacaca    25440
gccaagagcg taacgtgttc aatcaatgat atccattatt attacatgtc aaatcacatc    25500
tgacttctgt gattctactg gggaaaagga tgcaaaatcc tcttgccgtt ggggtgtcaa    25560
atattttagt acttatttcc aaattcattg gaggggtctt tccctgaagt ttacagatgt    25620
ggaatacacc attcaggcag gctttcttca gtagtgcagg tcatttcagg ggttctccac    25680
attctagaat aatttttttt tttacccact acagacacat ttactggcaa ggcccatgat    25740
aacaaaatga aattaataca ggctttacag tcagagacct aggcgacctt gggtaattca    25800
ttaatatctc tgagcctcta tttcctcagc tttgaaagag gcataagaat tgctctgaag    25860
aataatcatg agtataaaat aagataaatg agataactat gtaatatgca ttagtttagc    25920
accaagccat atacaaaggc acaataaaga gaatctaata tgtttccttt attcccactg    25980
ctatgaactg aatgtgtgtg tccccgccc accgcaaatt catatgatga agccctaatc    26040
cacattgtaa aggtatttgg aggtggggca tttgtgaggg aactaggttt aaatgaactc    26100
atgaaggtgg agcccccatg ctgagatcaa tgcccttatt taacaaaaat cagaaacaac    26160
aacaacacaa aggaagacag catgaaatct ctctctcttt ctcttttccc ctctccctct    26220
gccttcatcc ccatcgccat gcacccgcaa aagaaaggcc atgtgaggac ataaccagag    26280
ccctcccaag accctgaccc tgctggcgct ctgatctcag acttccagcc tccaggacca    26340
tgaaaaataa atgttggttg ttcaagccac ccagtctatg gtatttcagt gtagcagttt    26400
gaactgagat acctattaac agatgttcct ttccttcttc tccctcattt ttatggcaca    26460
ttaccagtgt ttggtactaa atactagctg ttaattctcc cttagtagaa gacaatagag    26520
taatgctgag ttggtctcag ctgtgggaaa ccttttgccc agagagaaaa attaagtctc    26580
ctaacagaaa gctggcactt tcccttactg ggcatcagcg aaaacctgat tcccatgggt    26640
aaagtgagta attgctaaag ggaaacagat catgtgcatt tacatagtca gagatgtttt    26700
atgggattag gtgggtgatg aagagtaatc attataataa ttttacaacc cagacataaa    26760
agagaaagag cagagaaaga ccagttctct tgtgaaatat ttgccatta atatcttttt    26820 atctttgggc aagccaactt attttcttac aaataagcag taactagaca cagatattta    26880
agaggagaaa tggaccttag atgttctgtg gcataatttt cctttcacat aggggaaaac    26940
caggaccaga gcagcggatg aagatgccaa gatcaggcac tgccaattgt tttgactacc    27000
tctagggaga tcctctcatg actcacacat tgcctctctc ttgaaaatga gtaaagagtt    27060
gcccaaccaa attcttgaaa taaggtcagt tataaatgcc tatagcagct accttctttt    27120
ttattattta gaaaatgatc attggaactt gttatcagaa gacacaggct gagagggaag    27180
ggatgtattt tttcacatgt caaggaacca ggggtaatat aacattcaca ttctagagaa    27240
```

```
aggtcaaata ataaattgcc ataaaataca gactgctcat gagctgtttt gaaatcttgg    27300
cttcttgtca aaaactaaa ggtggaggag agtaaaatcc ataactgtgt gcttttttgtg   27360 taggtgtgtt ggactgaatg tacatatgat tggatcatag agatgatcaa agaagtgtat    27420
actattcctc aacagaagag gacaaaaaac gaaattgaca tttgttgaca tttccttggc    27480
cttagaagtg tttgtaaatg acagagttag gatttgaacc cagttccagc gagtttaaag    27540
cccaggttat ttcccaataa gccaaagaaa tttccaatgc caacctattc ctggcatctt    27600
tagcagcaag agtgattata gtttccacag acagaaattg tgtacagagt tgggtgaaag    27660
aacagtagct ccaacatgct tggcatcaag gctgtgactg cacgaactat tccaggaaaa    27720
ctagtcatca caggtgattg aaaagagaag atatctttta gcagactaaa atctgcaggc    27780
atcttcatca ctccttaatg cagacagaca aaactgattg gctagactaa taagatcaga    27840
ctttgttttg gaaactaaat gtctattaag acacgcgaga agacaagatt tcctaaacat    27900
agactatgaa tagactatga atagtcaaga gggaggtcga ggaaaaggga attcccctta    27960
acatggcaga tcaaatattt aaattttaat gacatattag atggaatata agaagttttt    28020
gtgttatgaa ataaaaagaa ctcattcttt taaaaaatgg caatccaata tttatacacg    28080
ttcttctatc ttatagcatg actgaattcg aagtgttctt gttcatgtct ccttctctga    28140
gaaagagtaa gtgcctccac aaacacattc actgggagtc cagaagtgga gagtatcgtg    28200
ttttcactgt tcaaggtcac gtagtggttc ctggcccaaa caagtaggag ctttctaaaa    28260
ttaaaggcaa ctatccataa aggttccttc atctgctgtc tcctagtcca ttggcaggac    28320
ttggcaggga aagccctctt cttgatagag atattggacc tccaacctat ctcttcatct    28380
tctcccatac atctcctcca tacagggttg tcaggtcagt aatccctact ggccatttag    28440
aaggtgacat ttatcaatta taattaggtg acttaggagg cttactcaac tccccagaat    28500
ctcagtgtcc tcatctgtga aactggaaat aataaagcct atttcataaa cctaattctt    28560
catattaaat gggataacat atataaagca cttagcacat gctatgaccc cagaagatac    28620
agattcacag agcagatgga gcactgctgt gtctcatgat actcaagctt gaatatcaag    28680
cttgactccc attctgctaa ttctccctct ggctactagg acatcttgac tttcagggtc    28740
tggactctgg gccttaaggg aaagctaaga ctcgtccttg tatttctact ttatgtaggt    28800
agaagctgat ctgcattagg gctggttgct cccttctccc catctcaagc cccagaatct    28860
cttcttgtat taatctctct cccaaagttc ttgctgaggt cagatttcat agtcctgctt    28920
tttcagcacc tgttcttaat tagttcaaac ttttgcaggt tttctttcag gccatatttt    28980 atttgttttcc tcagaaactc ctcttagact acatccttta tctccagaca cctgggatcc    29040
acattgattc ttttattttc cacaatttct aaccctgaac agctgcatga atgtaagcaa    29100
gcttctaagc atagatgggt gggtggttgg gatgtgtaca cgttattcat tcattcagtc    29160
atacatttat tatttataaa ctacttattg aacacttcct agtgcttgga atttttttaa    29220
aaatctcaag cgatatgcat atcaatacaa ataatttca gttctcaaga aacttaatct    29280
tgggaaggat aaacaaagac ttataataca atatggtgca agatttacaa taaagcagtg    29340
gttctcagca ttggctgaat aatagaacca cctggctata ttatatagtg atgcttgact    29400
ccaactcaga ccaatgaaat caaatcccct gtgagtaaga cctgggcatt gctatgtttt    29460
gatagctttc caggtgattc cattctgcag ggaggtttga gaatcccttg gatagaggga    29520
agtatgggct gccttgggac cacaattaag aggtccctac tctaattggt aaggtgctaa    29580
aggctgcaaa gggaagatga catctgagct aagtcttttt tttttttttt tttttttttt    29640
```

```
tttgagacag agtctcgctc tgtcacccag gctgaagtgt agtggcataa tctcggctca   29700
ctgcaacctc cgcctcctgg gttcaagcaa ttctcctgcc tcagctgccc cagtagctgg   29760
gataacatgc acccgccact atgcttggct aatgttttgt attttttagta gagatggggt   29820 ttcaccatgt tgaccaggct ggctcaaact cctgacctca agtaatctac ccaccttggc   29880
ctcccaaagt gctgggatta caggcatgag ccaccacacc cggccctgag ctaagtcttg   29940
acaaatgagt tgcccaagtg aagatgtggg aaagccattt caagggcaga ggaacaagat   30000
gagttcatag aactgcctgt aattttgggt acagtttaga gagtgctaaa tgctaaagca   30060
tttagcctgt ctctggcagg caaaaggaga gtcattgaag gattgttaaa aaggaaataa   30120
tatggtcagt attatataca tctgaagtac caagacatca gttggggagc aaattttact   30180
ttcattgcat cttgccccag cagaactatc tcccttaat aagaccttta aaactgttgg   30240
cacctccctg gcttcaaaca ttagaaacag gaaactctac ccatgagcta accttcaccc   30300
catcctttcc tgaaacaaag aacatctgtt ctcccacttg gatgtgcctg gagtaaagag   30360
gggcgcctaa gtattctcag ttgactacag agaaatgatt ggcgtcacgt agattagtca   30420
tacatacatg cagatgatga catagtcaaa tgtattgaga cattttagtt ccaaaaagta   30480
agtgttttgt ttctgataca gtgctgtcac ccttggccag ggaaacccag ggatcatagc   30540
tgctacagat aaattatgat ttattccttg aagagggcc tgaactcaaa agaaattaag   30600
tagtaataac acttgaaaat tctctttctc caatttcagt atgcaaatct atttacatat   30660
caaccaagcc tttgggacag gttagttatt gtttgtggtg gtagtggttg tgttgtttat   30720
gtttgagttt tgtgttttt tttaattctg agatacatta tcaatttaat gacaactttg   30780
caggataaaa aaggaggagg agaaagaagg ggaggaagag aaaggggaag aggaggagaa   30840
gaagggaaaa aagagaaaaa atgattaaat ttaatttgtg ttctaattgt gaaacaatct   30900
aatttcaaaa atgttaaaat ctgtgtgttg ggttagagat gggaaaagta tgctgtataa   30960
taaaaaaaaa atccccagga ggaaaatgaa atatttttag aggtactagg aattttatag   31020
tcaatgggat ccaaagctgt attttagac agagaaatct gaggcacagg tagacgagaa   31080
attttcttca aattctcgag ggaattactt agtagtgaag ctggaatcag aaacctcatt   31140
tctcagcctc aagtttggtt tgcttttccat gacaccctag aatattccaa ctaatatctg   31200
agaagcaaaa aagcatctca tccttctac tcatatttct ggctgaggga actattcaaa   31260
gagataaagt acatgaataa ataaaaaatg tgtatcacag ctaagtacat cttagcaaag   31320
aaataagcaa aagactatgg tgcctcagtt ctcaacactc tcttttgttc atttatttag   31380
tggctgttat cttgagtagg tgattcttgc atatcaaatt gcattttggt gtgtcaaagt   31440
gactggtttt acttgtttgt tggttcctaa agctaattat tattttaac accttttgat   31500 atgctaaatc aggctaatga gactaaaatg ggatttctca tgggtttatt agtcatcaac   31560
accatcttac atatgtgtat atatgtttta atgctttcaa agtgtaaata aatgattata   31620
cttgagactc atacaaatat cataaagcag cttttttcctt agtattcctc ctagaaaata   31680
gatatttcat tggcagagtc gtggtgaaag atgtggtgtc atacaataaa tttacttcag   31740
ccagctgtgc gagcttaagt tacccagttc ttttctgcct cagtggcctc ttctgtaata   31800
tggactgata ggggatctca catgcctgtg tttagaatta agtcggataa ttcatgtaaa   31860
gtgcttagca agtcacctgg cctattataa ctagccatta tgtttgcta gaacatttat   31920 ctgttcacaa attatgcatt gattgcctat aataactaaa cttgaggaat gcttattacg   31980
taccacgtac tattcgaagc acatcacaag tagtaactca tttcattttt ataatgactc   32040
```

```
tttgaggtaa gaactattat taccatctct gctttacaaa tgaggaaatt gaggcataga    32100
gacgtaaagt cacttgttca aagcctagca tctgggaaac agtagaggtg ggactcaaac    32160
tcagaaagcc tggctatagg ctctgctctg ctgtctcccg ggattggcca catgctaagc    32220
attgggcaa cagcaatgag gcccataggg tttctgctct caaggagatc actataaatc     32280
agccccggga gatgatccct aaaagagaag tacgtcgttt gcaaaatgac agcacagacg    32340
cacgagttct gaactcttcc tcagagtttg gggaagttgt ttagccctgc tttctgccct    32400
ctctatgggt cacacacata ctccgagtga agaatgacgg agttacccat cttctggctc    32460
cttcccgtga cactggctac cctatgctaa aaaccagccc ccagattcca catccctgaa    32520
tgtcttattt acaggttctg tcattttcat gataacctt ctaatgttct aaatttcctt     32580
tctgtgggtt gtcaagcaaa ttcattctcg gcagtcagta agaactcctt gttcaaaatg    32640
ccacacatta cagagtcaat gattctaaac acattttttt ttagtgcatc caacttataa    32700
gctgcagtgc tagaaacaaa ttcacactcc ctttacacta cagtgccatc ttttccgagg    32760
gtggggctcg cgtttcttca ccatccagtt tctcatacgt agattatgat ttctgctttt    32820
gccaaacagg acattgtttg accaagtcct tatggggagga agcacagccc agtgagcaga   32880
acaatgattt gaaagtcctg ggttctattt tcagctcctc tgttgactag ctgcgcattc    32940
agccctagga aggtcaaaag cagaatggcc ttgctttgac gactttctct gcatgtacag    33000
ctctagatgg aaaatatatc aggcatctgg ctctcagcct tgaggagctg gtctttggag    33060
aatacatgtg tagtcacact ttgttttcat ttttaaagca aaagaacaaa acaaactctc    33120
taggggaaa atgggctggt agagaatgga agagagaaac ctaataacat tttaaacaat     33180
ccaggagtta agggattgct tgagtcattc agatcaaaga aggctctttg gcacaagttg    33240
gagtctccgg catttgaaaa tggaagaggc aaagaggagg aagctttgag agacttttc    33300
aaaccgggac ggtagcagat actcagaact ctgcctgtag ggaccaggcg gggaactcag    33360
gcaggttaag gcctgtgggc aaactggaaa gcccaggcca cctgtgaagt ggtctgctgc    33420
tagtgatacc agatgcttgt tgtggaagaa ggaagttact cttgccagaa cagctgaatt    33480
ttcaagagaa actgaacatt gagattttg tcattagaac ccctgatttt tttacatgat     33540
gaaatctaat catcattttt aaacttttaa aggggcactg agcaggcaag atcaaacata    33600
tagcctaagc aatgtactcc ccatgtctct tctatatgta gatgggtgt ggttccttaa     33660
gggctttagt tgtatgttct gtgaatgaat agaggctaga ttccagacaa aaatgattag    33720
cagtgactca actttagctg cactttggaa tacctgggtg ttacctggga ctgcagcctg    33780
agcactggga ttttataaat gcttctcaag tgattccagc atgcaaccat gaataagaac    33840
cactatgtta ggatattgcg agaaggttta agcattacag aaagttgggt tttaacttga    33900
taagatacat aatcttatca agacacatgt gatctctgaa catggatcag ggaattgaca    33960
ttcaatataa atggcatttt ctttttcttttt tttagactct tttgagagtt ccagttaaaa   34020
actctctagc atcattgctg atggccgtaa ttaatatctt tgggttcatt agcaatcagc    34080
taacaacaga catccattgg caaaacaagg gtatagtggt agaggtcaaa cacaacgaaa    34140
gccaaaggac aagtgcaagc cctgagcaca gataagtatt tacagggaaa attaactttt    34200
tttctgatgg ccatgaagca aaatagacag tagagcaaag ggagccttt acaagagcag     34260
ttcaatcttt gtccacattc taatggctat aaaactcacc atgaagctag caaatggtgc    34320
atacaactaa tactttcagt ctttttcttcc ttatttcaca ggtcttatgc attataaata    34380
acacgactaa gtctcagcgg ttgtatccat ggctagttct tatttcagct ttggttcctc    34440
```

```
ttgctattta ctatgtttct cataaaagat gttagtgtgg attgagtata tgaaatcatg   34500
tacaatggaa tgttaaatgg ggcattccct cttgtctagg tatatcagaa gaggcccaat   34560
acacttggtg ccaaggaagc tcaccttcta aaaccagatg gtagcttgcc tataaaagga   34620
tacactaaga ggttctaccc aagttatcac attggcagcc tccagcttat caagagagac   34680
tttaaagaac ttggcagtgg ggatctttct agagggcgtt gtcaatttag gaagcatctt   34740
cgtcttcatg cctcaccttt ccgataagtt tgtttcttcc ttaatgcaaa caaaatgaga   34800
gacactttga tgggaccact tgcagagctt gacatgtgtc atctggattt taacagacag   34860
atatcattga gatatctgac tcacacctga aaacactgta actagaacta ctctctctct   34920
ctctctctct ttctctctct ctctctctct ctctctctct ctctctttat gcctaaaaca   34980
gagctatgtg gaggctaagc aggacttcca aaatttgaaa caaataagga acctgttcaa   35040
agaaggcaga ttgaggcatc ttgaaagaaa ttgcctggca gggtgtcatg actccattag   35100
ggggaacgta ccatttgaag ccaagagaat aaagaagtca tggatgacta gcttgagaag   35160
gcgtaactgg agtcagggaa acagttactg agagagatgt cctgcaatgt agggaaaaag   35220
agggagcttc cccaaactca acacaatgct ctatgaaaca cacatcagtt gggatgttca   35280
ctaaactcag aggatcacaa tgacagatta taagagcgcc agtcaagtta gaacttctta   35340
ttccatctta cgaccttcct cttcctcccc tacactcctc tgtattcttc ctcttgctcc   35400
cccacagcct ctatactctg agaagcagtc tcttgctctg ctccttctgt gaattgttaa   35460
ttcaattatt tcaaatttct cacttcattc tctgtctagt gggtgtgagt cctgggtgtc   35520
tggggatctc atatgtgatt tattgtggtc agaatgcaaa aatataggca aaatcataac   35580
atagtagtta aatttataat tatttggatt attgaaatac atctataaaa agtatttat   35640 aatttgtttt gaatactttg tctttggaga ggccagaaat cacagacagg aaaggaggag   35700
gagatagaga gaggagaaga tggggaaacc aacctggcct ctcctcctac tcctggattt   35760
ccaatctgat aacagagttg tgagaaaaga cagagcttaa gtttacatgg ataagacttt   35820
tgactagact ttttactacc ttggaaaaaa gctttttaa aaaatttat acctgttggt   35880 aatcagaaaa gccaagagag aactactcag agttttatta gttagaggaa cctggggatt   35940
gagggtgagt actcaaaatg tcaggtttgg aggggcagaa gcaaaattta aaaaattgtt   36000
tatacctgca acctgtcaag tccagtttac acaataatac aaaataaacc aatttaactt   36060
gaacacataa aatgttttca tgatgtggat tcaatttaac aagggcacaa catgatacca   36120
cagtcatctt tcaaaattct catctttagg attcagctttt ggtaccttaa agatatattg   36180
ggttacagca acatttctgc aggaagctaa tatgtattcc ttaaaaagag ttccatgatc   36240
aaagatattg gtgacaaact tgttcactca aaaaataaat agaggccagc catggtggct   36300
catgcctgta atcccagaac tttggcagga caaggcagga ggatcacttg agccccagag   36360
ttggaaacca gcctagacaa tatagcaaga ccctgtctct aaaaaagaaa tagctgaaag   36420
tggtggcatg tgcctgtagt cccagctact gggaggctg aggtgtgatg atcatctgag   36480
tccaggaatt taaagctgct gtgaactatg aaggctccat tgcacccag cctgggtgac   36540 agagcaagac cctacctcaa aaagtaaaat aaataaataa gtaagtaggg ttttttttg   36600 ttgttttttg ttttgtttg ttttaactg taggtctcct agaatgtttt aatgtgtgtt   36660
gtaagggaac aattctataa gaaagaatac ctggtggtgg cattttcaag ctcatttgtt   36720
caaaggctgt tattattccc aaatatttag gcttccattt attaaatatt tgctgaacat   36780
ctaccatgtg caggcatggg ggatgggtgt tgggggttaa ttaaatatat caaatgggct   36840
```

```
cctctcactc aaagatctta tgatctaatg gattgcttat tttagtcctc atcttagttt   36900
gaaaatctct ttggagagat ctgttctatg ccatttttca gatttctgcc actgcaaaac   36960
tatttgttaa cacaaaaata caaattacct gaggaagaag ttgtgttgta aaatagatgt   37020
gtttttataa aacaaaattt aaaagtgcat tcacaaccaa gcataacaaa tatgctttgg   37080
tcacctttcc tttctgtcct tgatcaactt cagctgatta tggaaaattc ttgataaagt   37140
tataaagtca tccacctctt ttttctctag gtctaactcc tttccttgta ttggacgtca   37200
aatccccaca ttctactctt tctgctccct cagaaaagat ctgacatcag tcattcggat   37260
tggtgtgggc ttcctgtgag atattttgac aaaggttttc tttatgtgtt agcactgaac   37320
agttttggca atttcttcc ccttcaccag cctactacac atgaccacac aggtgtttac    37380
atatgtacat acacacacgt gcacacttac cttccttcaa aacaggccaa atgcaacatc   37440
ttgtctcctt cttgcaggca aagtaggaga cctgtgttga gtgacagaat tcctttacct   37500
tctgggctat agcatcccag agaatgtcct cacctgggag ttttctatgc atggctttcc   37560
ttgattccca ggaagatcta catccagtta acttaactat ggcagctgaa tcctgacaat   37620
ggtgtgaagg aaaacatggt ggatacaaat gagcaccatg ggtacagctt gatgatgtcc   37680
agctttatgc ataatgtgga ctggcagggc ctttgatcat gcctcaatag ctgtgaagat   37740
agcagatggc aaaagaagtg gtaggttcta agtaggttcc ccttctctac tggttgccac   37800
agactcaaaa ggaattttta ctacaggaag ggacccaaat attctagcct agcctctata   37860
ctctgaaaag cagtctcttg ctctactccc tctgtgaatt gttaattcaa ttctttcaaa   37920
tttctcaatg gattctctgt ctagtgggtg tgggtcctgg gtgtctgggg atctcataca   37980
tgatttcttg cggtcaaaat acaaaaatgt aggcaaaatt ataacatagt agttgaattt   38040
ataattattt ggattattga agtacatcca taaaaagtat tttataagtt gttttaaggc   38100
cttgacctgt tcaacatatt tcttaaatgt atctcaattc cttctacatt ttgctatcat   38160
acgtatcgcc atttatgtct aggctaccat catctaagac cacaataata ggtaccaact   38220
tatcttccca cttttgtcct ctgcaattga aaaataaatc aggggttttta cttctgacca   38280 aaatggaggt ctcaggtgtt tgactaaagg tagtatagca ctgtgatgct aaaataaggg   38340
aaagcaatga cgtgacattg agtgattgtg agtggccaac catccccatt ctcctagttt   38400
gcttgggact gagggagttc ccagaacatg agactttcag tgctaccact gaaaatgtcc   38460
tggccaaacc aggataagtt gttcatctga aagccctgtg ttttaccaa ttgacagctt    38520 gtagaaagtt tccagtctgt agtacaggaa ggagagactc ttatatagct tgccaggctt   38580
gagttgagga gatagaagca aaaatttaga gagacaagga ggctagaatt tgaagggtga   38640
gtagtaaaag gaagaaagct gcacaaagag ggagacagta gactacagat gtgcagaagg   38700 gtcccttttca gttaattgag ttctgatctc accattcatg agagatgtct tagtctgttc   38760
tgtgtttcta taatggaata gctgacactg ggtaatttat caagaaaaga ggtttatttc   38820
aatcatgctt ctggaggttg ggaagtccac aaagcatagc accagaatcc acttggcttc   38880
tcgtgagggc ctgtgctgca atagaacatg acaagaagta aaggggaag cagacagaga    38940 tcaaacacaa gaggcacccc actctcctaa gaactaatcc atccctgtga gagctaattc   39000
aatcttgtga gagcaagatg gcacttctca caatcttgtg agagtaagaa cccactgacc   39060
accgtgagaa tcgcaccaag cttcccatga aggcagaacc ctcatgaccc aaatgtctcc   39120
cattagattc cacatcttaa agttccatct cctggcattg ctgcactggg aattaaggtt   39180
ccaacatgag ttgtggagga gacactcaaa ccgtagcaag aggcaactat ctgagactgg   39240
```

```
ggaaagaaat atcagaaaaa agtaagtgaa aaacccatgg accctcacac agggctgcaa    39300
ttagtttgtg atcccaaaag aaggaaagga aattgtcata atccaataaa cattgggtag    39360
aatattcaga ggagccctgt gttagtaatg aggataaatt agccttaggc taaagactat    39420
tctggaccca tcctaacaaa gcttacagga taggatccaa ttgcttccaa ataactgtgt    39480
ttcagaaaaa caaaaacaa acaaaaaaaa actaacatta cttaaagaaa tataacaaaa    39540
tccataaatc aaggagcaag tcaagaaata gaaaagaat cagaaatgat ggagatgctg    39600
gaactaacag acaaaaatct aaaactatta taaatattcc ctacatgtcc agtaaggtag    39660
aggaaaagat gagcataata aagagaaaaa ttgaagatat taaaaaatac tcaaatggaa    39720
cttctagaga aaacaattat aaatgagtga tcaaaaaata aactacaggg ttttatagaa    39780
aattggacac tgtaaaagaa atattggtga acttgaacat aaagcaaaag aaaatgaccc    39840
caaacaaaca ctgagagtaa aaaaaaaaaa gacaaaaaac ccccagaaaa tcagtgagat    39900
atgggaaaat ataattgtta aacctacaa gtaattgaag ttcaggagga gaagtggaga    39960
atggaatatt ttgaaataat gatgactaaa agttccaaaa tttgatgaaa atgataaccc    40020
aaagactcaa gaatttccat gaacctcaag cagaagaaag gcttttaagc aataaaggaa    40080
gctaagaaaa atcatagtaa aattggcagg agagtgggaa gaacagtgaa aaaaacattt    40140
tttaagagca accagagaaa aaagataggt tacatggcaa ggaacaaagg tgagaataat    40200
gccatccttt ttgtcagaaa ctatttaagc caaataataa taggcatctt taaaatataa    40260
aaatgaaaaa aaagttaatc aagaattgtt tatacaatga aaatatcttt caaaaatcaa    40320
gtcaaagaca gattttcaga caacaaaagg aggagatgac tcataatcac caagtgtgca    40380
cttaaacaaa tattaaaata aattatctag gcagatgaaa aatgataaca ggtggaaaat    40440
ttgggcctac acaaaggaat gaagagagaa atgaataata tgtagataaa tgtagaacag    40500
attttttatt cttttccagc ctctttaaga gatgaataac tctttaaagt taaaaacaaa    40560
aaagaacaaa ttctggagtt tgtgtcatac atagaagtaa aaagcatggc aacctagcac    40620
aaaaggttaa ataggaaatg gatggatact gatgcaaggt ccatatacca tgagtgaagt    40680
cgtataatat tacatgaagg tgaactgtga taaatttaaa atgcatatgt actgtaaacc    40740
tcagaagaac cactaaaaat agttatgtct aacaagacaa tagtaaaaat aaaataaagt    40800
aataaaaata actaataaaa ataataacag ggagagagga ataaaaaaca aagagaagac    40860 aagtaaaatag aaaacaaata accaatatag aagatttaaa accaacagta tcaatagcta    40920
cactgcatgt taacagtcta gacacttgaa ttaaatggca gatactggcg ggattggatt    40980
aaaaggcaat acccaactat atactgcctg aaatatagta cttaccaagt ggattttaa    41040 aattaataat aaaagaatgg caaaagatat accatgcaaa cactaaccaa agaaagctg    41100 gagtaactat attaatatat gacatcttat agttccaata tttatagttg gaaaattaac    41160
acctcaatct cagtaattga tagcaaaagt agacagaaaa atcagtgaag atacagaaga    41220
cttgaataac actgtcaatc aacttgacct aattaacatt tatagaacac tccatacaac    41280
aagaggaaaa tctacattct ttccaaggtc attcagtaag atagacaata tcctgggtca    41340
taaaacaagg ctcaatcaat ttaagagaat taatgtaata caaagtatat tctctgacca    41400
caggagaatt aaactagaac tcaataacgc aaatatatct gcagaaaact ccaaatattt    41460 ggaaccaaa ccataggtca acgaggaaat cacaaatgat atcagaaaag attttccctg    41520
aatgaaaaca aaacacaata tatcaaaaat tgtggaatgc aactaaagca gtgcttgag    41580 aatttatagc attaaatatt tatgttagaa aagaaggctt tcttaaatca atgatctcag    41640
```

```
cttccacctt agaaaactag aaaaagaaga ggatattaag caaaagttaa aaataaaaat   41700
aaaagctacc tttattgaac acttaccagg cattatctta agtgatttat gctaagtgtc   41760
ttttccaatc tggtcataac attatgagtt agtcatgatt aatatcccac atttcagatg   41820
aggaaattaa atcttgctga acttctgtaa cttccaagtt tatgtagtta accaagagcc   41880
agagttatta tttgaactca ggtctctatg ctgttgtaac ttcaacatcc tacagattga   41940
gtgtatttat accgttaagc atattttatt atcttcaggt ttgatatttc tttgttgcat   42000
atatattata catatatata aatactatat acacatacat acacgaattc ttcatttacc   42060
tagaaccaaa aggaccttct cctagcatgc tggagaatgt ctagagacca gacattgcta   42120
ttatcatctc tgaaaactgt ggcatcagtg aaatgaccta ccatgaagga tgtcactggg   42180
aagtctgtga tggcagtcca tgaataattt gcacttgttc ctgccagtct ttcaagctac   42240
atgatctcga gtcatggaga tatgggtgag caactgagta tcacagtgct ctccatggcc   42300
accataactc actcaagtct taatatcttc tcgcaaggat aaacccagcc tccttaaaac   42360
aaaatcaagc tcatgttctt tacatgagaa gccaaattca tctttctcca agcacaaagt   42420
agtaaagagt gctggacatc tgatttctat ttgtagaact gccaggcaat tattgtgtgt   42480
cttgggcaag ggacttgatt ttctaaatcc tcagttttct ctgttgcaaa atggaagcaa   42540
aaagatctct ccaatgtcct ctccttgttt gctgctttct gcatcttttc tcctacacaa   42600
ttgacaattt taactgcctt atcggtataa ctactgaaga atcagttccc aatatccatg   42660
aaggtaaaag tcagatatta ttattcatcc actccaaatc ctccaatgac ttcccatttc   42720
actaaaataa aaatgtaagt ccttacgatg tcctcacaac atagtttctc ccatccctct   42780
gtacagccta ttatttcttt ggcttttatct attattcctt ccctctgtat tagtcagctg   42840
ggttcccgtg atgaaatacc actgactgag gagcttcaac aacacaaatg tatttattta   42900
tttattttat tttattttat tttattttat ttttgagaca aagtctcacc ctgttgccca   42960
aactggagtg cagtggcaaa atcttggctc actacaacct ccacctccca ggttcaagca   43020
attctcctac ctcagcctcc cgagtagctg ggactacagg catgcaccac catgcccggc   43080 taattttttgt attttagta gagatggagt ttctgtatgt tggccaggct ggtcttgaac   43140
tcctgatctc atgatctgcc cacctcagcc tcccaaagtg ctgggattac aggcgtgagc   43200
caccatgcct ggccacaaat ttattttctc acagtcctag aggctggaag tctaaaatca   43260
aggtgtcagc agatttcatt tcttctgacg cctctctcct tgacttgtag atgactgcct   43320
tcttgatgtg tccttacatg gtctttcctc tgtgcacgca catacctggt atctctgtgc   43380
atgcccaaat tcccttttct tataaggaca tcagtcagat tggatgaggg cccaacctga   43440
aggcctcatt ttaacttaat cacatcgtaa aaggccctat ctccaaggac tcttagatat   43500
attagaggtt agggcttcaa tgtgtgaatt tgataagggg agggacataa ttcagcccat   43560
aatactctca cttactgtgt tccagctaaa ctggtcttct gcatggtctt caaacacact   43620
cttgtctcaa ggcttttgca ctggctattc cttctccctg tgccgctgca aagaacgatc   43680
atgtttgccg caatcttgta gttttaagga ccttttcata acctaatgca catgtcaacc   43740
catggccaga accctatgta agatttatcc ccaattttt ttttggcctc cttgctcctc   43800
tcttttaatt tgttcccttt ggcttcctta agtattaact ctaacagata acagctttac   43860
agtttggctt cccttgtttt attcaactca gtttcaggtt attataatgt cttcatttcc   43920
gatgtggccg ccatattgga tggtgctgaa tcacccattc aaaagaaatg tgttaatgcc   43980
agtttatgtg ccagtcatcg ttagtatctg gaaatacaca ggaaaatatt agggttagga   44040
```

```
ttaatgaaga ctaatgaatt cagtagtggt atacacagag tatcatcaga gcccaaaaaa   44100
ggaacattta tatgaaagaa tatcaggaag gcgtctggaa agagttggta ctacagctac   44160
agtttgaaaa atgagcaact tagccaggta tacagagggg aagagaattt tctagactct   44220
gttagcatca tgcatgaaag tatggaagca tgaaacagta tgatacattt acagaaaagc   44280
gcatgtagag aagtatgaga taatgggggct tgattgatag aaggctagag aataaaaatc   44340
atgtgtgcta agataattta tcttgaaagg tccagggagc attttaaaat tcttaacaag   44400
ggaatcattt ggtcggatct ccaatttaga acgtttagta ttccatcatt gaagacagtg   44460
acatgtaaga gtgagttctg gatgaaggaa gccaggtagg gagttactgt agtaattctt   44520
ctatgaagaa atgaggacta aacaagagc agaggcaaca caaatataat ggaaggtacg   44580
gctatatgac acagtaagga aattgaatct atagaattgg tgctgggttt aaacatgaga   44640
attgaacgag aagaaaactc taaaataaat cccaggtttc tgggtttggc aaagaaagag   44700
atgatgatat tattcatcat tagaagggag agaaacatta acttgcagac acattgagag   44760
tagtgaaact tccgtaagag ctgtccagtg aacaggtatt tttatacatt ttgtcaaggg   44820
caagaaaatt tcccattgat tggggcctat ttagttgcct tcttcttctt gcaagagtac   44880 tattttctc aacacacctt gtaatcttag gcaagggaa gaaggctttt atttggagtt   44940
gcttttatat gagaccaagt ataactaaaa agatatagca tatcctcaac cccacccagc   45000
ccccattcat tgcagcacct cctaaggtgt agatgtcccc tgtatcccaa aaacgtgagt   45060
ggtgactaag tgtgatgtgg cacaaacgtt gaccacacta aagtgaccac atagtacttc   45120
gctgctccca ctgggaaaca aaacataata caaatataca atgcttcaca gagtagcagg   45180
tgattctttt ttttttttctt aaagtcagat ttattgaggt atagtttaca ctaaacagtt   45240 tacttttgt aacttttaag ttcagaggca tcttttgacc tcaaaaacct agttaagtaa   45300
gcaaaggaga acttttttttt tgttttcatt tcactgatga ggaagctgat gattaaagag   45360
gttaaatgac ttgtcccggg tcatacttag tcttgagtaa gcaagattaa gtcttctgac   45420
tcttaattct gcttttttcca agatatcaca gaggatcttc cagaacagct tacttagaaa   45480
ggacatataa tctgttcctc ataacagttt tatggtaata ggaattaat cttctaagta   45540 atcaactcag gcttttccac ttaccagtga aattgcagga ggaaactata gaacttgaaa   45600
cactatcttc cacatttctg tattgatcct gtttgatggt ttgtgatatt aagggaatac   45660
atgactatca tctagtgttt caagaccaag cccttcaaag tagagtaagc cacaacataa   45720
aaagtgctta gttaccttct tggctctaga gagtcattaa atccaacctt tctcttctgt   45780
ctagctgcct aggagtggct tctgttttaa tcatcatcat cattatttgt attagtctgt   45840
tctcgcattg ctataaagaa ctacccgaga ctgggtaatt tacaaagaaa agagatttaa   45900
ttgactcaca gttccacagg ctgtacaggg agcatggata tggaggcatc aggaaacaca   45960
atcatggtgg aaggtgaagg ggaagtaggc acatcttcac atggcagagc aagagagaca   46020
gagtgaaggg gaaggtaaca ctttttaaaca accagatctc agccgggcgt ggtggctcac   46080
acttgcaatc ctagcacttt gggaggccaa ggtgagtaga ttgcctgagc tcaggagtct   46140
gagaccagcc tggcagcat ggtaaaaact cgtgtctact aaaatacaaa aaattagccg   46200
agagcggtgg cacatacctg ttatcccagc tactcgggat gctgaggcac aagaattgct   46260
tgaacccagg aggcagaggt tgcagtgagt tgacattgtg ctactgcact ccagcctggg   46320
taacagggtg agactctctg tttccaaaat atatatacac acacacacac atacacacac   46380
acacacacac acacacatac atatatttat ttatttattt atttatttat ttatttgtgt   46440
```

```
gtgtgtgtgt gtgtgtgtgt gtgtgtatgt gtatctgtat gtgtatgtgt atatatataa   46500
acaaccagat ctcgtgagaa ctctataatg agaccgcacc agggagatgg tgctaaacta   46560
ttagaaacca cccccatgat tgaatcacct cccgccaggt cccacctcca acaccgcagg   46620
ttacaattca acatgagatt tgagtgggga cacagagcca aaccatacca ctattttatc   46680
atttctatta agagttccct gcatttcaat ctggcctaga atacctgctg agatcatatt   46740
cttatgggta ttaagtgata gtgtcataaa ttaccatctg caaaatacta tttcagaagc   46800
tgtaattctc tgtcaagttc tctgttatat tgctacactc tgcagatttt tagaaagtta   46860
aatattatat atgtatactt ctgcattaat gactttattt tgattcttgt ggtatctcag   46920
gaatgtaata tgcaaagttt gtatagatgt ttttctttag tgtaatgaat tattaggata   46980
tgactctttt gtaaaaggga gaaagaacag taatttgaat ccctgcagag atagcaatgt   47040
atttggagac aatttgaaat gttttatctt tatctactaa aaattccagg ttgaaaagaa   47100
taaaatcacc tcctctctct aaatgcttta ctctggtagt attattatgt aattattcac   47160
aaaaaggtgt gttcttgtta cacaatcact accttctcct tggagatttc aaaaataaat   47220
agatgagaaa ttatgtccct caaaaaagac cacaaaagtt tatccagaaa actttccctg   47280
tattgatttt tctttaataa atgaagctac atgttttcat ttttaagaaa tataaaacct   47340
taacttgttc ttctctcttg atacagttta ggaggtcttg catgcattct ctaacctcac   47400
ctccttcccc tttctccaac tacactgtcc tctttcagtt cactgaacac tccaagctca   47460
ttcatgcctc agggcctttg catatccaga tatctccttc tgctcactcc ttattaccac   47520
catggtccat ttgaactgga tcctcccagt ttttttctcta tcacttcacc ctattcattt   47580
ccttattaca atttacaaaa accaaaaagt gttacttctt atctctcttg ccagctctat   47640
cagagctgct accacatctg tgttggatgt catgtataac cagcggctag ttccatgcct   47700
ggtacatcat tgcttaatat cttttttgttg aatgaatgaa tgaatggatg aatgacaaaa   47760
attcctaatc aaattttctg ttgctacctt ttatacttac aacttaatat tacatcctta   47820
tactctaaac tcatacatac ttctataaat aggagaaact ttacctacag aaatagcaca   47880
ctaagattgt aagcaggaga aagataactg aagttttttcg aatttagaat ctattctggt   47940
cactttctaa tgagttccag aatctatgtt cccatatctt tgggaagcaa ataattgact   48000
gttaatagct tttcaaatat gtcatcagaa tggcagatga ggcctgaaat tctcaatgga   48060
ttgacaaaaa gcccctgtcc tcttggtaga atgaaatata gtacttgtaa cacttcctta   48120
cttcccccaa attacttatt ctttaagtta cagaaaagga attccacaaa ctacaatgaa   48180
aactcaaagg aagtaattac tttaggtaat atacaagtta atactatgtc ttttgtttgg   48240
tttttcttca gacagaaaat aacccaaact ttttttttaa ttcattcttg aattttagaa   48300
accattgtta aagtattaat catttctgag ccatccgtag attgagttta ttcatccttt   48360
ctttaagttc ctctcaacaa acttagccat gttttatgat gtataaaaca tgctaaaata   48420
tttttaatct aaaccaaaat ggattttggt caggtatgct gaccctgagc agtcagtata   48480
tgacagggag accaaaacaa cccaaccagt tctgatttta cacaagttcc ttgccttctc   48540
ctttaacata tatcggaatt gctaccttag atggttcagt gttatgggaa gttgacagac   48600
agaaaatgca gtattatatt aggtcaaagg ttgacaaact ttcctgtaa agtgaatatt   48660
tcagactttg tgagacatgt actcgctgtc acaatgacac aactaagcca tcttagaggg   48720
aaagcaatca cagacgatat ataggtgaat atgcataagc aggtgcctta cttcaggctg   48780
ctgtcacaaa gtaccataga ctgggtggct tacaaacata tttctcactg ttctggaagc   48840
```

```
tgaggagtcc taggtcagag tgtctctctt ctcagttaca gactgctgtc ttcttgtatc   48900
ctcacatggc aagaagagga caagagagct ctctggagtc cctttcatga ggacattaat   48960
cccattcatg agggctaaaa cctcataccc taatcacctc ccaaaggctc taccacctaa   49020
taagatcaca ctgggtgcta aaatttcaac atatgaattt tgggaagaac acaaacattc   49080
agtccactgc agtgtgctat aataaaactt gatttacaaa agtacactgt aggccagaca   49140
tggcttgcag accatagtcc gacaaccttt gaattaggtg atcactacaa catgtaaatg   49200
aatatgcatt gtgtcttagt tcaggctgct ataacaaagt accatagaca tggtggttta   49260
caaatatgtt tctcacagtt ctggaaacta gggagtccta agtcagagag tccctcttcc   49320
cagatataga ctattgtctt tttcttgtat cctcacatgg caaaaagagg ataagagcac   49380
gatacctaga tgtatttgtg atggggagtc agccatttta acatttatta aacacccact   49440
aaactccaag gtttccagac agtgtcataa ataagcttca caactgatct gtattcagta   49500
gatgtgaaaa ttgaaactgc ctggttatta atctgtgtgg ccaggccatg aacccattct   49560
cttccgtcag gttcagccct taagcacaca tgccacagag tcaaaaacaa cctaggtttg   49620
aatcttgctc agctatttac tgatggtgtg ctgtatggaa aattactaga cctctgtgta   49680
tctcagaatc ttcccctatc tcatggagtg gctaggagga ttaagaaata aaccacaaat   49740
agcactcgct tagaacagtg ctctctgctc aacgcatgtg gctagctttg accacaattc   49800
tgcagacact tcaggttcca gagagttctt tcagaagttc cacaaatgtt tgatttaaat   49860
gctgctaaaa aatattttc actcttaaa ataccttaat aaaaagaaac atatattcat    49920
gcaatgtata ccaaattgaa cacatattct cattctatat gttaacttgt gttgtcagtt   49980
aacttttaca cagacattga agcaaagctt ttcctgttct tcctgtttat ttaaaaattt   50040
tgcagagaat tcaaggtaag ctgataaaaa taattcttac cattgtaacc acttagctgt   50100
gtgaatcaga attgtcttga cactgtgcag ctgaagtaaa aacaatctaa aattggaggc   50160
tgaggtggac ataagattct catctctaat attgtgttaa tcagaaaaac tttattattc   50220
ccattgattg gctttacaat aagtaaatgt tataaatcgg ttttaaagcc tttatatgaa   50280
aatgactcac tttttctgtt ttatatattt aaggtttcat gtaaatttc atttggagct    50340 aaaaaagaca tttttcagca gaaacattta actagtactt aactagtcaa gatctgcctc   50400
tttagattgg ggcttttttt agatcaagac ttgattctta cgtatctttt ttaaaaatta   50460
gactctgata attaggtcaa gacaaagagt tacccaagca gagttcttca ttctccttta   50520
ctctcctacc cacatcatta tgtcctagtg gccttaatag atatttctc cttagatctt    50580 tataataatc ctctgagttt gccaggcagg tgatattagt ctcataaatg aagaaggtga   50640
atgagactca aagaatataa atgactccca agggcatatg actaaacaag tggtagggtc   50700
aagactcaaa tcagaaggct tctgactact aatcgagagt ttttcccacc cgttttgatg   50760
tcaaagatgg ctgagatttt ggggaggggc tttgggagtt cagaggtgac cctttagcca   50820
ctgctgaagc tgatagagat gcaagatcag taaacatatc ttattctttg tttgtttttc   50880
cataggttgg ctaggctttc tagtgattaa aaaaagcaat gtagacactt gtaaagtgtt   50940
ttaatttatt gtcctggact ctgtctcact tgttgcaaga gtcatttgac atgacgcctt   51000
gctaagaaat ccacacgtag gtctcaaatt cagtcctggt tgatttccta gggtctatgc   51060
tccatgaggg cagggacagt actagatatt tgtgtccaca acatctaga ggcatccaat    51120 tcttatctgt tcataaatat atgatagaat caaccatcat tctatacatt tttctttaga   51180
tcttttttcc ttttgctacc attgcttttt ggaccattat tgcaggcata tcataaactt   51240
```

```
ccttggtaac tcttggcatt ttggtcctgc ctccctcaga tttttttctg cataatctca   51300
aagcatccag caatgcttct ccagcgcctc tcagaacaag gcccagatta tcctcctggg   51360
attcaagttt cttcatgata tgggcatgcc ttatgaatac accttcgctc tggtctcatc   51420
accgtccctg cagtcctctc tctatatggg acatgctcat tgctgctttg tgtctctgcc   51480
gttgcttgtc tgtttgccag cttttcattt ctctacacaga tccaaattgt acccatgatt   51540
tcctacctaa ttcaactcta attttctatg atccctgccc cagtaatttt agcccataag   51600
aatttttata gcacaaattt tgtacttaat gacacttgta ttatttcatg ggttagttag   51660
tgcaatctct atgaggctgt aggcaatcaa gtaagatatt taaattgtac ccacattgtc   51720
ctaccttccc acactgtaga cacctactaa attggagtaa tgtgtaataa aataatttat   51780
agatttaagt aattgaaatc atcccaaggc acagagagaa caaacaaaca tattcctgag   51840
acatgtctaa ttcatgtgcc atggttatct tgagataatt ttccactgta cttttaataa   51900
aagagacacc taaattattt catagtttgc ttttgttttt cctccttgag cattgccatg   51960
gttattgata tttattaaat caaatctgcc actgaagcat atataaccac tcaagaatga   52020
attacagcaa atatttaact gcctgcctgc ctttgaattg gttaatcaga atgagtgatg   52080
cattagctgg ttcaactcct ttcacctgga aagatggcta tcgattccct ttattgtgat   52140 ttaaagatt tgaggaaagt ctaaaagcat ttcaaaagat ttcaataagt aagacataat   52200
tctgcttttc ataaccacta aatgaaaaaa aaaactaaat acaaaaaaga ttcttcgagt   52260
aaaattctgt cattctccac ttttttattgt gttaaaaaaa tcaactataa tatgagtgaa   52320
agtcaagttc tgctggtatg tatgaaatga aagagaggt gctgtaggtt attaataaca   52380
ggggatgttt tgtacctgtt ctggaagatg aaatatgcatt tttgtgttgg agccagtcca   52440
taagtcaaat tccctttaaaa caggcagagg ccagccttgt tctggctgca gcctgcacgg   52500
ccagaaaaac agaggaagaa gcgccttcca ccagcatgaa atgttatcca ctttgatatg   52560
taaacattct tccttcacct gaagttgatg tcagggtaac taaaacacaa gaacttggtt   52620
gactgagcag aagcaatctg ttgtattctt ctgtttttca aaaccagaga taatcaagga   52680
ctgttatgtc agatgctagc tgacctaact tttgagtgga aaacgaacca ggaatctgag   52740
ataactggat agtctccgca tattttaaaa aaatcagcat gtctcttgaa actgctcaga   52800
cttagctgat ttttgtagtt gttgttgttc tctttatagt ttttttttctt tttttctcgt   52860 attccagact cctggcattt aatctattgg gtgggaataa atgacgtaaa ttgtactcat   52920
atttgcaaaa agcccaaaaa agatgttaag gctgttaaca acagacgtct acgctacagt   52980
tgaaatgggc taggtgaatt gagacagaat tctatgaaca ttttatgaag ctttccttaa   53040
atttctaatt gaaaattgct actgtttgtg ttactgttga ttcatttcat ttaagtcttg   53100
gtcttgtaga ttctattgat accccattct tggggatgaa aaacaatgtt aaatgcgcac   53160
atttgttagg aaaatgggct gggtgggaga cggaaggctt tggccgccat cctagggcat   53220
tcctgtgcat tgcgatggtc agcatttctg tatctaaaca tcgaaaaagt acaataaaaa   53280
tacagtatta taatctggga ccactatcat acacgcagtc tttcttgacc aaaacatcct   53340
tatgccgtgc gtggctgtgc tgagaaggag gagcactcgt cctctccaag cacatccaat   53400
ttgcctcagt cctcatgact cccgcccgtg taccagaact gagctcattt gttattgaag   53460
ttgcttttct tatacccagc ccagttttcc attgatgctt ccgcttattc tatgtaggta   53520
ttttcattta tcacacaata tccctagtct aagacttcat ttgaggaaag aaaaaaaaaa   53580
aaacctctgc tgctaaaaat aatttgaaaa ctcctagaca ataggacctt tcaaatccct   53640
```

```
tacaattcta acaaccagtg aattcatgct tcacagccat tcagatctat acgtatgaaa   53700
tacaagacat atgtgttcaa cttccttca tcgcctcctt taaactttct tttttctttt    53760
ttgagtcagt ccctgcagga acagaccaag tgagcccatt aagagaacag ttcattccca   53820
cctgctacct cgagccagcc aacaatctca gcctcaccac tccattcttg attatgtaga   53880
accattccaa tcctgagtga caggatttgc aaagacagct gttgggctcc acaaacattt   53940
ggaggagggg aaaatgtgag gttggttgct acattctcct acttcttttt actgaaagga   54000
acagctgcga tcttcacatg taagatgaag taaacaaaag ctgacaatgc ccagcaccat   54060
tcagcagtaa gcattcaaat ggattttcc tcaccgcgtt tgcaggcccg gcacagtctc    54120
agttccccac agcacagaga ggaagcaagg tctttgcatg ccctgttcac ttggccaaac   54180
attgccctag atgtgcaatt caacccatat aaagcaagcg taattcaaga gccctgactc   54240
tttcaccatt tcatgatggc ttattactcg cacacggcat tgtcaggttc agcaactct    54300 gtgtgcagca ggcagaaatg cagtgtttat ctctgacagg caaacattct taggctcatc   54360
ggcatgagta tccacgctga actggctatc ggggaagtag atccctgcat gggaaagtca   54420
aggtatgttt agagggactc gatgattcaa ccccattggc tggttcattc cttttgtttc   54480
ctctgccttt ttatttgctt acacagaaaa cagagcattc atttatttct tttccctctc   54540
tcatctctat taaccactag ggccatctgc ccatctgaaa ctgtctttgg ctgcatggtt   54600
gtgaatccag gtgacagtga aaatgaagaa gtggtgattg tccctgcatg ttttctctga   54660
agggttaact aaaaaaaaaa aaaaaaaag cctttgtgtc tgtttcgagt tctccagttg    54720
aaatactgta ctcattgaac tgcaagaaat aaaacctgca agtaggcact gtgctaatgt   54780
aatagaaatg tgttagacag gggcactatt tcttaaatat gcttgaatta agcaagttct   54840 tttaaaagt gggtgggact tttgatgttt tacatagtta tattttcaat ttcttgtgct    54900
cagtttaaaa ctcaagattc tttgtttctg tgtgtgtcat tagggcaggt gttggatgac   54960
aagtaaatgc actgaaaaat gaaaaaaaaa gatttgtgcc ctaacctcca tgaatttggt   55020
gacttaatat atccatacag atctgacttt taatcaaagg tgctcacagg tggggtaagg   55080
gataaggagg aatttgtcta caggatcctt ttatcctaag ttgccttaca acatccaatt   55140
gtgttaccgt tttttttttt tttttacaa acccattgct aggctaagaa gtattgattc    55200
catctagtta aacatgtcga gtgagaggaa gtgatcaatg gattacttct tcaaaacatt   55260 tatccccct agtggaatcc tctgattttt ataacattaa agagccaggt ataggagttg    55320
ggagaagaat ttaaaatttg aaatgtcttc ttttttcaac tctgttcatg aaaactctag   55380
ttaatgcatg tgatttcctg ggtctccctc tctacttccc tccattatca ccaccttttg   55440
ttgctgctgg ggctgtgggt gccctgaagg agcatgagat ggccttcctc agatatctgg   55500
gttttaaatt cagttcgtat ctcttaagtg aagtgggtag ggccaaaaat gactcactgc   55560
ccagtggtgc ctggaaacat tatcagcaaa gacattcacc tagggagaaa ataaacacag   55620
aattctcata tgggcccatc tttccaacca tctcctggac tttggtagtc ttttctgagc   55680
cagatatctc tctaaagtca cttgctgtca gaccttttg tctcatattt aggaatggct    55740
gaagttcttt ataaatccca gatgaaacag gaggaaaact actttgaaat gatcatttcc   55800
atgatctcta aaatgcaaca aaccgtattt cttaagatta acggatgcga gcctatgaca   55860
ggttcaatgt gggaccaact caagggaaat tgatgaccga attattaaaa ggcattcatt   55920
acatcgcagt ttcacctgaa gaggggggtgt ccccccagtag tgcttctgca gcagaattgc  55980
ttagaaactg cagaacatcc acaaggcaag caccccaggc cattgtgtct gactgtcttt   56040
```

```
caaatagagg aatggctagt tgccatttgc tgagggcatc tcctgcactg agaactgtgt   56100
gcatatatgg atgatatcgc cgagactcac aagtatgcaa gatagaaact aggtgcattt   56160
ttttcagatt aggaacttga gaatggaaga taaactgaga aggggagcag ggaggatag    56220 ggagagattg ggcaacggtt aagaagttac agttaaatag gaataaatcc tggtgctcta   56280
ttgcacagca gggtgcctgt ggttgacaac attgcattgt ctatttcaaa gtagatagaa   56340
gagaggcttt tgaatgttct caccacaagg atatgataaa tgtttgaggt aatggatatg   56400
ctaaatactc tggttttgatt attacatagg gtatgccagt ttcaaagcat cacattttac   56460
cccataaata tgtacaacta tcatgtgtca attaaaaata aaattaaaaa aaatttattg   56520
ataaaagaat aaaaaatagc atgcttttgg ccactctatt tgataggcat catttaaaaa   56580
acataagact ataaggctgg gcatggtggc acatgcacct gtactcccag ctatttagga   56640
ggccgagaca agagggctgc ttgagcccag gagttcgaga tcagcctgag caacacagtg   56700
agaccctcat ctttaaaaaa tatacgtagt atagatgatg taaaaggacc acctttccaa   56760
atgagtcaat tcttcctta atttaataca ttcctaggta gtaagttttt agagagctaa    56820
actaattcct tgctatgtct taggttacca tttataagtg ttcttatggg ggttagcttc   56880
attttatgta ctaaacactt atttgaaagg atcgttgcct ttttccatgt gctaatttgt   56940
atagagagtt tacgtattgt gggaatttaa tttattcctg cattttatcc aggaaaatag   57000
agccagatgc ttttggacac ttgttatttg cttttaaataa gatatcaggt taagataaga   57060 aaatatatt gattggatat tgcgtcttcc tctggagaac gtaaaacctt tcacgtccta   57120
catctcatca taccttacaa ctttagaaca gactctaata aaaggaaaat gttttaactg   57180 tcccttttact tatagagggc agggatggga aagtgcactc aattatacta acagagctct   57240
caattaatct aaattcaaag cgaaggctcc tgttgtggat cagggaccct gaataaacat   57300
gctttctagg agacttcacc gccaggttcc aagagaggtc acagtactcc tgcactcctg   57360
atggcagacc cttggattcc attgcaggca gtgacacacc aagagtaaga ggagctggct   57420
tcagccctgt ccacgtgtgt ctgctggctc gcccttctgt ctggcatctc cacgcccctc   57480
ctcttccgga ctcccttgca tgaccttcca aacagaatga gctgttcttc caaatatgac   57540
cctaactcat tcaacagctg gaggcaagag caaactagag ctcatgcaaa gggtattagc   57600
attgagtctt tttttttcccc ctctttctct cagactaata gatatttgga aaattcatct   57660
aaaaaccttt tttaaaaaaa tttcattcat aaaaatagcc aagggggtttc tcagagagtt   57720 tccttttagc aagtcttttg gaaggaataa atgtctactt tattattttt ccttcctgtg   57780
cctgacctcg gagaggatta gagggtctgg gcaaggagag gagcctcaca cccagccacc   57840 cacactttc cttctgacga gacccaccgc catgccatgc tctgtacaag ttctctggag   57900
gaacataaga gccaccttat gtgtgaggga ataagaccat gctttgaaga gccagacttt   57960
ctccttttac ttgctcttga aattgttttc actctgatct gcaagtcaaa gaaatgatct   58020
attatacatg tagggacctc aaaatctgtt tgactctgtg caaataaggt acagtccctg   58080
ccttcttcct atagtttttct tatcactagg ggacttgaaa aggatttagt tcaacaactg   58140
agtcagcatg agctcacaca aaacaaatcg tttcacacca atgtcaattt ctttctttct   58200 tccccccgc ccccacttt ttatttaaat aattcggtca gggaaatccc acatgcttag   58260
tatcattttg tcagcaaggt acatgacaac tctggtcaca atagaaagtc gtttagtgaa   58320
ttaatgtcaa ctctggaaaa agtggctaat gtgtcttggg gagtttggtc cttgcctgta   58380
cacctgcctg aagatcacaa gagtaagaag gacaggtaac acacactgaa tgacaggatc   58440
```

```
agaggttagc aatatctcag aagcctgcca tatgagccaa acccaataca aaacaattta   58500
gcaatattaa gtaattatca cattttgtac ttcaataaaa aatttaatat catgactttg   58560
cggtaggaaa ggccaagttt aatgttggtt aaaaatagtt tggagattat atttgtctgt   58620
cttcaatatg atgtttcttt caaaatatcc caaataatct gaattaagag tagaaataat   58680
atctaccatt tattgagtac ctactatctg ctaaaataac aaatttataa tgaaggtgta   58740
actattccca ttttacagat gaaaaaaatg gaggaggtta agtaaccagc actaagtcaa   58800
aatggctagc aaagatcaaa accaacatgt tagccaatgt taggcagttc aagtcctttc   58860
ctctgtgcct gaaatgaaag aaattttcca ggaattttgc attggttatt catatcaagt   58920
ataaaaaatg ttattcattt caatgaacca aaattaagtc aagacactta aggactgtct   58980
agaggaaaat gaccaggata ggaaagagtc tggaagccat gcaagaaaag acacagatgg   59040
taaatattta acatgaaaaa tagaagattt gtgtgggata taggagatac cttcaaataa   59100
tgaagacctg tggtcaactg gggcaaatat tttaacccca aataagttct tcaacaataa   59160
cagtttcatt acaaataagg gaagagaaag tgcccaaaat gagcattctc agtcactaga   59220
tgcagaatca gaaagccacc tgccagggct gttattgagt gaaattctga ctttgaaaac   59280
atttggccta tacgagggat tcttaatctg atatccatgg aagaacttta ggtaaagtct   59340
ttgaatccct ggaaattata tgaaaaattg tatatgtgtt ttttttttctt gggaaatggt   59400 ggatatattt cttcaaatcc tcaaagcaat tctacaatat tggtggggca gtgaaaggaa   59460
atcacttcca attctacaat tctgtttttgt aaaagtagtc ttacccttca cagaggtgca   59520
cccaagagaa ctgtgtgatt gatttaatat taggggtgaa tgaacataaa caattgaaga   59580
aaacttcaag ttttttagcc ttgtaactaa gatgttcata caatttttaa aaatctttaa   59640
taaaagagaa gcaaatttag tggaagataa ttaagtagaa ataaataggc aaactgaagc   59700
ctgtctaaga ttccagtact gagagtactg agtacgtaat tcaaatattc ttttacatca   59760
tggcagaaaa atgctgaaat ctagggatat atgctgacta gtaactgagt cttatataaa   59820
taattttttt aaagccactt gaactttaga accataaaat gttataacac taactgttct   59880
agagactact tacttcagtc tcctaatgtt acaactgaag aaatcatgtc tcagaaaaac   59940
taagagacat attctggatt ctggggcctg gttcctgatt cacgtctctg tctgcaaatt   60000
taaggaaaaa aaattctaaa acattcaaat ctggaataaa cctatgcatt tttcaagaag   60060
aaaatatata tataaaaact agtcttaact acatataata cacaaaggtc cactttgtta   60120
tggtataagg caagaccgta aggaggtctt atgcctcctt atgaggcata agattgcccc   60180
ttacgagttt taaagtatga attccacacg tcagcatgct ctgggatgtt ttcacagtat   60240
ttttaacatt ggtcctcata gtcttaattt acctctggaa atttccatgg atgattaaac   60300
tatgaagaac aaagaagcac atggctgtgt tatttagagt ttagtgaatt aggtctgcaa   60360
gtctgttggt ttcctttttag atgttgtctt gtccgtttct aagatcagag ggagaccagc   60420
tccaggagtg ctcatgaatg catcagtggt cttccatacc atctgatgaa aagattcatt   60480
ctgtgtctca aaaggatatt ccagatccag ttctgagtca gcaggtcttt ggtgtatata   60540
tatatatata tatatatata taaatttttc cactgcttta tttttttaaa ttcatctgac   60600
aaggtcaagg tgggattgag acaagaaaaa tttggaacta gtcccatttg agacttattt   60660
ccttaaaaaa ggaactgttt tttaataatc tgaaagttta cataattttg acatgcaagt   60720
tatatacgtg tgtgtgtacg tttgcatgct tgtgtgtatg ttcatttttt ttaaagagac   60780
tcaaactaaa taaaattttg attgggggtg ttgctgaaag gactatagtg tcagctgtta   60840
```

```
taacttcagc tttaaacact aaaccaaaac atgggctaca tgttccaatt catactgaag    60900
ctttataata tatggcctta gagtagaagt ataatgatct cttgggagag gcaagatcca    60960
attaaaattc agtttgctgt cttttggaaa gacataagca gttatatatc ctttgagacg    61020
gtcttaagaa atacacacct gagctttaaa tggccactca tttgactgtg aagttgaatt    61080
tcaattcatc tgggagtcag agcacaagaa agaattcaaa taacaacact ctgatatttc    61140
ctggtgtgtt accagggaga aaagagctcc tggaaaatga acgccttaca catttgcaga    61200
tattaccaac cacttataaa acaaggcta ttgttatgca taaaagtcat tccttttagg     61260
ggaagcctaa gagtgaattg aaatgtggct gacatttcta ccacaagata aaatgttttt    61320
ttaatatcat gtttaagttc tcttagttaa aaagagaaa agggaaaaaa agaagaagaa     61380
agaaaaatat ctataatcca gtattcagaa gcaattccag acacttcacc catgaaataa    61440
ctcactggaa gacattacat ttctaaacac aaaagctatt agcagccttt tctaattctc    61500
ttttagttca ataagggaat tattgaccgt attttgcaat cccacatgtt tttaaaagac    61560
aaaaaacata gtacattgaa cagaaaacat acgaatgctt tctatttaat ttattagttc    61620
atgactaaga tgaaacactc caacatatac aataacctcc ccaccccac ttcactctga     61680 ggttcttttg gttacttctt ttttacaaca aaggtttgat gtattcttta aaatatataaa   61740 agaaaaagcc actatattgc ctcagaacta ctccatctca ctgcctcact ttaaattctg    61800
attgactgta atgagaccac agacagattg atgaaataaa tttagatact aaatagcatt    61860
gtacttgggg tgatttagtt atatagctca tttatttctt caacaaattt gttgaacagc    61920
agtattagtt aaggcaatgc aagctgatgt cataaataaa ccccccaaatc acaatggcct   61980 aaaaccttaa aggtgcaatt tttattcatg gaagcagggc aatgtaagta actacaggat    62040
tcaggcagcc agaattcttt catcctgtgt ttccatcatc ttctagagct tcaaagtctt    62100
ctgcatttat ccaagataag agaaaagaaa tttgagaagg tgtacctgtt tttagccatc    62160
ttctgctcac ttgctcttgg aattaacaaa tcacacaacc atacctaagt gcaaagtggt    62220
tgagaaatgt atttcctgat gggacaacca ccttccagtg ataacttcac actctgaaag    62280
ggctcagctg caacacctgt aataatactg tgctggacat tgtggaattt tctaaaagaa    62340
acaaaactgg gaccttgtct tccacgagca tgcacgttag caattttttg caaggaattt    62400
attcccttac caataataat agttaatata tatataaagt ttgttatgta tcaggctcat    62460
tattggacca gaggctgtgt gggtggtatt tcaggactca aaccctggta tctgcgctgt    62520
ccaaattcat gctcttgcct cctgccctcc gtagacttct aatcacttaa ggcaagagac    62580
tcaagtctag ttctcttaga agttcctacc acagggcaga gcccacacca gacagtgaag    62640
gaatgtggat tatactaaac aaaaccctag gatcgattgt ataggtaact gttggcaata    62700
aattagagct caattccaac tcataaaaag ctgtactcca aaatacaatt caccataaat    62760
gaaagctttt taaagatatg agttgcctat actataaata ttgatttttt ttcatctgag    62820
tcaattgaga tgcaaatgct aatttgagta gatgagcata tgagcattag tggaaaaact    62880
cacctaaaaa ggtacaagag agagcaagat gcccaagata gattaacaca acactttaac    62940
cagaatgttc tatcattttc tttctgcaca tacaccttct aacttgcaaa tctgtcttgc    63000
ttcacatgat ctcttcccat ctaatttgat gggttttttct ctgaaagaaa tgaagggagg   63060
attcctccag ttcttgtttt ctatggtaat tatcctaagt tttaggggaa gaattttaaa    63120
agaggaattc taggcactttc tcaacttgga gcagaataga gatgtattcc agtaaggaat   63180
atagttcatg ggcataagtg acttgaatat gaggtagaat tgggggtaaa taacctatga    63240
```

```
aatgtataga tgatattcta tcagacaaga gatattacct atagttttac aaaagaaata   63300
aacttttagc taggccttttt agaaacatgt aaaattaact gagtttacca agtatagaaa   63360
aaataggaaa ttgtcattta gaagggcatg atctattcag ctagccaacc aagaaatatg   63420
tcgagtgctc cgatgcaagg tagggtatga agagcagtgg ggagaagggg gcagtgaaaa   63480
gtgcaagaca acacctattc ccatataggt cagcagctaa gagcaacaac aaaagagaac   63540
aatgggcatg tacagtgcat ccacctgtac caggtaacat gccaggtgaa ttattcaaat   63600
tatctcattt ggcactaatg catgtaaagt acatagcaag gtgcctgtca cagaaagaat   63660
gtacaataag tgatagctgt gatttaaatg ccagttttat gtggaggtta ttatctgttt   63720
tcaaattaaa gaaagtgagg catggtgagg ctatgtgatg ctataaactg aatgttttta   63780
tccccacaaa atttatatgt tggaacctaa tcacgaaagt aatcgtgagg ccccgtaaag   63840
gtagggtctt tgggggttga ttaggtcatg aaaactccac cttcatgaat gctgttataa   63900
taataataat tagtactctt ataagagagg actgggggag ctcatttgtc ccttctacta   63960
tgtgaggatg tagcaacaaa gtaccatctt tgaagcagag agtgagctct catcagacat   64020
tgaatctgtc agtacattga tcttggactt cccagcctcc aggaccgtaa gcaataaatt   64080
tctgttgttt ataaattatc ccatctgagg tattttctta cagtaggcta agatagatga   64140
tatatccaaa gccccttagc tggagaaacc agacatacac gcatgaaaag ttcaataaca   64200
atgagattct ttgtgaaagt tgctctcctg gcagttctat tttactagta gaatattcat   64260
cttagttcat gggttgttat tcctcaatct ggctgctgag tgcccttttgg gtgtttatga   64320 ttttaactgc ctgcccctgg ttctagttgc ctgggttagg caatgagggt attttgtgca   64380
aattgtgtcc tgagtgccta tgctgcagct ccccatgagt cttccattct aattctaatc   64440
aacttccagc tatctatctt aagcagagta ccttttagga cagggtgata gggggagcct   64500
agaggtcaca tgcgaggcct cccatctgtg gaggtttagt tggagagagc tgacaatgag   64560
atgattcctg tgcagcagta gtcatgaacc tggggcagga atgagagcac catgctatct   64620
cccagggccc agagagtgtg gccctgagag acagatcagt gaaatctcta aagagcaatg   64680
cgccagattg atgagattat cttgggggta cttgctagtc tctttggctt cggaggggcg   64740
tggagggagg ggaacagata ggctcagatc ctctctgccc ttgaggctgg tcaaacatat   64800
tgcaggtttg tagagaagtg tcttctcctt gtacttgtac agatgatttg ctaaccggac   64860
ctgaaactgt cctatctccc tccattccag tgactcaagt gtcctcagag ctaatccagg   64920
taactagagc caggggcagg cagttaaaat cataaacacc caagggaac ccagcagcca    64980 gattgaggaa taacaacaac ccatgcccca agatgaacat tctactagta aaatagaact   65040
tccagaagaa acagatgaca actttaacaa agaatcaaaa gtatacttac aaaaattgaa   65100
aaatagcatt aaaataactt tccagcattc aaaaacatgg cttttcaatt aaaaacatca   65160
attcagttaa ggaaaggatg gcctaggatg agacagactc acttgcaata taagacatta   65220
tagggtaaat accaaatgag tcgttttgat tctcaggtgg aattgaccat tagactcacc   65280
tgttaaaaac acagacttca acttacccag ccctaataaa tcaggaactc tggaagccga   65340
gccaatgaaa gtgcattttg gttggaagtg gccactggtt ttgggcactg gttatggggg   65400
ctgtggaaac tggcagtaca tgttaatga gttatcaggg tgagagatca ctgggtctgc    65460
agggatggtg gtaaggaccg cgggagagag atgagaactg aaatgagcat gagaggtggg   65520
tagagtttat tgatagtgac ctaaaaatat gaaacaagga ttgatgaatg ttttgtctgc   65580
atgatcccaa gttttcacca gatttagaca caaatacttg tcacacccgt agatcaaata   65640
```

```
gcaagtctaa aatttttta  agtttagctt taaataatat aatacacatc agataaataa  65700
gaagttgaag tatcgcgatt ttgcaaatgt ttaggaagct tgtgttcatc cggttcacat  65760
ttccttcact ctatgtgtgc atgtttgaaa ctgaaatata caagttaaat ctttagtctt  65820
acttttttaa ccactgacaa tgatgatggt ccatttatct cccaatgttc catttcaaga  65880
cagatggatc agtttgtcaa ggtctgagta ggaataaatg gagtgctcca aaggcaaatc  65940
tgtagtggtg tgttcaattt gataaaatca cgcttgcata ttttttttcct aaatttcctg  66000 aaccactcca ctaagggaga caacctagta cttcttggtt ttttttctctt caaatggctg  66060 cttctgagtc acagatgtga aataacagga atcaaaggat tcatggatca agaaaaatga  66120
ctcctgatca tttccagtag gttatttcct tggagctgtt ctgctctgcc cccaggaggt  66180
gtaatggatt tgaactaaat gtaatcaaaa attttcacct gcatcctat  ttcctgaaag  66240 tagctcagtc ccatgaagct gaactttctg cagctgtgag acccacggca tggctgcttc  66300 cttagggaa  ataaactcga tgtttctctg agtcagaacc acagaacaac agtctcatga  66360
aatgctctat gccaaacaaa aagcactctg cactcagatt tgggatgaga ttcacatgcc  66420
atcagctctc agagggtgat agagcacatc caagcttctg gagcccctgc agcagagaaa  66480
tcattttatt cataactctc tgtaacttag tcacttgtat tcattttga  gtgctgcctt  66540 aacaaagtaa caactgggta gtttagacaa cagaaatgta ttgtctcaca gttccagagg  66600
ctagaagttc aaagtcaaag tgttggcagc tctgtcccaa gcttccctcc ttggcttgta  66660
gatggctgat ttcatgttca cagggcattc tccccatata ggtgtctatc tccaaattcc  66720
atctgtttgc aaagacacca gtcatagtgg attagagtcc atctaacgac ttcatttaa   66780 cttgattacc tctgtaaaga ccctatctcc acataaggtc acattctgag gtactgaggt  66840
ttagaactta catctgaatt tgaggaggga gatgtaattc aactgattat accactgaat  66900
cctttttttc ccatgtcatc tattaacagc ctgaagaaca cgtttagagg gatgttactg  66960
tggcttcaca gataccatgc tcttcctcaa tggttcccaa atgccatttg cagaatatat  67020
gcagaatcac tgggagtgct ttttagaatt ctaaatctgc caggcatggt ggctaacacc  67080
tgtaatccca gtactttggg agaccaaggc aggcagatcg cttgagccca ggagttcgag  67140
accagcctgg gcaacatggt gaaaccccat ccctactaaa aatacaaaaa attagctggg  67200
tgttgtggca tgcacctgta gtcccagcta cttgagaagg ttaggctgca atgagccatg  67260
agcccatgat cctccactgc actccagcct gggcaagaag agtgaaacct gtcaaaaaaa  67320
aaaaagaaga attatagatt cttgggtctc acctccacaa attaaaatcc actggatcta  67380
aggaggaact caggaatttg caatttacaa agttgcccag acattctga  tgcatcacca  67440 ggttggagtt ccacagccag ttagtgctcc cttattattt tttagacttg atttgggcca  67500
taaatcttat aatagctacc taagaagtac acttcttctt taaacaatat gaacatagaa  67560
ttgttttctc atctctgttt ttattacatc ttctatcttc ctccactgca gtacaaacca  67620
cttgatgtgc atagattctg ccttactcat ctttttattc tcagtgtgta ccagagaatc  67680
cacacataaa taacattcaa taagcgttta ttgaagaaat aaatacctcc agcaacacag  67740
gcaaactgta caattgtttc atcatttaaa gaagttcctg gccgggcgca gtggctcatg  67800
cctgtatccc agcactttag gaggccaaga caggtggatc tcttaagctc aggagttcga  67860
gaccagcctg gccaacatgg tgaaacctca tctctattaa aaatacaaaa aaaaaggtag  67920
ctgggcatgt tggtgtgcac ctgtggtccc agctactcag gtgattgagg caggagaatt  67980
acttgaacct gggaggcaga ggttgcagtg agctgagatc acgtcactgc actccagcct  68040
```

```
gggcaacaga gtgagactcc atctaaaaaa aaaaaaaga aaaagaaaaa aagaaaaaga    68100
aaaaagaaga aaaatgttat tgacattgac atatctttat acttgagaga attcagctac    68160
tcttaagagt ttaacccgtg cagccatgcc cgctgtcctg actcattttt actcctgcca    68220
tgatagctta cctgtggttt caggacacat ctttcttttt ccagcctcaa ggatcttttg    68280
cacatgctat tttggaactc ttctgcctac cctctttctc cacccatcc ccagttgcca     68340 cgactatttc caaatgaata tttgttctgc ccttcaaatt agaagtggtg ccctgttaa     68400 acgttttcat aatgcttcat ttttttttcc atggagacac tgatcatgct tgtaatgaat    68460
agttcaatgg ttgctctctc tgacaaactc taatctacat gtaggcaggc ttcatgtctg    68520
ttgtgttcat ttttgaagcc acagaaactt gaacagagta ggaactcaaa tattaattga    68580
gtcgttatgc gctttaccat gattatgtgt tttttcccac cattaaactg ggagcttctc    68640
tacagcaggg actagattta atttattttt ctattttggg cacctggcac agtgcctgga    68700
aggcagaaca agcacaataa attttcttaa aatttgtaag gttttgtttt atttgaatgg    68760
ttgtttagtt tttgccttga tgaaagcctg ggatagaaat ttagaacaag gttggatgtt    68820
ggtgatcata taaaaataga tttgttcttt tttgtcatta gagcccaaac ttaaaaaata    68880
tgtcaaataa aaaataaac tagaataaca gggaacattt aatggaacca aggcacctca    68940
aacagctgac atacttctaa aaagcagaaa gtaaatagtaa gggagataat agcatacgag    69000
ttagttttcc aattgccaaa agatcacttc aaatacagct cttggcagtc atcttcttat    69060
ggagaaactg caacacttat ggaatggcaa ttccaccaat ccccttttc taacagcaga    69120 aaaacctgaa ggagacaagc ccagctatag tccagctggg acctgtggca ataacctgac    69180
ctaaagttac ataagtgatc aggaccgtat gtggtccgta cccctctgcc tgaggatgct    69240
acgcagctgt ttaactctct caaacatttt gttcttttac tgacaaccca ctgcagtcaa    69300
gttgtctatt cccataatat ggaatattgg gtctatagta atttcctatt cctatttcta    69360
ggcaatcatg taagataagg ggaatgggca cctatttctc tggggaaggt ataaatgtgt    69420
cttttatctc tttccagtat ccccactgtg tagagctggt ccacaatgga gaggaggaaa    69480
agttttgcat tggaccaaat cactgcctta gaaggaaaga gattgcaatc ccattcattt    69540
ttaagatctg caatgggttg ggatgatacc catttaaaaa agaaaaaaaa agaggttacc    69600
tctttggcct cttttggcaaa ggatatgaac tagtaataaa gcctcagcat caaggcttgg    69660
gagtctggct caaagtggct aagactagaa gcatcttcta acataaatat ggcagcatta    69720
ggaaaatagc ttggccttta gagagaccca gattatcttc accttaaaaa ctaccaagac    69780
cctggtccag caagaccacc atcacagcag taaatacata gccaccaact tcacagaagg    69840
ttttccactg agacattgtg aaaaccacaa tccattaccg gtggatgagt cccagctctc    69900
ttactacctg gagcttccaa gcaagactta cctgtccttt gttccagatt ggttcctggg    69960
atcctggacc aacacaaaga gaagaggaaa gcctcaaggg aaataaaagt gaaggtttca    70020
gtgatagttt aaatatatat ttttaaatgt tagcttttt ttaaatactt cacagtgatg     70080
gatggagtat ttcaaccaca atggcaaaga atgaattacc ggcagtgtca gagtttcttg    70140
ttgctgtggg aagacagctg ccatgttgag aggtgccttg tggagaggct catgtggcga    70200
ggaactgaga ctggcttcta tccaacaacc agtgaggaac taaggcccta aagtcctata    70260
gtccacaagg aactaaatcc taccaacaac tacatgagtg agcctggaat ctgatttttcc    70320 ccagtgggga cttaaggtac ctacaacctg gctgttatgg gctaaactgc atcctgccca    70380
aatttatatg tttgagtctt aactcccagc acttcagaac atggttttgt ttggagacat    70440
```

```
agtcattaaa gaggtaatga agttaaaatg aggtcattag gatgagtcct aatccaatag   70500
gactggtgtt cttatatgaa gaggaaattt gaacacagac acatatacag gaaagaccat   70560
gcgaagaaga cacagagagg aaacggccat ctacaatcca aggagagagg cctcagaaca   70620
agccaaccct gcagatacct tgatctaggc atccagaatt gtatgaaaat acattttgt    70680
tatttaagct acccagtctg tggtgctttg ttatggcaat cccagaaaac taattaacta   70740
attgactgca gccttgcaag ggaccctgaa ccagaggacc cagttaagcc atgtgcagat   70800
tcctgactca cagaactagg agataacaaa tgtttgttgt tctaaggtgc taaatgttgg   70860
gaaaatatgt tatgtggcta tgttgttttg cacatgtgcc acataatgat gttttggtca   70920
acaacagacc acacatatga tggtgggccc ataagattgt aatactgtgt ttctattatg   70980
cattctctat ttatagatac acaaatactt gccactgtgt tacaattgcc tactgtcttc   71040
agtactgtaa catgctgtac aggtttgtag cccagaagca atagactata ccatacagtc   71100
tgggtgtgta gtaggctata ccatctatgt ttgtgaagta cactctatga tgttcacata   71160
attatgaagt tgcctagtga tgcatttctc agaatgcatg cccgacatta agtgacactt   71220
ggctttatgt ctatcatgca tttaagatat tgcaatatag ttaacttatg ttttaataca   71280
cctcttaatt ctgttttgat cccacaccaa ccaagatgca aaactaattt tttcgcccat   71340
ttccataaaa aacacaatta caatgggcct aatgtggttt atgtcatttt ccctgaagat   71400
ttgtggtggt ataggaagca gtcacagcac cctgtataaa gctcttccat ggcctgcccc   71460
cttttcgcag tcacctctat tatttgaagg aatggtccaa ccaacctcaa agctctggaa   71520
atttgcccca aaataatttt accctgaagc cattgaagct taagtttcag accccagttt   71580
cacattcctg tgagttctgc aagtcactgg gagctataga gtcttctacg tagatttggg   71640
aaacaaggtg aaaataccte aagaaatctc agaagccagg ggcctgcatc tccaagcctc   71700
tggcaatttt cttgtggttt ctatcctcac tctagatatt tgcttttgag actgattttg   71760
aattcagaat tttatattct ctcaaaaaga gaattctcca aattctataa gcttcaggct   71820
ctacaaaact tgtctattct gcctaactag atttatcata gcacgtacca aagatggccc   71880
tgcctcatga ggacttttca tatcagaccc ttagataata atattccctc atgtaagtaa   71940
taatatttcc gcatgtagtt atgtatgaat aattttcatt catctatatc atgttggcca   72000
tagtcagtgt ccatgtccaa tttatttttt gtgtccttgg tgctcagaaa gttaccagat   72060
gttcagtcag aattttattt aaaatatttt gatgaactag atttaaagat agattaaatt   72120
aattcctaca catgatttaa tttaatggat aaaataaggg actgagcatt agcctgaact   72180
gtgtacttgc attagccctg atgttcccca gagggaataa tatgtgaaga atactgcata   72240
ggctgaaaaa caagagttcc cagcagacca atattctttc tttctgcaag ctgtgagaca   72300
cctggggaaa gttctccaca tttggttttt cagctactcc acccatgact agaaggaaga   72360
ttttatttta ttattttatt ttattgtatt ttttaacagt aaaagaaaaa ttattgttat   72420
tttaatgaaa aagaaccacc tggaaagtct agtgacattt ttgaaggcag ggaccacttt   72480
ttccagggat ttgtttccct atgctagtgc tccattcacc cttgcaccac ttcagcaaag   72540
cacatagtag gtgtagcagg gagatgttaa gatggaaact tggccctgac cataggccaa   72600
gccagggtgt ctagtcggga tttatccata aacatcaata tttatcacta gatgatatat   72660
tgatttctta tctgcctcct atacctattg atctattttt cacagcttat agtggggagg   72720
gtcatgttca gttattatcc ttaaaccaaa acaatctctt cttgaaaaat aggatgctat   72780
gctctgatgt ttgcagaggc caggaaattc ttgctctgag agttccagaa aaaaagattt   72840
```

```
gtccagattt gaactaattt cagaaaaaca aaacaaaaac aaaaaaccat ccaaggttaa   72900
gaggtgactt ctgactcaca gaatgaacaa gaaggcaggg gaaaaaataa gtcccccaag   72960
attcaggtca aaggaaatga acagaaggat gatggagtgg cccagaggag gatcacgtga   73020
cagaaaagtc aagataaatt agtggcagga cagaggaaaa gaactaaaga cctgcaggat   73080
cctgaaagaa agaatgaaag gaagcagatg aagattctag agcccagctg aatagccagg   73140
ccgcctgagg gtaaagaggg agagaaagag gaagcagtga atcaaatcaa aaaaggatag   73200
aaaaatacag agaaacaagc cagggcacgg tggctctcac ctgtaatccc agcactttgg   73260
gatgacaagg aaggcggatc acatgaggcc aggaatttga ccacgctg gccaacatgg   73320
caaaaccctg tctctactag aaaaatatgg aggaatgttt gagagattgt gcactgccag   73380
gggtgaggac ataaatttat ttgctatgtg aatgtttttt gagactcatc tagttccttt   73440
acaattttaa tttagaattt ctttagctcc aaatcaggat cattagctgg gagttcttat   73500
aaatcaaaag caaaacaaag ctattgcaaa caagtgggag ttctcataac cttaatcaga   73560
aaggcttgag ttgcatttcc aaatcctgtc tctagagacc atgagttttt aatgatagta   73620
tttccatgaa agcccaattg aatacaatca ccacccagac caaagtgtag gggaaatcat   73680
aaagctactt tcaaatccga gtcttctttg aaatttaaaa ttatattcca tgataatggt   73740
tctcataaac cttaatgcaa gggaaaaaaa aaaaactaca gcagaataaa gaagatttaa   73800
aagaagcag gataggaaaa aagacaagcc agaggctagc tatatctttt cataaagcac   73860
acctggtctc ataagcacat gagagctagg cccagaagtt tcgagccttg gagactcact   73920
tcaaacaaat tccagggaaa gacactcaat taagtgttca ggacaattgt atatccccag   73980
tgcactcatg tactggaagt gcttaaactc tgccctcagt ggtcaataaa atggtattaa   74040
gtcacagaca acccattgcc attggtattg gctgatgtct ctggtagttt atgtgatgac   74100
aaacattagc cttaacagca gagccttcct ttctttgatt tccgtgtgaa attctgtggc   74160
tgggagatgt ttatgttcac atgaacataa ctgtaagcaa accatcttat ggtagacatc   74220
tctccagaaa aagcaaattc catctttta aatagaaaaa aaaaacagca gcaaaatgaa   74280
attaatgcct ttggctcatt gtgttgtaaa attatccttg aagttatttc acactgccct   74340
aaaaaatcat tgaattcaga ttataacaca gctcttatga agctgttagg cagttgcatc   74400
tttaatgagg ctgagtaggt aagaggaaca gatactctag attgaaagcc atcgcaaaaa   74460
atgtgaaaca actgtattaa atttaattta atttaaccaa tgggtgtatt tattccctgc   74520
cttcttccag aaaggattta gggagcttag gtaatgtgga ggtctgaagg tgtagatact   74580
catgaaagcc tcagattaat atctagaaca tataatgtgt ccagatagtt ttcaattatc   74640
aatgcattaa tctaagcttg gaaaggactt ttaaactgca atgaaacctc aactagtttc   74700
aaacctgcat ttttagtaa gctattttgt catttggaga cccacacaaa aaacctattg   74760
ttcctttaaa aaggagagag agaaaaaaag aaaaacaacc tgctggtgtt gctttgttca   74820
tcttatcacc ttatcattca gcagcctatt caggatcaaa tgtgggaaag tctgtgtgtg   74880
agattaagcc ctatactcag cacaggaatt tcttggataa atgtctttct taaatggata   74940
gctatgtaaa aaacagaaga gaaactctat tattacaatg cagttgggtt ttttttgtttg   75000
gtatgtttca aatctaatat ttaaaattaa gaaaattcaa agcaaaccat ctgtgtggat   75060
gttttcatac tccattttg tgacaatagc ttgcttaacc gagattatta gtggattctt   75120
tcaataagag gaagagagta ccatcattaa gatggtatgc ctccactagc ctttattttt   75180
gagattaaag aatgacaaaa atatttatat atattttttc attattaaga cggagtctca   75240
```

```
ctctatcgcc aaggctggag tgcagtggcg ccatcttggc tcactgcaac ctctgcctcc   75300
caggttcaag caattctccc acttcggcct cctgagtagc tgggatcaca ggcacccgcc   75360
accacacctg gctaatttt gtatttttag tagagatggg gtttcaccac attgcccagg    75420
ctggtctcaa attcctgacc tcaagtgatc cgcctgcctc agcatcccac agtgctggga   75480
ttacaggcat gagccaccac aactagccaa aaatatata ttttctttaa aaaaagtta     75540 ttttctgcct aattacttca atatttcatg aacattgtgg gggaaagaat attcatacag   75600
ttctctaaat atatcagtga gttgaggtac caaatacaga attctattga attctaattg   75660
caacactgaa gcagacttac tctaagatcc tgctacctgg actaaccaca gactataccc   75720
agattccatc tgcaagatgt agtggagcca aacatcacat cactgaggaa tatttattat   75780
atatctttct gtagaggtga gagagtattt atagatataa caaacaattg gtcagatact   75840
actggagatt tggaagcttc actaggtttt tcactaaatt tgttgatagc caactctaaa   75900
gctcattcta ctactactag ccatcttccc ttggacaatt tcatgggcat cgcttcactg   75960
aaaagaaaaa tgagtaagta taatctcact agtacatgaa taactattat aaacacaata   76020
ctttctacaa ggtttattac taatctatgt catttaagtt ctagatttta cagtattttg   76080
gagtgatgaa taaatagcat gctgttcttc tatagctagc aaacaagact cagctttgga   76140
gacaagaaga aggaatacag gagatgtttc cttgaatgag tcttcttcct aaactctgct   76200
agaagtatgt cagaaagcga aggttacctc agtctccaag tcatgaaaac atgaggtctt   76260 tctgtttct agggaaagta tttcatcatt tcctagtgtg gcttttgca caccccagaa     76320 ggaggaagac aagccatcgt gtcacctta catggtagtt gagatgcttc acatttgtac    76380
ataacatctt atatgatcga aagaggaact caaactcgac aggggagaat aaggaaatac   76440
atctaaaact gacaattatg ttaatccctc aattccctgg gcccccaaaa tagtctcctc   76500
tatttgccat ttcaaaatag ctaatgagag ggtaattgga catgtagaca ctgaatttcc   76560
actgctcatg gtttccttcc ctgggctccc agtcacccgg aaggccccgg attacctcaa   76620
atgtcataac gggttcatcg cattacgaat tacctccttc tgccaataaa ctacaagttc   76680
tttgaggaca gaaactgtga tttatgggca tttgtatccc cagagattca aagagtgcct   76740
gatacagagt ggtgatagat gattttatca tcttatcatc atcatcctca tcatcgttgt   76800
acctaaatag aggttacttc ctgtttcttt tatttaacaa taacctatta taatatatac   76860
tatgcatttt taatgcactt tacaaatatt gtcctcattt aatccctgta aggtgaatac   76920
tattattggc tccatttgc agataagaca ctgagtcgtg aaaaggctaa gtacctcaca    76980
caagatcaca cagccagtga cagaactagg atttggctgg actcttaaag actctggttt   77040
gccatttaaa ggtacgctga gctccacaac actgccttag aacttgctca gagcaattgt   77100
catattacta tggtaggttt ccctgtctcc cttaagactt aaagcttctg gagatcagaa   77160
actgtattgt ttacttgcaa aatcatgggc ttaggagcca gaaagatctc gatctaagtc   77220
ctgcctcatc tgcttcttct tcatgggatt agtagactga ttttcccctt gcttagccat   77280
gcagtttgaa tggaattcac cccattctca gctacaacca cggatcttgt ttgctttaaa   77340
ccaatcatca ctgcccaatt ttctggcctt tgattgattt aaaggtgaac acatgaccgc   77400
tttggaccaa tgaggctcag gtggtatttt gtgagggtct ctggaataga aaatcatttc   77460
tcttctgaca gaactacaag gcaaggcgca atcactgatg gtgaaagata aagatcatta   77520
tattaggaac tgttggctgt catactgcta atgtgaggtg agttagcctt agaaagagga   77580
tgctaccttg aaaggcaggg cagatctatg gaaataaact gagtttgtgg tgacattgat   77640
```

```
agccacttta gttcatcagc tgaatcccaa tctacttggt tttttcagct ctgtaagcca    77700
acaaataccc tgctagtgtt ttagcctatg ccagttgttt tttctgctgc ttgttaataa    77760
gacacataca gtcttggaca aattatataa aaatatgaat ctttggccag gcatggaggc    77820
tcacgcctgt aatcccaaca ctttgggagg ccgaagcggt cggatcacag ggtcaggagt    77880
tcgagaccag cctggccaat atggtgaaac cccgtctcta ctaaaaatac aaaaattagc    77940
tggatgtggt ggcacatgcc tgttgtccca gctactcagg aggctgaggc agaagaatcg    78000
cttgaacccg ggaggcagag gttgcagtga gctgagatca tgccactgaa ctccagcctg    78060
ggagacagaa tgacactcgg tctcaaaaaa aaaaaaaaat tctgaatctt tgaatgttat    78120
cgtatagctt tttaaaagac tagattaagc tatggatgta agcaccaatg catttttta    78180 aaagtatatt ggatgaatga gttaaagtct aagtgaattc agcaagtttg taacccttga    78240
gctcttgtga gctcaatctg ccctcaatca tctgagaatg aacaaaacag actcaaccat    78300
tttgtgtcat ccagatgaat agaaagggcc tgaatatatt cttttttat attttttgtc    78360 ataggcccta gcgttttcat ctgctcagtt tttgagtgtg cttgttaggg ctttaatgct    78420
aaactcaatg taagctgggt ttatgtaatt tagtggtttc tagacttagg cttcctaaat    78480
gttccattag acaagaagac aaaatatgaa acaaataac atcaaactac cattaacaat     78540
tagcattgtc agagtcagta aaactgtttt tgaaataaag cagcttttca ggccagtatt    78600
tgagaactaa tgatagagtt tttttgtagg caatgaatga agtgttgtgg aacaaatgtg    78660
gatttggact ttcaagacca acttgaacca gagtcttgaa tctgcaactt tactagctgt    78720
ggcttctttt taattgatta actttctttt tctgtaaaat gggaataatg attcctacct    78780
cttacaagcg ttgtggtagg aggtattcca aatgagataa atatgtgaaa tcactaaaac    78840
ttccagaata catggaaata atatatgtct gtattggcaa attatgagtg tagtaatgag    78900
ggatttacat ggacacattt acattcttta gttcagactc cctttgacga cacataacaa    78960
acacacacaa gaatatttgc cctgtgtcca gcactctttt gagaatttct ctcttctcct    79020
ccttctgata tcccaaccaa ccaaccagta ggaatgtgcc ctagaaacta tgttttacag    79080
ctcagtccac atctttcac cttacaaatt acttattgtt agtttcttgg gaaagtaaaa     79140
ttgagatatt aagattctat gaaattggtt ggtggtattg aagactgtgc tgctgctgct    79200
gctactgctc cagaactcta gtggagatat tacaaatggg agcagaaaaa gtgagaaggt    79260
ggtctgtaga gacagagcac agcacagagg tagaaaggtt gagataaaga aacaatgcag    79320
tgagagaagg agagaacaca gacatagaaa cagagacata aaggcaccag acacgagagc    79380
agagataatt taataaggcc gtagtttctc ttggatttcc agttccttct tttagtcaat    79440
tctgatattt agcacactgc actgcaccag atatcttgtc gccttcaaat aaagtatttt    79500 tccccttaa acatgctaat ttgggcttgt attatttgca atcaatagaa ttgagaaaaa     79560
cactctatgt catatctgaa ctagtatatc agaatggttt tctgccattg gtaacagaga    79620
cccagctcaa tggcttaaac acacaagggt ttatcctgtc acattaacaa aaaaaaaagt    79680
gcagagtagc agtccggggt tggaataggg tccacaaagt catctggggc caggcttcat    79740
ctatctttct cttacatcac aagtgacttc tgtctacaag gcccctcatg gtccacaatt    79800
gattgttttt acaacagctt tccaaagagc agaaagaaaa acaagtagaa gagcttgtac    79860
tttcttttct atttatgtca cctctgctta catctcacta gccagatata gacatatggc    79920
cccatctacc tgcacagaaa tctcagaaat gtaatttttc agcttggcca ttgcccaggg    79980
ttctgttact agggaagaag                                                80000
```

<210> SEQ ID NO 6
<211> LENGTH: 2260
<212> TYPE: RNA
<213> ORGANISM: Homo sapiens
<220> FEATURE:
<221> NAME/KEY: mRNA
<222> LOCATION: (1)...(2260)
<223> OTHER INFORMATION: Corresponds to a cDNA detected by cDNA cloning.
      It includes two exons. It is transcribed from the
      +strand of Seq_ID_06.doc.

<400> SEQUENCE: 6

| | | | | | |
|---|---|---|---|---|---|
| auuugaauug | gugaacuuag | uaaagcagac | ggcucucacc | aauaagggca | ggcaucaucc | 60 |
| aaucugucga | aagcuugaau | aaaacaaaaa | gaggaaggga | aaauuugcuu | cuuuucuucu | 120 |
| ugaucuagua | uaucaucuuc | uccugcccuu | ggaugugagu | gggccuucag | acuuaaacca | 180 |
| ggaguuacac | cuuuggcuuc | ccugguucuc | aguucuuugg | acuuggacug | aauuacacug | 240 |
| ccagguuucc | ugguucucca | gcuugcagau | ggcagaucau | gggacuucuu | ggccuccaua | 300 |
| auuguuuca | uaucuccagg | ccuuucauug | ggucagguug | gcauuucgcu | gcccuuuaug | 360 |
| ugugugacaa | gugaaaauaa | ggaagaaaa | aaacucaagu | gaagaaaauc | agaaucugcg | 420 |
| cagcaguucc | ugggcguuuc | agcugcuucc | cacaucaccu | gccucaucaa | gccccagcau | 480 |
| ccaucuccuu | gcucaucuua | cacccugugu | gcaugacagg | cccaccauuc | auuuaucaga | 540 |
| gcaaaggcuc | ucccacuauu | cugguucacc | cccuacuua | gccagauaua | caagaauauc | 600 |
| ugcacggaug | accugccuca | ccugggagcu | cagaggagcu | cagauccau | acuaucgca | 660 |
| ccaaggacag | aucucccagc | aagaaugaca | gaaaagacua | acugccccca | aaaucucccu | 720 |
| uccaaaacac | aguucucuua | auucucccaa | gaaaccagaa | ugugacugcu | caccucucua | 780 |
| aggaccugaa | acaacuggc | cauuucagcu | auuuaaauca | acuuuaaaaa | auccaaccgc | 840 |
| caaaauauua | aaccauuuug | guuggaauga | uaacauaacu | aaccugcuga | cagcugcuuc | 900 |
| ugcuagguc | aaaaauggaa | aaaaaaauac | uucuaaucag | gucaaaucac | ucuaccuuug | 960 |
| ggauucuaaa | uuuacucaua | uucucaaaga | aauauauuca | gucauagugg | ggaaaauagg | 1020 |
| auuauuccuu | uagcucgaua | agcaaccaga | aguucuuccu | ucaaaucuug | acauuuaauc | 1080 |
| aaucagaaau | ugauuuuugg | aaaacuguuu | ccaugaagc | uaucucugcc | ugaaggauuu | 1140 |
| uucuuuuaca | auccagacua | uagaaggaaa | uucacaaccu | ggacuuucac | cuccauuggu | 1200 |
| cagaguuuua | cugaccaauu | cccaccucug | ccuuacaccu | aacggaaguu | uaugccuguu | 1260 |
| uucucuucac | auaccccaac | aguuacaaau | gguuguauu | auuaagcauc | uuuuauuuug | 1320 |
| uggccucuga | uuacaugguc | cccuaaauuu | ugaccaauc | acaaaagauu | gguaaaauuu | 1380 |
| cuuaacauau | uaauaauauu | uuguuuaugu | gucaauaucu | uagcauguau | caauuaagac | 1440 |
| agaggucuua | acguucucuu | uuugaaagag | aauauuagga | uucagagaua | uuaagagauu | 1500 |
| cucccaggau | cacaguuagg | uaacagagcu | ggauuuuagu | ccaggucugu | cuacagcucu | 1560 |
| aacguauaua | cacccuuugu | auaacaugu c | acgaauucag | cauaaaggga | ucuucaguga | 1620 |
| ucuaagucag | gggucagcaa | ccuuuucuaa | aaaggaccaa | auaguaauau | uucaggcuuu | 1680 |
| guggacccua | uggucucuau | cauaacuguu | caaaucacca | uguaguguaa | aaggagccau | 1740 |
| aagcaaaaua | uaaacuaacg | aauguggcug | uuuuauggga | uuuuuuuua | acucuuuauu | 1800 |
| uacaaaagca | ggugggcagau | cagaacucac | uuaugggcca | uaguucucug | accccugacc | 1860 |
| ugagaaaauc | uuauauuuau | ggacaacauu | uagacuguga | cuugccaagu | aagaacaaga | 1920 |
| agcucuguca | acugaaggu c | aaggcuggag | uucugaaagc | aaagagcugu | cugguguuaa | 1980 |

| | | |
|---|---|---|
| ugauaaguga auaguuaaa guuagaagau cccaguuaua agaagcacaa agaauaauga | 2040 | |
| ccauagacuc cugaacaaga augucuggac uucuggcuua ggcacucuug uuguaugguc | 2100 | |
| caggccaagu uaccuaaucu cuccaggccu ccauuuucuu aucauuaaau gaagauaaua | 2160 | |
| aaaguauuuu ccucagagag cuguaagaau aaacugagcu aacccauguc aagcacauag | 2220 | |
| aauagggccc agccuauauu aauuuaucaa uaaaugccag | 2260 | |

<210> SEQ ID NO 7
<211> LENGTH: 2817
<212> TYPE: RNA
<213> ORGANISM: Homo sapiens
<220> FEATURE:
<221> NAME/KEY: mRNA
<222> LOCATION: (1)...(2817)
<223> OTHER INFORMATION: Corresponds to a cDNA detected by cDNA cloning.
      It includes three exons, the first and third are
      identical to the two exons in Seq_ID_06.doc. It is
      transcribed from the +strand of Seq_ID_06.doc

<400> SEQUENCE: 7

| | | |
|---|---|---|
| auuugaauug gugaacuuag uaaagcagac ggcucucacc aauaagggca ggcaucaucc | 60 | |
| aaucugucga aagcuugaau aaaacaaaaa gaggaaggga aaauuugcuu cuuuucuucu | 120 | |
| ugaucuagua uaucaucuuc uccugcccuu ggaugugagu gggccuucag acuuaaaccca | 180 | |
| ggaguuacac cuuuggcuuc ccugguucuc aguucuuugg acuggacug aauuacacug | 240 | |
| ccagguuucc ugguucucca gcuugcagau ggcagaucau gggacuucuu ggccuccaua | 300 | |
| auuguggggca aaaggaaag agacaaaaca gcaugaaaug augagaccaa gugaugaaaa | 360 | |
| uucauucaca augauugcuu ucaagaguaa uuucucuugg guaauucagc agccuguuac | 420 | |
| uauggcucuc uggagugaua gcuaauguaa augaagccuc uaaaagugga uuauccugac | 480 | |
| aagaauauac ucagccaaua augcaacaga aauccauuca aagcauucgg aaaaauuca | 540 | |
| aaagaauaaa uauucuuuuu uuuuuuuaa aguuaaugac cuacgauccaa uuucuuccuu | 600 | |
| gacuaacaag cagcaagcac uuaaaaauau ccagccagga ugaauagaa acccaccuga | 660 | |
| cuuguuaaua uuuuuguuug gucccagga cucagauucu aagccaaauu cuuugaauga | 720 | |
| ucuuggcaaa ugucucgaau uauuuugcc aacuuucuu uaucuuggaa aaaaguuuc | 780 | |
| augaaugggu gucaaaauug auuaguuuua aaaccuuuc uugcagauac guauggcacc | 840 | |
| cuaaaacugu auuagaaaaa aauuucauau cuccaggccu ucauuggggu caggguuggca | 900 | |
| uuucgcugcc cuuuaugugu gugacaagug aaaauaagga agaaaaaaa cucaagugaa | 960 | |
| gaaaaucaga aucugcgcag caguccuggg cguuucagc ugcuucccac aucaccugcc | 1020 | |
| ucaucaagcc ccagcaucca ucuccuugcu caucuuacac ccugugugca ugacaggccc | 1080 | |
| accauucauu uaucagagca aaggcucucc cacuauucug guucaccccc cuacuuagcc | 1140 | |
| agauauacaa gaauaucugc acggaugacc ugccucaccu gggagcucag aggagcucag | 1200 | |
| auuccauuac uaucgcacca aggacagauc ucccagcaag aaugacagaa aagacuaacu | 1260 | |
| gccccccaaaa ucucccuucc aaaacacagu ucucuuaauu cucccaagaa accagaaugu | 1320 | |
| gacugcucac cucucuaagg accugaaaac aacuggccau uucagcuauu uaaaucaacu | 1380 | |
| uuaaaaaauc caaccgccaa aauauuaaac cauuuugguu ggaaugauaa cauaacuaac | 1440 | |
| cugcugacag cugcuucugc uaggugcaaa aauggaaaaa aaauacuuc uaaucagguc | 1500 | |
| aaaucacucu accuuuggga uucuaaauuu acucauauuc ucaaagaaau auauucaguc | 1560 | |
| auaguggggga aaauaggauu auuccuuuag cucgauaagc aaccagaagu ucuuccuuca | 1620 | |

| aaucuugaca uuuaaucaau cagaaauuga uuuuuggaaa acuguuuccu augaagcuau | 1680 |
| cucugccuga aggauuuuuc uuuuacaauc cagacuauag aaggaaauuc acaaccugga | 1740 |
| cuuucaccuc cauuggucag aguuuuacug accaauuccc accucugccu acaccuaac | 1800 |
| ggaaguuuau gccuguuuuc ucuucacaua ccccaacagu acaaauggu uguuauuauu | 1860 |
| aagcaucuuu uauuuugugg ccucugauua cauggucccc uaaauuuuga ccuaaucaca | 1920 |
| aaagauuggu aaaauuucuu aacauauuaa uaauauuuug uuuaugaguc aauaucuuag | 1980 |
| caugauacaa uuaagacaga ggucuuaacg uucucuuuuu gaaagagaau auuaggauuc | 2040 |
| agagauauua agagauucuc ccaggaucac aguuagguaa cagagcugga uuuuagucca | 2100 |
| ggucugucua cagcucuaac guauauacac ccuuuguaua acaugucacg aauucagcau | 2160 |
| aaagggaucu ucagugaucu aagucagggg ucagcaaccu uuucuaaaaa ggaccaaaua | 2220 |
| guaauauuuc aggcuuugug gacccuaugg ucucuaucau aacguucaa ucaccaugu | 2280 |
| aguguaaaag gagccauaag caaaauauaa acuaacgaau guggcuguuu auggggauuu | 2340 |
| uuuuuaacu cuuuauuuac aaaagcaggu ggcagaucag aacucacuua ugggccauag | 2400 |
| uucucugacc ccugaccuga gaaaaucuua uauuuaugga caacauuuag acugugacuu | 2460 |
| gccaaguaag aacaagaagc ucugucaacu gaaggucaag gcuggaguuc ugaaagcaaa | 2520 |
| gagcugucug guguuaauga uaagugaaau aguuaaaguu agaagauccc aguuauaaga | 2580 |
| agcacaaaga auaaugacca uagacuccug aacaagaaug ucuggacuuc uggcuuaggc | 2640 |
| acucuuguug uaugguccag gccaaguuac cuaaucucuc caggccucca uuucuuauc | 2700 |
| auuaaaugaa gauaauaaaa guauuuuccu cagagagcug uaagaauaaa cugagcuaac | 2760 |
| ccaugucaag cacauagaau agggcccagc cuauauuaau uuaucaauaa augccag | 2817 |

```
<210> SEQ ID NO 8
<211> LENGTH: 1970
<212> TYPE: RNA
<213> ORGANISM: Homo sapiens
<220> FEATURE:
<221> NAME/KEY: mRNA
<222> LOCATION: (1)...(1970)
<223> OTHER INFORMATION: Corresponds to a cDNA detected by cDNA cloning.
      It includes two exons, the last is also present as
      "exon-2" in a human cDNA clone (sequence acc. no.
      BC036936). It is transcribed from the +strand of Seq_ID_06.doc

<400> SEQUENCE: 8
```

| auuugaauug gugaacuuag uaaagcagac ggcucucacc aauaagggca ggcaucaucc | 60 |
| aaucugucga aagcuugaau aaaacaaaaa gaggaaggga aaauuugcuu cuuucuucu | 120 |
| ugaucuagua uaucaucuuc uccugcccuu ggaugugagu gggccuucag acuuaaacca | 180 |
| ggaguuacac cuuuggcuuc ccugguucuc aguucuuugg acuggacug aauuacacug | 240 |
| ccagguuucc ugguucucca gcuugcagau ggcagaucau gggacuucuu ggccuccaua | 300 |
| auugugauc cccacugugu agagcugguc cacaauggag aggaggaaaa guuugcauu | 360 |
| ggaccaaauc acugccuuag aaggaaagag auugcaaucc cauucauuuu uaagaucugc | 420 |
| aauggguugg gaugauaccc auuuaaaaaa gaaaaaaaaa gagguuaccu cuuuggccuc | 480 |
| uuuggcaaag gauaugaacu aguaauaaag ccucagcauc aaggcuuggg agucuggcuc | 540 |
| aaaguggcua agacuagaag caucuucaa cauaaauaug gcagcauuag gaaauagcu | 600 |
| uggccuuuag agagcccag auuaucuuca ccuuaaaaac uaccaagacc cugguccagc | 660 |
| aagaccacca ucagcagu aaauacauag ccaccaacuu cacagaaggu uuccacuga | 720 |
| gacauuguga aaaccacaau ccauuaccgg uggaugaguc ccagcucucu uacuaccugg | 780 |

-continued

| | |
|---|---|
| agcuuccaag caagacuuac cuguccuuug uuccagauug guuccuggga uccuggacca | 840 |
| acacaaagag aagaggaaag ccucaaggga aauaaaagug aagguuucag ugauaguuua | 900 |
| aauauauauu uuuaaaauguu agcuuuuuuu uaaauacuuc acagugaugg auggaguauu | 960 |
| ucaaccacaa uggcaaagaa ugaauuaccg gcagugucag aguuucuugu ugcuguggga | 1020 |
| agacagcugc cauguugaga ggugccuugu ggagaggcuc auguggcgag gaacugagac | 1080 |
| uggcuucuau ccaacaacca gugaggaacu aaggcccuaa aguccuauag uccacaagga | 1140 |
| acuaaauccu accaacaacu acaugaguga gccuggaauc ugauuuuccc caguggggac | 1200 |
| uuaagguacc uacaaccugg cuguuauggg cuaaacugca uccugccaa auuuauaugu | 1260 |
| uugagucuua acucccagca cuucagaaca ugguuuuguu uggagacaua gucauuaaag | 1320 |
| agguaaugaa guuaaaauga ggucauuagg augaguccua auccaauagg acuggguguuc | 1380 |
| uuauaugaag aggaaauuug aacacagaca cauauacagg aaagaccaug cgaagaagac | 1440 |
| acagagagga aacggccauc uacaauccaa ggagagaggc cucagaacaa gccaacccug | 1500 |
| cagauaccuu gaucuaggca uccagaauug uaugaaaaua cauuuuuguu auuuaagcua | 1560 |
| cccagucugu ggugcuuugu uauggcaauc ccagaaaacu aauuaacuaa ugacugcag | 1620 |
| ccuugcaagg gacccugaac cagaggaccc aguuaagcca ugugcagauu ccugacucac | 1680 |
| agaacuagga gauaacaaau guuuguuguu cuaaggugcu aaaugaugugg aaaauaugu u | 1740 |
| auguggcuau guuguuuugc acaugugcca cauaaugaug uuuuggucaa caacagacca | 1800 |
| cacauaugau gguggggccca uaagauugua auacuguguu ucuauuaagc auucucuauu | 1860 |
| uauagauaca caaauacuug ccacuguguu acaauugccu acugucuuca guacuguaac | 1920 |
| augcuguaca gguuuguagc ccagaagcaa uagacuauac cauacaguca | 1970 |

```
<210> SEQ ID NO 9
<211> LENGTH: 1989
<212> TYPE: RNA
<213> ORGANISM: Homo sapiens
<220> FEATURE:
<221> NAME/KEY: mRNA
<222> LOCATION: (1)...(1989)
<223> OTHER INFORMATION: Corresponds to a human cDNA sequence (sequence
      acc. no. BC036936). It is transcribed from the
      +strand of Seq_ID_06.doc

<400> SEQUENCE: 9
```

| | |
|---|---|
| uuugcaggcc cggcacaguc ucaguuccccc acagcacaga gaggaagcaa ggucuuugca | 60 |
| ugcccuguuc acuggccaa acauugcccu agaugugcaa uucaacccau auaaagcaag | 120 |
| cguaauucaa gagcccugac ucuuucacca uuucaugaug gcuuauuacu cgcacacggc | 180 |
| auugucaggu uccagcaacu cugugugcag caggcagaaa ugcaguguuu aucucugaca | 240 |
| ggcaaacauu cuuaggcuca ucggcaugag uauccacgcu gaacuggcua ucggggaagu | 300 |
| agaucccugc augggaaagu caagguaucc ccacugugua gagcuggucc acaauggaga | 360 |
| ggaggaaaag uuuugcauug gaccaaauca cugccuuaga aggaaagaga uugcaauccc | 420 |
| auucauuuuu aagaucugca auggguuggg augauaccca uuuaaaaaag aaaaaaaaag | 480 |
| agguuaccuc uuuggccucu uuggcaaagg auaugaacua guaauaaagc cucagcauca | 540 |
| aggcuuggga gucuggcuca aaguggcuaa gacuagaagc aucuucuaac auaaauaugg | 600 |
| cagcauuagg aaaauagcuu ggccuuuaga gagacccaga uuaucuucac cuuaaaaacu | 660 |
| accaagaccc ugguccagca agaccaccau cacagcagua aauacauagc caccaacuuc | 720 |
| acagaagguu uuccacugag acauugugaa aaccacaauc cauuaccggu ggaugagucc | 780 |

```
cagcucucuu acuaccugga gcuuccaagc aagacuuacc uguccuuugu uccagauugg    840
uuccugggau ccuggaccaa cacaaagaga agaggaaagc cucaagggaa auaaaaguga    900
agguuucagu gauaguuuaa auauauauuu uuaaauguua gcuuuuuuu aaauacuuca    960 cagugaugga uggaguauuu caaccacaau ggcaaagaau gaauuaccgg cagugucaga    1020
guuucuuguu gcugugggaa gacagcugcc auguugagag gugccuugug gagaggcuca    1080 ugggcgagg aacugagacu ggcuucuauc caacaaccag ugaggaacua aggcccuaaa    1140
guccuauagu ccacaaggaa cuaaauccua ccaacaacua caugagugag ccuggaaucu    1200
gauuuucccc agugggacu uaagguaccu acaaccuggc uguuaugggc uaaacugcau    1260
ccugcccaaa uuuauauguu ugagucuaaa cucccagcac uucagaacau gguuuuguuu    1320
ggagacauag ucauuaaaga gguaaugaag uuaaaaugag gcauuagga ugaguccuaa    1380 uccaauagga cugguguucu uauaugaaga ggaaauuuga acacagacac auauacagga    1440
aagaccaugc gaagaagaca cagagaggaa acggccaucu acaauccaag gagagaggcc    1500
ucagaacaag ccaacccugc agauaccuug aucaggcau ccagaauugu augaaaauac    1560
auuuuuguua uuuaagcuac ccagucugu gugcuuugu auggcaaucc cagaaaacua    1620
auuaacuaau ugacugcagc cuugcaaggg acccugaacc agaggaccca guuaagccau    1680
gugcagauuc cugacucaca gaacuaggag auaacaaaug uuguuguuc uaaggugcua    1740 aauguuggga aaauauguua uguggcuaug uuguuugca caugugccac auaaugaugu    1800
uuuggucaac aacagaccac acauagaug gugggcccau aagauuguaa uacguguuu    1860 cuauuaugca uucucuauuu auagauacac aaauacuugc cacuguguua caauugccua    1920
cugucuucag uacuguaaca ugcuguacag guuuguagcc cagaagcaau agacuauacc    1980
auacaguca    1989
```

<210> SEQ ID NO 10
<211> LENGTH: 3931
<212> TYPE: RNA
<213> ORGANISM: Homo sapiens
<220> FEATURE:
<221> NAME/KEY: mRNA
<222> LOCATION: (1)...(3931)
<223> OTHER INFORMATION: Corresponds to a cDNA detected partly by cDNA
      cloning, partly by PCR analysis. It includes two
      exons, the last is identical to the last exon in Seq_ID_06 and
      Seq_ID_07.doc. It is transcribed from the +strand of Seq_ID_06.doc

<400> SEQUENCE: 10

```
gaagguaaaa aaagagggga ggucugagaa auagaaauau cagaggaagg aaauaaagga    60
gggugagagu aaauucucuu uuagcauuca gauuccacag auuccacaaa ucacauuucu    120
uuuuuuacca acuaaggaaa aauaacacuu gaccuaacau uucauugcag uuagcuaaag    180
gaugcuagaa aaacuauguu gcaguggguu gcucuaauuu cuucaggaau agagaaaagu    240
gacaaaaaga ucagagaaga gaagaaagga aacuaucaga aaaauacaga auuggaguag    300
gauauaacau auuuggguug aagguaaaau uuuauauugu aaucuuaagu aucuugcuac    360
uucaguuugg ucccuggaac agcagcauca gaaucugccg agggcuuguu aaaaaggcag    420
aaucucaggu cccaucccag acucacugaa ucagaauaua aauacugaca agaugccccg    480
ggauucauau gcacaguaga gcuggcgaag uuccauugua gccugugauu guuucugca    540 acuuaguauu ucgaguuuuu cccaaggaag aaaacccagg ccuuagcuuc uggcagacuu    600
guguuucucc uuuacuuacu agcugcauga cucaugagca aggaaaucaa acuuuaugug    660
```

| | |
|---|---|
| ccugaguuuc cucaucuaua aaauggagac uauaauaauc aucuccuagg cuuguuuuga | 720 |
| ggauguucaa caaaugcucc uuucauuccu cuauuuacag accugccgca gacaauucug | 780 |
| cuagcagccu uugugcuauu aucuguuuuc uaaacuuagu aauugagugu gaucuggaga | 840 |
| cuaacucuga aauaaauaag cugauuauuu auuuauuuuc ucaaaacaac agaauacgau | 900 |
| uuagcaaauu acuucuuaag auauuauuuu acauuucuau auucuccuac ccugaguuga | 960 |
| ugugugagca auaugucacu uucauaaagc cagguauaca uuauggacag guaaguaaaa | 1020 |
| aacauauuau uuauucuacg uuuuugucca aaaauuuuaa auuucaacug uugcgcgugu | 1080 |
| guugguaaug uaaaacaaac ucaguacagu aguauucagu acaguauuua agccccugua | 1140 |
| cuuaaacaua uuccucguac caaugaaguu acaugaaaag caaauuugug ugagauaucg | 1200 |
| uagauggaag uaaauuaguc uuuauguucc ccacaaauug aaaugcauuu caaaacucu | 1260 |
| gugugug uau guguguguu gacagagugu gugugagaga gagacagaga gauacgcuuu | 1320 |
| gguugccucc auaagcuggc ugcuaugauu aauaagacca aguuuucuaa agaaaaugag | 1380 |
| aucauaacaa aagcccucuu uaugacuauc uuuuaucagg ggcaaaaagg aaagagacaa | 1440 |
| aacagcauga aaugaugaga ccaagugaug aaaauucauu cacaaugauu gcuuucaaga | 1500 |
| guauuucuc uuggguaauu cagcagccug uuacuauggc ucucuggagu gauagcuaau | 1560 |
| guaaaugaag ccucuaaaag uggauuauec ugacaagaau auacucagcc aauaaugcaa | 1620 |
| cagaaaucca uucaaagcau ucgggaaaaa uucaaaagaa uaaauauucu uuuuuuuuu | 1680 |
| uuaaaguuaa ugaccuacga uccauuucuu cccugacuaa caagcagcaa gcacuuaaaa | 1740 |
| auauccagcc aggaugaaau agaaacccac cugacuuguu aauauuuuug uuugguccca | 1800 |
| gggacucaga uucuaagcca aauucuuuga augaucuugg caaagucuc gaauuauuuu | 1860 |
| ugccaacuuu ucuuuaucuu ggaaaaaaag uuucaugaau ggguguucaaa auugauuagu | 1920 |
| uuuaaaaacc uuucuugcag auacguaugg caccccuaaaa cuguauuaga aaaaaauuuc | 1980 |
| auaucuccag gccuuucauu gggucagguu ggcauuucgc ugcccuuuau gugugugaca | 2040 |
| agugaaaaua aggaaagaaa aaaacucaag ugaagaaaau cagaaucugc gcagcaguuc | 2100 |
| cugggcguuu cagcugcuuc ccacaucacc ugccucauca agcccagca uccaucuccu | 2160 |
| ugcucaucuu acaccugug ugcaugacag gcccaccauu cauuuaucag agcaaaggcu | 2220 |
| cucccacuau ucugguucac ccccuacuu agccagauau acaagaauau cugcacggau | 2280 |
| gaccugccuc accugggagc ucagaggagc ucagauucca uuacuaucgc accaaggaca | 2340 |
| gaucucccag caagaaugac agaaaagacu aacugccccc aaaaucuccc uuccaaaaca | 2400 |
| caguucucuu aauucuccca agaaaccaga augugacugc ucaccucucu aaggaccuga | 2460 |
| aaacaacugg ccauuucagc uauuuaaauc aacuuuaaaa auccaaccg ccaaauauu | 2520 |
| aaaccauuuu gguuggaaug auaacauaac uaaccugcug acagcugcuu cugcuaggug | 2580 |
| caaaaaugga aaaaaaaaua cuucaaauca ggucaaauca cucuaccuuu gggauucuaa | 2640 |
| auuuacucau auucucaaag aaauauauuc agucauagug gggaaaauag gauuauuccu | 2700 |
| uuagcucgau aagcaaccag aaguucuccc uucaaaucuu gacauuuaau caaucagaaa | 2760 |
| uugauuuuug gaaaacuguu uccuaugaag cuaucucugc cugaaggauu uucuuuuac | 2820 |
| aauccagacu auagaaggaa auucacaacc uggacuuuca ccuccauugg ucagaguuuu | 2880 |
| acugaccaau ucccaccucu gccuuacacc uaacggaagu uuaugccugu uucucuuca | 2940 |
| cauaccccaa caguuacaaa ugguuguauu auuaagcau cuuuuauuuu guggccucug | 3000 |
| auuacauggu ccccuaaauu uugaccuaau cacaaaagau ugguaaaauu ucuuaacaua | 3060 |

-continued

```
uuaauaaauau uuuguuuaug ugucaauauc uuagcaugua ucaauuaaga cagagguucuu    3120 aacguucucu uuuugaaaga gaauauuagg auucagagau auuaagagau ucucccagga    3180
ucacaguuag guaacagagc uggauuuuag uccaggucug ucuacagcuc uaacguauau    3240
acacccuuug uauaacaugu cacgaauuca gcauaaaggg aucuucagug aucuaaguca    3300
ggggucagca accuuuucua aaaggacca aauaguaaua uuucaggcuu uguggacccu    3360
auggucucua ucauaacugu ucaaaucacc auguagugua aaaggagcca uaagcaaaau    3420
auaaacuaac gaauguggcu guuuuauggg auuuuuuuu aacucuuuau uuacaaaagc    3480 aggugggcaga ucagaacuca cuuaugggcc auaguucucu gaccccugac cugaaaaau    3540 cuuauauuua uggacaacau uuagacugug acuugccaag uaagaacaag aagcucuguc    3600
aacugaaggu caaggcugga guucugaaag caaagagcug ucggguguua augauaagug    3660
aaauaguuaa aguuagaaga ucccaguuau aagaagcaca aagaauaaug accauagacu    3720
ccugaacaag aaugucugga cuucggcuu aggcacucuu guuguauggu ccaggccaag    3780
uuaccuaauc ucuccaggcc uccauuuucu uaucauuaaa ugaagauaau aaaaguauuu    3840
uccucagaga gcuguaagaa uaacugagc uacccaugu caagcacaua gaauagggcc    3900
cagccuauau uaauuuauca auaaaugcca g                                  3931
```

<210> SEQ ID NO 11
<211> LENGTH: 9458
<212> TYPE: RNA
<213> ORGANISM: Homo sapiens
<220> FEATURE:
<221> NAME/KEY: mRNA
<222> LOCATION: (1)...(9458)
<223> OTHER INFORMATION: Corresponds to a cDNA detected by cDNA cloning.
      It includes one exon. The sequence includes the last
      two exons in Seq_ID_07.doc. It is transcribed from
      the +strand of Seq_ID_06.doc

<400> SEQUENCE: 11

```
auuugaauug gugaacuuag uaaagcagac ggcucucacc aauaagggca ggcaucaucc      60
aaucugucga aagcuugaau aaaacaaaaa gaggaaggga aaauuugcuu cuuuucuucu     120
ugaucuagua uaucaucuuc uccugcccuu ggaugugagu gggccuucag acuuaaacca     180
ggaguuacac cuuuggcuuc ccugguucuc aguucuuugg acuuggacug aauuacacug     240
ccagguuucc ugguucucca gcuugcagau ggcagaucau gggacuucuu ggccuccaua     300
auugugugag ucaauuucca uuuuauuuac auauccaguu augcauugcu uaacaaugga     360
gacagguucu gagaaaugca uuguuaagug auuucaucau ugugcaaaca ucauagagug     420
uaacuacaca aaccuggaca gcauagacua cuacacaucu aggcuacaug uguuagcuug     480
uaaccucaug auaaguaugu auaacaucau gauaaguaug uauguaucua ccauaucuaa     540
auguagaaaa gguacaguaa aaauaugguu uaaucuuaug ggaucaccau cauauaugca     600
auccuuugua gacugaaaug ucauguguua gugcaugacu guauacgcac acauacacaa     660
acacacacaa auauacuauu gguucuuuu cucugaagag cccuaauaca auaguuuaua     720
cauuuauauu gacucuauuu caaaauuuau gguuuuggug aaacauaugu ggagauggg     780 cauaggugug ugaacuggga uaguguccug cugaugaaug ggugggaggc aucauuuggg     840
acaagcccag ggcaucagcu uauagauauc aagagcucaa caagagcacu uuauggcaaa     900
accucccaca agaccucuca gaaguugaga aacugcuaaa aguuucuuua ugacagauga     960
cauuuaugga uaaaauaggg auuagcagga uucuuuaaau acuuucgaac acuaaccuuc    1020
auuucuacca ggcagugggg ccccaagugc agggccauag gaaguacaag ucugggagau    1080
```

-continued

```
acuaggcugc acugucugua gagaaucuga aaaaauaaua gagucacuga aaugcaguuu    1140
gguauaauua uugccaugca ucauaauucu aaaucauacu aguggucaaa uacucuuccc    1200
ugaaaaaaca uuuucuuggu uugaauucua aauaauuguu guggucacca cugagcuuuu    1260
aaauauauaa auacuuucaa guuugcauau uuuuauuacc uguccuuaa caaacauuga     1320 auucaacaug aaaaugauua ugggaaacau ucggguauac aguccugac ucuuaaggac     1380 ucagguaaau acuuagggua uuucauggcc cuagucuuug ggguaccaca uguuucuucu    1440
ucaaaucaca gauucaaaau caagaaugau aacacaguga uuguguagac aaaauaagug    1500
aaccaaaauu gcuugcuucu gucauucuau ggaaccacug agaguuuuua cuugugcuua    1560
aaauuuugaa uaguaaaaca gagugucaac uucaugcugg aauauuuuug gcuuuuuaga    1620
cacaauuuua aguacaugaa guauuuuuac aagacuaagu aacaucacug aaauuacagc    1680
uuucuucuuu uuaaaacugg uauuuguuau aaaacuaaag agcgaaucaa gaaaagcaua    1740
auuauuacug auuauuacag gauuauuacu gaaaagaaa uguacggaau agaggaggaa     1800
ggaguuaaca aaugauccac ucggguguu gaaaacacca auaagccugc uuccaggaag     1860
ugccuaagac agagcuggcu cagcuugcug ggucacagca guaaggaaa cugcugggcu     1920 acaugccacc auccucaguu guccagauag auaaucccau agccccaugg ggaaauaauc    1980
uuuaauuaug auauagcuga caccauucaa agcacauagc uaaguccuuu augugaauua    2040
acuuuuguca aauuuauuuu ucauaaauaa cccaaauaug uauaccacua uuauccuacc    2100
uuaaagagga gaaacugagc uccuaaaguu uaaauaucua acccaaguua agacugcuag    2160
ucacccuagg cuauuaacuc aggcagucua acucagguau aauaacauua ugcuacuguu    2220
ugcagcuuuu acuaugccug aauuauaacg ucaugcuauc uaacuaaaaa gcuaagggaa    2280
auaaaaugag ccauagggcu caauuucaua aaggagaga aaauacuggg gaaaagugau     2340
aaugcagagu uuaaaauauu uuuguaaaag ugccagagau ugaguauaac aagugugacc    2400 aaaaaaaaa aaaaaaaaa aaaaggaaga agguaaaaaa aagagggagg ucugagaaau     2460
agaaauauca gaggaaggaa auaaaggagg gugagaguaa auucucuuuu agcauucaga    2520
uuccacagau uccacaaauc acauuucuuu uuuuaccaac uaaggaaaaa uaacacuuga    2580
ccuaacauuu cauugcaguu agcuaaagga ugcuagaaaa acuauguugc agugguuugc    2640
ucuaauuucu ucaggaauag agaaaaguga caaaaagauc agagaagaga agaaaggaaa    2700
cuaucagaaa aauacagaau uggaguagga uauaacauau uugggugaa gguaaaauuu     2760 uauauuguaa ucuuaaguau cuugcuacuu caguugguc ccuggaacag cagcaucaga     2820
aucugccgag ggcuuguuaa aaaggcagaa ucucaggucc cauccagac ucacugaauc     2880 agaauauaaa uacugacaag augccccggg auucauaugc acaguagagc uggcgaaguu    2940
ccauuguagc cuguaauugu uuucugcaac uuaguauuuc ugaguuuccc caaggaagaa    3000
aacccaggcc uuagcuucug gcagacuugu guuucuccuu uacuuacuag cugcaugacu    3060
caugagcaag gaaaucaaac uuuaugcugc ugaguuccu caucauaaa auggagacua     3120 uaauaaucau cuccuaggcu uguuugagg auguucaaca aaugcuccuu ucauuccucu     3180
auuuacagac cugccgcaga caauucgcag agcagccuuu gugcuauuau cguuuucua     3240 aacuuaguaa uugagugugaa ucuggagacu aacucugaaa uaaauaagcu gauuauuuau    3300
uuauuuucuc aaaacaacag aauacgauuu agcaaauuac uucuuaagau auuauuuuac    3360 auucuauau ucuccuaccc ugaguugaug ugugagcaau augucacuuu cauaaagcca    3420
gguauacauu auggacaggu aaguaaaaaa cauauuauuu auucuacguu uuuguccaaa    3480
```

-continued

| | |
|---|---|
| aauuuuaaau uucaacuguu gcgcgugugu ugguaaugua aaacaaacuc aguacaguag | 3540 |
| uauucaguac aguauuuaag ccccuguacu uaaacauauu ccucguacca augaaguuac | 3600 |
| augaaaagca aauuugugug agauaucgua gauggaagua aauuagucuu uauguucccc | 3660 |
| acaaauugaa augcauuuca aaacucugu guguguaugu gugugugugu cagagugugu | 3720 |
| gugagagaga gacagagaga uacgcuuugg uugccuccau aagcuggcug cuaugauuaa | 3780 |
| uaagaccaag uuuucuaaag aaaaugagau cauaacaaaa gcccucuuua ugacuaucuu | 3840 |
| uuaucagggg caaaaaggaa agagacaaaa cagcaugaaa ugaugagacc aagugaugaa | 3900 |
| aauucauuca caaugauugc uuucaagagu aauuucucuu ggguaauuca gcagccuguu | 3960 |
| acuauggcuc ucuggaguga uagcuaaugu aaaugaagcc ucuaaaagug gauuauccug | 4020 |
| acaagaauau acucagccaa uaaugcaaca gaaauccauu caaagcauuc gggaaaaauu | 4080 |
| caaaagaaua aauauucuuu uuuuuuuuu aaaguuaaug accacgauc cauucuucc | 4140 |
| cugacuaaca agcagcaagc acuuaaaaau auccagccag gaugaaauag aaacccaccu | 4200 |
| gacuuguuaa uauuuugu uggcccagg acucagauu cuaagccaaa uucuuugaau | 4260 |
| gaucuuggca aaugucucga auuauuuug ccaacuuuuc uuuaucuugg aaaaaaaguu | 4320 |
| ucaugaaugg gugucaaaau ugauuaguuu uaaaaaccuu ucuugcagau acguauggca | 4380 |
| cccuaaaacu guauuagaaa aaaguaagu acucuguagu gugaaaaauu cuuaaaggac | 4440 |
| accccucuuuu acaaacucac aaaacagcc uuggaauac ccacaugaag uagcuguugu | 4500 |
| uauugcuuuc uauauaccua caucuugcu auuauaaaaa gacuguuuu uggcaggugu | 4560 |
| gguggcucac accguaauu ccagcacuuu gggaggccaa ggcgggcgga ucaccugaga | 4620 |
| ucaggaguuc aggaccagcc ugaucaauau ggugaaaccc agucuuuacu gaaaauacaa | 4680 |
| aaaucacccg ggugugguga cgggcgccug uagcccagc uacucgggua gcugaggcag | 4740 |
| gagaaucacu ugaacucagg agucagaggu ugcagugagc ugaucaug ccacugcacu | 4800 |
| ccagccuggg ugacagagca agacuccauc ucaaaaaaaa aaaaaaaaaa gacugguuuu | 4860 |
| ucaacagcua uucccacccc ucugcaugga aauauucacc cagucaauug uuuuccuagu | 4920 |
| uuggguaaug gcccucuggg caggacugga guggggcaca caggagaagc ugcaaacuau | 4980 |
| guuuagaagc augucuggga aaugucaugc aagaaaagac auauuuaaag guaggcuuug | 5040 |
| caugaaugga aaggagagu aauucuaugu agagcagagc cucuuacuug cagugagaga | 5100 |
| agcaaaagug ggaagcaag aggaauuaug cuuuucauca gccaaauuug caggauggag | 5160 |
| gauuggcuca gucaucuugg cugaggcuca ugaaccagg uguaaagaaa guggacuaga | 5220 |
| uuaauuucau ccauuacagg aagaggagcc gugaaagaua auccagaaau cauugggauu | 5280 |
| ugauggaga agguauuug ggacuauucc auuugaaaug agaagguacc ugacauucuu | 5340 |
| ugaauuccuu ucaagcaaag gauuaaauuu acccaugagu ugacucagaa aaaacauaaa | 5400 |
| aaguauuguu gcucugcuca gauuuuauc uaacucauuc ucacuucuua uuccaugaug | 5460 |
| aaaugacaua aaugagguuu uuuauuguug uguuguugu uuucuggaca caaggcaagg | 5520 |
| uagcuaccug ggcagagcug uuuuauuucu cuaugccgug gagagaaauu gguuaauggu | 5580 |
| ccauggaagg cagucauuaa gauguuccca ugcgagugaa cuuuccaggg uucccagcuu | 5640 |
| cugcauccuu cccugucccu caauuccauu guuggugaug acaaugucuc ucccaucagc | 5700 |
| cucaugaagu ucucucucau uuauuaaaau uggcuucag gaaaauuuuu gaaaaugugu | 5760 |
| ccaguaaugc cugauuggcc ccuuauccua aaggcuuaaa cuggaggaag gaagcuaaac | 5820 |
| ugagaaaucu ugcaaaucau ugagccaaaa acguauuaau agcaagaucu aucauuuauu | 5880 |

|  |  |
| --- | --- |
| gacuaguaug uggcaggcag ugcccuuuua uuuaggcagg gagaguugau gggggggggcg | 5940 |
| ggguucacac aucuuaaaga ggugcuaucu ccuccuauau aaaucaugua agucaagaga | 6000 |
| guaaggaauu gucuuuguuu gguuauauuc aggggauuag aguauacagu agaagauccc | 6060 |
| aagaaaccuu gggaucauuu uagacuaaga aaugccaaua ccgccgggcg cgguggcuca | 6120 |
| cgccuguaau cccagcacuu ugagaggccg agguggggcgg aucacaaggu caggagauug | 6180 |
| agaccguccu ggcuaacgug gugaaacccu gucucuacua aaaauacaaa aaauuagccg | 6240 |
| ggcguggugg cgggcgccug uagucccagc uacucgggag gcggaggcag gagaaugguug | 6300 |
| ugaacucagg aggcggagcu ugcagucagc cgagauugcc ccaaugcacu ccagccuggg | 6360 |
| cgacagaacg agacuccguc ucagaacaaa acaaaaggaa augccaauac cagcagaaau | 6420 |
| agagccaaau caugaacaua agcuaaacaa auguuggcag cguagccuag gguuaagag | 6480 |
| agcagacucu uaacuagaac acugcacucc auguccucac uguagacccu cacuguggg | 6540 |
| uucuaauuaa cccguuac uuaccaguag cagucuaag gcauuccuua aguucguugu | 6600 |
| gccccaauuu guucaucugu agaaggggua ggaugacagu aguguuuacu uuauaggcuu | 6600 |
| acugugagca uuaaaugagu uacuacugua uuguaaagu gcuuaaaaug cugcuccaaa | 6720 |
| agaguuuguu aaacacuuaa gaacugauuu acuugcaucu aaacugacag cucucaauaa | 6780 |
| cuggaaauga ucaagcauag gcccuggau auaagcaggu cuacaugaag gcaaaaaugu | 6840 |
| ucguuucuuu uguucagccc ugugccuaga ucaauaucua gugaucaugc ucaagaaaua | 6900 |
| uuguugaaug aaucaaugaa ccuaccgagg uaguuacaua aaagaguucu gcaugaguac | 6960 |
| aaaucugggc aaagugaccu ccaaggaaau uccacuuuu agauucugug auuccuuaa | 7020 |
| ggaacugaua aauggugug auacaaugua aaaaaaugug ccauaaugau uugagaaaaa | 7080 |
| cuuauuuucu cuccccucuuu uuuccuuccu uccuuccuc cucccuuccu uccuccucc | 7140 |
| cucccuuccu uccucccucc cucccuuccu uccuucucu ucuucuuuuc uuucuuucuu | 7200 |
| ucuuucuuc uuucuuucu ucuucuuuc uuucuuucu cucuucuucuu uccuucuuu | 7260 |
| cuuccuuucu uugugccuuu cuuucuuucu ucuuucuuc ucugccuuuu cuuucuuccu | 7320 |
| uucuuucuuu cugccuuucu uucuuuugu uuucuuucu uccuucuuu uuccuuuaa | 7380 |
| gcagaccaug ucuguuagau gaaugccuuu uucuaguuaa aagguuaaac aggaaaguga | 7440 |
| agcacaauua ucaagggucu ccagucaucu ccacauguuc uuaaucauua ucuucuuuua | 7500 |
| caguuucaua ucuccaggcc uuucauuggg ucagguuggc auuucgcugc ccuuuaugug | 7560 |
| ugugacaagu gaaaauaagg aagaaaaaa acucaaguga agaaaaucag aaucugcgca | 7620 |
| gcaguuccug ggcguuucag cugcuucca caucaccugc cucaucaagc cccagcaucc | 7680 |
| aucuccuugc ucaucuuaca cccguguggc augacaggcc caccauucau uuaucagagc | 7740 |
| aaaggcucuc ccacuauucu gguucacccc ccuacuuagc cagauauaca agaauaucug | 7800 |
| cacggaugac cugccucacc ugggagcuca gaggagcuca gauccauua cuaucgcacc | 7860 |
| aaggacagau cucccagcaa gaaugacaga aaagacuaac ugcccccaaa aucccccuuc | 7920 |
| caaaacacag uucucuuaau ucucccaaga aaccagaaug ugacugcuca ccucucuaag | 7980 |
| gaccugaaaa caacuggcca uuucagcuau uuaaaucaac uuuaaaaaau ccaaccgcca | 8040 |
| aaauauuaaa ccauuuggu uggaaugaua acauaacuaa ccugcugaca gcugcuucug | 8100 |
| cuaggugcaa aaauggaaaa aaaaauacuu cuaaucaggu caaaucacuc uaccuuuggg | 8160 |
| auucuaaauu uacucauauu cucaaagaaa uauauucagu cauaguggg aaauaaggau | 8220 |
| uauuccuuua gcucgauaag caaccagaag uucuuccuuc aaaucuugac auuuaaucaa | 8280 |

-continued

| | |
|---|---|
| ucagaaauug auuuuuggaa aacuguuucc uaugaagcua ucucugccug aaggauuuuu | 8340 |
| cuuuuacaau ccagacuaua gaaggaaauu cacaaccugg acuuucaccu ccauugguca | 8400 |
| gaguuuuacu gaccaauucc caccucugcc uuacaccuaa cggaaguuua ugccuguuuu | 8460 |
| cucuucacau accccaacag uuacaaaugg uuguuauuau uaagcaucuu uuauuuugug | 8520 |
| gccucugauu acaugguccc cuaaauuuug accaaucac aaaagauugg uaaaauuucu | 8580 |
| uaacauauua auaauauuuu guuuaugugu caauaucuua gcauguauca auuaagacag | 8640 |
| aggucuuaac guucucuuuu ugaaagagaa uauuaggauu cagagauauu aagagauucu | 8700 |
| cccaggauca caguuaggua acagagcugg auuuuagucc aggucugucu acagcucuaa | 8760 |
| cguauauaca cccuuuguau aacaugucac gaauucagca uaaagggauc uucagugauc | 8820 |
| uaagucaggg gucagcaacc uuuucuaaaa aggaccaaau aguaauauuu caggcuuugu | 8880 |
| ggacccuaug gucucuauca uaacuguuca aaucaccaug uaguguaaaa ggagccauaa | 8940 |
| gcaaauaua aacuaacgaa uguggcuguu uuaugggauu uuuuuuaac ucuuuauuua | 9000 |
| caaaagcagg uggcagauca gaacucacuu auggggccaua guucucugac cccugaccug | 9060 |
| agaaaaucuu uauuuuaugg acaacauuua gacugugacu ugccaaguaa gaacaagaag | 9120 |
| cucugucaac ugaaggucaa ggcuggaguu cugaaagcaa agagcugucu gguguuaaug | 9180 |
| auaagugaaa uaguuaaagu uagaagaucc caguuauaag aagcacaaag aauaaugacc | 9240 |
| auagacuccu gaacaagaau gucuggacuu cuggcuuagg cacucuuguu guauggucca | 9300 |
| ggccaaguua ccuaaucucu ccaggccucc auuuucuuau cauuaaauga agauaauaaa | 9360 |
| aguauuuucc ucagagagcu guaagaauaa acugagcuaa cccaugucaa gcacauagaa | 9420 |
| uagggcccag ccuauauuaa uuuaucaaua aaugccag | 9458 |

<210> SEQ ID NO 12
<211> LENGTH: 552
<212> TYPE: DNA
<213> ORGANISM: Homo sapiens
<220> FEATURE:
<221> NAME/KEY: exon
<222> LOCATION: (1)...(552)
<223> OTHER INFORMATION: Exon 1

<400> SEQUENCE: 12

| | |
|---|---|
| attatgtaga accattccaa tcctgagtga caggatttgc aaagacagct gttgggctcc | 60 |
| acaaacattt ggaggagggg aaaatgtgag gttggttgct acattctcct acttcttttt | 120 |
| actgaaagga acagctgcga tcttcacatg taagatgaag taaacaaaag ctgacaatgc | 180 |
| ccagcaccat tcagcagtaa gcattcaaat ggatttttcc tcaccgcgtt tgcaggcccg | 240 |
| gcacagtctc agttccccac agcacagaga ggaagcaagg tctttgcatg ccctgttcac | 300 |
| ttggccaaac attgccctag atgtgcaatt caacccatat aaagcaagcg taattcaaga | 360 |
| gccctgactc tttcaccatt tcatgatggc ttattactcg cacacggcat tgtcaggttc | 420 |
| cagcaactct gtgtgcagca ggcagaaatg cagtgtttat ctctgacagg caaacattct | 480 |
| taggctcatc ggcatgagta tccacgctga actggctatc ggggaagtag atccctgcat | 540 |
| gggaaagtca ag | 552 |

<210> SEQ ID NO 13
<211> LENGTH: 305
<212> TYPE: DNA
<213> ORGANISM: Homo sapiens
<220> FEATURE:
<221> NAME/KEY: exon

```
<222> LOCATION: (1)...(305)
<223> OTHER INFORMATION: Exon 1a

<400> SEQUENCE: 13
atttgaattg gtgaacttag taaagcagac ggctctcacc aataagggca ggcatcatcc    60
aatctgtcga aagcttgaat aaaacaaaaa gaggaaggga aaatttgctt cttttcttct   120
tgatctagta tatcatcttc tcctgcccctt ggatgtgagt gggccttcag acttaaacca   180
ggagttacac ctttggcttc cctggttctc agttctttgg acttggactg aattacactg   240
ccaggtttcc tggttctcca gcttgcagat ggcagatcat gggacttctt ggcctccata   300
attgt                                                              305

<210> SEQ ID NO 14
<211> LENGTH: 307
<212> TYPE: DNA
<213> ORGANISM: Homo sapiens
<220> FEATURE:
<221> NAME/KEY: exon
<222> LOCATION: (1)...(307)
<223> OTHER INFORMATION: Exon 1b

<400> SEQUENCE: 14
atttgaattg gtgaacttag taaagcagac ggctctcacc aataagggca ggcatcatcc    60
aatctgtcga aagcttgaat aaaacaaaaa gaggaaggga aaatttgctt cttttcttct   120
tgatctagta tatcatcttc tcctgcccctt ggatgtgagt gggccttcag acttaaacca   180
ggagttacac ctttggcttc cctggttctc agttctttgg acttggactg aattacactg   240
ccaggtttcc tggttctcca gcttgcagat ggcagatcat gggacttctt ggcctccata   300
attgtgt                                                            307

<210> SEQ ID NO 15
<211> LENGTH: 557
<212> TYPE: DNA
<213> ORGANISM: Homo sapiens
<220> FEATURE:
<221> NAME/KEY: exon
<222> LOCATION: (1)...(557)
<223> OTHER INFORMATION: Exon 2

<400> SEQUENCE: 15
gggcaaaaag gaaagagaca aaacagcatg aaatgatgag accaagtgat gaaaattcat    60
tcacaatgat tgcttttcaag agtaatttct cttgggtaat tcagcagcct gttactatgg   120
ctctctggag tgatagctaa tgtaaatgaa gcctctaaaa gtggattatc ctgacaagaa   180
tatactcagc caataatgca acagaaatcc attcaaagca ttcgggaaaa attcaaaaga   240
ataaatattc ttttttttttt tttaaagtta atgacctacg atccatttct tccctgacta   300
acaagcagca agcacttaaa aatatccagc caggatgaaa tagaaaccca cctgacttgt   360
taatattttt gtttggtccc agggactcag attctaagcc aaattcttttg aatgatcttg   420 gcaaatgtct cgaattattt ttgccaactt ttctttatct tggaaaaaaa gtttcatgaa   480
tgggtgtcaa aattgattag ttttaaaaac ctttcttgca gatacgtatg gcaccctaaa   540
actgtattag aaaaaaa                                                 557

<210> SEQ ID NO 16
<211> LENGTH: 1955
<212> TYPE: DNA
<213> ORGANISM: Homo sapiens
<220> FEATURE:
<221> NAME/KEY: exon
```

<222> LOCATION: (1)...(1955)
<223> OTHER INFORMATION: Exon 3

<400> SEQUENCE: 16

```
tttcatatct ccaggccttt cattgggtca ggttggcatt tcgctgccct ttatgtgtgt      60
gacaagtgaa ataaggaaa gaaaaaaact caagtgaaga aaatcagaat ctgcgcagca     120
gttcctgggc gtttcagctg cttcccacat cacctgcctc atcaagcccc agcatccatc     180
tccttgctca tcttacaccc tgtgtgcatg acaggcccac cattcattta tcagagcaaa     240
ggctctccca ctattctggt tcaccccct acttagccag atatacaaga atatctgcac     300
ggatgacctg cctcacctgg gagctcagag gagctcagat tccattacta tcgcaccaag     360
gacagatctc ccagcaagaa tgacagaaaa gactaactgc ccccaaaatc tcccttccaa     420
aacacagttc tcttaattct cccaagaaac cagaatgtga ctgctcacct ctctaaggac     480
ctgaaaacaa ctggccattt cagctattta atcaacttt aaaaaatcca accgccaaaa      540
tattaaacca ttttggttgg aatgataaca taactaacct gctgacagct gcttctgcta     600
ggtgcaaaaa tggaaaaaaa aatacttcta atcaggtcaa atcactctac ctttgggatt     660
ctaaatttac tcatattctc aaagaaatat attcagtcat agtggggaaa ataggattat     720
tcctttagct cgataagcaa ccagaagttc ttccttcaaa tcttgacatt taatcaatca     780
gaaattgatt tttggaaaac tgtttcctat gaagctatct ctgcctgaag gattttctt      840
ttacaatcca gactatagaa ggaaattcac aacctggact ttcacctcca ttggtcagag     900
ttttactgac caattcccac ctctgcctta cacctaacgg aagtttatgc ctgttttctc     960
ttcacatacc ccaacagtta caaatggttg ttattattaa gcatctttta ttttgtggcc    1020
tctgattaca tggtccccta aattttgacc taatcacaaa agattggtaa aatttcttaa    1080
catattaata atattttgtt tatgtgtcaa tatcttagca tgtatcaatt aagacagagg    1140
tcttaacgtt ctctttttga aagagaatat taggattcag agatattaag agattctccc    1200
aggatcacag ttaggtaaca gagctggatt ttagtccagg tctgtctaca gctctaacgt    1260
atatacaccc tttgtataac atgtcacgaa ttcagcataa agggatcttc agtgatctaa    1320
gtcaggggtc agcaaccttt tctaaaaagg accaaatagt aatatttcag gctttgtgga    1380
ccctatggtc tctatcataa ctgttcaaat caccatgtag tgtaaaagga gccataagca    1440
aaatataaac taacgaatgt ggctgtttta tgggattttt ttttaactct ttatttacaa    1500
aagcaggtgg cagatcagaa ctcacttatg ggccatagtt ctctgacccc tgacctgaga    1560
aaatcttata tttatggaca acatttagac tgtgacttgc caagtaagaa caagaagctc    1620
tgtcaactga aggtcaaggc tggagttctg aaagcaaaga gctgtctggt gttaatgata    1680
agtgaaatag ttaaagttag aagatcccag ttataagaag cacaaagaat aatgaccata    1740
gactcctgaa caagaatgtc tggacttctg gcttaggcac tcttgttgta tggtccaggc    1800
caagttacct aatctctcca ggcctccatt ttcttatcat taaatgaaga taataaaagt    1860
attttcctca gagagctgta agaataaact gagctaaccc atgtcaagca catagaatag    1920
ggcccagcct atattaattt atcaataaat gccag                              1955
```

<210> SEQ ID NO 17
<211> LENGTH: 366
<212> TYPE: DNA
<213> ORGANISM: Homo sapiens
<220> FEATURE:
<221> NAME/KEY: CDS
<222> LOCATION: (1)...(366)

<400> SEQUENCE: 17

```
atg ttc aac aaa tgc tcc ttt cat tcc tct att tac aga cct gcc gca      48
Met Phe Asn Lys Cys Ser Phe His Ser Ser Ile Tyr Arg Pro Ala Ala
1               5                   10                  15 gac aat tct gct agc agc ctt tgt gct att atc tgt ttt cta aac tta      96
Asp Asn Ser Ala Ser Ser Leu Cys Ala Ile Ile Cys Phe Leu Asn Leu
            20                  25                  30 gta att gag tgt gat ctg gag act aac tct gaa ata aat aag ctg att     144
Val Ile Glu Cys Asp Leu Glu Thr Asn Ser Glu Ile Asn Lys Leu Ile
        35                  40                  45 att tat tta ttt tct caa aac aac aga ata cga ttt agc aaa tta ctt     192
Ile Tyr Leu Phe Ser Gln Asn Asn Arg Ile Arg Phe Ser Lys Leu Leu
    50                  55                  60 ctt aag ata tta ttt tac att tct ata ttc tcc tac cct gag ttg atg     240
Leu Lys Ile Leu Phe Tyr Ile Ser Ile Phe Ser Tyr Pro Glu Leu Met
65                  70                  75                  80 tgt gag caa tat gtc act ttc ata aag cca ggt ata cat tat gga cag     288
Cys Glu Gln Tyr Val Thr Phe Ile Lys Pro Gly Ile His Tyr Gly Gln
                85                  90                  95 gta agt aaa aaa cat att att tat tct acg ttt ttg tcc aaa aat ttt     336
Val Ser Lys Lys His Ile Ile Tyr Ser Thr Phe Leu Ser Lys Asn Phe
            100                 105                 110 aaa ttt caa ctg ttg cgc gtg tgt tgg taa                             366
Lys Phe Gln Leu Leu Arg Val Cys Trp *
            115                 120
```

<210> SEQ ID NO 18
<211> LENGTH: 1253
<212> TYPE: DNA
<213> ORGANISM: Homo sapiens
<220> FEATURE:
<221> NAME/KEY: exon
<222> LOCATION: (1)...(1253)
<223> OTHER INFORMATION: ESTbc03936 Exon 2

<400> SEQUENCE: 18

```
tatccccact gtgtagagct ggtccacaat ggagaggagg aaaagttttg cattggacca      60
aatcactgcc ttagaaggaa agagattgca atcccattca tttttaagat ctgcaatggg     120
ttgggatgat acccatttaa aaagaaaaa aaagaggtt acctctttgg cctctttggc      180
aaaggatatg aactagtaat aaagcctcag catcaaggct gggagtctg gctcaaagtg     240
gctaagacta gaagcatctt ctaacataaa tatggcagca ttaggaaaat agcttggcct     300
ttagagagac ccagattatc ttcaccttaa aaactaccaa gaccctggtc cagcaagacc     360
accatcacag cagtaaatac atagccacca acttcacaga aggttttcca ctgagacatt     420
gtgaaaacca caatccatta ccggtggatg agtcccagct ctcttactac ctggagcttc     480
caagcaagac ttacctgtcc tttgttccag attggttcct gggatcctgg accaacacaa     540
agagaagagg aaagcctcaa gggaaataaa agtgaaggtt tcagtgatag tttaaatata     600
tattttttaaa tgttagcttt tttttaaata cttcacggtg atggatggag tatttcaacc     660
acaatggcaa agaatgaatt accggcagtg tcagagtttc ttgttgctgt gggaagacag     720
ctgccatgtt gagaggtgcc ttgtggagag gctcatgtgg cgaggaactg agactggctt     780
ctatccaaca accagtgagg aactaaggcc ctaaagtcct atagtccaca aggaactaaa     840
tcctaccaac aactacatga gtgagcctgg aatctgattt tccccagtgg ggacttaagg     900
tacctacaac ctggctgtta tgggctaaac tgcatcctgc ccaaatttat atgtttgagt     960
cttaactccc agcacttcag aacatggttt tgtttggaga catagtcatt aaagaggtaa    1020
```

```
tgaagttaaa atgaggtcat taggatgagt cctaatccaa taggactggt gttcttatat    1080
gaagaggaaa tttgaacaca gacacatata caggaaagac catgcgaaga agacacagag    1140
aggaaacggc catctacaat ccaaggagag aggcctcaga acaagccaac cctgcagata    1200
ccttgatcta ggcatccaga attgtatgaa aatacatttt tgttatttaa gct           1253

<210> SEQ ID NO 19
<211> LENGTH: 21
<212> TYPE: RNA
<213> ORGANISM: Homo sapiens
<220> FEATURE:
<221> NAME/KEY: mRNA
<222> LOCATION: (1)...(21)
<223> OTHER INFORMATION: siRNA targeting Exon 1

<400> SEQUENCE: 19
aauaagggca ggcaucaucc a                                               21

<210> SEQ ID NO 20
<211> LENGTH: 21
<212> TYPE: RNA
<213> ORGANISM: Homo sapiens
<220> FEATURE:
<221> NAME/KEY: mRNA
<222> LOCATION: (1)...(21)
<223> OTHER INFORMATION: siRNA targeting Exon 1 B

<400> SEQUENCE: 20
aauuacacug ccagguuucc u                                               21

<210> SEQ ID NO 21
<211> LENGTH: 21
<212> TYPE: RNA
<213> ORGANISM: Homo sapiens
<220> FEATURE:
<221> NAME/KEY: mRNA
<222> LOCATION: (1)...(21)
<223> OTHER INFORMATION: siRNA targeting Exon 2 A

<400> SEQUENCE: 21
aauucauuca caaugauugc u                                               21

<210> SEQ ID NO 22
<211> LENGTH: 21
<212> TYPE: RNA
<213> ORGANISM: Homo sapiens
<220> FEATURE:
<221> NAME/KEY: mRNA
<222> LOCATION: (1)...(21)
<223> OTHER INFORMATION: siRNA targeting Exon 2 B

<400> SEQUENCE: 22
aauuucucuu ggguaauuca g                                               21

<210> SEQ ID NO 23
<211> LENGTH: 21
<212> TYPE: RNA
<213> ORGANISM: Homo sapiens
<220> FEATURE:
<221> NAME/KEY: mRNA
<222> LOCATION: (1)...(21)
<223> OTHER INFORMATION: siRNA targeting Exon 3 (DDend) A

<400> SEQUENCE: 23
aaaaucagaa ucugcgcagc a                                               21

<210> SEQ ID NO 24
```

```
<211> LENGTH: 21
<212> TYPE: RNA
<213> ORGANISM: Homo sapiens
<220> FEATURE:
<221> NAME/KEY: mRNA
<222> LOCATION: (1)...(21)
<223> OTHER INFORMATION: siRNA targeting Exon 3 (DDend) B

<400> SEQUENCE: 24
aaugaugaug ggaagaagga a                                               21

<210> SEQ ID NO 25
<211> LENGTH: 21
<212> TYPE: RNA
<213> ORGANISM: Homo sapiens
<220> FEATURE:
<221> NAME/KEY: mRNA
<222> LOCATION: (1)...(21)
<223> OTHER INFORMATION: siRNA targeting CDS A

<400> SEQUENCE: 25
aaacuuagua auugagugug a                                               21

<210> SEQ ID NO 26
<211> LENGTH: 21
<212> TYPE: RNA
<213> ORGANISM: Homo sapiens
<220> FEATURE:
<221> NAME/KEY: mRNA
<222> LOCATION: (1)...(21)
<223> OTHER INFORMATION: siRNA targeting CDS B

<400> SEQUENCE: 26
aauaugucac uuucauaaag c                                               21

<210> SEQ ID NO 27
<211> LENGTH: 14
<212> TYPE: DNA
<213> ORGANISM: Homo sapiens
<220> FEATURE:
<221> NAME/KEY: primer_bind
<222> LOCATION: (1)...(14)
<223> OTHER INFORMATION: Exon overlapping oligonucleotide primer F26

<400> SEQUENCE: 27
agacggctct cacc                                                       14

<210> SEQ ID NO 28
<211> LENGTH: 21
<212> TYPE: DNA
<213> ORGANISM: Homo sapiens
<220> FEATURE:
<221> NAME/KEY: primer_bind
<222> LOCATION: (1)...(21)
<223> OTHER INFORMATION: Exon overlapping oligonucleotide primer FDP5

<400> SEQUENCE: 28
cacttgtcac acacataaag g                                               21

<210> SEQ ID NO 29
<211> LENGTH: 21
<212> TYPE: DNA
<213> ORGANISM: Homo sapiens
<220> FEATURE:
<221> NAME/KEY: primer_bind
<222> LOCATION: (1)...(21)
<223> OTHER INFORMATION: cDNA oligonucleotide primer FDP5

<400> SEQUENCE: 29
```

```
cctttatgtg tgtgacaagt g                                              21

<210> SEQ ID NO 30
<211> LENGTH: 22
<212> TYPE: DNA
<213> ORGANISM: Homo sapiens
<220> FEATURE:
<221> NAME/KEY: primer_bind
<222> LOCATION: (1)...(22)
<223> OTHER INFORMATION: cDNA oligonucleotide primer F10

<400> SEQUENCE: 30
atccagccag gatgaaatag aa                                             22

<210> SEQ ID NO 31
<211> LENGTH: 20
<212> TYPE: DNA
<213> ORGANISM: Homo sapiens
<220> FEATURE:
<221> NAME/KEY: primer_bind
<222> LOCATION: (1)...(20)
<223> OTHER INFORMATION: upstream primer human VH family leader sequence
      VH1

<400> SEQUENCE: 31
ccatggactg gacctggagg                                                20

<210> SEQ ID NO 32
<211> LENGTH: 21
<212> TYPE: DNA
<213> ORGANISM: Homo sapiens
<220> FEATURE:
<221> NAME/KEY: primer_bind
<222> LOCATION: (1)...(21)
<223> OTHER INFORMATION: upstream primer human VH family leader sequence
      VH2

<400> SEQUENCE: 32
atggacatac tttgttccag c                                              21

<210> SEQ ID NO 33
<211> LENGTH: 20
<212> TYPE: DNA
<213> ORGANISM: Homo sapiens
<220> FEATURE:
<221> NAME/KEY: primer_bind
<222> LOCATION: (1)...(20)
<223> OTHER INFORMATION: upstream primer human VH family leader sequence
      VH3

<400> SEQUENCE: 33
ccatggagtt tgggctgagc                                                20

<210> SEQ ID NO 34
<211> LENGTH: 20
<212> TYPE: DNA
<213> ORGANISM: Homo sapiens
<220> FEATURE:
<221> NAME/KEY: primer_bind
<222> LOCATION: (1)...(20)
<223> OTHER INFORMATION: upstream primer human VH family leader sequence
      VH4

<400> SEQUENCE: 34
atgaaacacc tgtggttctt                                                20

<210> SEQ ID NO 35
<211> LENGTH: 20
<212> TYPE: DNA
```

```
<213> ORGANISM: Homo sapiens
<220> FEATURE:
<221> NAME/KEY: primer_bind
<222> LOCATION: (1)...(20)
<223> OTHER INFORMATION: upstream primer human VH family leader sequence
      VH5

<400> SEQUENCE: 35
atggggtcaa ccgcgatcct                                                     20

<210> SEQ ID NO 36
<211> LENGTH: 20
<212> TYPE: DNA
<213> ORGANISM: Homo sapiens
<220> FEATURE:
<221> NAME/KEY: primer_bind
<222> LOCATION: (1)...(20)
<223> OTHER INFORMATION: upstream primer human VH family leader sequence
      VH6

<400> SEQUENCE: 36
atgtctgtct ccttcctcat                                                     20

<210> SEQ ID NO 37
<211> LENGTH: 21
<212> TYPE: DNA
<213> ORGANISM: Homo sapiens
<220> FEATURE:
<221> NAME/KEY: primer_bind
<222> LOCATION: (1)...(21)
<223> OTHER INFORMATION: down stream primer C1

<400> SEQUENCE: 37
gaggctcagc gggaagacct t                                                   21

<210> SEQ ID NO 38
<211> LENGTH: 21
<212> TYPE: DNA
<213> ORGANISM: Homo sapiens
<220> FEATURE:
<221> NAME/KEY: primer_bind
<222> LOCATION: (1)...(21)
<223> OTHER INFORMATION: down stream primer C 2

<400> SEQUENCE: 38
ggggaagacc gatgggcccc t                                                   21

<210> SEQ ID NO 39
<211> LENGTH: 20
<212> TYPE: DNA
<213> ORGANISM: Homo sapiens
<220> FEATURE:
<221> NAME/KEY: primer_bind
<222> LOCATION: (1)...(20)
<223> OTHER INFORMATION: northern blot primer

<400> SEQUENCE: 39
tcacctggga gctcagagga                                                     20

<210> SEQ ID NO 40
<211> LENGTH: 20
<212> TYPE: DNA
<213> ORGANISM: Homo sapiens
<220> FEATURE:
<221> NAME/KEY: primer_bind
<222> LOCATION: (1)...(20)
<223> OTHER INFORMATION: northern blot primer

<400> SEQUENCE: 40
```

-continued

```
gtgatcctgg gagaatctct                                              20

<210> SEQ ID NO 41
<211> LENGTH: 25
<212> TYPE: DNA
<213> ORGANISM: Homo sapiens
<220> FEATURE:
<221> NAME/KEY: primer_bind
<222> LOCATION: (1)...(25)
<223> OTHER INFORMATION: RACE antisence primer

<400> SEQUENCE: 41
tacattacca acacacgcgc aacag                                        25

<210> SEQ ID NO 42
<211> LENGTH: 30
<212> TYPE: DNA
<213> ORGANISM: Homo sapiens

<400> SEQUENCE: 42
tgacggggtc acccacactg tgcccatcta                                   30

<210> SEQ ID NO 43
<211> LENGTH: 30
<212> TYPE: DNA
<213> ORGANISM: Homo sapiens

<400> SEQUENCE: 43
ctagaagcat ttgcggtgga cgatggaggg                                   30

<210> SEQ ID NO 44
<211> LENGTH: 25
<212> TYPE: PRT
<213> ORGANISM: Homo sapiens

<400> SEQUENCE: 44

Cys Asp Leu Glu Thr Asn Ser Glu Ile Asn Lys Leu Ile Ile Tyr Leu
1               5                   10                  15

Phe Ser Gln Asn Asn Arg Ile Arg Phe
            20                  25

<210> SEQ ID NO 45
<211> LENGTH: 18
<212> TYPE: PRT
<213> ORGANISM: Homo sapiens

<400> SEQUENCE: 45

Cys Gln Val Ser Lys Lys His Ile Ile Tyr Ser Thr Phe Leu Ser Lys
1               5                   10                  15

Asn Phe
```

The invention claimed is:

1. A method for establishing a diagnosis of a subtype of B-cell chronic lymphocytic leukemia (B-CLL) in an individual comprising detecting the presence or absence of at least one transcription product, wherein said at least one transcription product comprises a RNA nucleotide sequence selected from the group consisting of SEQ ID No: 6, SEQ ID No: 7, and SEQ ID No: 11 in a biological sample isolated from the individual, wherein the biological sample is selected from the group consisting of blood, lymph node biopsy, bone marrow, and spleen biopsy.

2. A method for establishing the prognosis of a subtype of B-CLL in an individual comprising detecting the presence or absence of at least one transcription product, wherein said at least one transcription product comprises a RNA nucleotide sequence selected from the group consisting of SEQ ID No: 6, SEQ ID No: 7, and SEQ ID No: 11 in a biological sample isolated from the individual, wherein the biological sample is selected from the group consisting of blood, lymph node biopsy, bone marrow, and spleen biopsy.

3. A method for determining whether an individual has a B-CLL subtype with poor prognosis, the method comprising detecting the presence or absence of at least one transcription product, which comprises a RNA nucleotide sequence selected from the group consisting of SEQ ID No: 6, SEQ ID No: 7, and SEQ ID No: 11 in a biological sample isolated from said individual, wherein the biological sample is selected from the group consisting of blood, lymph node biopsy, bone marrow, and spleen biopsy and wherein the presence of at least one of the transcriptional product(s) indicates that the individual has a subtype of B-CLL associated with a poor prognosis.

4. The method of claim 3, wherein the determination is performed at several time points at intervals as part of a monitoring of a cancer patient after or during the treatment for primary cancer.

5. The method according to claim 1, 2, or 3, wherein said at least one transcriptional product comprises a nucleotide sequence spanning the junction between Exon-2 and Exon-3.

6. The method according to claim 5, wherein the nucleotide sequence spanning the junction between Exon-2 and Exon-3 is the last 20 nucleotides of the 3'-end of SEQ ID No: 15 and the first 20 nucleotides of the 5'-end of SEQ ID No: 16.

7. The method of claim 1 or 2, wherein the presence of at least one of the transcriptional product(s) indicates that the individual has a subtype of B-CLL associated with a poor prognosis.

8. The method according to any one of claim 1, 2, or 3, wherein the presence or absence of the transcriptional product(s) is/are determined by a method selected from the group consisting of a nucleic acid hybridization based technique and a PCR based technique.

9. A method for determining whether an individual has a B-CLL sub-type with poor prognosis, the method comprising detecting the presence or absence of at least one transcriptional product, wherein said at least one transcriptional product includes the nucleotide sequence of SEQ ID No: 11 in a biological sample isolated from the individual, wherein the biological sample is selected from the group consisting of blood, lymph node biopsy, bone marrow, and spleen biopsy and wherein the presence of at least one of the transcriptional product(s) indicates that the individual has a subtype of B-CLL associated with a poor prognosis.

10. The method according to claim 9, wherein said at least one transcriptional product comprises a nucleotide sequence spanning the junction between Exon-2 and Exon-3.

11. The method according to claim 9, wherein the method further detects for a nucleotide sequence spanning the junction between Exon-2 and Exon-3 wherein said detected sequence is the last 20 nucleotides of the 3'-end of SEQ ID No: 15 and the first 20 nucleotides of the 5'-end of SEQ ID No: 16.

12. A method for determining whether an individual has a B-CLL sub-type with poor prognosis, the method comprising detecting the presence or absence of at least one transcriptional product, wherein said at least one transcriptional product includes the nucleotide sequence of SEQ ID No: 6 in a biological sample isolated from the individual, wherein the biological sample is selected from the group consisting of blood, lymph node biopsy, bone marrow, and spleen biopsy and wherein the presence of at least one of the transcriptional product(s) indicates that the individual has a subtype of B-CLL associated with a poor prognosis.

13. A method for diagnosing or prognosing a subtype of B-CLL in an individual comprising detecting the presence or absence of at least one transcription product comprising the Exon2-Exon3 junction in a biological sample of the individual, wherein the biological sample is blood, lymph node biopsy, bone marrow, or spleen biopsy.

\* \* \* \* \*

UNITED STATES PATENT AND TRADEMARK OFFICE
CERTIFICATE OF CORRECTION

PATENT NO. : 8,586,298 B2  Page 1 of 1
APPLICATION NO. : 10/535500
DATED : November 19, 2013
INVENTOR(S) : Hertz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 840 days.

Signed and Sealed this
Twenty-second Day of September, 2015

Michelle K. Lee
*Director of the United States Patent and Trademark Office*